United States Patent
Oniciu et al.

(10) Patent No.: US 9,085,585 B2
(45) Date of Patent: Jul. 21, 2015

(54) COMPOUNDS, COMPOSITIONS AND METHODS USEFUL FOR CHOLESTEROL MOBILIZATION

(71) Applicant: CERENIS THERAPEUTICS HOLDING SA, Labege (FR)

(72) Inventors: Daniela Carmen Oniciu, Toulouse (FR); Jean-Louis Henri Dasseux, Toulouse (FR); Otto Geoffroy, Gainesville, FL (US); Ronald Barbaras, Seilh (FR)

(73) Assignee: Cerenis Therapeutics Holding SA, Lebege (FR)

( * ) Notice: Subject to any disclaimer, the term of this patent is extended or adjusted under 35 U.S.C. 154(b) by 12 days.

(21) Appl. No.: 13/673,799

(22) Filed: Nov. 9, 2012

(65) Prior Publication Data

US 2013/0267554 A1   Oct. 10, 2013

Related U.S. Application Data

(62) Division of application No. 13/276,238, filed on Oct. 18, 2011, now Pat. No. 8,349,833.

(60) Provisional application No. 61/394,136, filed on Oct. 18, 2010, provisional application No. 61/444,212, filed on Feb. 18, 2011.

(51) Int. Cl.

| A61K 31/4365 | (2006.01) |
|---|---|
| C07D 513/04 | (2006.01) |
| C07D 493/04 | (2006.01) |
| A61K 31/155 | (2006.01) |
| A61K 31/194 | (2006.01) |
| A61K 31/198 | (2006.01) |
| A61K 31/20 | (2006.01) |
| A61K 31/201 | (2006.01) |
| A61K 31/353 | (2006.01) |
| A61K 31/5377 | (2006.01) |
| A61K 31/575 | (2006.01) |
| A61K 31/7032 | (2006.01) |
| C07D 495/04 | (2006.01) |
| G01N 33/92 | (2006.01) |
| C07D 471/04 | (2006.01) |
| C07D 401/14 | (2006.01) |
| C07D 401/04 | (2006.01) |

(52) U.S. Cl.
CPC ............ *C07D 493/04* (2013.01); *A61K 31/155* (2013.01); *A61K 31/194* (2013.01); *A61K 31/198* (2013.01); *A61K 31/20* (2013.01); *A61K 31/201* (2013.01); *A61K 31/353* (2013.01); *A61K 31/4365* (2013.01); *A61K 31/5377* (2013.01); *A61K 31/575* (2013.01); *A61K 31/7032* (2013.01); *C07D 401/04* (2013.01); *C07D 401/14* (2013.01); *C07D 471/04* (2013.01); *C07D 495/04* (2013.01); *C07D 513/04* (2013.01); *G01N 33/92* (2013.01); *G01N 2800/52* (2013.01)

(58) Field of Classification Search
CPC .......................... A61K 31/4365; C07D 513/04
USPC ........................................... 514/301; 546/114
See application file for complete search history.

(56) References Cited

U.S. PATENT DOCUMENTS

| 3,935,222 A | 1/1976 | Hoehn |
|---|---|---|
| 3,939,159 A | 2/1976 | Dornauer et al. |
| 5,288,726 A | 2/1994 | Koike et al. |
| 5,763,448 A | 6/1998 | Carling et al. |
| 6,410,729 B1 | 6/2002 | Spohr et al. |
| 6,632,814 B1 | 10/2003 | Bourzat et al. |
| 8,349,833 B2 | 1/2013 | Oniciu et al. |
| 2007/0249555 A1 | 10/2007 | Barbaras et al. |
| 2012/0129856 A1 | 5/2012 | Oniciu et al. |

FOREIGN PATENT DOCUMENTS

| CA | 1147658 | * 6/1983 | .................... 548/200 |
|---|---|---|---|
| WO | WO 2005/076007 | 8/2005 | |
| WO | WO 2007/143724 | 12/2007 | |
| WO | WO 2009/046606 | 4/2009 | |
| WO | WO 2012/054535 | 4/2012 | |

OTHER PUBLICATIONS

Database Accession No. 1214529-66-4, Database Registry [Online], Chemical Abstracts Service, Columbus, Ohio, Mar. 25, 2010, XP002724959.
Database Accession No. 1240167-51-4, Database Registry [Online], Chemical Abstracts Service, Columbus, Ohio, Sep. 7, 2010, XP002724960.
Database Accession No. 1214614-28-4, Database Registry [Online], Chemical Abstracts Service, Columbus, Ohio, Mar. 25, 2010, XP002724961.
Kim, Y-C. et al., "Synthesis of pyridoxal phosphate derivatives with antagonist activity at the P2Y13 receptor," Biochem Pharmacol., 70(2):266-274 (2005).
Supplementary European Search Report for European Application No. 11835025, mailed Jun. 17, 2014.
International Search Report and Written Opinion for International Application No. PCT/US2011/056780, mailed May 31, 2012, 22 pages.
Fabre, A. C. et al., "P2Y13 receptor is critical for reverse cholesterol transport," Hepatology, 52:1477-1483 (2010).
Jacquet, S. et al., "The nucleotide receptor $P2Y_{13}$ is a key regulator of hepatic high-density lipoprotein (HDL) endocytosis," Cell Mol. Life Sci., 62:2508-2515 (2005).
Martinez, L. O. et al., "Ectopic β-chain of ATP synthase is an apolipoprotein A-I receptor in hepatic HDL endocytosis," Nature, 421:75-79 (2003).

(Continued)

Primary Examiner — Samantha Shterengarts
(74) Attorney, Agent, or Firm — Cooley LLP

(57) ABSTRACT

The invention relates to classes of pharmaceutically-active heterocyclic compounds and pharmaceutically acceptable salts, and hydrates thereof, and compositions comprising the same. The invention also relates to methods for treating or preventing a disease or disorder, which comprises administering a therapeutically or prophylactically effective amount a compound described herein.

11 Claims, 28 Drawing Sheets

(56) References Cited

OTHER PUBLICATIONS

Zhan, C. et al., "Molecular modeling of purinergic receptor P2Y12 and interaction with its antagonists," Journal of Molecular Graphics and Modelling, 26(1):20-31 (2007).

Mackey, R. H. et al., "High-Density Lipoprotein Cholesterol and Particle Concentrations, Carotid Atherosclerosis, and Coronary Events," Journal of the American College of Cardiology, 60(6):508-516 (2012).

Tardy, C. et al., "CER-001, a HDL-mimetic, stimulates the reverse lipid transport and atherosclerosis regression in high cholesterol diet-fed LDL-receptor deficient mice," Atherosclerosis, 232:110-118 (2014).

Blom, D. et al., "Altered lipoprotein metabolism in $P2Y_{13}$ knockout mice," Biochimica et Biophysica Acta, 1801:1349-1360 (2010).

Goffinet, M. et al., "P2Y13 Receptor Regulates HDL Metabolism and Atherosclerosis In Vivo," Plos One, 9(4):e95807 (2014).

* cited by examiner

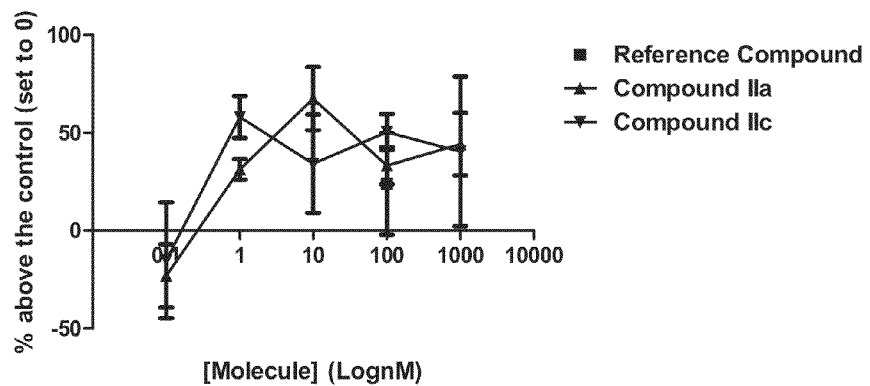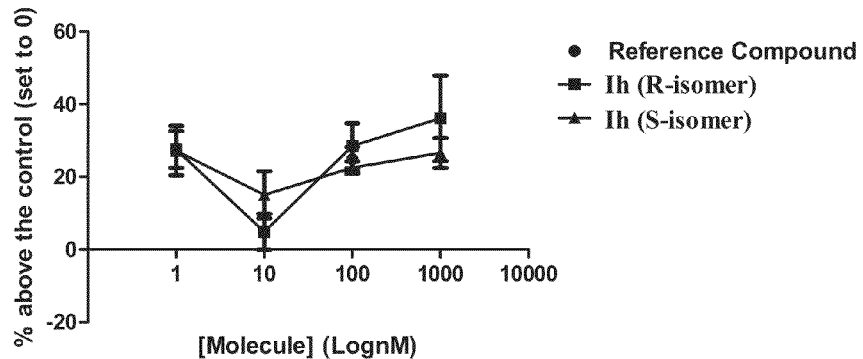
FIG. 4A-B

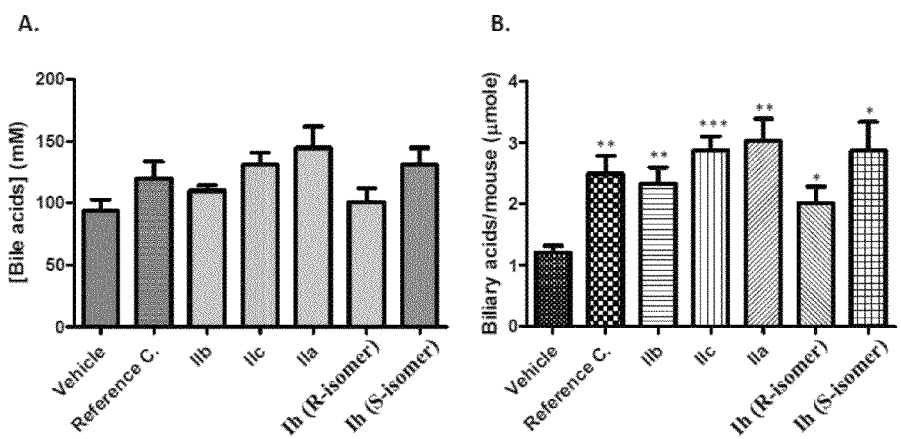
FIG. 5A-B

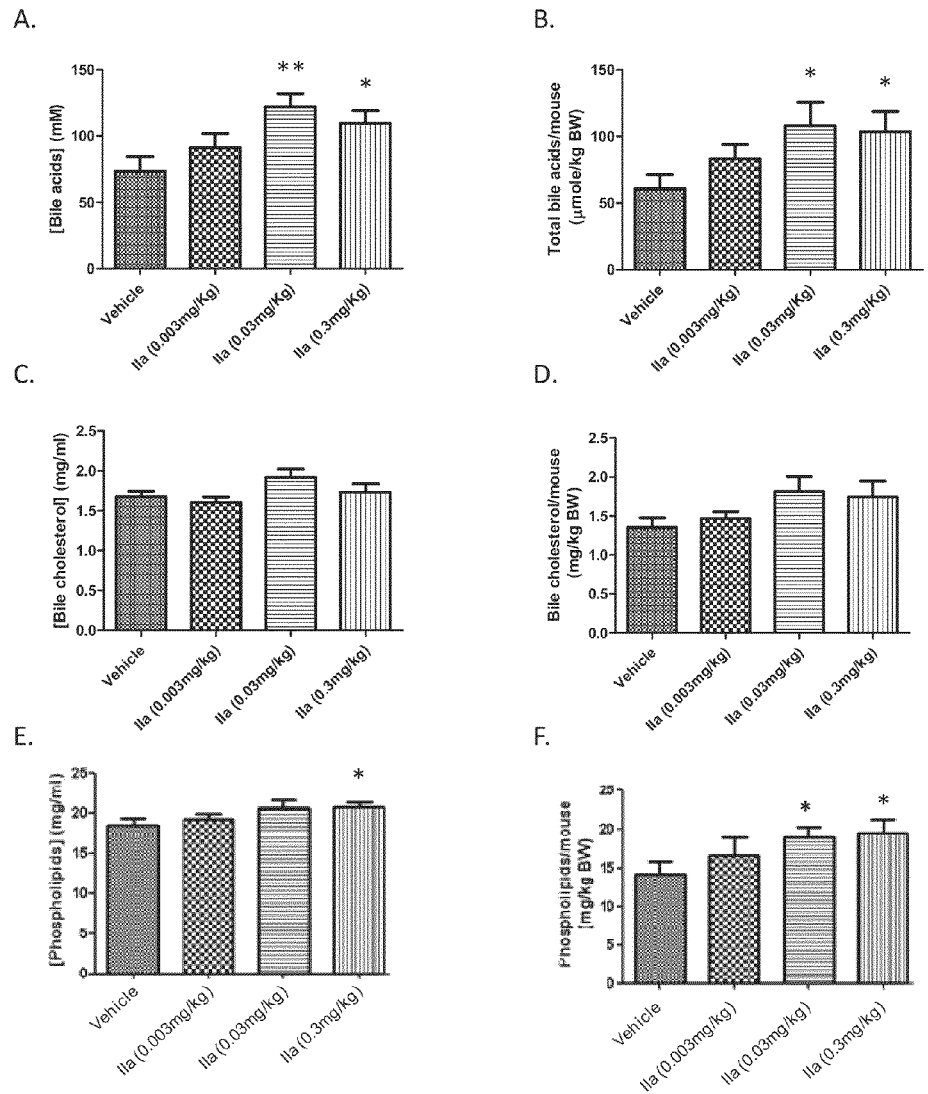
FIG. 6A-F

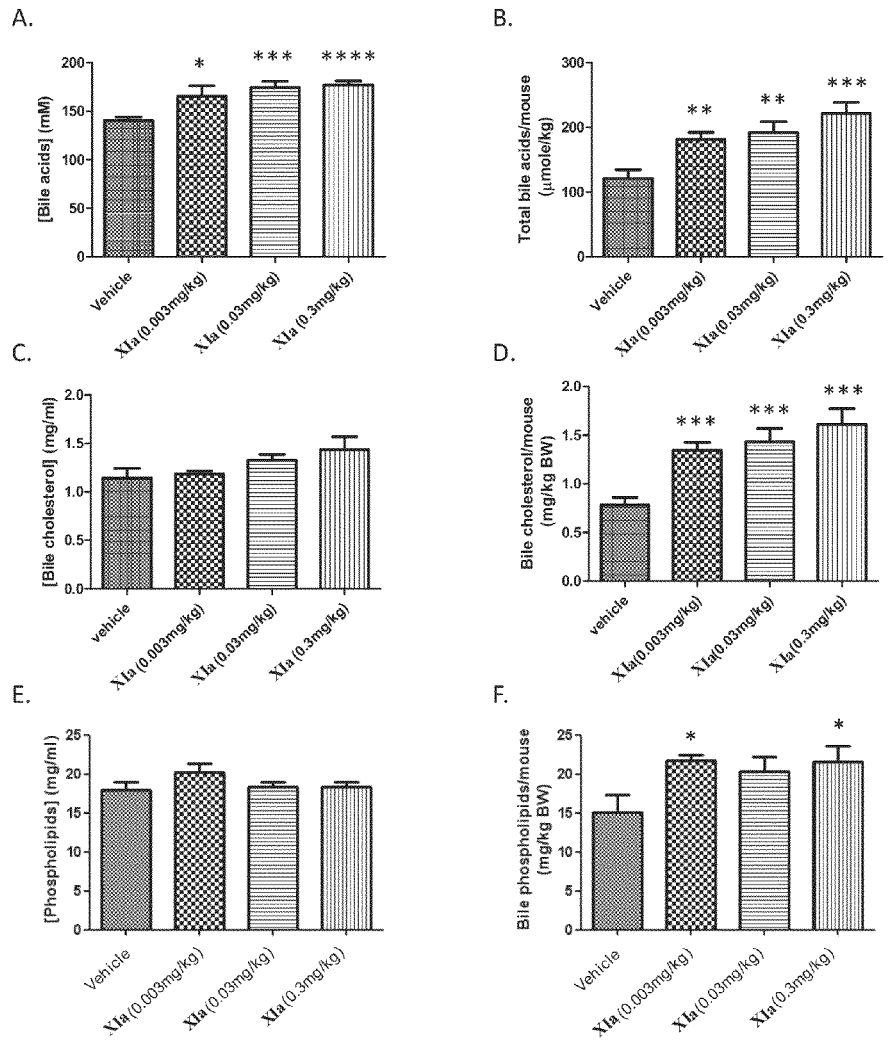
FIG. 7A-F

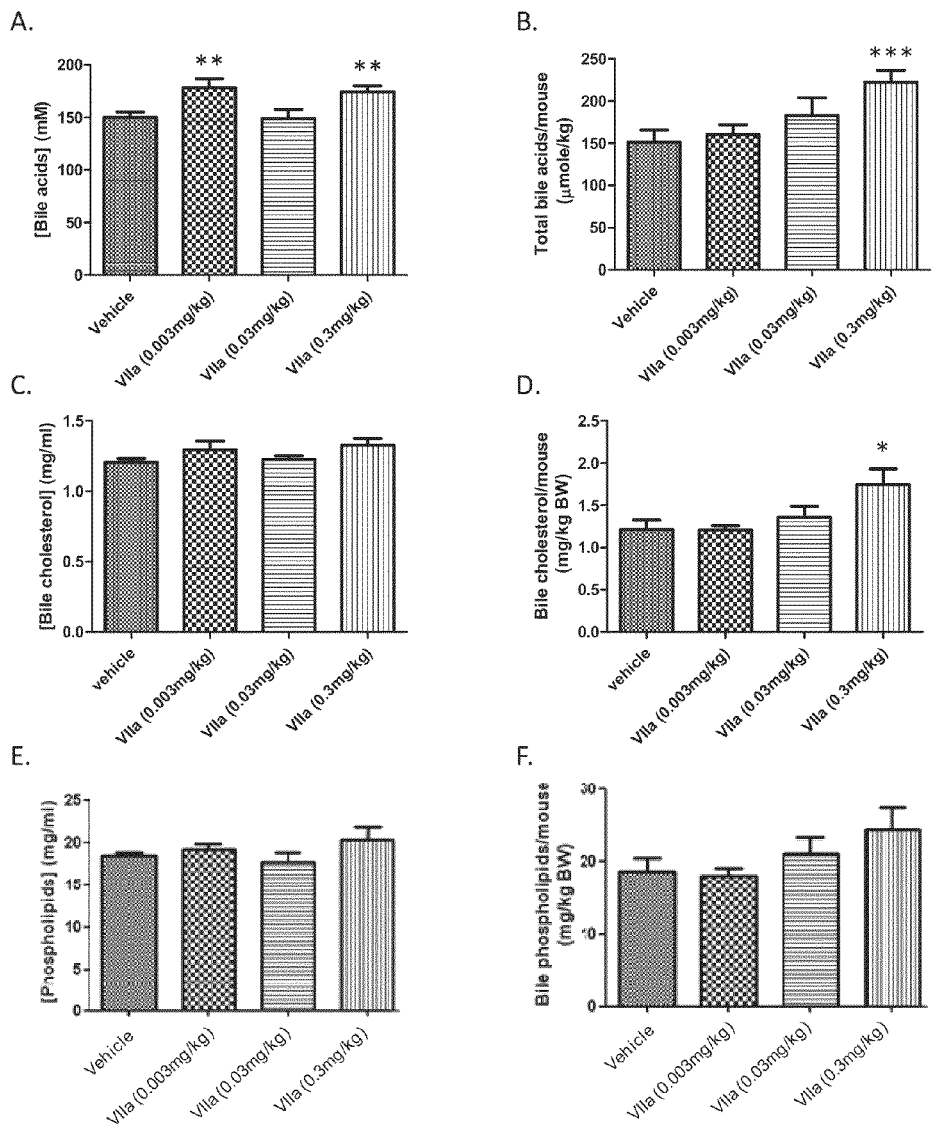
FIG. 8A-F

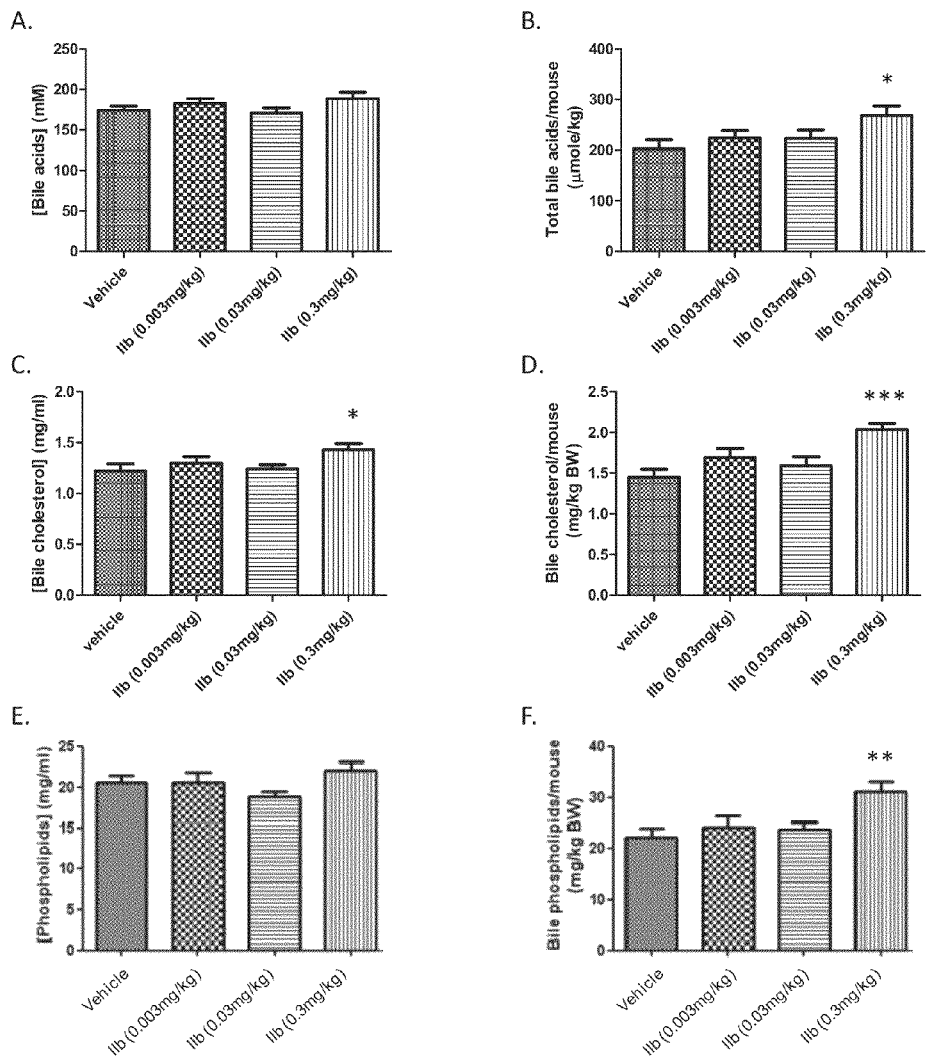
FIG. 9A-F

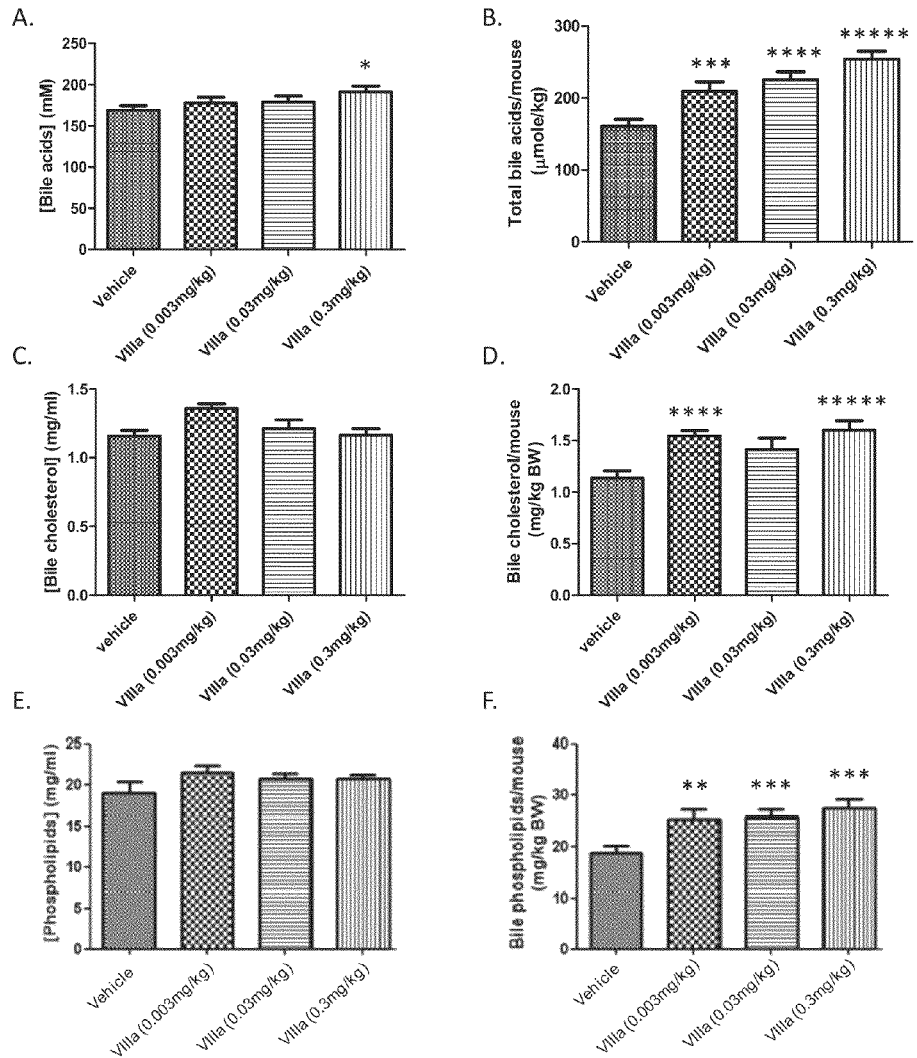
FIG. 10A-F

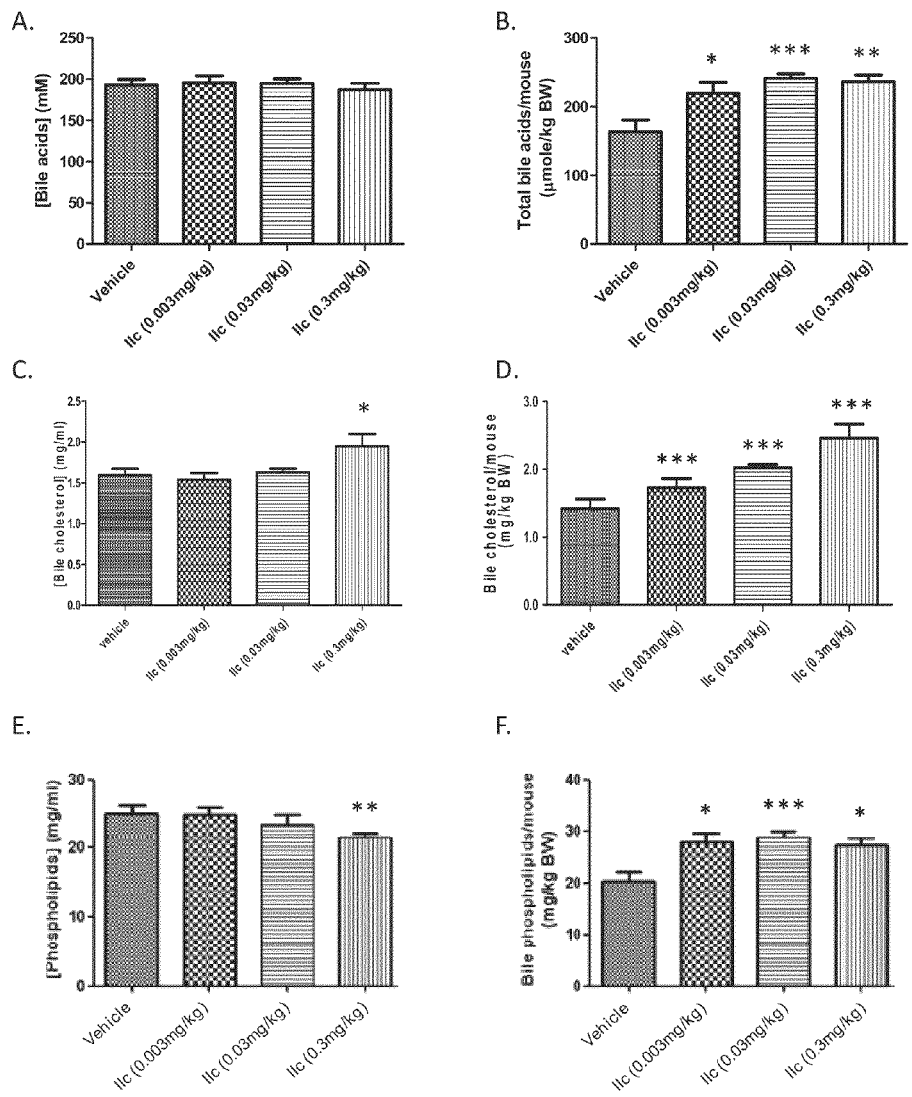
FIG. 11A-F

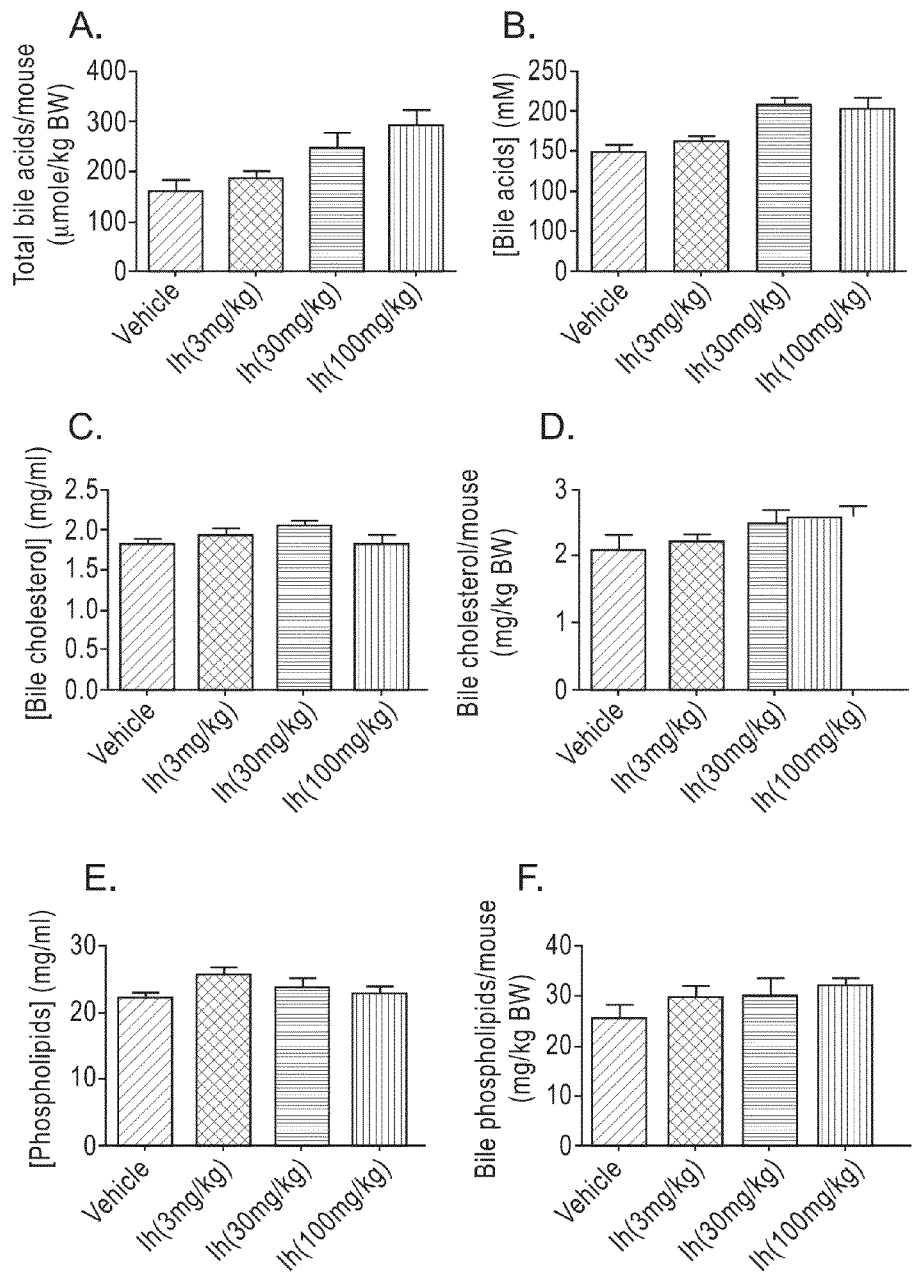
FIG. 12A-F

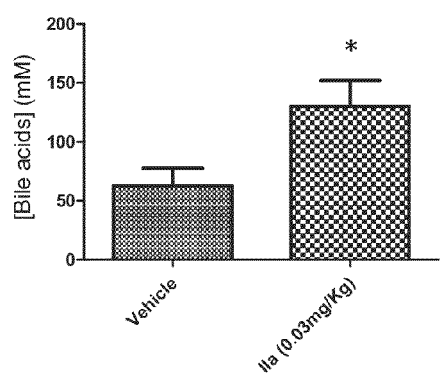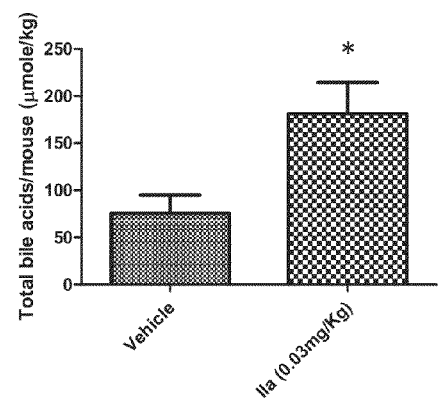
FIG. 13A-B

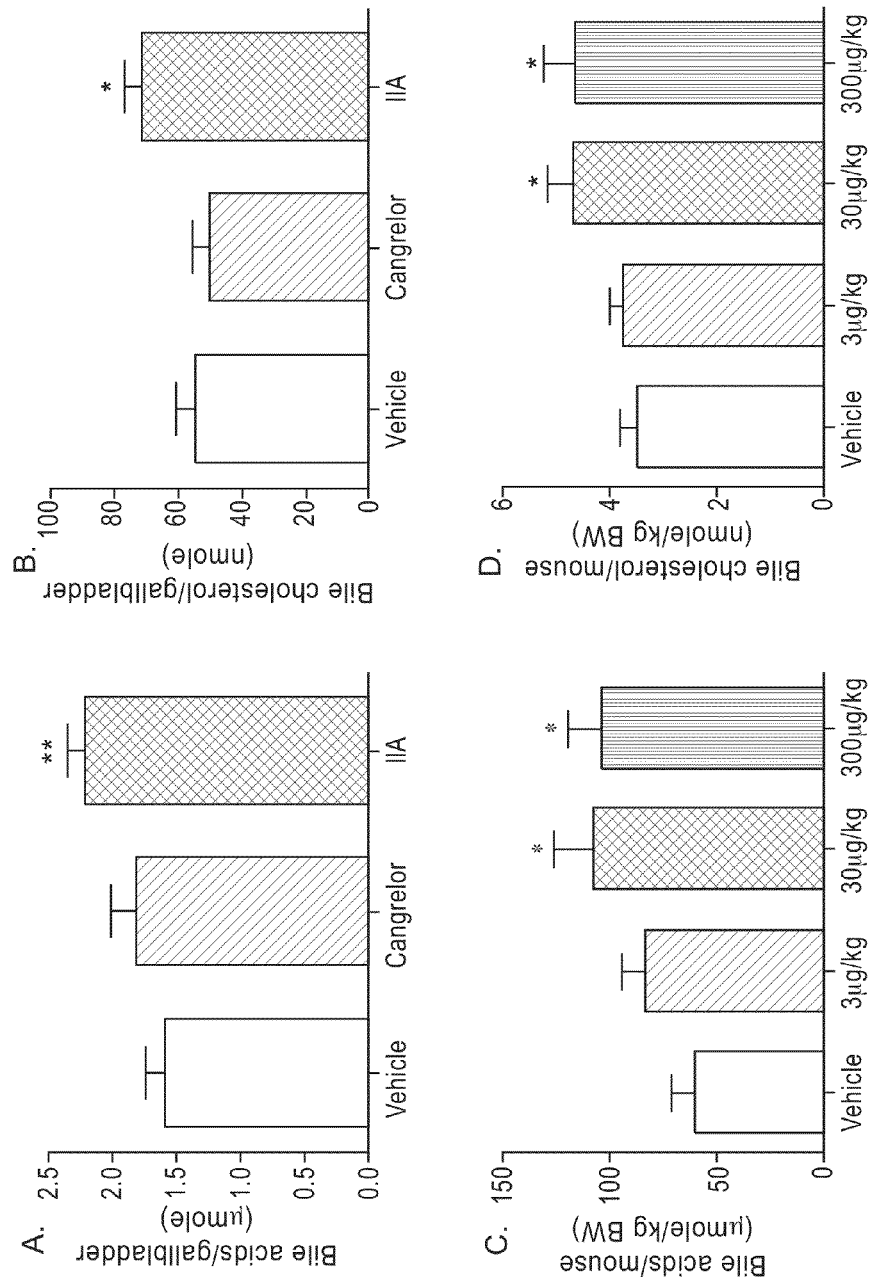
FIG. 16A-D

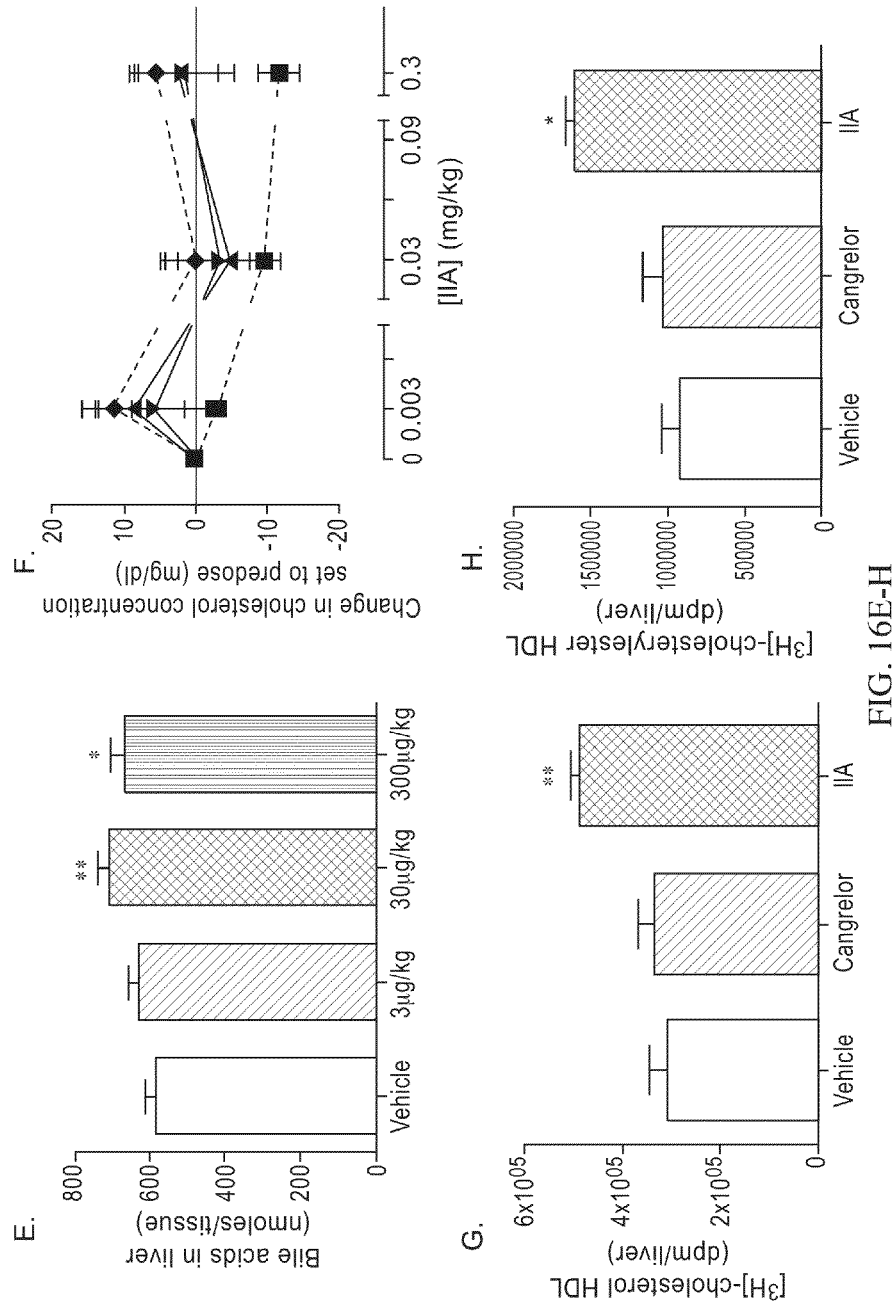
FIG. 16E-H

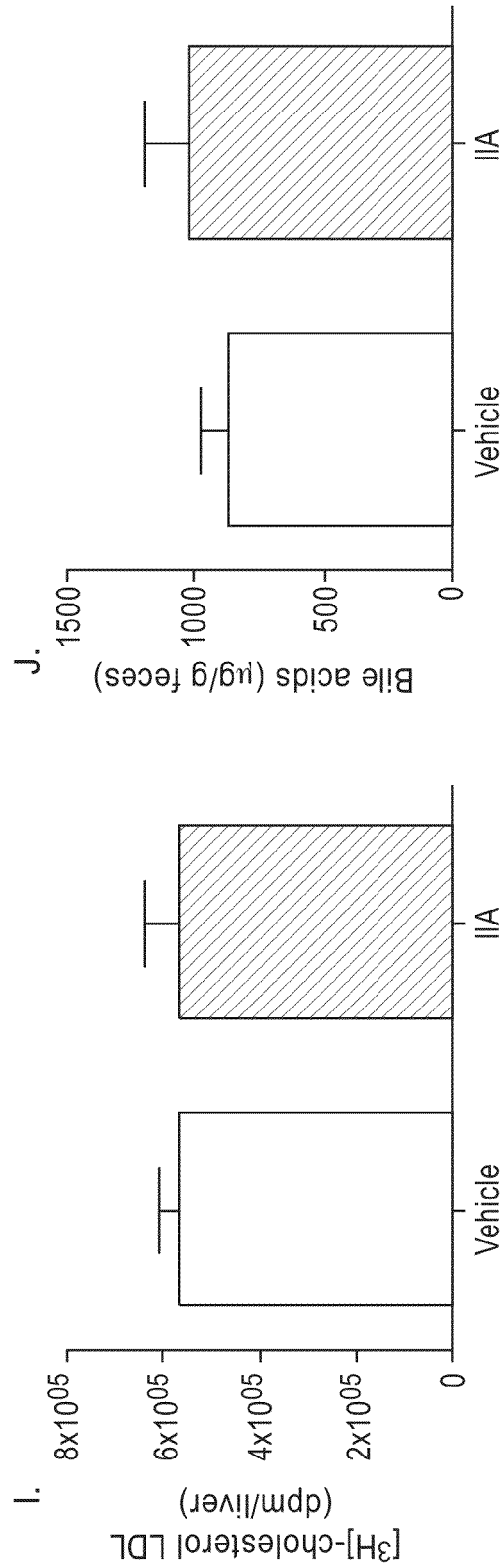
FIG. 16 I-J

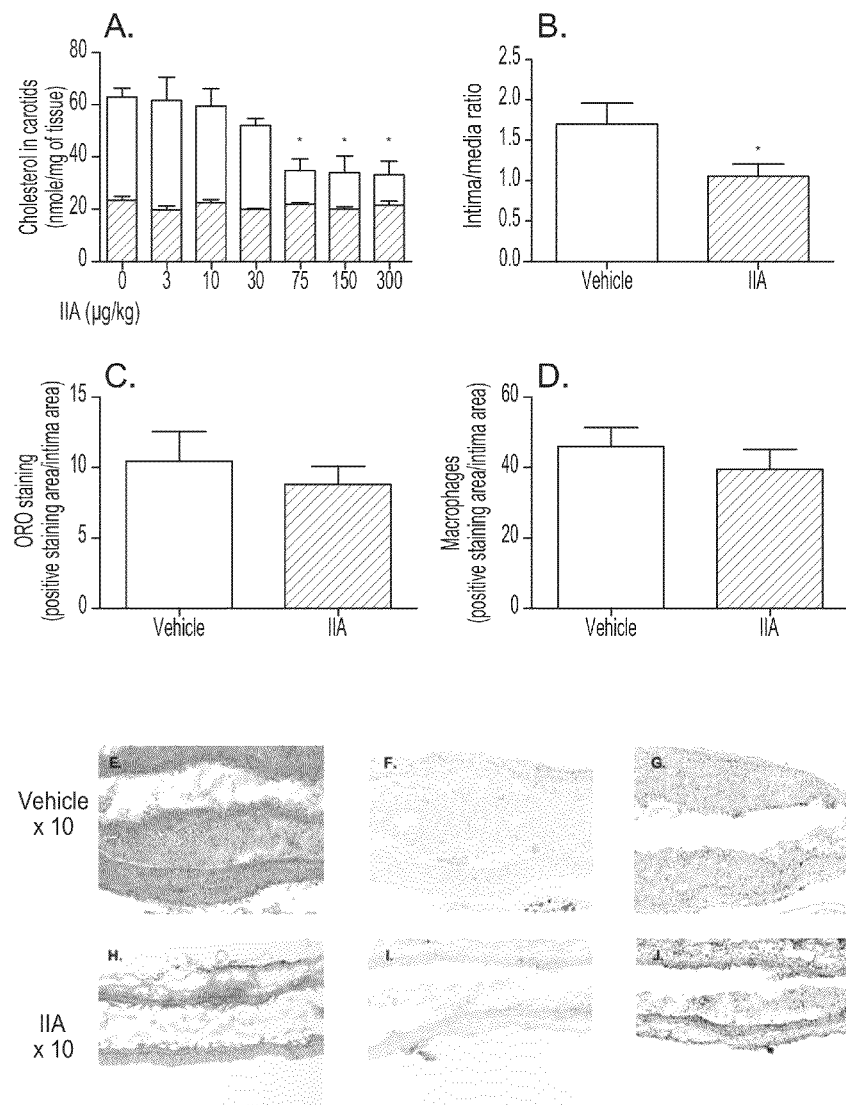
FIG. 17A-J

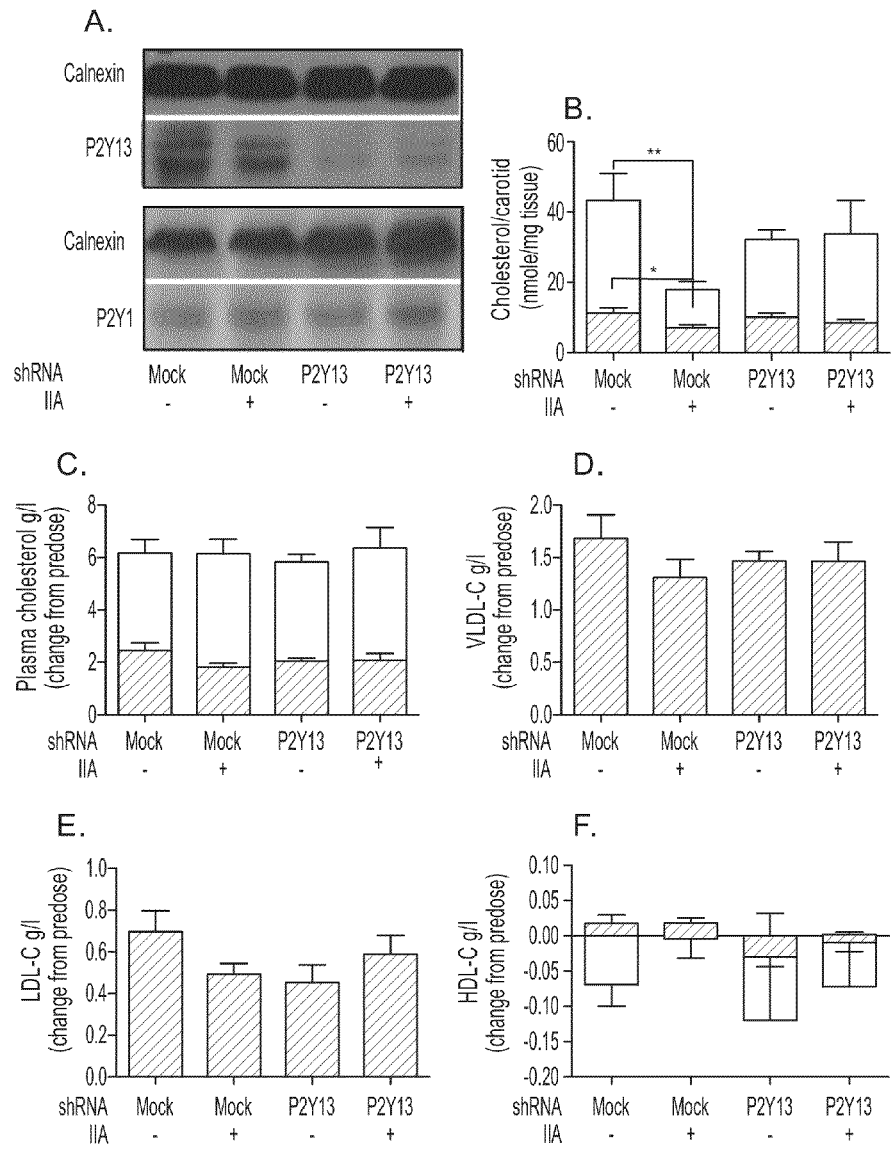
FIG. 18A-F

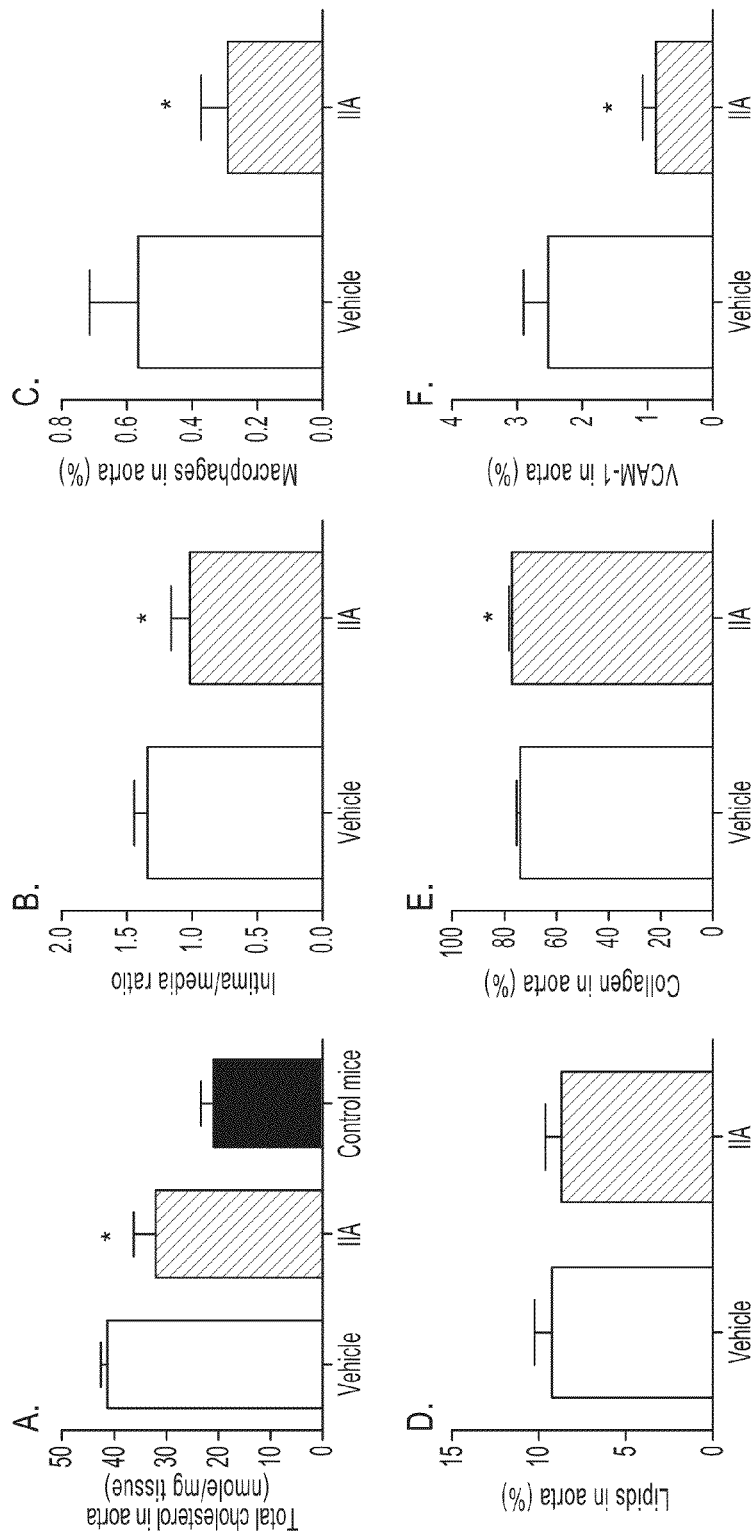
FIG. 19A-F

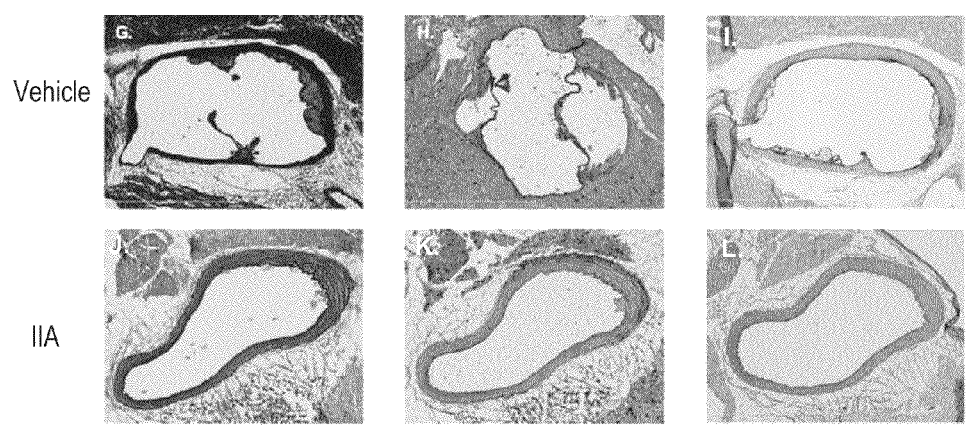
FIG. 19G-L

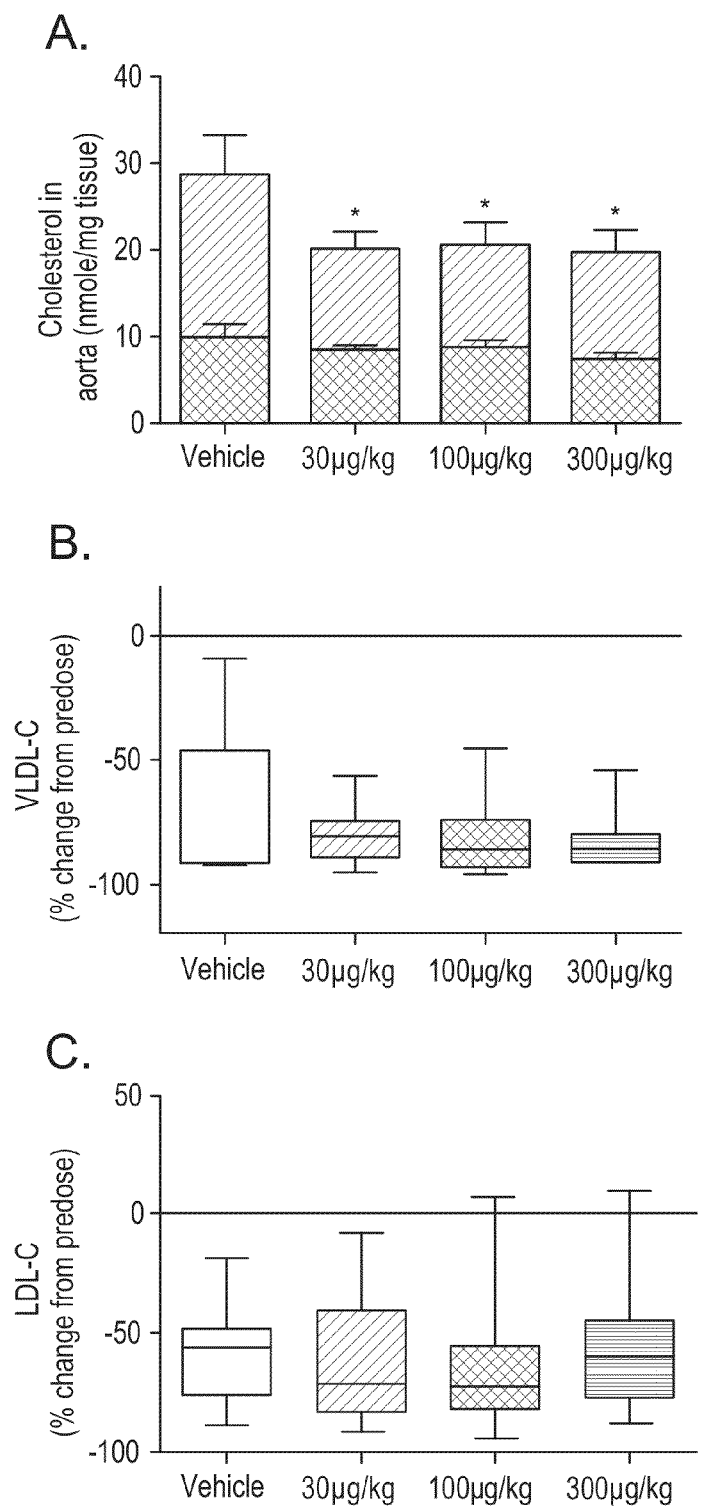
FIG. 20A-C

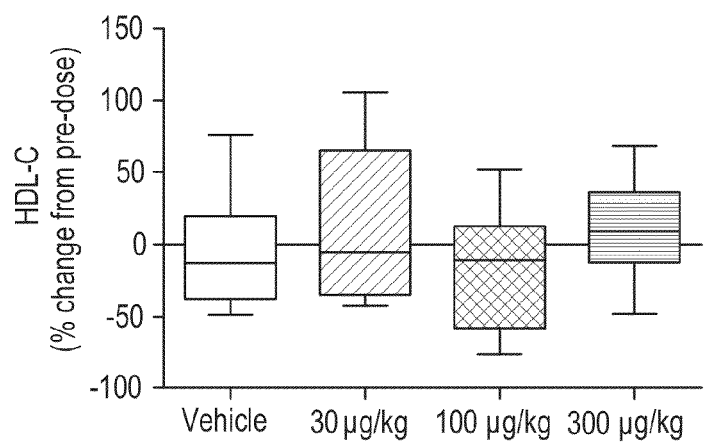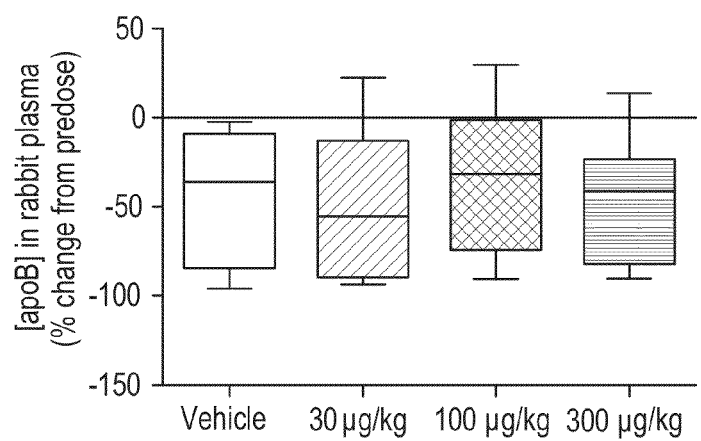
FIG. 20D-E

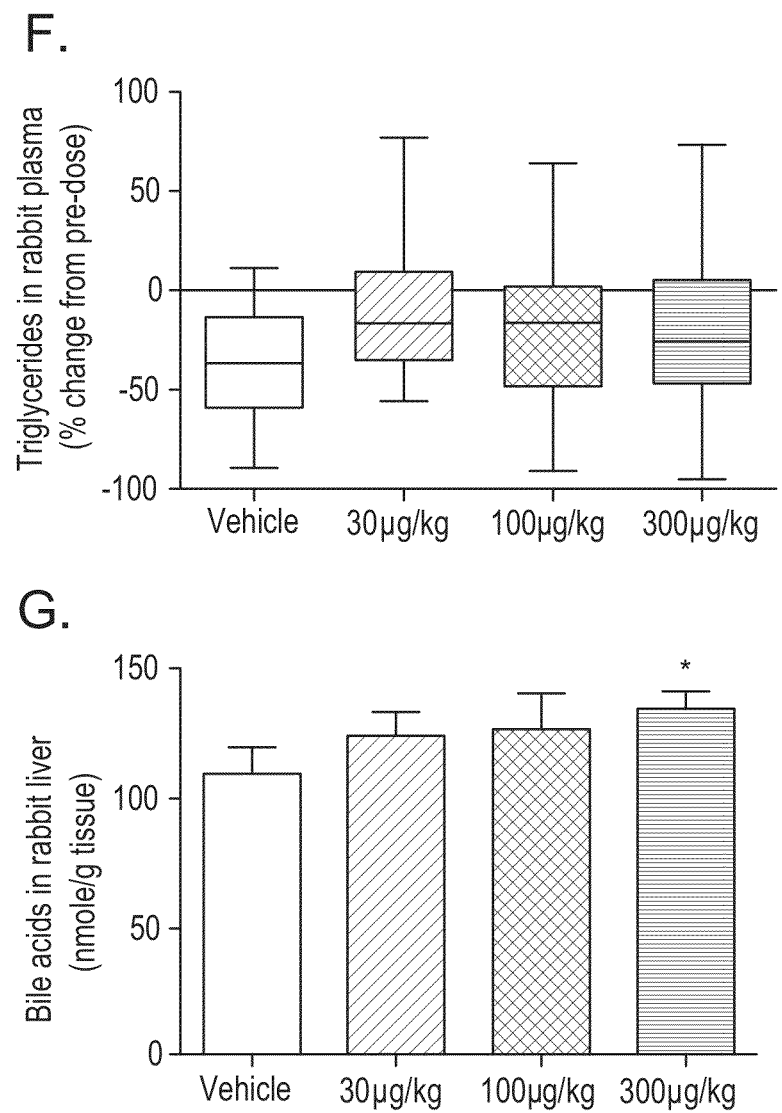
FIG. 20F-G

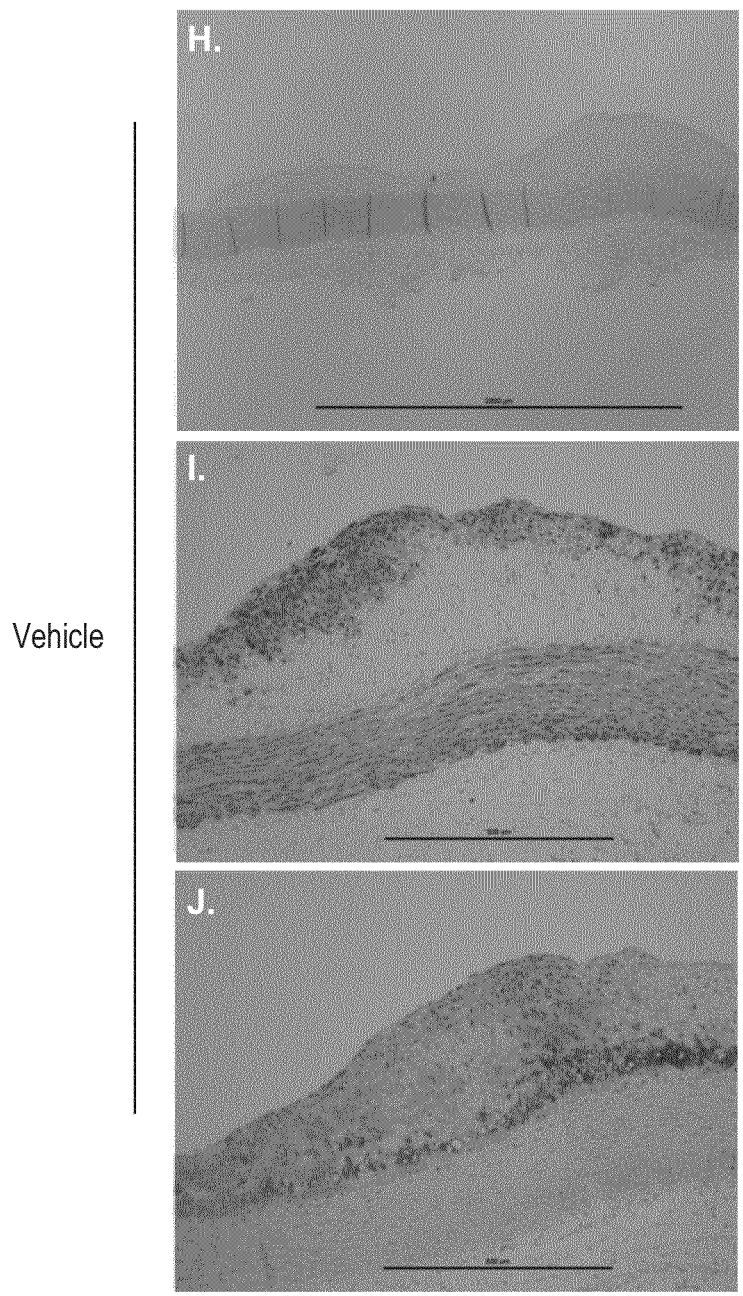
FIG. 20H-J

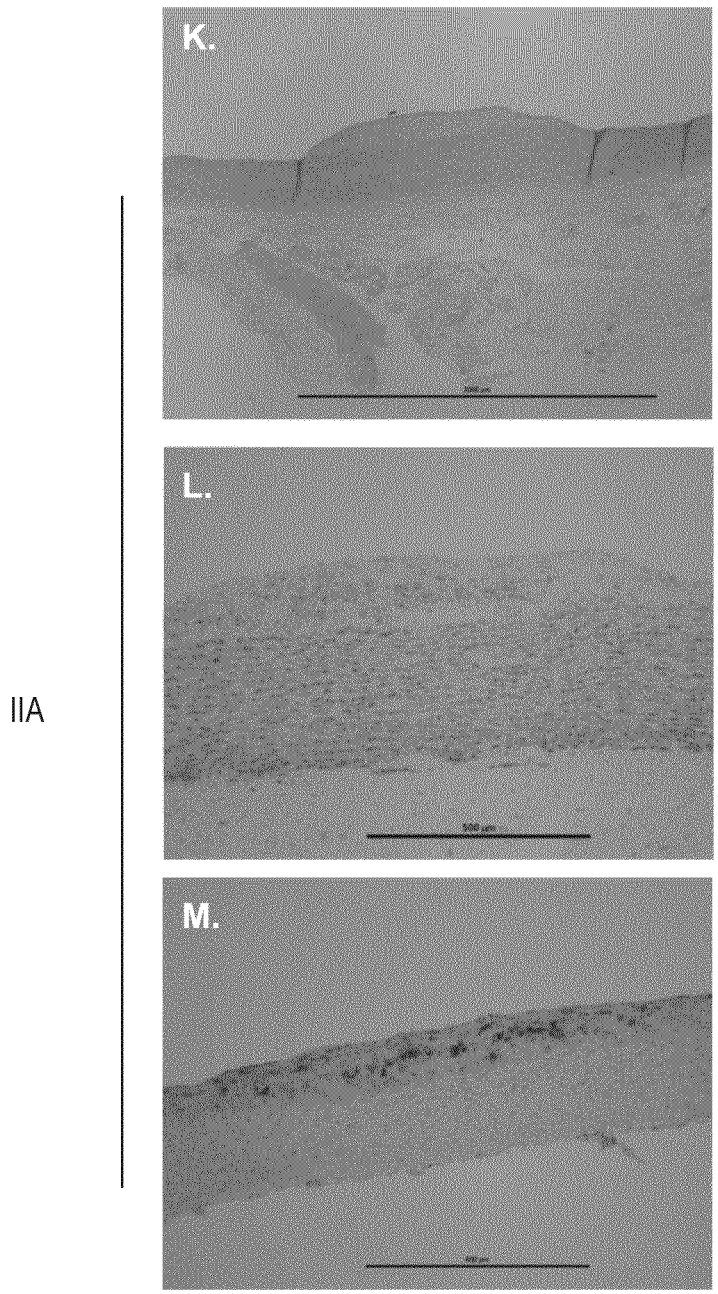
FIG. 20K-M

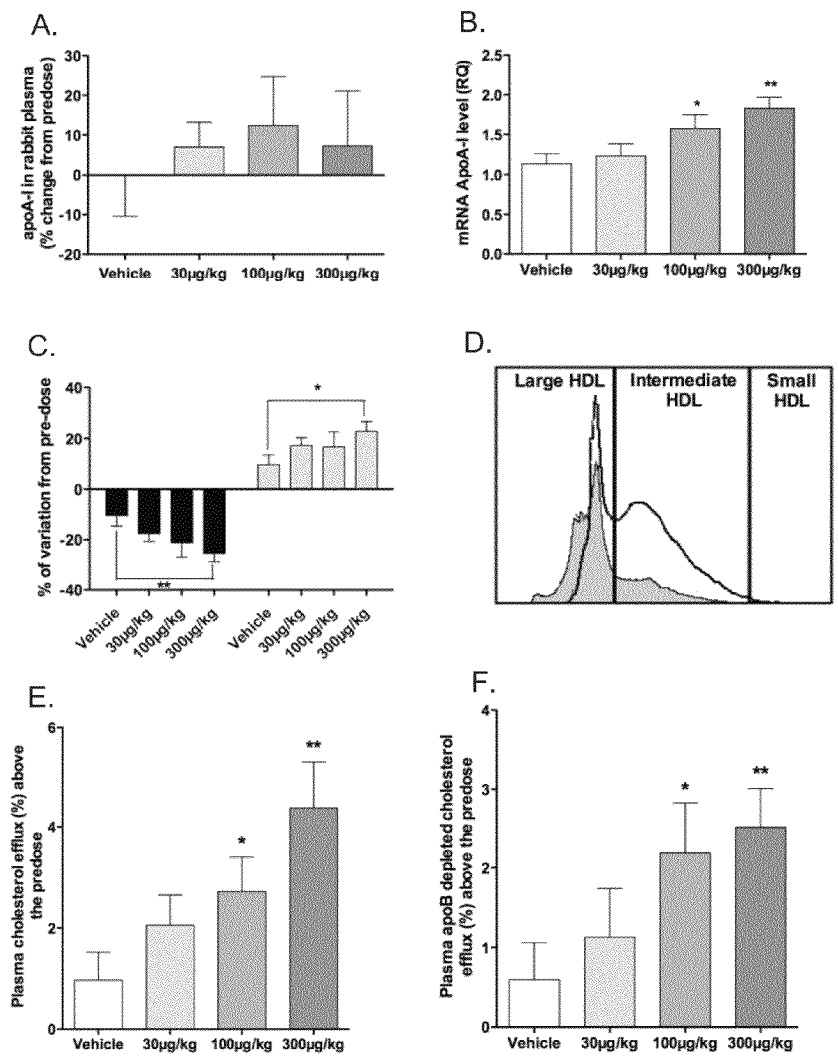
FIG. 21A-F

COMPOUNDS, COMPOSITIONS AND METHODS USEFUL FOR CHOLESTEROL MOBILIZATION

This application is a division of U.S. application Ser. No. 13/276,238, now U.S. Pat. No. 8,349,833, filed Oct. 18, 2011, which claims the benefit of U.S. Provisional Application No. 61/394,136, filed Oct. 18, 2010, and U.S. Provisional Application No. 61/444,212, filed Feb. 18, 2011, the disclosure of each of which is hereby incorporated by reference herein in its entirety.

FIELD OF THE INVENTION

The invention provides compounds, compositions, and methods of treatment or prevention of abnormal conditions in a subject.

BACKGROUND OF THE INVENTION

Cholesterol circulating in the human body is carried by plasma lipoproteins, which are particles of complex lipid and protein composition that transport lipids in the blood. Two types of plasma lipoproteins that carry cholesterol are low density lipoproteins ("LDL") and high density lipoproteins ("HDL"). LDL particles are believed to be responsible for the delivery of cholesterol from the liver (where it is synthesized or obtained from dietary sources) to extrahepatic tissues in the body. HDL particles, on the other hand, are believed to aid in the transport of cholesterol from the extrahepatic tissues to the liver, where the cholesterol is catabolized and eliminated. Such transport of cholesterol from the extrahepatic tissues to the liver is referred to as "reverse cholesterol transport."

The reverse cholesterol transport ("RCT") pathway has three main steps: (i) cholesterol efflux, i.e., the initial removal of cholesterol from various pools of peripheral cells; (ii) cholesterol esterification by the action of lecithin:cholesterol acyltransferase ("LCAT"), thereby preventing a re-entry of effluxed cholesterol into cells; and (iii) uptake of the cholesteryl ester by HDL and delivery of the HDL-cholesteryl ester complex to liver cells.

The RCT pathway is mediated by HDL particles. A pathway in the liver involving F1-ATPase and the P2Y13 receptor (Martinez et al. 2003 Nature 421; 75-79) that regulates HDL-cholesterol removal was recently described. The presence of a nucleotidase activity of F1-ATPase subunit at the cell surface of hepatocytes, allowing the hydrolysis of ATP to ADP, which in turn stimulates the P2Y13 receptor activities resulting in the uptake of the HDL by the cells was recently described. (Jacquet et al. 2005 Cell Mol Life Sci 62; 2508-2515). More recently, Fabre et al (Fabre et al. Hepatology 52; 1477-1483) confirmed the relationship between P2Y13r and the reverse cholesterol transport in mice.

SUMMARY OF THE INVENTION

In one embodiment, the invention provides compounds of the following Formula (I)

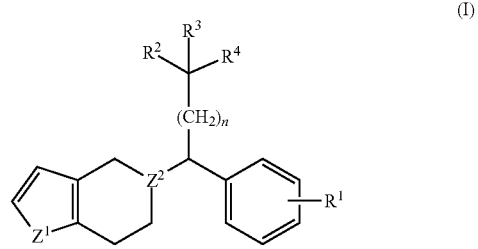

and pharmaceutically acceptable salts thereof, wherein
each of $R^1$, $R^2$, and $R^3$ is independently H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$;
$R^4$ is —H, —OH, —COOH, —NH(alkyl), —N(alkyl)(alkyl), -hydrocarbyl, —O-hydrocarbyl, -aryl, —O-aryl, -aralkyl, —O-aralkyl, -heteroaryl, —O-heteroaryl, -heterocyclyl, —O-heterocyclyl, -halo, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), or —OC(O)N(alkyl)(alkyl);
$Z^1$ is CH$_2$, S, O, NH, N-hydrocarbyl, N-aryl, N-heteroaryl, or N-heterocyclyl;
$Z^2$ is CH or N; and
n is an integer from 1-6.

In another embodiment, the invention provides compounds of the following Formula (II)

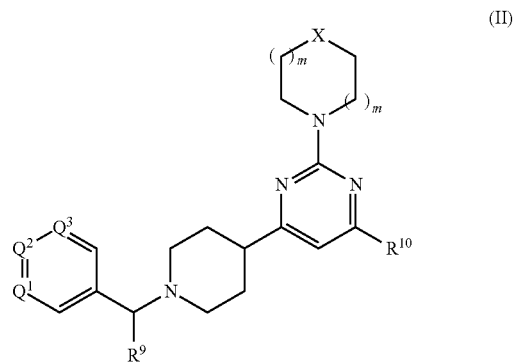

and pharmaceutically acceptable salts thereof, wherein
each $R^9$ is independently —H, -hydrocarbyl, -aryl, -aralkyl, -heteroaryl, -heterocyclyl, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), or —SO$_2$NH$_2$;
each $R^{10}$ is independently —H, —OH, —NH$_2$, —NH(alkyl), —N(alkyl)(alkyl), hydrocarbyl, —O-alkyl, —O-alkenyl, aryl, —O-aryl, aralkyl, —O-aralykl, heteroaryl, —O- heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), NHC(O)(C$_2$-C$_{10}$-alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$;

each of Q$^1$, Q$^2$, and Q$^3$ is independently CR$^{10}$ or N;

X is CHR$^{10}$, S, O, or NR$^9$; and each m is independently an integer from 0-3.

In another embodiment, the invention provides compounds of the following Formula III:

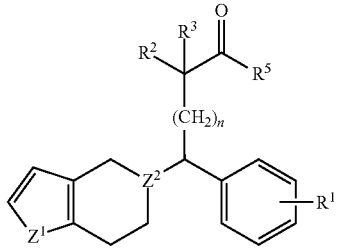

Formula III and pharmaceutically acceptable salts thereof, wherein each of R$^1$, R$^2$, and R$^3$ is independently H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$;

R$^5$ is —H, —OH, —NH$_2$, —NH(alkyl), —N(alkyl)(alkyl), hydrocarbyl, —O-hydrocarbyl, aryl, —O-aryl, aralkyl, —O-aralkyl, heteroaryl, —O-heteroaryl, heterocyclyl, or —O-heterocyclyl;

Z$^1$ is CH$_2$, S, O, NH, N-hydrocarbyl, N-aryl, N-heteroaryl, or N-heterocyclyl;

Z$^2$ is CH or N; and n is an integer from 1-6.

In another embodiment, the invention provides compounds of the following Formula IV:

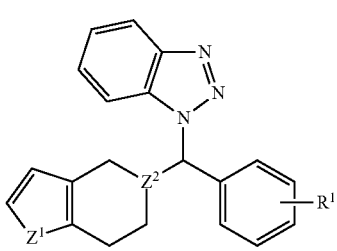

Formula IV and pharmaceutically acceptable salts thereof, wherein

R$^1$ is H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$;

Z$^1$ is CH$_2$, S, O, NH, N-hydrocarbyl, N-aryl, N-heteroaryl, or N-heterocyclyl; and Z$^2$ is CH or N.

In another embodiment, the invention provides compounds of the following Formula V:

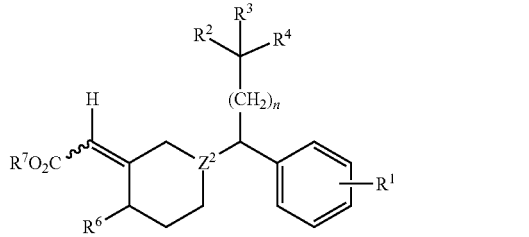

Formula V and pharmaceutically acceptable salts thereof, wherein each of R$^1$, R$^2$, and R$^3$ is independently H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$;

R$^4$ is —H, —OH, —COOH, —NH$_2$, —NH(alkyl), —N(alkyl)(alkyl), hydrocarbyl, —O-hydrocarbyl, aryl, —O-aryl, aralkyl, —O-aralkyl, heteroaryl, —O-heteroaryl, heterocyclyl, —O-heterocyclyl, halo, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), or —OC(O)N(alkyl)(alkyl);

R$^6$ is —H, —OH, —SH, —S-hydrocarbyl, —COOH, —NH$_2$, —NH(alkyl), —N(alkyl)(alkyl), hydrocarbyl, —O-hydrocarbyl, aryl, —O-aryl, aralkyl, —O-aralkyl, heteroaryl, —O-heteroaryl, heterocyclyl, —O-heterocyclyl, halo, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), or —OC(O)N(alkyl)(alkyl);

R$^7$ is H, hydrocarbyl, aryl, aralkyl, heteroaryl, or heterocyclyl;

Z$^2$ is CH or N; and n is an integer from 1-6.

In one embodiment, the invention provides compounds of the following Formula VI:

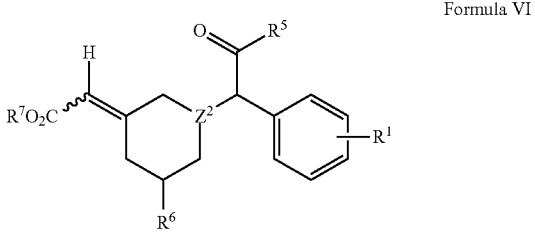

Formula VI and pharmaceutically acceptable salts thereof, wherein

R$^1$, is H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$;

R$^5$ is —H, —OH, —NH(alkyl), —N(alkyl)(alkyl), hydrocarbyl, —O-hydrocarbyl, aryl, —O-aryl, aralkyl, —O-aralkyl, heteroaryl, —O-heteroaryl, heterocyclyl, —O-heterocyclyl, or halo;

R$^6$ is —H, —OH, —SH, —S-hydrocarbyl, —COOH, —NH$_2$, —NH(alkyl), —N(alkyl)(alkyl), hydrocarbyl, —O-hydrocarbyl, aryl, —O-aryl, aralkyl, —O-aralkyl, heteroaryl, —O-heteroaryl, heterocyclyl, —O-heterocyclyl, halo, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), or —OC(O)N(alkyl)(alkyl);

R$^7$ is H, hydrocarbyl, aryl, aralkyl, heteroaryl, or heterocyclyl; and

Z$^2$ is CH or N.

In one embodiment, the invention provides compounds of the following Formula VII:

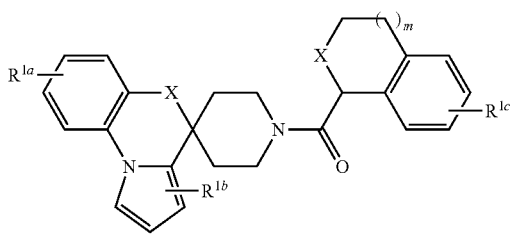

Formula VII and pharmaceutically acceptable salts thereof, wherein each of R$^{1a}$, R$^{1b}$, and R$^{1c}$ is independently —H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$;

each X is independently CHR$^{10}$, S, O, or NR$^9$;

each R$^9$ is independently H, hydrocarbyl, aryl, aralkyl, heteroaryl, heterocyclyl, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), or —SO$_2$NH$_2$;

each R$^{10}$ is independently —H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$; and m is an integer from 0-3.

In another embodiment, the invention provides compounds of the following Formula VIII:

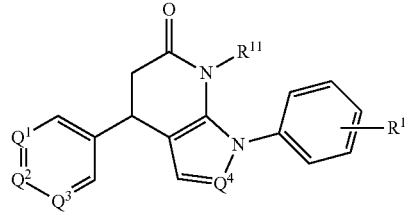

Formula VIII and pharmaceutically acceptable salts thereof, wherein

R$^1$ is —H, —OH, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$;

R$^{11}$ is H, hydrocarbyl, aryl, aralkyl, heteroaryl, heterocyclyl, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), or —SO$_2$NH$_2$;

each of Q$^1$, Q$^2$, Q$^3$, and Q$^4$ is independently CR$^{10}$ or N; and each R$^{10}$ is independently —H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$.

In another embodiment, the invention provides compounds of the following Formula IX:

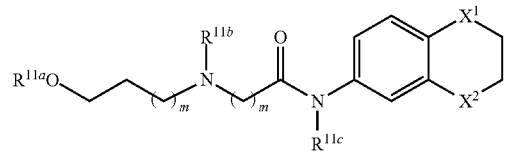

Formula IX and pharmaceutically acceptable salts thereof, wherein each of R$^{11a}$, R$^{11b}$, and R$^{11c}$ is independently H, hydrocarbyl, aryl, aralkyl, heteroaryl, heterocyclyl, —C(O)(alkyl), —C(O)O(alkyl), —C(O)NH$_2$, —C(O)NH(alkyl), —C(O)N(alkyl)(alkyl), or —SO$_2$NH$_2$;

each of X$^1$ and X$^2$ is independently CHR$^{10}$, S, O, NR$^9$, or N-acyl;

each R$^9$ is independently H, hydrocarbyl, aryl, aralkyl, heteroaryl, heterocyclyl, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), or —SO$_2$NH$_2$;

each R$^{10}$ is independently —H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH₂, —C(O)NH(alkyl), —C(O)N(alkyl)(alkyl), —NHC(O)(alkyl), N(alkyl)C(O)(alkyl), —OC(O)O(alkyl), —OC(O)NH₂, —OC(O)NH(alkyl), —OC(O)N(alkyl)(alkyl), —CHNH, —CHN(alkyl), or —SO₂NH₂; and each m is independently an integer from 1-3.

In another embodiment, the invention further provides compounds of the following Formula X:

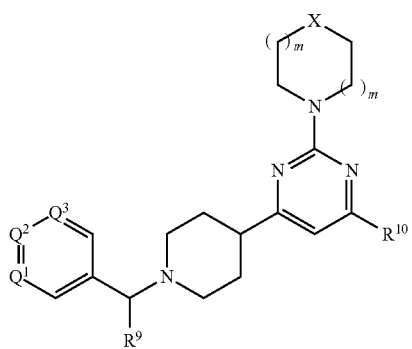

(X)

and pharmaceutically acceptable salts thereof, wherein each $R^9$ is independently —H, -hydrocarbyl, -aryl, -aralkyl, -heteroaryl, -heterocyclyl, —C(O)O(alkyl), —OC(O)(alkyl), —C(O)NH₂, —C(O)NH(alkyl), —C(O)N(alkyl)(alkyl), —NHC(O)(alkyl), N(alkyl)C(O)(alkyl), or —SO₂NH₂;

each $R^{10}$ is independently —H, —OH, —NH₂, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF₃, —C(O)O(alkyl), —OC(O)(alkyl), —C(O)NH₂, —C(O)NH(alkyl), —C(O)N(alkyl)(alkyl), —NHC(O)(alkyl), N(alkyl)C(O)(alkyl), —OC(O)O(alkyl), —OC(O)NH₂, —OC(O)NH(alkyl), —OC(O)N(alkyl)(alkyl), —CHNH, —CHN(alkyl), or —SO₂NH₂;

each of $Q^1$, $Q^2$, and $Q^3$ is independently $CR^{10}$ or N;

X is $CHR^{10}$, S, O, or $NR^9$; and each m is independently an integer from 0-3.

In another embodiment, the invention further provides compounds of the following Formula XI:

Formula XI

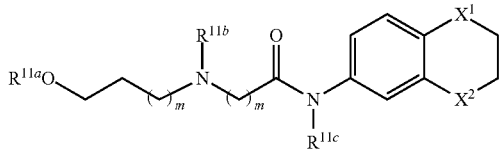

and pharmaceutically acceptable salts thereof, wherein each of $R^{11a}$, $R^{11b}$, and $R^{11c}$ is independently H, hydrocarbyl, aryl, aralkyl, heteroaryl, heterocyclyl, —C(O)(alkyl), —C(O)O(alkyl), —C(O)NH₂, —C(O)NH(alkyl), —C(O)N(alkyl)(alkyl), or —SO₂NH₂;

each of $X^1$ and $X^2$ is independently $CHR^{10}$, S, O, $NR^9$, or N-acyl;

each $R^9$ is independently H, hydrocarbyl, aryl, aralkyl, heteroaryl, heterocyclyl, —C(O)O(alkyl), —OC(O)(alkyl), —C(O)NH₂, —C(O)NH(alkyl), —C(O)N(alkyl)(alkyl), —NHC(O)(alkyl), N(alkyl)C(O)(alkyl), —OC(O)O(alkyl), or —SO₂NH₂;

each $R^{10}$ is independently —H, —OH, —NH₂, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF₃, —C(O)O(alkyl), —OC(O)(alkyl), —C(O)NH₂, —C(O)NH(alkyl), —C(O)N(alkyl)(alkyl), —NHC(O)(alkyl), N(alkyl)C(O)(alkyl), —OC(O)O(alkyl), —OC(O)NH₂, —OC(O)NH(alkyl), —OC(O)N(alkyl)(alkyl), —CHNH, —CHN(alkyl), or —SO₂NH₂; and each m is independently an integer from 0-3.

In another embodiment, the invention provides compounds of the following Formula (XII)

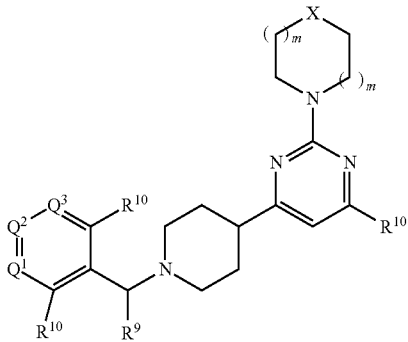

(XII)

and pharmaceutically acceptable salts thereof, wherein each $R^9$ is independently —H, -hydrocarbyl, -aryl, -aralkyl, -heteroaryl, -heterocyclyl, —C(O)O(alkyl), —OC(O)(alkyl), —C(O)NH₂, —C(O)NH(alkyl), —C(O)N(alkyl)(alkyl), —NHC(O)(alkyl), N(alkyl)C(O)(alkyl), or —SO₂NH₂;

each $R^{10}$ is independently —OH, —NH₂, —NH(alkyl), —N(alkyl)(alkyl), hydrocarbyl, —O-alkyl, —O-alkenyl, aryl, —O-aryl, aralkyl, —O-aralykl, heteroaryl, —O-heteroaryl, heterocyclyl, —O-heterocyclyl, halo, —OCF₃, —C(O)O(alkyl), —OC(O)(alkyl), —C(O)NH₂, —C(O)NH(alkyl), —C(O)N(alkyl)(alkyl), NHC(O)(C₂-C₁₀-alkyl), N(alkyl)C(O)(alkyl), —OC(O)O(alkyl), —OC(O)NH₂, —OC(O)NH(alkyl), —OC(O)N(alkyl)(alkyl), —CHNH, —CHN(alkyl), —SO₂NH₂, —S-alkyl, —S-aryl, —S-heteroaryl, —S-heterocycle, or —S— hydrocarbyl;

each of $Q^1$, $Q^2$, and $Q^3$ is independently $CR^{10}$ or N;

X is $CHR^{10}$, S, O, or $NR^9$; and each m is independently an integer from 0-3.

In another embodiment, the invention provides compounds of the following Formula XIII:

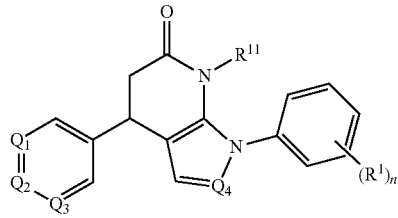

(XIII)

and pharmaceutically acceptable salts thereof, wherein $R^1$ is independently —H, —OH, —NH₂, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O (alkyl), —OC(O)(alkyl), —C(O)NH$_2$, —C(O)NH(alkyl), —C(O)N(alkyl)(alkyl), —NHC(O)(alkyl), N(alkyl)C(O) (alkyl), —OC(O)O(alkyl), —OC(O)NH$_2$, —OC(O)NH (alkyl), —OC(O)N(alkyl)(alkyl), —CHNH, —CHN(alkyl), or —SO$_2$NH$_2$;

R$^{11}$ is H, hydrocarbyl, aryl, aralkyl, heteroaryl, heterocyclyl, —C(O)O(alkyl), —OC(O)(alkyl), —C(O)NH$_2$, —C(O) NH(alkyl), —C(O)N(alkyl)(alkyl), —NHC(O)(alkyl), N(alkyl)C(O)(alkyl), or —SO$_2$NH$_2$;

each of Q$^1$, Q$^2$, Q$^3$, and Q$^4$ is independently CR$^{10}$ or N;

n is an integer from 1-4, and each R$^{10}$ is independently —H, —OH, —NH$_2$, —NH (alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH (alkyl), —C(O)N(alkyl)(alkyl), —NHC(O)(alkyl), N(alkyl) C(O)(alkyl), —OC(O)O(alkyl), —OC(O)NH$_2$, —OC(O)NH (alkyl), —OC(O)N(alkyl)(alkyl), —CHNH, —CHN(alkyl), or —SO$_2$NH$_2$.

A compound or pharmaceutically acceptable salt of the compound of any of Formulas (I)-(XIII) is a "compound of the invention."

In another embodiment, the invention provides compositions comprising an effective amount of a compound of the invention and a pharmaceutically acceptable vehicle or carrier.

In another embodiment, the invention provides methods for treating or preventing a disorder of lipoprotein metabolism, a disorder of glucose metabolism, a cardiovascular disorder or a related vascular disorder, a disorder involving abnormal modulation of C-reactive protein or a related disorder, aging, Alzheimer's Disease, Parkinson's Disease, pancreatitis, pancreatitius, or abnormal bile production (each being a "Condition"), the method comprising administering to a subject in need thereof an effective amount of a compound of the invention.

In another embodiment, the invention encompasses methods for monitoring the progress of a therapy for a cardiovascular disorder in a subject, the method comprising:

a. determining the level of free cholesterol in the high-density lipoprotein in the blood of the subject;

b. administering to the subject a compound of the invention;

c. monitoring the level of free cholesterol in the blood of the subject for a period of time after administration of the compound; and d. evaluating the level of improvement in the subject based on a comparison of the results of steps a. and c.

In another embodiment, the invention encompasses methods of determining the level of P2Y13 activity in a subject, the method comprising:

a. determining the level of free cholesterol in the high-density lipoprotein in the blood of the subject;

b. administering to the subject a compound of the invention;

c. monitoring the level of free cholesterol in the blood of the subject for a period of time after administration of the compound; and d. evaluating the level of P2Y13 activity in the subject based on a comparison of the results of steps a. and c.

BRIEF DESCRIPTION OF THE FIGURES

FIG. 1A), Compound Ih (R-isomer) (dark triangle; FIG. 1B) and Compound Ih (S-isomer) (dark triangle; FIG. 1C) activity on 1321 N1 cells transfected with P2Y13 receptor. Non-transfected 1321 N1 cells were used as negative control (dark circle). Each data point was a mean of triplicate wells.

FIG. 4A-B: Dose responses of selected molecules on HDL internalization by HepG2 cells. Cells were incubated for 10 min at 37° C. with 75 μg/ml $^3$H cholesterol Cholesteryl Oleate [Cholesteryl-1,2-$^3$H(N)] HDL, Reference Compound (100 nM) and increased concentrations of the selected molecules. FIG. 4A: Compounds IIa and IIc (0.1, 1, 10, 100 and 1000 nM). FIG. 4B: Compound Ih (S-isomer) and compound Ih (R-isomer) (1, 10, 100 and 1000 nM). Data are expressed as the percentage of internalized radioactivity with respect to the control value (set as 0).

FIG. 5A-B: Single-dose effect of the illustrative compounds of the invention on bile acids secretion after IV injection. Mice were fasted for 2 hours and then injected in the caudal vein with the selected molecules (10 nmol/kg) in PBS solution (100 μl). 4 hours later the bile content was analyzed. FIG. 5A. Data are expressed as the concentration of bile acids. FIG. 5B. Data are expressed as the pool of bile acids per mouse (*p<0.05, p<0.005, *p<0.0001). Group of animals n=5.

FIG. 6A-F: Dose-response effect of Compound IIa on bile acids, bile phospholipids and bile cholesterol secretions. Mice were fasted for 2 hours and then treated with increased concentrations of Compound IIa (0.003, 0.03 and 0.3 mg/kg) by oral gavage. 6 hours later the bile content was analyzed. FIG. 6A. Data are expressed as the concentration of bile acids. FIG. 6B. Data are expressed as the pool of bile acids per mouse weight. FIG. 6C. Data are expressed as the concentration of bile cholesterol. FIG. 6D. Data are expressed as the pool of bile cholesterol per mouse weight. FIG. 6E. Data are expressed as the concentration of bile phospholipids. FIG. 6F. Data are expressed as the pool of bile phospholipids per mouse weight. Group of animals n=10. (*p<0.05, **p<0.005)

FIG. 7A-F: Dose-response effect of Compound XIa on bile acids, bile phospholipids and bile cholesterol secretions Mice were fasted for 2 hours and then treated with increased concentrations of Compound XIa (0.003, 0.03 and 0.3 mg/kg) by oral gavage. 6 hours later the bile content was analyzed. FIG. 7A. Data are expressed as the concentration of bile acids. FIG. 7B. Data are expressed as the pool of bile acids per mouse weight. FIG. 7C. Data are expressed as the concentration of bile cholesterol. FIG. 7D. Data are expressed as the pool of bile cholesterol per mouse weight. FIG. 7E. Data are expressed as the concentration of bile phospholipids. FIG. 7F. Data are expressed as the pool of bile phospholipids per mouse weight. Group of animals n=10. (*p<0.05, p<0.005, *p<0.0005, ****p<0.0001)

FIG. 8A-F: Dose-response effect of Compound VIIa on bile acids, bile phospholipids and bile cholesterol secretions. Mice were fasted for 2 hours and then treated with increased concentrations of Compound VIIa (0.003, 0.03 and 0.3 mg/kg) by oral gavage. 6 hours later the bile content was analyzed. FIG. 8A. Data are expressed as the concentration of bile acids. FIG. 8B. Data are expressed as the pool of bile acids per mouse weight. FIG. 8C. Data are expressed as the concentration of bile cholesterol. FIG. 8D. Data are expressed as the pool of bile cholesterol per mouse weight. FIG. 8E. Data are expressed as the concentration of bile phospholipids. FIG. 8F. Data are expressed as the pool of bile phospholipids per mouse weight. Group of animals n=10. ($*p<0.05$, $p<0.01$, $*p<0.005$)

FIG. 9A-F: Dose-response effect of Compound IIb on bile acids, bile phospholipids and bile cholesterol secretions. Mice were fasted for 2 hours and then treated with increased concentrations of Compound IIb (0.003, 0.03 and 0.3 mg/kg) by oral gavage. 6 hours later the bile content was analyzed. FIG. 9A. Data are expressed as the concentration of bile acids. FIG. 9B. Data are expressed as the pool of bile acids per mouse weight. FIG. 9C. Data are expressed as the concentration of bile cholesterol. FIG. 9D. Data are expressed as the pool of bile cholesterol per mouse weight. FIG. 9E. Data are expressed as the concentration of bile phospholipids. FIG. 9F. Data are expressed as the pool of bile phospholipids per mouse weight. Group of animals n=10. ($*p<0.05$, $p<0.005$, $*p<0.0005$)

FIG. 10A-F: Dose-response effect of Compound VIIIa on bile acids, bile phospholipids and bile cholesterol secretions. Mice were fasted for 2 hours and then treated with increased concentrations of Compound VIIIa (0.003, 0.03 and 0.3 mg/kg) by oral gavage. 6 hours later the bile content was analyzed. FIG. 10A. Data are expressed as the concentration of bile acids. FIG. 10B. Data are expressed as the pool of bile acids per mouse weight. FIG. 10C. Data are expressed as the concentration of bile cholesterol. FIG. 10D. Data are expressed as the pool of bile cholesterol per mouse weight. FIG. 10E. Data are expressed as the concentration of bile phospholipids. FIG. 10F. Data are expressed as the pool of bile phospholipids per mouse weight. Group of animals n=10. ($*p<0.05$, $p<0.01$, $*p<0.005$, $**p<0.001$, $***p<0.0005$)

FIG. 11A-F: Dose-response effect of Compound IIc on bile acids, bile phospholipids and bile cholesterol secretions. Mice were fasted for 2 hours and then treated with increased concentrations of Compound IIc (0.003, 0.03 and 0.3 mg/kg) by oral gavage. 6 hours later the bile content was analyzed. FIG. 11A. Data are expressed as the concentration of bile acids. FIG. 11B. Data are expressed as the pool of bile acids per mouse weight. FIG. 11C. Data are expressed as the concentration of bile cholesterol. FIG. 11D. Data are expressed as the pool of bile cholesterol per mouse weight. FIG. 11E. Data are expressed as the concentration of bile phospholipids. FIG. 11F. Data are expressed as the pool of bile phospholipids per mouse weight. Group of animals n=10. ($*p<0.05$, $p<0.005$, $*p<0.0005$)

FIG. 12A-F: Effect of Compound Ih (racemate) on bile acids, bile phospholipids and bile cholesterol secretions. Mice were fasted for 2 hours and then treated with increased concentrations of Compound Ih (racemate) (3, 30 and 100 mg/kg) by oral gavage. Six hours later the bile content was analyzed. FIG. 12A: data are expressed as the concentration of bile acids. FIG. 12B: data are expressed as the pool of bile acids per mouse weight. FIG. 12C: data are expressed as the concentration of bile cholesterol. FIG. 12D: data are expressed as the pool of bile cholesterol per mouse weight. FIG. 12E: data are expressed as the concentration of bile phospholipids. FIG. 12F: data are expressed as the pool of bile phospholipids per mouse weight. Group of animals n=10. ($*p<0.05$, $p<0.005$, $*p<0.0001$).

FIG. 13A-B: Single-dose effect of Compound IIa on bile acids secretion after one week treatment. Mice were treated daily with Compound IIa (0.03 mg/kg) by oral gavage. On the day of sacrifice, the mice were fasted for 3 hours followed by an oral gavage (same concentration). 4 hours later the bile content was analyzed. FIG. 13A: data are expressed as the concentration of bile acids. FIG. 13B: data are expressed as the pool of bile acids per mouse weight ($*p<0.05$). Group of animals n=10.

FIG. 16A-J: Increase of bile secretion following activation of P2Y13r pathway in mice. C57Bl/6J mice (n=10) were fasted for 2 h and then intravenously injected with Cangrelor® or Compound IIa (10 nmoles/kg). Four hours later the gallbladders were removed and analyzed for: Bile acids content (FIG. 16A); Bile cholesterol content (FIG. 16B). C57Bl/6J mice (n=10) were fasted for 2 h followed by single oral dose of P2Y13r agonist Compound IIa at 3, 30 or 300 µg/kg. Six hours later bile acids contents (FIG. 16C); bile cholesterol content (FIG. 16D), and bile acid content of liver (FIG. 16E) were evaluated using HPLC and enzymatic kits for gallbladders. Plasma samples were collected at time 0 and after 6 h of treatment, then analyzed for: total cholesterol (▲), unesterified cholesterol (●), esterified cholesterol (■) and HDL cholesterol (▼) determined using either enzymatic kits or Lipoprint® for HDL cholesterol (FIG. 16F). C57Bl/6J mice (n=5) were intravenously injected with [$^3$H]-cholesterol-labelled mouse HDL (FIG. 16G), [$^3$H]-cholesteryl oleate-labelled mouse HDL (FIG. 16H) or [$^3$H]-cholesterol-labelled mouse LDL (FIG. 16I), and with Cangrelor® or Compound IIa (10 nmoles/kg). Radioactivity present in the liver was determined 2 hours later for the HDL or 5 hours later for the LDL. Cholesterol content of feces from treated animals (100 µg/kg) was determined by Charge aerosol detection (FIG. 16J). $*p<0.05$, $**p<0.01$.

FIG. 17A-J: Dose-response effect of P2Y13 agonist on atherosclerotic plaque progression in ApoE$^{-/-}$ mice. ApoE$^{-/-}$ mice (n=7) were ligated on the upper part of the left carotids. On the day of the surgery the animals were placed on a Western diet and given an oral gavage of vehicle or increasing doses of Compound IIa. Ligated carotids were lipid extracted in 2:1 chloroform/methanol. FIG. 17A: the concentrations in unesterified cholesterol (dark bars) and total cholesterol (superimposed gray bars) were measured by HPLC. FIG. 17E and FIG. 17H: hematoxylin eosin staining of longitudinal sections of ApoE$^{-/-}$ mice carotids. FIG. 17F and FIG. 17I: Oil Red O staining of longitudinal sections of ApoE$^{-/-}$ mice carotids. FIG. 17G and FIG. 17J: CD-68 antibody staining of longitudinal sections of ApoE$^{-/-}$ mice carotids. FIG. 17B: quantification of the intima/media ratio (n=10). FIG. 17C: Oil Red O positive staining quantification (n=10). FIG. 17D: CD68 antibody staining quantification (n=10). The mice were dosed for 2 weeks with vehicle (FIG. 17E, FIG. 17F and FIG. 17G) or Compound IIa at 100 µg/kg (FIG. 17H, FIG. 17I and FIG. 17J).

FIG. 18A-F: Effect of P2Y13 silencing on atherosclerotic plaque progression in ApoE$^{-/-}$ mice. ApoE$^{-/-}$ mice (n=10) were infected with 5×10$^9$ adenoviral particles coding empty vector (mock) or vector encoding P2Y13r shRNA, 3 days before the ligation of the left carotid. On the day of surgery the animals were placed on a Western diet and also given oral gavage of vehicle or Compound IIa at 100 µg/kg, once a day for 2 weeks. FIG. 18A: Western-blot of liver homogenates blotted with anti-P2Y13r or anti-P2Y1r antibodies. FIG. 18B: ligatured carotids were lipid extracted in 2:1 chloroform/methanol. The concentrations in unesterified cholesterol (dark bars) and total cholesterol (superimposed gray bars) were measured by HPLC. FIG. 18C: esterified (dark bars) and total cholesterol (superimposed gray bars) concentrations in mice plasma were measured using enzymatic kit. FIG. 18D, FIG. 18E and FIG. 18F: plasma VLDL cholesterol, LDL cholesterol and HDL cholesterol content were resolved by HPLC using a Superose 6 column and an inline enzymatic detection. Dark bars represent unesterified cholesterol and gray bars esterified cholesterol. *p<0.05, **p<0.001.

FIG. 19A-L: Effect of P2Y13 agonist on atherosclerotic plaque progression in aortas of apoE$^{-/-}$ mice. ApoE$^{-/-}$ mice (n=20) were placed on a Western diet for 8 weeks followed by a 4 weeks oral gavage of vehicle or 100 µg/kg of Compound IIa. Aortas (n=10) were lipid extracted in 2:1 chloroform/methanol. FIG. 19A: the concentrations in total cholesterol were measured by HPLC and GC/MS and compared to parallel apoE−/− mice (n=10) on normal Chow diet as a baseline. FIG. 19B: quantification of the intima/media ratio (n=10). FIG. 19C: F4/80 antibody staining quantification (n=10). FIG. 19D: Oil Red O positive staining quantification (n=10). FIG. 19E: quantification of Sirius Red staining (n=10). FIG. 19F: anti-VCAM1 antibody staining quantification (n=10). The quantifications were expressed as the percentage of staining as compared to the sum of the intima and media area. *p<0.05. FIG. 19G to FIG. 19L: typical example of staining of aorta slides used for the quantifications. FIG. 19G and FIG. 19J: hematoxylin eosin staining of transversal sections of apoE$^{-/-}$ mice aortas. FIG. 19H and FIG. 19K: Oil Red O staining of transversal sections of apoE$^{-/-}$ mice aortas. FIG. 19I and FIG. 19L: VCAM1 antibody staining of transversal sections of apoE$^{-/-}$ mice aortas.

FIG. 20A-M: Plaque regression in rabbits treated with Compound IIa. New Zealand rabbits (n=15) with atherosclerotic plaques developed after 2 months of high-cholesterol diet, were treated with Compound IIa at 30, 100 and 300 µg/kg once a day by oral gavage for 4 weeks. FIG. 20A: lipids extracted from aortas were analyzed by GC/MS for cholesterol concentration. Dark bars, unesterified cholesterol; superimposed gray bars, total cholesterol. *p<0.05. FIG. 20B, FIG. 20C and FIG. 20D: Plasma VLDL cholesterol, LDL cholesterol and HDL cholesterol were resolved as described in FIG. 2. The results are expressed as the percentage from pre-dose. FIG. 20E: apoB concentration in plasma was determined by Western blot analysis. FIG. 20F: triglycerides were measured in the plasma using the kit from Biolabo. FIG. 20G: the bile acids concentrations in liver were determined using an enzymatic kit. FIG. 20H and FIG. 20K: hematoxylin/eosin staining of aortas from rabbits dosed with vehicle (FIG. 20H) or Compound IIa at 300 µg/kg (FIG. 20K). FIG. 20I and FIG. 20L: smooth muscle cells staining of aortas from rabbits dosed with vehicle (FIG. 20I) or Compound IIa at 300 µg/kg (FIG. 20L). FIG. 20J and FIG. 20M: macrophages and monocytes staining of aortas from rabbits dosed with vehicle (FIG. 20J) or Compound IIa at 300 µg/kg (FIG. 20M).

FIG. 21A-F: Functionality of plasma from high-cholesterol diet fed rabbits treated with Compound IIa. FIG. 21A: ApoA-I concentration in plasma was measured by SELDI-TOF analysis. Purified ApoA-I from homo-sapiens (MW$_{SELDI}$=28083 Da) was used as a reference for determination of rabbit ApoA-I (MW$_{SELDI}$=27838 Da) concentration. The results are expressed as the percentage from pre-dose. FIG. 21B: ApoA-I mRNA level was determined using the QPCR technique. Note the overall decrease in the HDL particle size of treated animals. FIG. 21C; HDL from rabbit plasma were separated according to the size of the different HDL particles using the Lipoprint® system. The data were expressed as the percentage for each HDL subpopulation set to the HDL population in the pre-dose animals. Two main HDL particle sub-populations were quantified (high and intermediate—dark and gray bars respectively). FIG. 21D: example of lipoprotein profiles of rabbit treated with vehicle (gray line) and with Compound IIa (300 µg/kg, dark line) using the Lipoprint® separation technique. FIG. 21E and FIG. 21F: determination of cholesterol efflux capacity of plasma and rabbit HDL, respectively, using pre-loaded [$^3$H]-cholesterol-oxLDL macrophages. The results are expressed as a percentage of cholesterol efflux. *p<0.05, **p<0.005.

DETAILED DESCRIPTION OF THE INVENTION

I. Definitions

Figure 1:
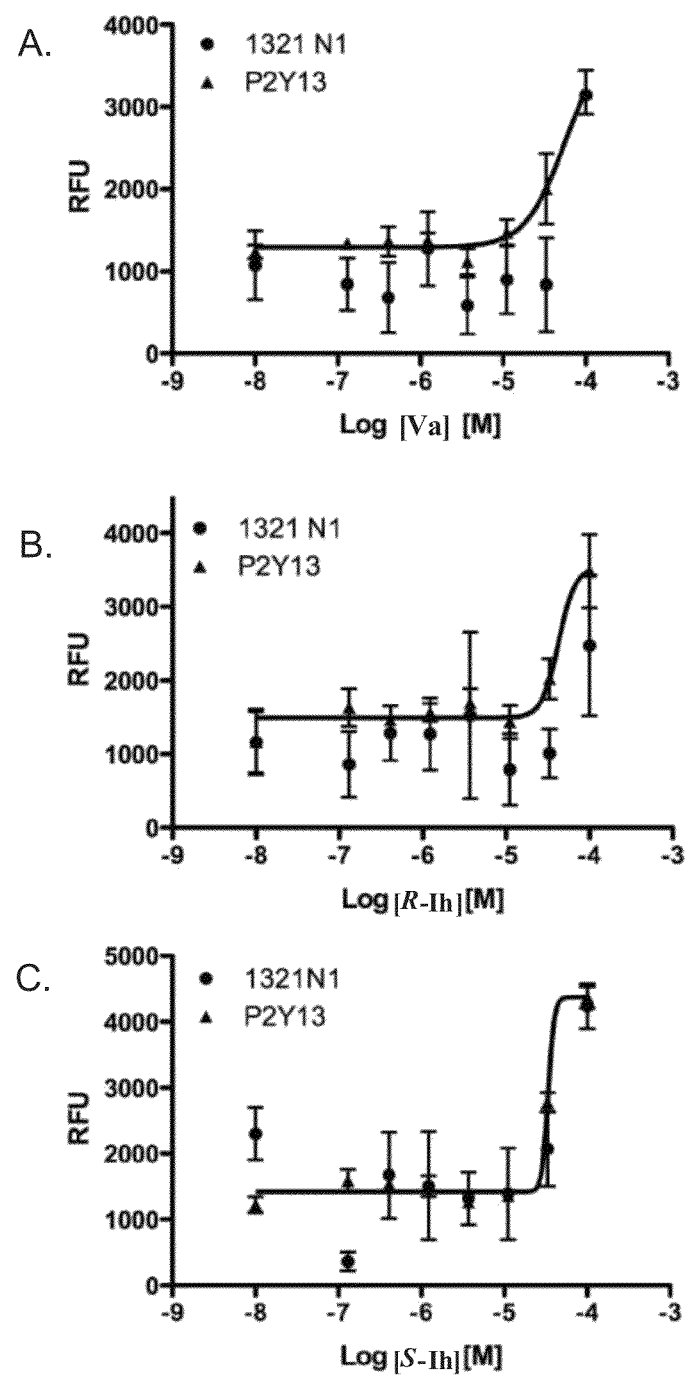
FIG. 1A-C: Compound Va (dark triangle.

The following definitions are used in connection with the invention disclosed herein:

The term "alkyl," as used herein unless otherwise defined, refers to a straight, branched, or cyclic saturated group derived form the removal of a hydrogen atom from an alkane. Representative straight chain alkyl groups include -methyl, -ethyl, -n-propyl, -n-butyl, -n-pentyl, and n-heptyl. Representative branched alkyl groups include -isopropyl, -sec-butyl, -isobutyl, -tert-butyl, -isopentyl, -neopentyl, 1-methylbutyl, 2-methylbutyl, 3-methylbutyl, 1,1-dimethylpropyl and 1,2-dimethylpropyl. Representative cyclic alkyl groups include cyclohexyl, cyclopentyl, and cyclopropyl.

The term "alkenyl" refers to a straight, branched, or cyclic hydrocarbon group containing at least one double bond. Representative alkenyl groups include, but are not limited to, ethylene, propylene, 1-butylene, 2-butylene, isobutylene, sec-butylene, 1-pentene, 2-pentene, isopentene, 1-hexene, 2-hexene, 3-hexene and isohexene.

The term "alkynyl" refers to a straight or branched chain hydrocarbon containing at least one triple bond. Representative alkynyl groups include, but are not limited to, acetylene, propyne, 1-butyne, 2-butyne, isobutyne, sec-butyne, 1-pentyne, 2-pentyne, isopentyne, 1-hexyne, 2-hexyne, 3-hexyne and isohexyne.

The term "hydrocarbyl," as used herein unless otherwise defined, refers to a substituent derived from the removal of hydrogen atom from a hydrocarbon molecule. Non-limiting examples of hydrocarbyl include alkyl, alkenyl, alkynyl; cyclic groups consisting of hydrogen and carbon such as aryl as described herein, including both aromatic and non-aromatic groups as described herein; and aralkyl described herein.

The term "aryl" as used herein unless otherwise defined, refers to an aromatic group. Non-limiting examples of aryl include phenyl, naphthyl, pyridyl, phenanthryl, anthryl, furanyl, azolyl, imidazolyl, and indolyl. In one embodiment, the aryl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless specified otherwise, the aryl is unsubstituted.

The term "heteroaryl" as used herein unless otherwise defined, refers to an aromatic group, wherein the aromatic group contains at least one ring atom that is not carbon. Non-limiting examples of heteroaryl include pyridyl, furanyl, azolyl, imidazolyl, thiophenyl, and indolyl. In one embodiment, the aryl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless specified otherwise, the heteroaryl is unsubstituted.

The term "aralkyl" as used herein unless otherwise defined, refers to an alkyl group, which is substituted with an aryl group. Non-limiting examples of an aralkyl group include benzyl, picolyl, naphthylmethyl.

The term "heterocyclyl" as used herein unless otherwise defined, refers to a cyclic group, wherein the cyclic group contains at least one ring atom that is not carbon. Representative examples heterocyclyl group include, but are not limited to, furanyl, furazanyl, imidazolidinyl, imidazolinyl, imidazolyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, triazolyl. In one embodiment, the aryl group is substituted with one or more of the following groups: -halo, —O—($C_1$-$C_6$ alkyl), —OH, —CN, —COOR', —OC(O)R', —N(R)$_2$, —NHC(O)R' or —C(O)NHR' groups wherein each R' is independently —H or unsubstituted —$C_1$-$C_6$ alkyl. Unless specified otherwise, the heterocyclyl is unsubstituted.

The term "alkoxy," as used herein unless otherwise defined, refers to —O-(alkyl), wherein alkyl is as defined above. Representative examples of a $C_1$-$C_6$ alkoxy include, but are not limited to, —OCH$_3$, —OCH$_2$CH$_3$, —OCH$_2$CH$_2$CH$_3$, —OCH(CH$_3$)CH$_3$, —OCH$_2$CH$_2$CH$_2$CH$_3$, —OCH$_2$CH(CH$_3$)CH$_3$, —OCH(CH$_3$)CH$_2$CH$_3$, —OC(CH$_3$)$_3$, —OCH$_2$CH$_2$CH$_2$CH$_2$CH$_3$, —OCH$_2$CH(CH$_3$)CH$_2$CH$_3$, —OCH$_2$CH$_2$CH$_2$CH$_2$CH$_3$, and —OCH$_2$CH$_2$CH(CH$_3$)CH$_2$CH$_3$.

The terms "halo" and "halogen," as used herein unless otherwise defined, refers to —F, —Cl, —Br or —I.

The term "subject," as used herein unless otherwise defined, is a mammal, e.g., a human, mouse, rat, guinea pig, dog, cat, horse, cow, pig, or non-human primate, such as a monkey, chimpanzee, or baboon. In one embodiment, the subject is a human.

The term "pharmaceutically acceptable salt," as used herein unless otherwise defined, is a salt of a basic group, such as an amino group, or of an acidic group, such as a carboxyl group, on the compounds of the invention. Illustrative salts of a basic group include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, and pamoate (i.e., 1,1'-methylene-bis-(2-hydroxy-3-naphthoate)) salts. Illustrative salts of an acidic group include, but are not limited, to lithium, sodium, potassium, calcium, magnesium, aluminum, chromium, iron, copper, zinc, cadmium, ammonium, guanidinium, pyridinium, and organic ammonium salts.

The terms "hydrate" and "solvate" as used herein and unless otherwise defined, describe a compounds of the invention or salts thereof, which further include a stoichiometric or non-stoichiometric amount of water or other solvent bound by non-covalent intermolecular forces.

The term "reverse cholesterol transport" (RCT) as used herein unless otherwise defined, describes the transport of cholesterol from extrahepatic tissues to the liver where it is catabolized and eliminated. HDL particles can play a major role in the reverse transport process, acting as scavengers of tissue cholesterol.

The term "altering lipid metabolism" as used herein and unless otherwise defined, indicates an observable (measurable) change in at least one aspect of lipid metabolism including, but not limited to, total blood lipid content, blood HDL cholesterol, blood LDL cholesterol, blood VLDL cholesterol, blood TG, blood Lp(a), blood Apo A-I, blood Apo E and blood NEFA.

The term "altering glucose metabolism" as used herein and unless otherwise defined, indicates an observable (measurable) change in at least one aspect of glucose metabolism, including but not limited to total blood glucose content, blood insulin, the blood insulin to blood glucose ratio, insulin sensitivity, and oxygen consumption.

An "effective amount," when used in connection with a compound of the invention, is an amount that is effective for treating or preventing a Condition as described herein.

An "effective amount" when used in connection with another therapeutic agent is an amount that is effective for treating or preventing a Condition in combination with a compound of the invention. "In combination with" includes administration within the same composition and via separate compositions; in the latter instance, the other therapeutic agent is effective for treating or preventing a Condition during a time when the compound of the invention exerts its prophylactic or therapeutic effect, or vice versa.

The language "substantially free of its corresponding opposite enantiomer" means having no more than about 10 mol %, in another embodiment no more than about 5 mol %, in another embodiment no more than about 2 mol %, in another embodiment no more than about 1 mol %, in another embodiment no more than about 0.5 mol % and in another embodiment no more than about 0.1 mol %, of its corresponding opposite enantiomer.

The language "substantially free of another stereoisomer" means having no more than about 10 mol %, in another embodiment no more than about 5 mol %, in another embodiment no more than about 2 mol %, in another embodiment no more than about 1 mol %, in another embodiment no more than about 0.5 mol % and in another embodiment no more than about 0.1 mol %, of another stereoisomer.

The term "about" when used in connection with a referenced numeric indication means the referenced numeric indication plus or minus up to 10% of that referenced numeric indication. For example, the language "about 50" covers the range of 45 to 55.

As used herein, the term "elderly human" refers to a human 65 years or older.

As used herein, the term "human adult" refers to a human that is 18 years or older.

As used herein, the term "human child" refers to a human that is 1 year to 18 years old.

As used herein, the term "human toddler" refers to a human that is 1 year to 3 years old.

As used herein, the term "human infant" refers to a newborn to 1 year old year human.

As used herein, the term "premature human infant" refers to a human infant born at less than 37 weeks of gestational age.

As used herein, the term "Apo(a)" refers to apolipoprotein (a).

As used herein, the term "Apo A-I" refers to apolipoprotein A-I.

As used herein, the term "Apo B" refers to apolipoprotein B.

As used herein, the term "Apo E" refers to apolipoprotein E.

As used herein, the term "FA" refers to fatty acids.

As used herein, the term "HDL" refers to High density lipoprotein.

As used herein, the term "IDL" refers to Intermediate density lipoprotein.

As used herein, the term "IDDM" refers to Insulin dependent diabetes mellitus.

As used herein, the term "LDH" refers to Lactate dehydrogenase

As used herein, the term "LDL" refers to Low density lipoprotein.

As used herein, the term "Lp(a)" refers to Lipoprotein (a).

As used herein, the term "NIDDM" refers to Non-insulin dependent diabetes mellitus.

As used herein, the term "NEFA" refers to non-esterified fatty acids.

As used herein, the term "P2Y13" refers to a GPCR receptor.

As used herein the term "P2Y13r" refers to the P2Y13 receptor

As used herein the terms "P2Y13r" and "P2Y13 receptor" are used interchangeably.

As used herein, the term "RXR" refers to Retinoid X receptor.

As used herein, the term "TG" refers to Triglicerides.

As used herein, the term "VLDL" refers to Very low density lipoprotein.

II. Compounds of the Invention

In one embodiment, the invention provides compounds of the following Formula I:

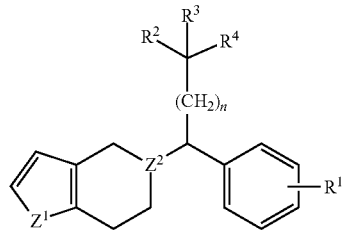

Formula I and pharmaceutically acceptable salts thereof, wherein
each of $R^1$, $R^2$, and $R^3$ is independently H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$;

$R^4$ is —H, —OH, —COOH, —NH$_2$, —NH(alkyl), —N(alkyl)(alkyl), -hydrocarbyl, —O-hydrocarbyl, -aryl, —O-aryl, -aralkyl, —O-aralkyl, -heteroaryl, —O-heteroaryl, -heterocyclyl, —O-heterocyclyl, -halo, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), or —OC(O)N(alkyl)(alkyl);

$Z^1$ is CH$_2$, S, O, NH, N-hydrocarbyl, N-aryl, N-heteroaryl, or N-heterocyclyl;

$Z^2$ is CH or N; and n is an integer from 1-6.

In some embodiments, the compounds of Formula I are those wherein $Z^2$ is N. In other embodiments, $Z^2$ is CH.

In some embodiments, $R^1$ is halo. In other embodiments, $R^1$ is chloro. In other embodiments, $R^1$ is 2-halo. In other embodiments, R' is 2-chloro. In other embodiments, $R^1$ is H.

In some embodiments, $Z^1$ is S. In other embodiments, $Z^1$ is O. In other embodiments, $Z^1$ is NH. In other embodiments, $Z^1$ is N-alkyl.

In some embodiments, each of $R^2$ and $R^3$ is independently H or alkyl. In other embodiments, each of $R^2$ and $R^3$ is H. In other embodiments, each of $R^2$ and $R^3$ is alkyl. In other embodiments, each of $R^2$ and $R^3$ is methyl.

In some embodiments, $R^4$ is —OH, —COOH, —C(O)O(alkyl), or —OC(O)(alkyl). In other embodiments, $R^4$ is —OH. In other embodiments, $R^4$ is —COOH. In other embodiments, $R^4$ is —C(O)O(alkyl) or —OC(O)(alkyl). In other embodiments, $R^4$ is —COOEt. In other embodiments, $R^4$ is —COOMe.

In some embodiments, n is an integer from 1-6. In other embodiments, n is 1. In other embodiments, n is 2. In other embodiments, n is 3. In other embodiments, n is 4. In other embodiments, n is 5. In other embodiments, n is 6.

In some embodiments, each of $R^2$ and $R^3$ is alkyl and $R^4$ is —C(O)O-alkyl. In other embodiments, each of $R^2$ and $R^3$ is methyl and $R^4$ is —C(O)O-alkyl. In other embodiments, each of $R^2$ and $R^3$ is alkyl and $R^4$ is —C(O)OEt. In other embodiments, each of $R^2$ and $R^3$ is methyl and $R^4$ is —C(O)OEt.

In some embodiments, each of $R^2$ and $R^3$ is H and $R^4$ is —C(O)O-alkyl. In other embodiments, each of $R^2$ and $R^3$ is H and $R^4$ is —C(O)OEt.

In some embodiments, each of $R^2$ and $R^3$ is alkyl and $R^4$ is —C(O)OH. In other embodiments, each of $R^2$ and $R^3$ is methyl and $R^4$ is —C(O)OH.

In some embodiments, each of $R^2$ and $R^3$ is H and $R^4$ is —C(O)OH.

In some embodiments, each of $R^2$ and $R^3$ is alkyl and $R^4$ is —OH. In other embodiments, each of $R^2$ and $R^3$ is methyl and $R^4$ is —OH.

In some embodiments, each of $R^2$ and $R^3$ is H and $R^4$ is —OH.

In some embodiments, $Z^1$ and $Z^2$ of the compounds of Formula I are the following:

|  | $Z^1$ | $Z^2$ |
| --- | --- | --- |
| I-1 | CH$_2$ | CH |
| I-2 | S | CH |
| I-3 | O | CH |
| I-4 | NH | CH |

-continued
|  | $Z^1$ | $Z^2$ |
|---|---|---|
| I-5 | N-hydrocarbyl | CH |
| I-6 | N-aryl | CH |
| I-7 | N-heteroaryl | CH |
| I-8 | N-heterocyclyl | CH |
| I-9 | $CH_2$ | N |
| I-10 | S | N |
| I-11 | O | N |
| I-12 | NH | N |
| I-13 | N-hydrocarbyl | N |
| I-14 | N-aryl | N |
| I-15 | N-heteroaryl | N |
| I-16 | N-heterocyclyl | N |
In some embodiments, a compound of Formula I has the structure:
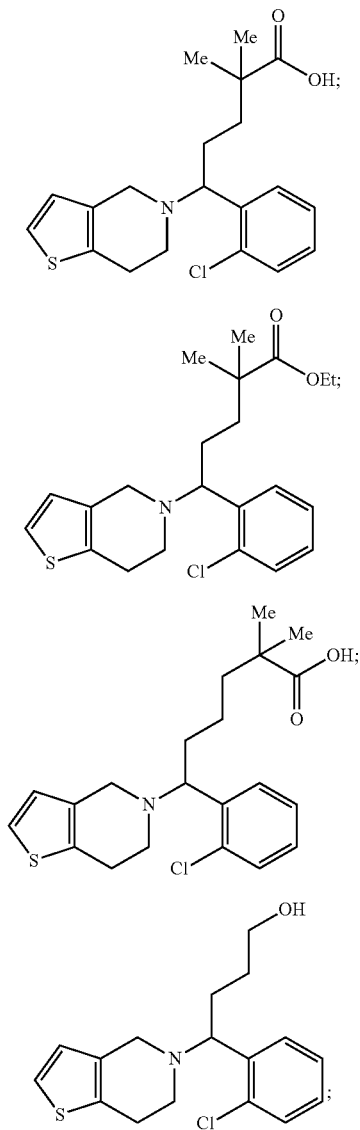
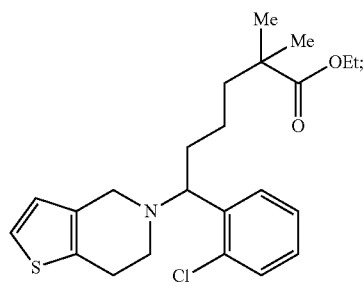
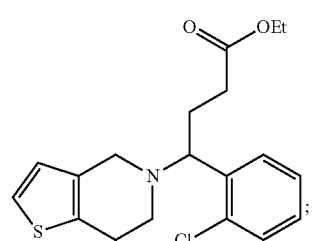
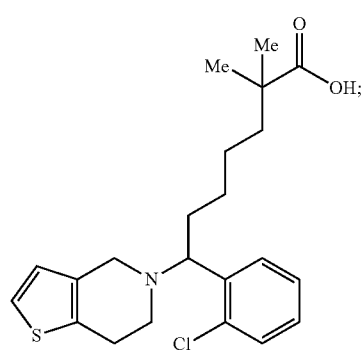
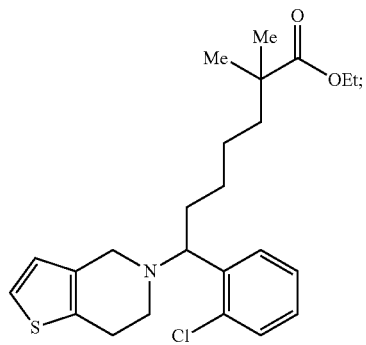
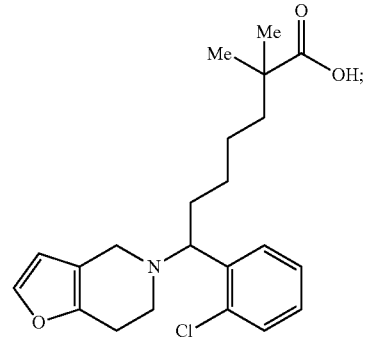

Ij
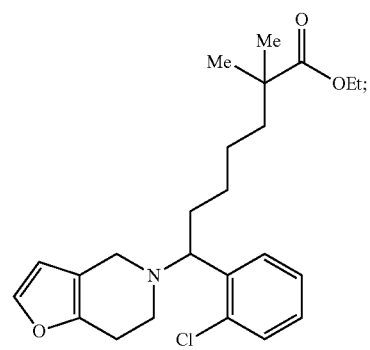
Ik
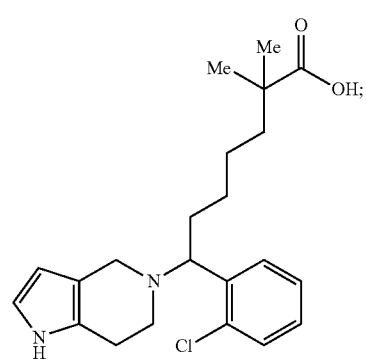
Il
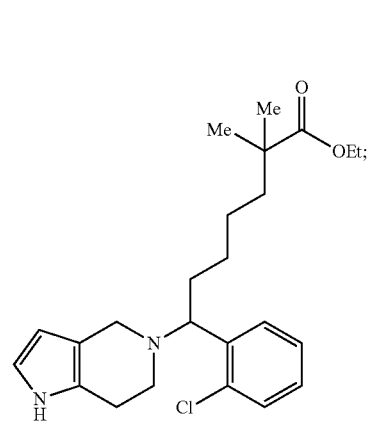
Im
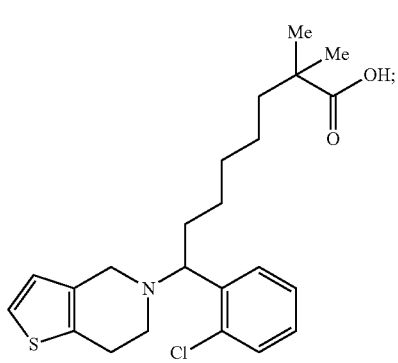
In
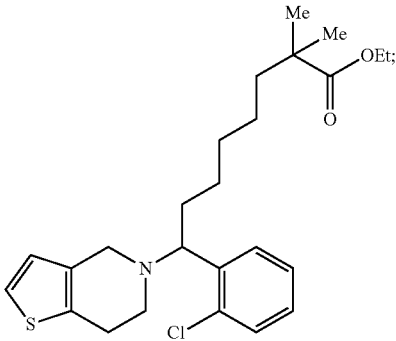
Io
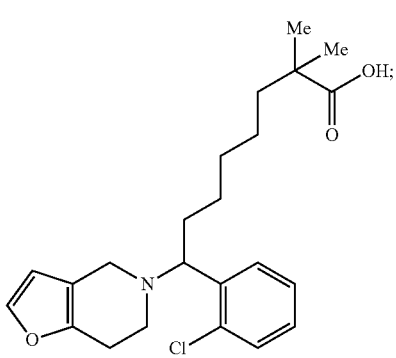
Ip
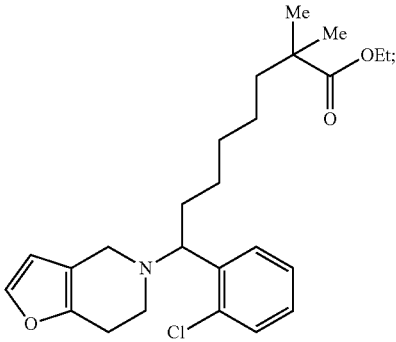
Iq
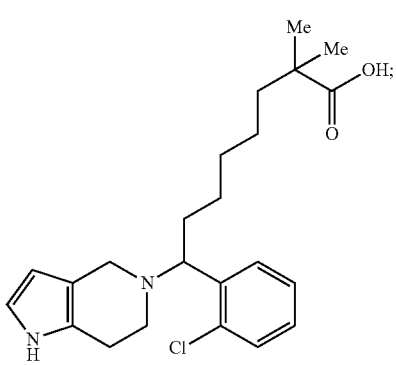

-continued

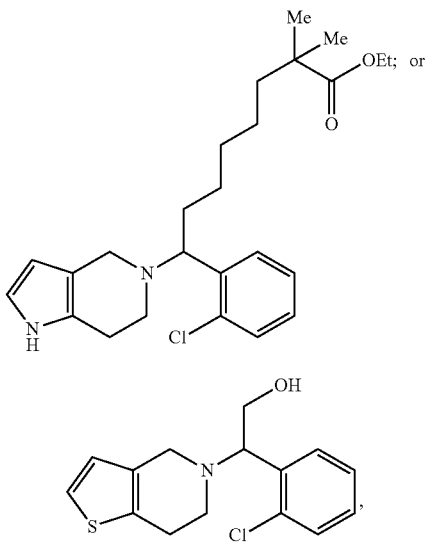

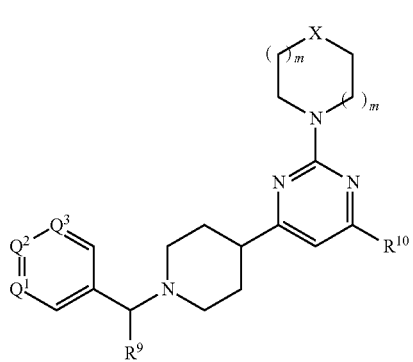

or a pharmaceutically acceptable salt of any of the foregoing.

In another embodiment, the invention provides compounds of the following Formula II:

Formula II and pharmaceutically acceptable salts thereof, wherein
each $R^9$ is independently —H, -hydrocarbyl, -aryl, -aralkyl, -heteroaryl, -heterocyclyl, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), or —SO$_2$NH$_2$;
each $R^{10}$ is independently —H, —OH, —NH(alkyl), —N(alkyl)(alkyl), hydrocarbyl, —O-alkyl, —O-alkenyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), NHC(O)(C$_2$-C$_{10}$-alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$;
each of $Q^1$, $Q^2$, and $Q^3$ is independently $CR^{10}$ or N;
X is $CHR^{10}$, S, O, or $NR^9$; and
each m is independently an integer from 0-3.

In some embodiments, the compounds of Formula II are those wherein $R^9$ is H or hydrocarbyl. In other embodiments, $R^9$ is H. In other embodiments, $R^9$ is hydrocarbyl. In other embodiments, $R^9$ is alkyl. In other embodiments, $R^9$ is methyl. In other embodiments, $R^9$ is ethyl. In other embodiments, $R^9$ is phenyl.

In some embodiments, the compounds of Formula II are those wherein
$R^{10}$ is H, —OH, or hydrocarbyl. In other embodiments, $R^{10}$ is H. In other embodiments, $R^{10}$ is —OH. In other embodiments, $R^{10}$ is —OMe. In other embodiments, $R^{10}$ is —OEt. In other embodiments, $R^{10}$ is —NH$_2$. In other embodiments, $R^{10}$ is —NHMe. In other embodiments, $R^{10}$ is —NMe$_2$. In other embodiments, $R^{10}$ is hydrocarbyl. In other embodiments, $R^{10}$ is alkyl. In other embodiments, $R^{10}$ is methyl. In other embodiments, $R^{10}$ is ethyl. In other embodiments, $R^{10}$ is phenyl.

In another embodiment, $R^9$ is H and $R^{10}$ is —OH.

In some embodiments, the compounds of Formula II are those wherein each of $Q^1$, $Q^2$, and $Q^3$ is N. In other embodiments, each of $Q^1$, $Q^2$, and $Q^3$ is $CR^{10}$. In other embodiments, each of $Q^1$, $Q^2$ is N and $Q^3$ is $CR^{10}$.

In some embodiments, the compounds of Formula II are those wherein X is CH$_2$. In other embodiments, X is O. In other embodiments, X is NH. In other embodiments, X is NMe. In other embodiments, X is N-benzyl.

In some embodiments, the compounds of Formula II are those wherein each m is independently an integer from 0-3. In other embodiments, each m is independently an integer from 1-3. In other embodiments, m is 0. In other embodiments, m is 1. In other embodiments, in is 2. In other embodiments, m is 3.

In other embodiments, $Q^1$ and $Q^3$ are N, $Q^2$ is $CR^{10}$ and $R^{10}$ is —N(alkyl)(alkyl). In other embodiments, $Q^1$ and $Q^3$ are N, $Q^2$ is $CR^{10}$ and $R^{10}$ is —N(H)(alkyl). In other embodiments, $Q^1$ and $Q^3$ are N, $Q^2$ is $CR^{10}$ and $R^{10}$ is —N(CH$_3$)$_2$.

In other embodiments, $Q^1$ and $Q^3$ are N, $Q^2$ is $CR^{10}$ and $R^{10}$ is —N(H)(CH$_3$).

In other embodiments, each m is 1, X is $NR^9$ and $R^9$ is H. In other embodiments, each m is 1 and X is O.

In some embodiments, $Q^1$, $Q^2$, $Q^3$ and X of the compounds of Formula II are the following:

|  | X | $Q^2$ | $Q^3$ | $Q^1$ |
|---|---|---|---|---|
| II-1 | $CHR^{10}$ | $CR^{10}$ | $CR^{10}$ | $CR^{10}$ |
| II-2 | S | $CR^{10}$ | $CR^{10}$ | $CR^{10}$ |
| II-3 | O | $CR^{10}$ | $CR^{10}$ | $CR^{10}$ |
| II-4 | $NR^9$ | $CR^{10}$ | $CR^{10}$ | $CR^{10}$ |
| II-5 | $CHR^{10}$ | N | $CR^{10}$ | $CR^{10}$ |
| II-6 | S | N | $CR^{10}$ | $CR^{10}$ |
| II-7 | O | N | $CR^{10}$ | $CR^{10}$ |
| II-8 | $NR^9$ | N | $CR^{10}$ | $CR^{10}$ |
| II-9 | $CHR^{10}$ | $CR^{10}$ | N | $CR^{10}$ |
| II-10 | S | $CR^{10}$ | N | $CR^{10}$ |
| II-11 | O | $CR^{10}$ | N | $CR^{10}$ |
| II-12 | $NR^9$ | $CR^{10}$ | N | $CR^{10}$ |
| II-13 | $CHR^{10}$ | $CR^{10}$ | $CR^{10}$ | N |
| II-14 | S | $CR^{10}$ | $CR^{10}$ | N |
| II-15 | O | $CR^{10}$ | $CR^{10}$ | N |
| II-16 | $NR^9$ | $CR^{10}$ | $CR^{10}$ | N |
| II-17 | $CHR^{10}$ | N | N | $CR^{10}$ |
| II-18 | S | N | N | $CR^{10}$ |
| II-19 | O | N | N | $CR^{10}$ |
| II-20 | $NR^9$ | N | N | $CR^{10}$ |
| II-21 | $CHR^{10}$ | $CR^{10}$ | N | N |
| II-22 | S | N | $CR^{10}$ | N |

-continued

|       | X     | $Q^2$     | $Q^3$     | $Q^1$ |
|-------|-------|-----------|-----------|-------|
| II-23 | O     | N         | $CR^{10}$ | N     |
| II-24 | $NR^9$| N         | $CR^{10}$ | N     |
| II-25 | $CHR^{10}$ | $CR^{10}$ | N    | N     |
| II-26 | S     | $CR^{10}$ | N         | N     |
| II-27 | O     | $CR^{10}$ | N         | N     |
| II-28 | $NR^9$| $CR^{10}$ | N         | N     |
| II-29 | $CHR^{10}$ | N    | N         | N     |
| II-30 | S     | N         | N         | N     |

-continued

|       | X     | $Q^2$ | $Q^3$ | $Q^1$ |
|-------|-------|-------|-------|-------|
| II-31 | O     | N     | N     | N     |
| II-32 | $NR^9$| N     | N     | N     |

In some embodiments, a compound of Formula II exists as a single tautomer or a mixture of tautomers. One of skill in the art will recognize structures possessing tautomeric forms, and will understand that the illustration of a single tautomer implies the structure of all possible tautomeric forms. In some embodiments, $R^{10}$ is OH, and the compound of Formula II exists in one, two, or three tautomeric forms of Formula II, as illustrated in Equation I.

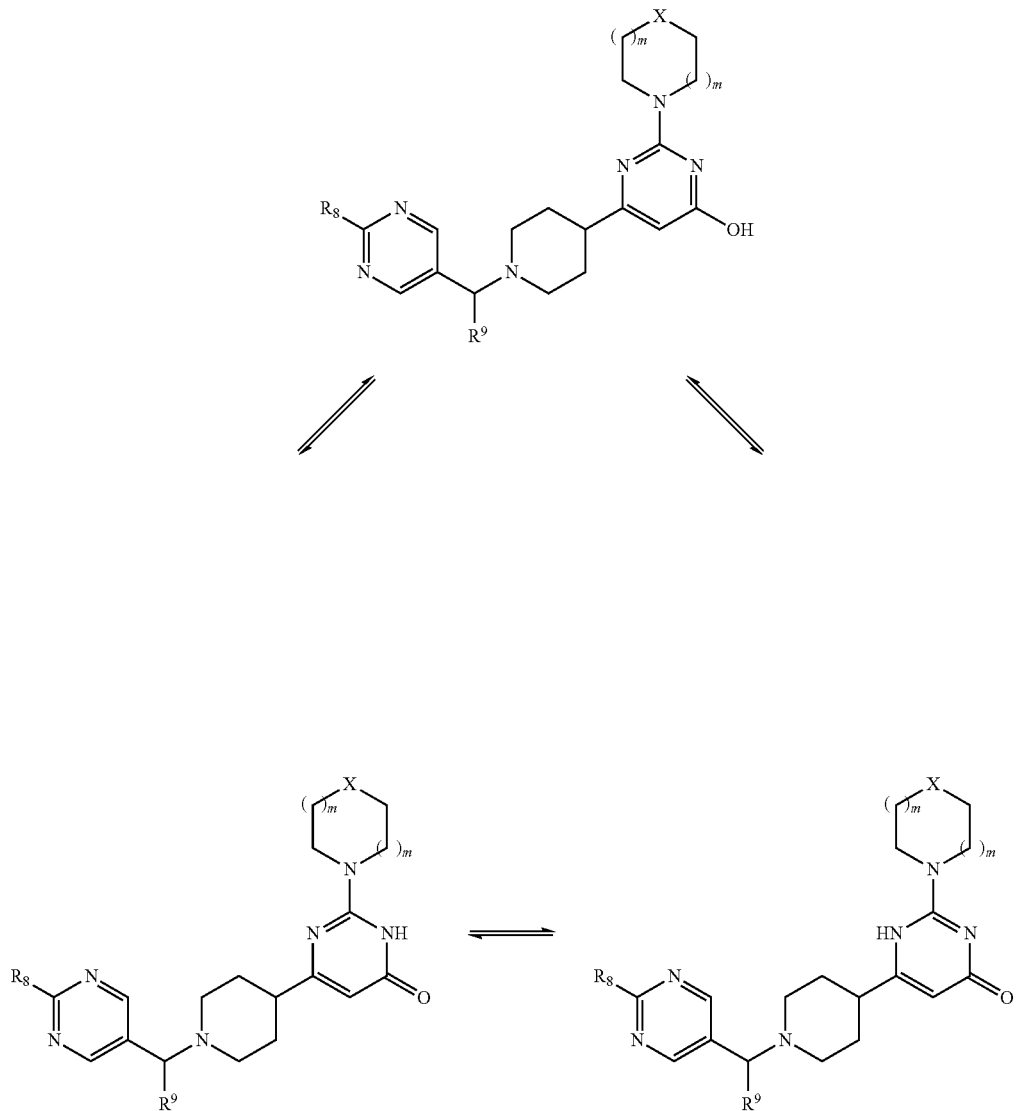

Equation I

In some embodiments, a compound of Formula II has the structure:
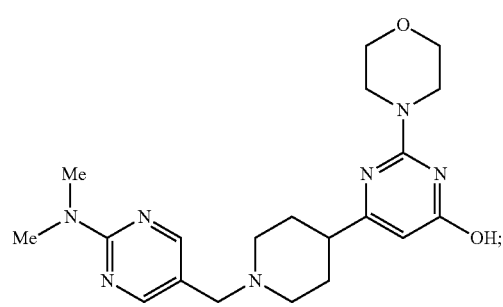
IIa
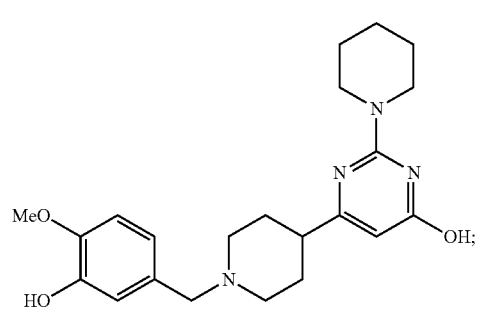
IIb
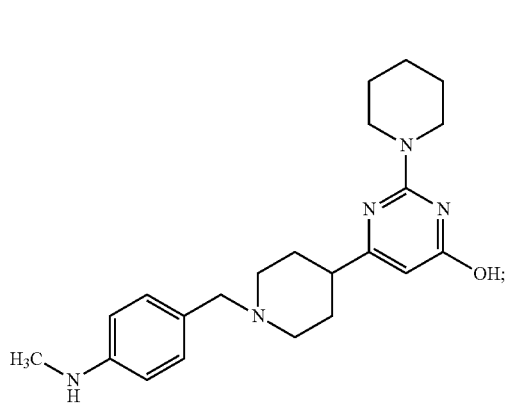
IIc
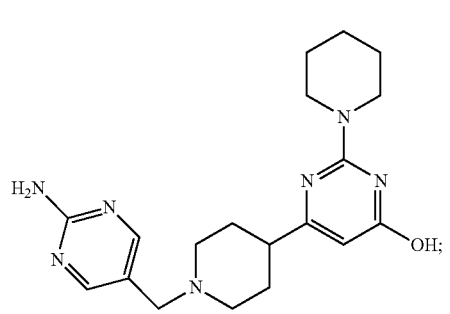
IId
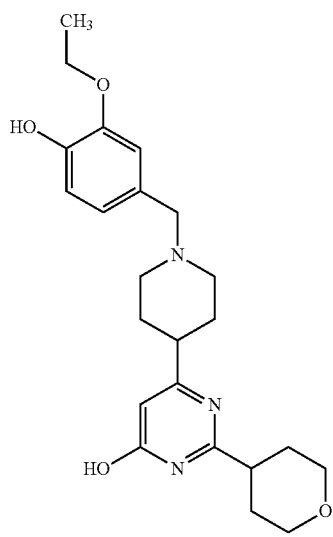
IIe
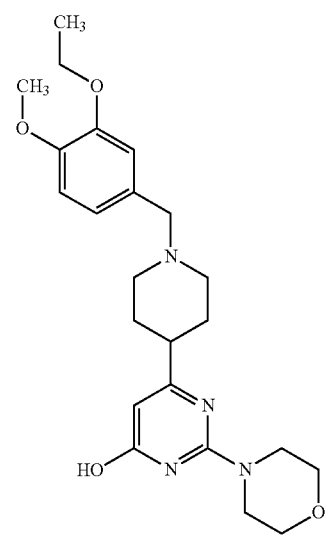
IIf
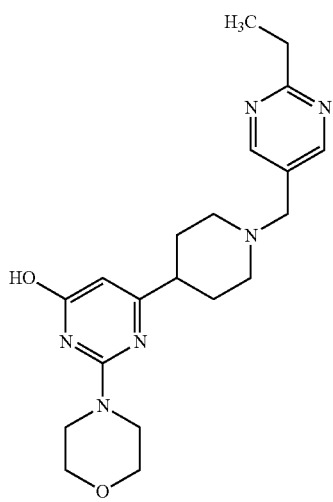
IIg -continued
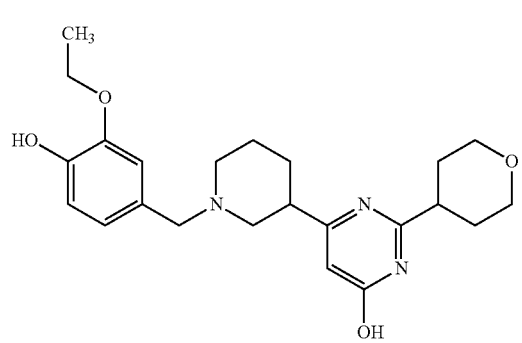
IIh
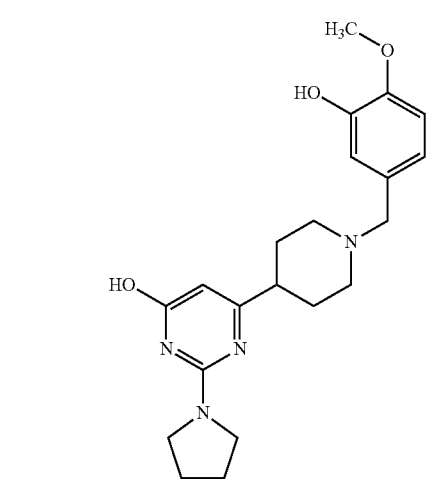
IIi
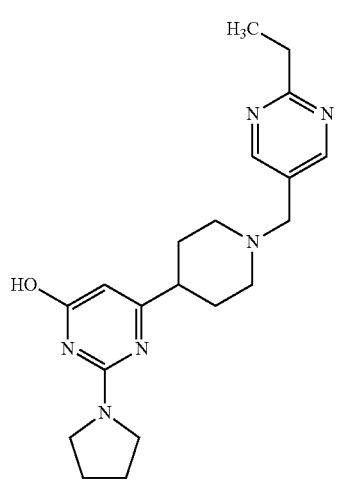
IIj
-continued
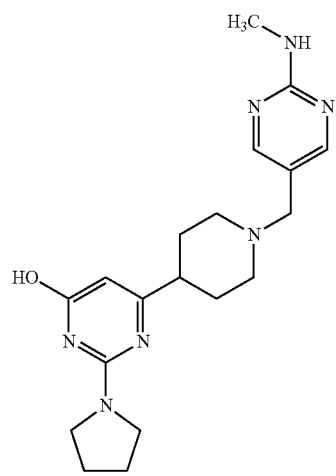
IIk
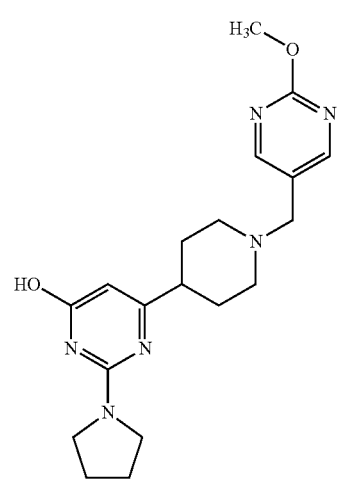
IIl
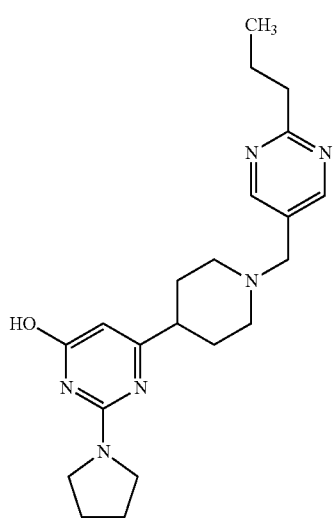
IIm -continued
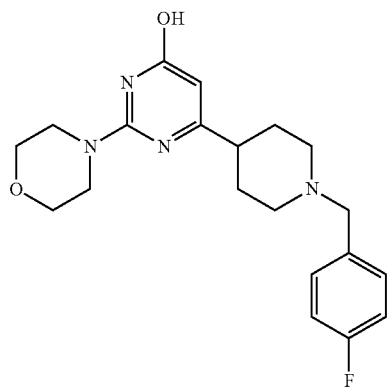
IIn
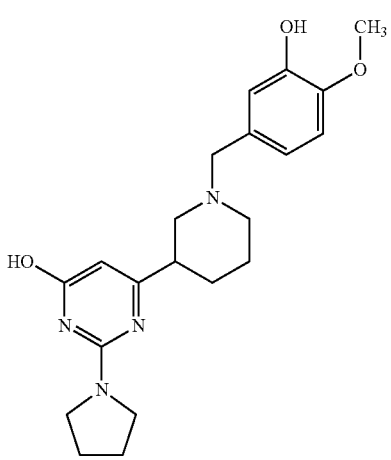
IIq
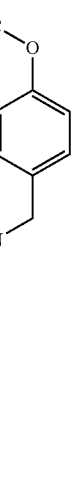
IIo
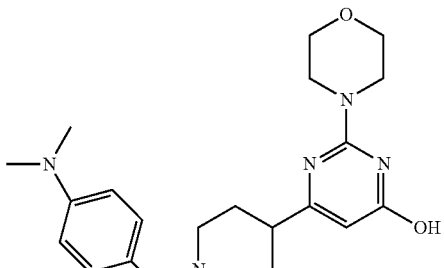
IIr
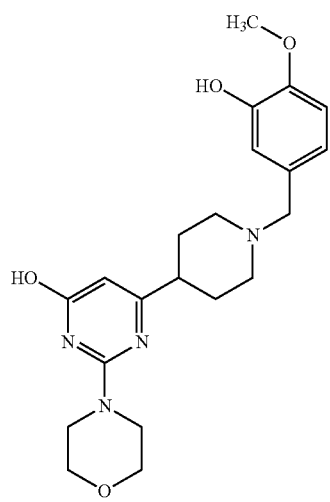
IIp
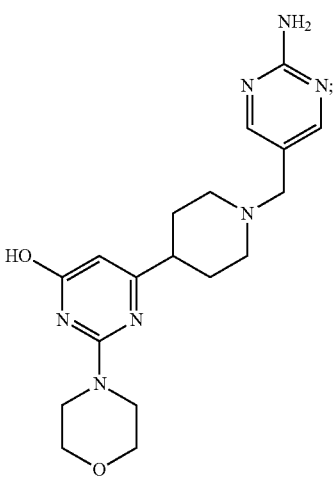
IIs -continued
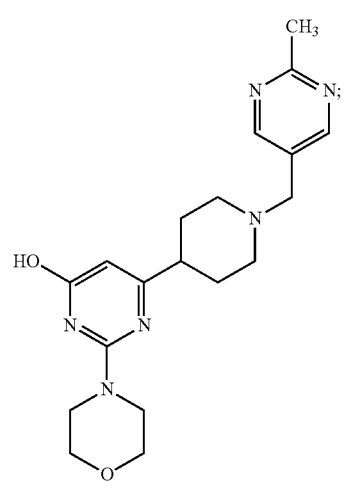
IIt
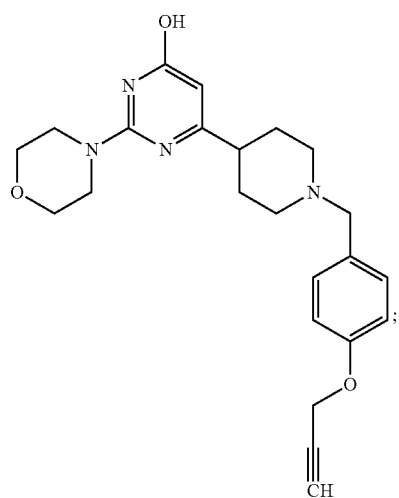
IIu
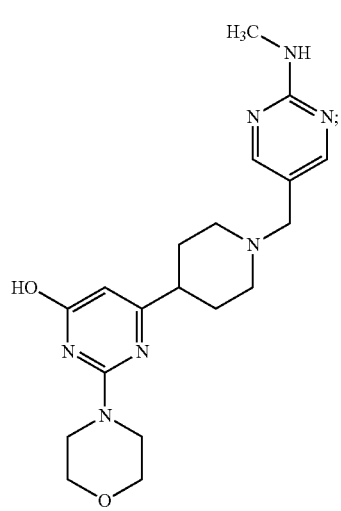
IIv
-continued
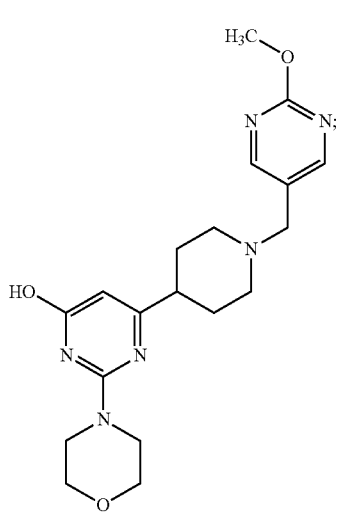
IIw
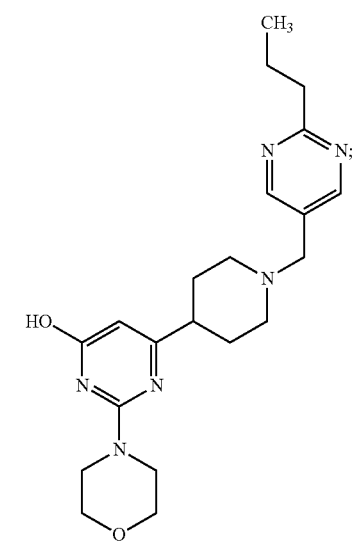
IIx
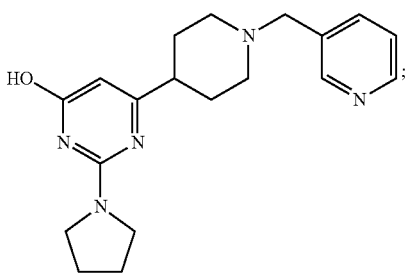
IIy

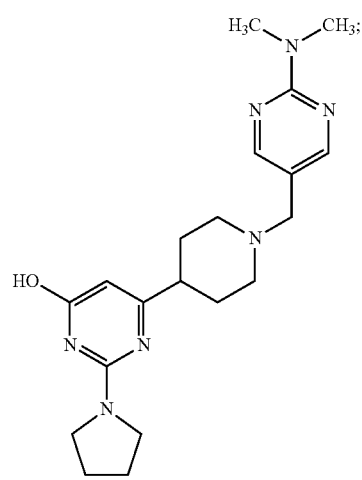
IIz
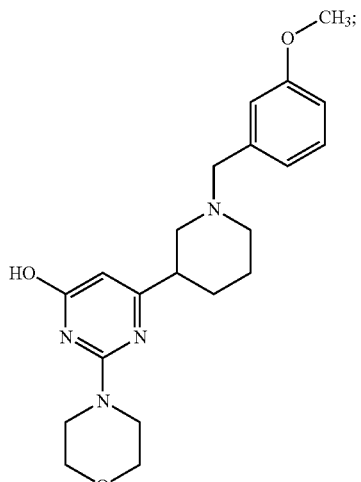
IIcc
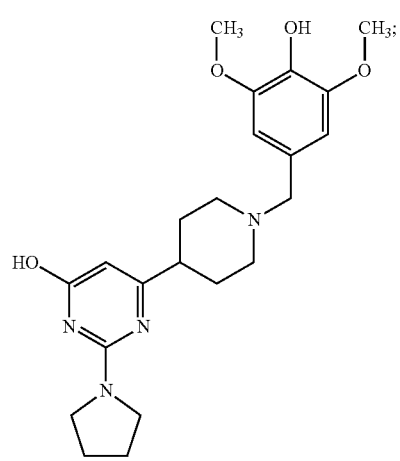
IIaa
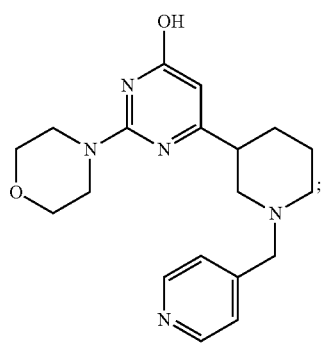
IIdd
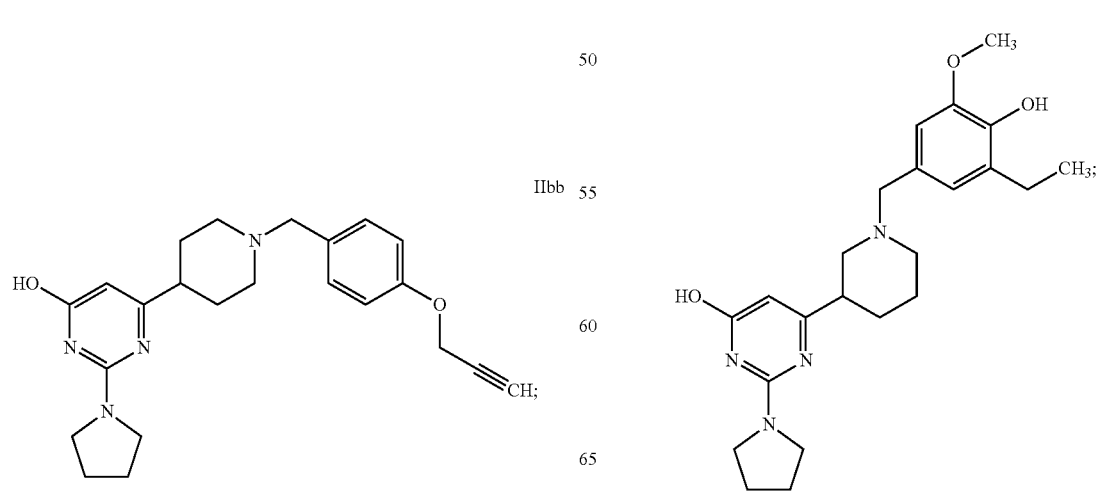
IIbb
IIee 37
-continued

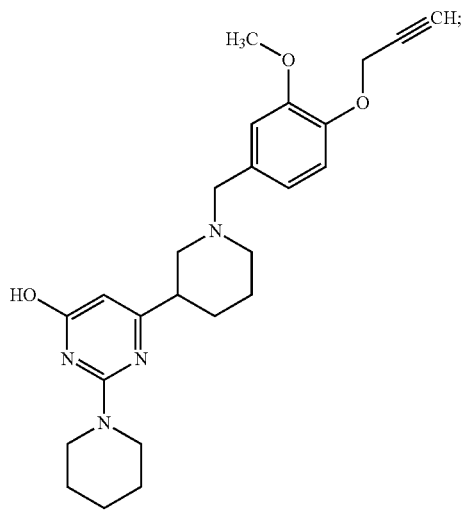
IIff

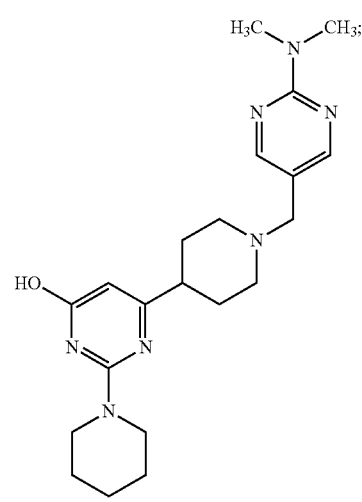
IIgg

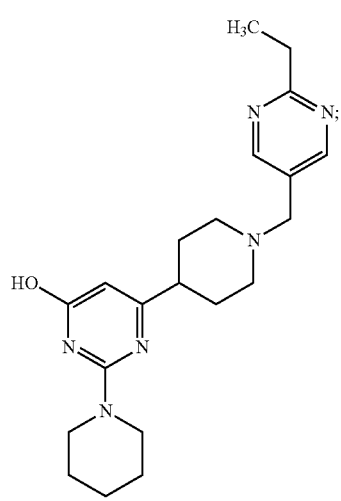
IIhh

38
-continued

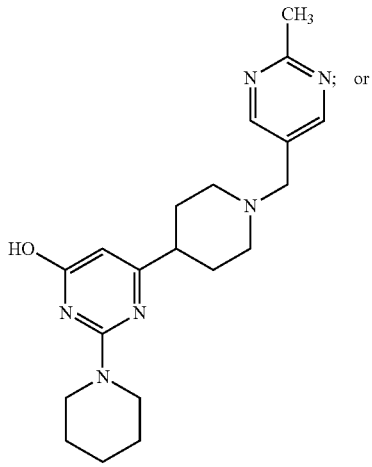
IIii

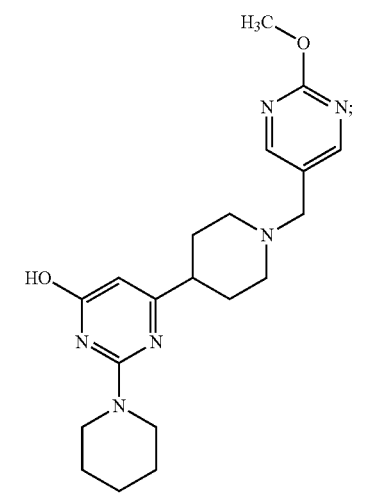
IIjj or a pharmaceutically acceptable salt of any of the foregoing.

In another embodiment, the invention encompasses compounds of the following Formula III:

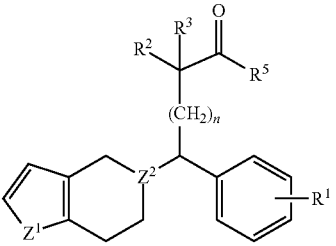
Formula III and pharmaceutically acceptable salts thereof, wherein
each of $R^1$, $R^2$, and $R^3$ is independently H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH (alkyl), —C(O)N(alkyl)(alkyl), —NHC(O)(alkyl), N(alkyl) C(O)(alkyl), —OC(O)O(alkyl), —OC(O)NH$_2$, —OC(O)NH (alkyl), —OC(O)N(alkyl)(alkyl), —CHNH, —CHN(alkyl), or —SO$_2$NH$_2$;

$R^5$ is —H, —OH, —$NH_2$, —NH(alkyl), —N(alkyl)(alkyl), hydrocarbyl, —O-hydrocarbyl, aryl, —O-aryl, aralkyl, —O-aralkyl, heteroaryl, —O-heteroaryl, heterocyclyl, or —O-heterocyclyl;

$Z^1$ is $CH_2$, S, O, NH, N-hydrocarbyl, N-aryl, N-heteroaryl, or N-heterocyclyl;

$Z^2$ is CH or N; and n is an integer from 1-6.

In some embodiments, the compounds of Formula III are those wherein $Z^2$ is N. In other embodiments, $Z^2$ is CH.

In some embodiments, $R^1$ is halo. In other embodiments, $R^1$ is chloro. In other embodiments, $R^1$ is 2-halo. In other embodiments, $R^1$ is 2-chloro. In other embodiments, $R^1$ is H.

In some embodiments, $Z^1$ is S. In other embodiments, $Z^1$ is O. In other embodiments, $Z^1$ is NH. In other embodiments, $Z^1$ is N-alkyl.

In some embodiments, each of $R^2$ and $R^3$ is independently H or alkyl. In other embodiments, each of $R^2$ and $R^3$ is H. In other embodiments, each of $R^2$ and $R^3$ is methyl.

In some embodiments, $R^5$ is —OH, —O-alkyl, or —O-aralkyl. In other embodiments, $R^5$ is —OH. In other embodiments, $R^5$ is —O-benzyl. In other embodiments, $R^5$ is —OEt. In other embodiments, $R^5$ is —OMe.

In some embodiments, n is an integer from 1-6. In other embodiments, n is 1. In other embodiments, n is 2. In other embodiments, n is 3. In other embodiments, n is 4. In other embodiments, n is 5. In other embodiments, n is 6.

In some embodiments, $Z^1$ and $Z^2$ of the compounds of Formula III are the following:

|  | $Z^1$ | $Z^2$ |
|---|---|---|
| III-1 | $CH_2$ | CH |
| III-2 | S | CH |
| III-3 | O | CH |
| III-4 | NH | CH |
| III-5 | N-hydrocarbyl | CH |
| III-6 | N-aryl | CH |
| III-7 | N-heteroaryl | CH |
| III-8 | N-heterocyclyl | CH |
| III-9 | $CH_2$ | N |
| III-10 | S | N |
| III-11 | O | N |
| III-12 | NH | N |
| III-13 | N-hydrocarbyl | N |
| III-14 | N-aryl | N |
| III-15 | N-heteroaryl | N |
| III-16 | N-heterocyclyl | N |

In another embodiment, the invention provides compounds of the following Formula IV:

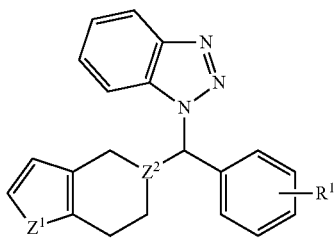

Formula IV and pharmaceutically acceptable salts thereof, wherein $R^1$ is H, —OH, —$NH_2$, —NH(alkyl), —N(alkyl)(alkyl), hydrocarbyl, —O-hydrocarbyl, aryl, —O-aryl, aralkyl, —O-aralkyl, heteroaryl, —O-heteroaryl, heterocyclyl, —O-heterocyclyl, halo, —$OCF_3$, —C(O)O(alkyl), —OC(O)(alkyl), —C(O)$NH_2$, —C(O)NH(alkyl), —C(O)N(alkyl)(alkyl), —NHC(O)(alkyl), N(alkyl)C(O)(alkyl), —OC(O)O(alkyl), —OC(O)$NH_2$, —OC(O)NH(alkyl), —OC(O)N(alkyl)(alkyl), —CHNH, —CHN(alkyl), or —$SO_2NH_2$;

$Z^1$ is $CH_2$, S, O, NH, N-hydrocarbyl, N-aryl, N-heteroaryl, or N-heterocyclyl; and $Z^2$ is CH or N.

In some embodiments, the compounds of Formula IV are those wherein $Z^2$ is N. In other embodiments, $Z^2$ is CH.

In some embodiments, $R^1$ is halo. In other embodiments, $R^1$ is chloro. In other embodiments, $R^1$ is 2-halo. In other embodiments, $R^1$ is 2-chloro. In other embodiments, $R^1$ is H.

In some embodiments, $Z^1$ is S. In other embodiments, $Z^1$ is O. In other embodiments, $Z^1$ is NH. In other embodiments, $Z^1$ is N-alkyl.

In some embodiments, $Z^1$ and $Z^2$ of the compounds of Formula IV are the following:

|  | $Z^1$ | $Z^2$ |
|---|---|---|
| IV-1 | $CH_2$ | CH |
| IV-2 | S | CH |
| IV-3 | O | CH |
| IV-4 | NH | CH |
| IV-5 | N-hydrocarbyl | CH |
| IV-6 | N-aryl | CH |
| IV-7 | N-heteroaryl | CH |
| IV-8 | N-heterocyclyl | CH |
| IV-9 | $CH_2$ | N |
| IV-10 | S | N |
| IV-11 | O | N |
| IV-12 | NH | N |
| IV-13 | N-hydrocarbyl | N |
| IV-14 | N-aryl | N |
| IV-15 | N-heteroaryl | N |
| IV-16 | N-heterocyclyl | N |

In some embodiments, a compound of Formula IV has the structure:

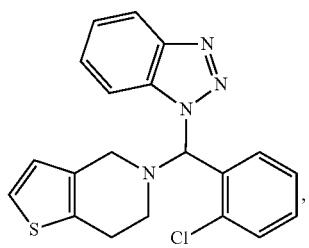

IVa or a pharmaceutically acceptable salt thereof.

In one embodiment, the invention encompasses compounds of the following Formula V:

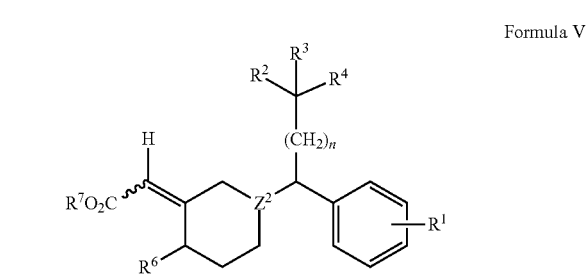

Formula V and pharmaceutically acceptable salts thereof, wherein each of $R^1$, $R^2$, and $R^3$ is independently H, —OH, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, $OCF_3$, —C(O)O(alkyl), —OC(O)(alkyl), —C(O)$NH_2$, —C(O)NH(alkyl), —C(O)N(alkyl)(alkyl), —NHC(O)(alkyl), N(alkyl)C(O)(alkyl), —OC(O)O(alkyl), —OC(O)$NH_2$, —OC(O)NH(alkyl), —OC(O)N(alkyl)(alkyl), —CHNH, —CHN(alkyl), or —$SO_2NH_2$;

$R^4$ is —H, —OH, —COOH, —NH(alkyl), —N(alkyl)(alkyl), hydrocarbyl, —O-hydrocarbyl, aryl, —O-aryl, aralkyl, —O-aralkyl, heteroaryl, —O-heteroaryl, heterocyclyl, —O-heterocyclyl, halo, —C(O)O(alkyl), —OC(O)(alkyl), —C(O)$NH_2$, —C(O)NH(alkyl), —C(O)N(alkyl)(alkyl), —NHC(O)(alkyl), N(alkyl)C(O)(alkyl), —OC(O)O(alkyl), —OC(O)$NH_2$, —OC(O)NH(alkyl), or —OC(O)N(alkyl)(alkyl);

$R^6$ is —H, —OH, —SH, —S-hydrocarbyl, —COOH, —$NH_2$, —NH(alkyl), —N(alkyl)(alkyl), hydrocarbyl, —O-hydrocarbyl, aryl, —O-aryl, aralkyl, —O-aralkyl, heteroaryl, —O-heteroaryl, heterocyclyl, —O-heterocyclyl, halo, —C(O)O(alkyl), —OC(O)(alkyl), —C(O)$NH_2$, —C(O)NH(alkyl), —C(O)N(alkyl)(alkyl), —NHC(O)(alkyl), N(alkyl)C(O)(alkyl), —OC(O)O(alkyl), —OC(O)$NH_2$, —OC(O)NH(alkyl), or —OC(O)N(alkyl)(alkyl);

$R^7$ is H, hydrocarbyl, aryl, aralkyl, heteroaryl, or heterocyclyl;

$Z^2$ is CH or N; and n is an integer from 1-6.

In some embodiments, the compounds of Formula V are those wherein $Z^2$ is N. In other embodiments, $Z^2$ is CH.

In some embodiments, $R^1$ is halo. In other embodiments, $R^1$ is chloro. In other embodiments, $R^1$ is 2-halo. In other embodiments, $R^1$ is 2-chloro. In other embodiments, $R^1$ is H.

In some embodiments, each of $R^2$ and $R^3$ is independently H or alkyl. In other embodiments, each of $R^2$ and $R^3$ is H. In other embodiments, each of $R^2$ and $R^3$ is alkyl. In other embodiments, each of $R^2$ and $R^3$ is methyl.

In some embodiments, $R^4$ is —OH, —COOH, —C(O)O(alkyl), or —OC(O)(alkyl). In other embodiments, $R^4$ is —OH. In other embodiments, $R^4$ is —COOH. In other embodiments, $R^4$ is —C(O)O(alkyl) or —OC(O)(alkyl). In other embodiments, $R^4$ is —COOEt. In other embodiments, $R^4$ is —COOMe.

In some embodiments, $R^6$ is —OH, —O-alkyl, —SH, —S-alkyl, or alkyl. In other embodiments, $R^6$ is —OH. In other embodiments, $R^6$ is —OMe. In other embodiments, $R^6$ is H. In other embodiments, $R^6$ is methyl. In other embodiments, $R^6$ is SH. In other embodiments, $R^6$ is —SMe.

In some embodiments, $R^7$ is H. In other embodiments, $R^7$ is methyl. In other embodiments, $R^7$ is ethyl. In other embodiments, $R^7$ is benzyl.

In some embodiments, n is an integer from 1-6. In other embodiments, n is 1. In other embodiments, n is 2. In other embodiments, n is 3. In other embodiments, n is 4. In other embodiments, n is 5. In other embodiments, n is 6.

In some embodiments, a compound of Formula V has the structure:

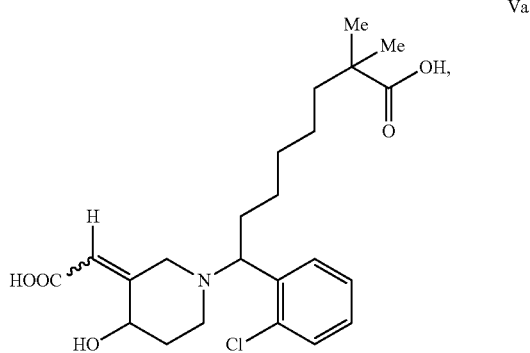 [SMILES: CC(C)(CCCCCC(c1ccccc1Cl)N1CCC(O)C(=CC(=O)O)C1)C(=O)O]

Va or a pharmaceutically acceptable salt thereof.

In one embodiment, the invention encompasses compounds of the following Formula VI:

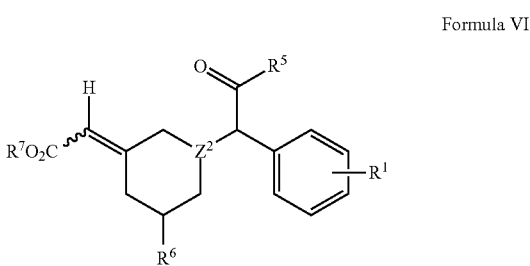

Formula VI and pharmaceutically acceptable salts thereof, wherein $R^1$, is H, —OH, —$NH_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —$OCF_3$, —C(O)O(alkyl), —OC(O)(alkyl), —C(O)$NH_2$, —C(O)NH(alkyl), —C(O)N(alkyl)(alkyl), —NHC(O)(alkyl), N(alkyl)C(O)(alkyl), —OC(O)O(alkyl), —OC(O)$NH_2$, —OC(O)NH(alkyl), —OC(O)N(alkyl)(alkyl), —CHNH, —CHN(alkyl), or —$SO_2NH_2$;

$R^5$ is —H, —OH, —NH(alkyl), —N(alkyl)(alkyl), hydrocarbyl, —O-hydrocarbyl, aryl, —O-aryl, aralkyl, —O-aralkyl, heteroaryl, —O-heteroaryl, heterocyclyl, —O-heterocyclyl, or halo;

$R^6$ is —H, —OH, —SH, —S-hydrocarbyl, —COOH, —$NH_2$, —NH(alkyl), —N(alkyl)(alkyl), hydrocarbyl, —O-hydrocarbyl, aryl, —O-aryl, aralkyl, —O-aralkyl, heteroaryl, —O-heteroaryl, heterocyclyl, —O-heterocyclyl, halo, —C(O)O(alkyl), —OC(O)(alkyl), —C(O)$NH_2$, —C(O)NH(alkyl), —C(O)N(alkyl)(alkyl), —NHC(O)(alkyl), N(alkyl)C(O)(alkyl), —OC(O)O(alkyl), —OC(O)$NH_2$, —OC(O)NH(alkyl), or —OC(O)N(alkyl)(alkyl);

$R^7$ is H, hydrocarbyl, aryl, aralkyl, heteroaryl, or heterocyclyl; and $Z^2$ is CH or N.

In some embodiments, the compounds of Formula VI are those wherein $Z^2$ is N. In other embodiments, $Z^2$ is CH.

In some embodiments, $R^1$ is halo. In other embodiments, $R^1$ is chloro. In other embodiments, $R^1$ is 2-halo. In other embodiments, $R^1$ is 2-chloro. In other embodiments, $R^1$ is H.

In some embodiments, $R^5$ is OH, O-alkyl, or O-aralkyl. In other embodiments, $R^5$ is OH. In other embodiments, $R^5$ is O-benzyl. In other embodiments, $R^5$ is OEt. In other embodiments, $R^5$ is OMe.

In some embodiments, $R^6$ is —OH, —O-alkyl, —SH, —S-alkyl, or alkyl. In other embodiments, $R^6$ is —OH. In other embodiments, $R^6$ is —OMe. In other embodiments, $R^6$ is —H. In other embodiments, $R^6$ is methyl. In other embodiments, $R^6$ is —SH. In other embodiments, $R^6$ is —SMe.

In some embodiments, $R^7$ is H. In other embodiments, $R^7$ is methyl. In other embodiments, $R^7$ is ethyl. In other embodiments, $R^7$ is benzyl.

In some embodiments, a compound of Formula VI has the structure:

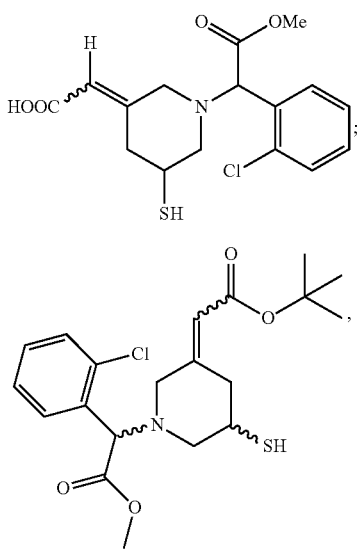

or a pharmaceutically acceptable salt thereof.

In one embodiment, the invention encompasses compounds of the following Formula VII:

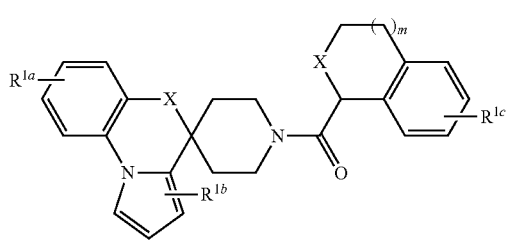

Formula VII and pharmaceutically acceptable salts thereof, wherein
each of $R^{1a}$, $R^{1b}$, and $R^{1c}$ is independently —H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$;
each X is independently CHR$^{10}$, S, O, or NR$^9$;
each R$^9$ is independently H, hydrocarbyl, aryl, aralkyl, heteroaryl, heterocyclyl, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), or —SO$_2$NH$_2$;

each R$^{10}$ is independently —H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$; and
m is an integer from 0-3.

In some embodiments, one or more of $R^{1a}$, $R^{1b}$, and $R^{1c}$ is halo. In other embodiments, one or more of $R^{1a}$, $R^{1b}$, and $R^{1c}$ is chloro. In other embodiments, each of $R^{1a}$, $R^{1b}$, and $R^{1c}$ is H.

In some embodiments, X is CH$_2$. In other embodiments, X is O. In other embodiments, X is NH. In other embodiments, X is NMe. In other embodiments, X is N-benzyl.

In some embodiments, $R^9$ is H or hydrocarbyl. In other embodiments, $R^9$ is H. In other embodiments, $R^9$ is hydrocarbyl. In other embodiments, $R^9$ is alkyl. In other embodiments, $R^9$ is methyl. In other embodiments, $R^9$ is ethyl. In other embodiments, $R^9$ is phenyl.

In some embodiments, $R^{10}$ is H, —OH, or hydrocarbyl. In other embodiments, $R^{10}$ is H. In other embodiments, $R^{10}$ is —OH. In other embodiments, $R^{10}$ is —OMe. In other embodiments, $R^{10}$ is —OEt. In other embodiments, $R^{10}$ is —NH$_2$. In other embodiments, $R^{10}$ is —NHMe. In other embodiments, $R^{10}$ is —NMe$_2$. In other embodiments, $R^{10}$ is hydrocarbyl. In other embodiments, $R^{10}$ is alkyl. In other embodiments, $R^{10}$ is methyl. In other embodiments, $R^{10}$ is ethyl. In other embodiments, $R^{10}$ is phenyl.

In some embodiments, m is an integer from 0-3. In other embodiments, m is an integer from 1-3. In other embodiments, m is 0. In other embodiments, m is 1. In other embodiments, m is 2. In other embodiments, m is 3.

In some embodiment, the invention encompasses compounds of the following Formula VII-1:

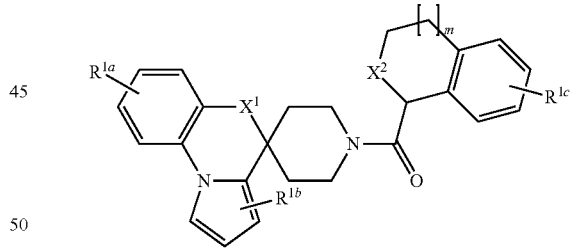

Formula VII-1

Wherein $R^{1a}$, $R^{1b}$, $R^{1c}$, m, $R^9$, and $R^{10}$ are defined as above, and $X^1$ and $X^2$ are defined as X above.

In some embodiments, $X^1$ and $X^2$ of the compounds of Formula VII-1 are the following:

|  | $X^1$ | $X^2$ |
| --- | --- | --- |
| VII-1-1 | CHR$^{10}$ | CHR$^{10}$ |
| VII-1-2 | CHR$^{10}$ | S |
| VII-1-3 | CHR$^{10}$ | O |
| VII-1-4 | CHR$^{10}$ | NR$^9$ |
| VII-1-5 | S | CHR$^{10}$ |
| VII-1-6 | S | S |
| VII-1-7 | S | O |
| VII-1-8 | S | NR$^9$ |

| | X¹ | X² |
|---|---|---|
| VII-1-9 | N | CHR¹⁰ |
| VII-1-10 | N | S |
| VII-1-11 | N | O |
| VII-1-12 | N | NR⁹ |
| VII-1-13 | NR⁹ | CHR¹⁰ |
| VII-1-14 | NR⁹ | S |
| VII-1-15 | NR⁹ | O |
| VII-1-16 | NR⁹ | NR⁹ |

In some embodiments, a compound of Formula VII has the structure:

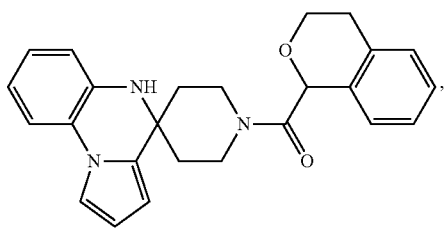

VIIa or a pharmaceutically acceptable salt thereof.

In another embodiment, the invention encompasses compounds of the following Formula VIII:

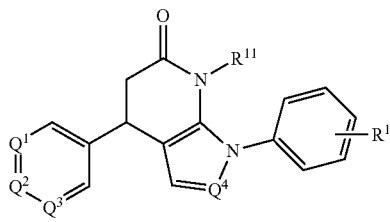

Formula VIII or pharmaceutically acceptable salts thereof, wherein $R^1$ is —H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$;

$R^{11}$ is H, hydrocarbyl, aryl, aralkyl, heteroaryl, heterocyclyl, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), or —SO$_2$NH$_2$;

each of $Q^1$, $Q^2$, $Q^3$, and $Q^4$ is independently CR¹⁰ or N; and each $R^{10}$ is independently —H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$.

In some embodiments, $R^1$ is alkyl. In other embodiments, $R^1$ is 2-alkyl.

In other embodiments, $Q^1$ is H, $Q^2$ is CR¹⁰ and $R^1$ is —OH and $Q^3$ is CR¹⁰ and $R^{10}$ is O-alkyl. In other embodiments, $Q^1$ is CR¹⁰ and $R^{10}$ is —O-alkyl, $Q^2$ is CR¹⁰ and $R^{10}$ is —OH and $Q^3$ is H.

In other embodiments, $Q^4$ is N. In other embodiments, $Q^4$ is CR¹⁰. In other embodiments, $Q^4$ is C(H).

In some embodiments, $R^{10}$ is H, —OH, or hydrocarbyl. In other embodiments, $R^{10}$ is H. In other embodiments, $R^{10}$ is —OH. In other embodiments, $R^{10}$ is —OMe. In other embodiments, $R^{10}$ is —OEt. In other embodiments, $R^{10}$ is —NH$_2$. In other embodiments, $R^{10}$ is —NHMe. In other embodiments, $R^{10}$ is —NMe$_2$. In other embodiments, $R^{10}$ is hydrocarbyl. In other embodiments, $R^{10}$ is alkyl. In other embodiments, $R^{10}$ is methyl. In other embodiments, $R^{10}$ is ethyl. In other embodiments, $R^{10}$ is phenyl.

In some embodiments, $R^{11}$ is H. In other embodiments, $R^{11}$ is methyl. In other embodiments, $R^{11}$ is ethyl. In other embodiments, $R^{11}$ is benzyl.

In some embodiments $Q^1$, $Q^2$, $Q^3$, and $Q^4$ of the compounds of Formula VIII are defined as follows:

| | Q1 | Q2 | Q3 | Q4 |
|---|---|---|---|---|
| VIII-1 | CR¹⁰ | CR¹⁰ | CR¹⁰ | CR¹⁰ |
| VIII-2 | CR¹⁰ | N | CR¹⁰ | CR¹⁰ |
| VIII-3 | CR¹⁰ | CR¹⁰ | N | CR¹⁰ |
| VIII-4 | CR¹⁰ | CR¹⁰ | CR¹⁰ | N |
| VIII-5 | CR¹⁰ | N | N | CR¹⁰ |
| VIII-6 | CR¹⁰ | N | CR¹⁰ | N |
| VIII-7 | CR¹⁰ | CR¹⁰ | N | N |
| VIII-8 | CR¹⁰ | N | N | N |
| VIII-9 | N | CR¹⁰ | CR¹⁰ | CR¹⁰ |
| VIII-10 | N | N | CR¹⁰ | CR¹⁰ |
| VIII-11 | N | CR¹⁰ | N | CR¹⁰ |
| VIII-12 | N | CR¹⁰ | CR¹⁰ | N |
| VIII-13 | N | N | N | CR¹⁰ |
| VIII-14 | N | N | CR¹⁰ | N |
| VIII-15 | N | CR¹⁰ | N | N |
| VIII-16 | N | N | N | N |

In some embodiments, a compound of Formula VIII has the structure:

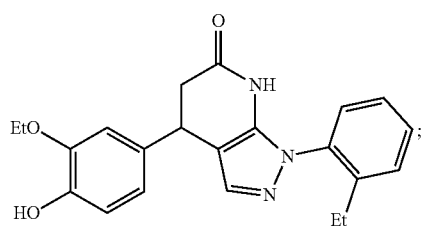

VIIIa

-continued

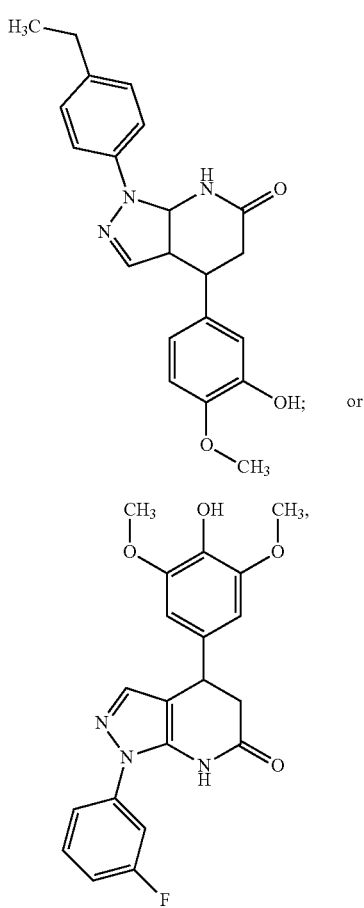

or a pharmaceutically acceptable salt thereof.

In another embodiment, the invention encompasses compounds of the following Formula IX:

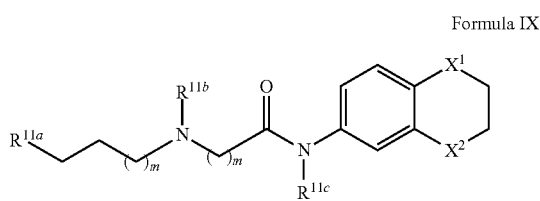

Formula IX and pharmaceutically acceptable salts thereof, wherein each of $R^{11a}$, $R^{11b}$, and $R^{11c}$ is independently H, hydrocarbyl, aryl, aralkyl, heteroaryl, heterocyclyl, —C(O)(alkyl), —C(O)O(alkyl), —C(O)NH$_2$, —C(O)NH(alkyl), —C(O)N(alkyl)(alkyl), or —SO$_2$NH$_2$;

each of $X^1$ and $X^2$ is independently CHR$^{10}$, S, O, NR$^9$, or N-acyl;

each $R^9$ is independently H, hydrocarbyl, aryl, aralkyl, heteroaryl, heterocyclyl, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), or —SO$_2$NH$_2$;

each $R^{10}$ is independently —H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$; and each m is independently an integer from 1-3.

In some embodiments, each of $X^1$ and $X^2$ is CH$_2$. In other embodiments, each of $X^1$ and $X^2$ is O. In other embodiments, each of $X^1$ and $X^2$ is NH. In other embodiments, each of $X^1$ and $X^2$ is NMe. In other embodiments, each of $X^1$ and $X^2$ is N-benzyl.

In some embodiments, $R^9$ is H or hydrocarbyl. In other embodiments, $R^9$ is H. In other embodiments, $R^9$ is hydrocarbyl. In other embodiments, $R^9$ is alkyl. In other embodiments, $R^9$ is methyl. In other embodiments, $R^9$ is ethyl. In other embodiments, $R^9$ is phenyl.

In some embodiments, $R^{10}$ is H, —OH, or hydrocarbyl. In other embodiments, $R^{19}$ is H. In other embodiments, $R^{10}$ is —OH. In other embodiments, $R^{10}$ is —OMe. In other embodiments, $R^{10}$ is —OEt. In other embodiments, $R^{10}$ is —NH$_2$. In other embodiments, $R^{10}$ is —NHMe. In other embodiments, $R^{10}$ is —NMe$_2$. In other embodiments, $R^{10}$ is hydrocarbyl. In other embodiments, $R^{10}$ is alkyl. In other embodiments, $R^{10}$ is methyl. In other embodiments, $R^{10}$ is ethyl. In other embodiments, $R^{10}$ is phenyl.

In some embodiments, each of $R^{11a}$, $R^{11b}$, and $R^{11c}$ is H. In other embodiments, one or more of $R^{11a}$, $R^{11b}$, and $R^{11c}$ is methyl. In other embodiments, one or more of $R^{11a}$, $R^{11b}$, and $R^{11c}$ is ethyl. In other embodiments, one or more of $R^{11a}$, $R^{11b}$, and $R^{11c}$ is benzyl. In other embodiments, one or more of $R^{11a}$, $R^{11b}$, and $R^{11c}$ is acetyl. In other embodiments, one or more of $R^{11a}$, $R^{11b}$, and $R^{11c}$ is benzoyl.

In some embodiments, each m is independently an integer from 1-3. In other embodiments, m is 1. In other embodiments, m is 2. In other embodiments, in is 3.

In some embodiments, $X^1$ and $X^2$ of the compounds of Formula IX are the following:

|       | $X^1$      | $X^1$      |
|-------|------------|------------|
| IX-1  | CHR$^{10}$ | CHR$^{10}$ |
| IX-2  | S          | CHR$^{10}$ |
| IX-3  | O          | CHR$^{10}$ |
| IX-4  | NR$^9$     | CHR$^{10}$ |
| IX-5  | N-acyl     | CHR$^{10}$ |
| IX-6  | CHR$^{10}$ | S          |
| IX-7  | S          | S          |
| IX-8  | O          | S          |
| IX-9  | NR$^9$     | S          |
| IX-10 | N-acyl     | S          |
| IX-11 | CHR$^{10}$ | O          |
| IX-12 | S          | O          |
| IX-13 | O          | O          |
| IX-14 | NR$^9$     | O          |
| IX-15 | N-acyl     | O          |
| IX-16 | CHR$^{10}$ | NR$^9$     |
| IX-17 | S          | NR$^9$     |
| IX-18 | O          | NR$^9$     |
| IX-19 | NR$^9$     | NR$^9$     |
| IX-20 | N-acyl     | NR$^9$     |
| IX-21 | CHR$^{10}$ | N          |
| IX-22 | S          | N          |
| IX-23 | O          | N          |
| IX-24 | NR$^9$     | N          |
| IX-25 | N-acyl     | N          |

The compounds disclosed herein can include one or more chiral centers and/or double bonds and, therefore, exist as stereoisomers, such as geometric isomers, enantiomers, or diastereomers. Illustrations herein of the compounds of the invention encompass all possible isomers as mixtures or in purified forms. Purified forms can be geometrically-enriched, enantiomerically-enriched, diastereomerically-enriched, optically-enriched, geometrically-pure, enantiomerically-pure, diastereomerically-pure, or optically-pure. Mixtures can include any combination of isomers, such as and enantiomeric, diastereomeric, racemic, and stereoisomeric mixtures. In one embodiment, the compounds of the invention exist as a single stereoisomer, substantially free of another stereoisomer. In another embodiment, the compounds of the invention exist as a single enantiomer, substantially free of its corresponding opposite enantiomer. In another embodiment, the compounds of the invention exist as racemates.

Compounds of the invention can be obtained, isolated, or purified such that they are racemic, substantially free of another stereoisomer or substantially free of corresponding opposite enantiomers using methods known to one of skill in the art, including chiral high performance liquid chromatography, selective crystallization, and reaction with a chiral resolving agent or chiral auxiliary.

In one embodiment, the compound of the invention is a compound or pharmaceutically acceptable salt of the compound of the following Formula X:

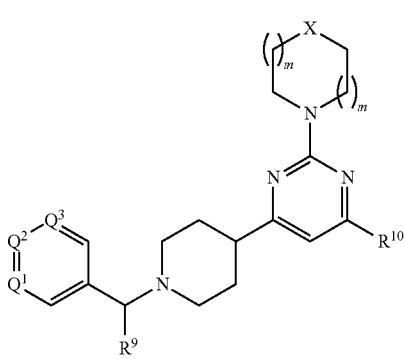

(X)

wherein each $R^9$ is independently —H, -hydrocarbyl, -aryl, -aralkyl, -heteroaryl, -heterocyclyl, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), or —SO$_2$NH$_2$;

each $R^{10}$ is independently —H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$;

each of $Q^1$, $Q^2$, and $Q^3$ is independently $CR^{10}$ or N;
X is $CHR^{10}$, S, O, or $NR^9$; and
each m is independently an integer from 0-3.

In some embodiments, $Q^1$, $Q^2$, $Q^3$ and X of the compounds of Formula X are the following:

| | X | $Q^2$ | $Q^3$ | $Q^1$ |
|---|---|---|---|---|
| X-1 | $CHR^{10}$ | $CR^{10}$ | $CR^{10}$ | $CR^{10}$ |
| X-2 | S | $CR^{10}$ | $CR^{10}$ | $CR^{10}$ |
| X-3 | O | $CR^{10}$ | $CR^{10}$ | $CR^{10}$ |
| X-4 | $NR^9$ | $CR^{10}$ | $CR^{10}$ | $CR^{10}$ |

-continued

| | X | $Q^2$ | $Q^3$ | $Q^1$ |
|---|---|---|---|---|
| X-5 | $CHR^{10}$ | N | $CR^{10}$ | $CR^{10}$ |
| X-6 | S | N | $CR^{10}$ | $CR^{10}$ |
| X-7 | O | N | $CR^{10}$ | $CR^{10}$ |
| X-8 | $NR^9$ | N | $CR^{10}$ | $CR^{10}$ |
| X-9 | $CHR^{10}$ | $CR^{10}$ | N | $CR^{10}$ |
| X-10 | S | $CR^{10}$ | N | $CR^{10}$ |
| X-11 | O | $CR^{10}$ | N | $CR^{10}$ |
| X-12 | $NR^9$ | $CR^{10}$ | N | $CR^{10}$ |
| X-13 | $CHR^{10}$ | $CR^{10}$ | $CR^{10}$ | N |
| X-14 | S | $CR^{10}$ | $CR^{10}$ | N |
| X-15 | O | $CR^{10}$ | $CR^{10}$ | N |
| X-16 | $NR^9$ | $CR^{10}$ | $CR^{10}$ | N |
| X-17 | $CHR^{10}$ | N | N | $CR^{10}$ |
| X-18 | S | N | N | $CR^{10}$ |
| X-19 | O | N | N | $CR^{10}$ |
| X-20 | $NR^9$ | N | N | $CR^{10}$ |
| X-21 | $CHR^{10}$ | N | $CR^{10}$ | N |
| X-22 | S | N | $CR^{10}$ | N |
| X-23 | O | N | $CR^{10}$ | N |
| X-24 | $NR^9$ | N | $CR^{10}$ | N |
| X-25 | $CHR^{10}$ | $CR^{10}$ | N | N |
| X-26 | S | $CR^{10}$ | N | N |
| X-27 | O | $CR^{10}$ | N | N |
| X-28 | $NR^9$ | $CR^{10}$ | N | N |
| X-29 | $CHR^{10}$ | N | N | N |
| X-30 | S | N | N | N |
| X-31 | O | N | N | N |
| X-32 | $NR^9$ | N | N | N |

In one embodiment, the compound of the invention is a compound or pharmaceutically acceptable salt of the compound of the following Formula XI:

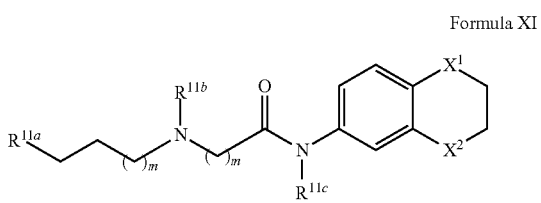

Formula XI and pharmaceutically acceptable salts thereof, wherein each of $R^{11a}$, $R^{11b}$, and $R^{11c}$ is independently H, hydrocarbyl, aryl, aralkyl, heteroaryl, heterocyclyl, —C(O)(alkyl), —C(O)O(alkyl), —C(O)NH$_2$, —C(O)NH(alkyl), —C(O)N(alkyl)(alkyl), or —SO$_2$NH$_2$;

each of $X^1$ and $X^2$ is independently $CHR^{10}$, S, O, $NR^9$, or N-acyl;

each $R^9$ is independently H, hydrocarbyl, aryl, aralkyl, heteroaryl, heterocyclyl, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), or —SO$_2$NH$_2$;

each $R^{10}$ is independently —H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$; and each m is independently an integer from 0-3.

In some embodiments, $X^1$ and $X^2$ of the compounds of Formula XI are the following:

|  | $X^1$ | $X^1$ |
| --- | --- | --- |
| XI-1 | $CHR^{10}$ | $CHR^{10}$ |
| XI-2 | S | $CHR^{10}$ |
| XI-3 | O | $CHR^{10}$ |
| XI-4 | $NR^9$ | $CHR^{10}$ |
| XI-5 | N-acyl | $CHR^{10}$ |
| XI-6 | $CHR^{10}$ | S |
| XI-7 | S | S |
| XI-8 | O | S |
| XI-9 | $NR^9$ | S |
| XI-10 | N-acyl | S |
| XI-11 | $CHR^{10}$ | O |
| XI-12 | S | O |
| XI-13 | O | O |
| XI-14 | $NR^9$ | O |
| XI-15 | N-acyl | O |
| XI-16 | $CHR^{10}$ | $NR^9$ |
| XI-17 | S | $NR^9$ |
| XI-18 | O | $NR^9$ |
| XI-19 | $NR^9$ | $NR^9$ |
| XI-20 | N-acyl | $NR^9$ |
| XI-21 | $CHR^{10}$ | N |
| XI-22 | S | N |
| XI-23 | O | N |
| XI-24 | $NR^9$ | N |
| XI-25 | N-acyl | N |

In one embodiment, a compound of Formula XI has the structure:

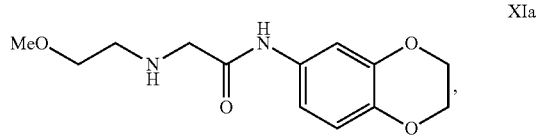 [SMILES: COCCNCC(=O)Nc1ccc2c(c1)OCCO2]

XIa or a pharmaceutically acceptable salt thereof.

In another embodiment, the invention provides compounds of the following Formula XII:

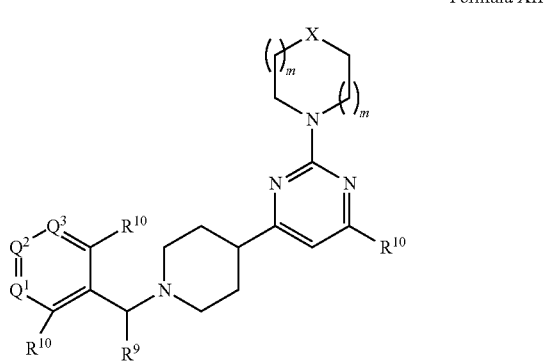

Formula XII and pharmaceutically acceptable salts thereof, wherein
each $R^9$ is independently —H, -hydrocarbyl, -aryl, -aralkyl, -heteroaryl, -heterocyclyl, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), or —SO$_2$NH$_2$;
each $R^{10}$ is independently —H, —OH, —NH$_2$, —NH(alkyl), —N(alkyl)(alkyl), hydrocarbyl, —O-alkyl, —O-alkenyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH (alkyl), —C(O)N(alkyl)(alkyl), NHC(O)(C$_2$-C$_{10}$-alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), —SO$_2$NH$_2$, —S-alkyl, —S-aryl, —S-heteroaryl, —S-heterocycle, or —S— hydrocarbyl;
each of $Q^1$, $Q^2$, and $Q^3$ is independently $CR^{10}$ or N;
X is $CHR^{10}$, S, O, or $NR^9$; and
each m is independently an integer from 0-3.

In some embodiments, the compounds of Formula XII are those wherein $R^9$ is H or hydrocarbyl. In other embodiments, $R^9$ is H. In other embodiments, $R^9$ is hydrocarbyl. In other embodiments, $R^9$ is alkyl. In other embodiments, $R^9$ is methyl. In other embodiments, $R^9$ is ethyl. In other embodiments, $R^9$ is phenyl.

In some embodiments, the compounds of Formula XII are those wherein $R^{10}$ is H, —OH, or hydrocarbyl. In other embodiments, $R^{10}$ is H. In other embodiments, $R^{10}$ is —OH. In other embodiments, $R^{10}$ is —OMe. In other embodiments, $R^{10}$ is —OEt. In other embodiments, $R^{10}$ is —NH$_2$. In other embodiments, $R^{10}$ is —NHMe. In other embodiments, $R^{10}$ is —NMe$_2$. In other embodiments, $R^{10}$ is hydrocarbyl. In other embodiments, $R^{10}$ is alkyl. In other embodiments, $R^{10}$ is methyl. In other embodiments, $R^{10}$ is ethyl. In other embodiments, $R^{10}$ is phenyl. In other embodiments, $R^{10}$ is —S-alkyl In another embodiment, $R^9$ is H and $R^{10}$ is —OH.

In some embodiments, the compounds of Formula XII are those wherein each of $Q^1$, $Q^2$, and $Q^3$ is N. In other embodiments, each of $Q^1$, $Q^2$, and $Q^3$ is $CR^{10}$. In other embodiments, each of $Q^1$, $Q^2$ is N and $Q^3$ is $CR^{10}$.

In some embodiments, the compounds of Formula XII are those wherein X is CH$_2$. In other embodiments, X is O. In other embodiments, X is NH. In other embodiments, X is NMe. In other embodiments, X is N-benzyl.

In some embodiments, the compounds of Formula XII are those wherein each m is independently an integer from 0-3. In other embodiments, each m is an integer from 1-3. In other embodiments, m is 0. In other embodiments, m is 1. In other embodiments, m is 2. In other embodiments, m is 3.

In other embodiments, $Q^1$ and $Q^3$ are N, $Q^2$ is $CR^{10}$ and $R^{10}$ is —N(alkyl)(alkyl). In other embodiments, $Q^1$ and $Q^3$ are N, $Q^2$ is $CR^{10}$ and $R^{10}$ is —N(H)(alkyl). In other embodiments, $Q^1$ and $Q^3$ are N, $Q^2$ is $CR^{10}$ and $R^{10}$ is —N(CH$_3$)$_2$. In other embodiments, $Q^1$ and $Q^3$ are N, $Q^2$ is $CR^{10}$ and $R^{10}$ is —N(H)(CH$_3$).

In other embodiments, each m is 1, X is $NR^9$ and $R^9$ is H. In other embodiments, each m is 1 and X is O.

In some embodiments, $Q^1$, $Q^2$, $Q^3$ and X of the compounds of Formula XII are the following:

|  | X | $Q^2$ | $Q^3$ | $Q^1$ |
| --- | --- | --- | --- | --- |
| XII-1 | $CHR^{10}$ | $CR^{10}$ | $CR^{10}$ | $CR^{10}$ |
| XII-2 | S | $CR^{10}$ | $CR^{10}$ | $CR^{10}$ |
| XII-3 | O | $CR^{10}$ | $CR^{10}$ | $CR^{10}$ |
| XII-4 | $NR^9$ | $CR^{10}$ | $CR^{10}$ | $CR^{10}$ |
| XII-5 | $CHR^{10}$ | N | $CR^{10}$ | $CR^{10}$ |
| XII-6 | S | N | $CR^{10}$ | $CR^{10}$ |
| XII-7 | O | N | $CR^{10}$ | $CR^{10}$ |
| XII-8 | $NR^9$ | N | $CR^{10}$ | $CR^{10}$ |
| XII-9 | $CHR^{10}$ | $CR^{10}$ | N | $CR^{10}$ |
| XII-10 | S | $CR^{10}$ | N | $CR^{10}$ |
| XII-11 | O | $CR^{10}$ | N | $CR^{10}$ |
| XII-12 | $NR^9$ | $CR^{10}$ | N | $CR^{10}$ |
| XII-13 | $CHR^{10}$ | $CR^{10}$ | $CR^{10}$ | N |

-continued

| | X | Q² | Q³ | Q¹ |
|---|---|---|---|---|
| XII-14 | S | CR¹⁰ | CR¹⁰ | N |
| XII-15 | O | CR¹⁰ | CR¹⁰ | N |
| XII-16 | NR⁹ | CR¹⁰ | CR¹⁰ | N |
| XII-17 | CHR¹⁰ | N | N | CR¹⁰ |
| XII-18 | S | N | N | CR¹⁰ |
| XII-19 | O | N | N | CR¹⁰ |
| XII-20 | NR⁹ | N | N | CR¹⁰ |
| XII-21 | CHR¹⁰ | N | CR¹⁰ | N |
| XII-22 | S | N | CR¹⁰ | N |
| XII-23 | O | N | CR¹⁰ | N |
| XII-24 | NR⁹ | N | CR¹⁰ | N |
| XII-25 | CHR¹⁰ | CR¹⁰ | N | N |
| XII-26 | S | CR¹⁰ | N | N |
| XII-27 | O | CR¹⁰ | N | N |
| XII-28 | NR⁹ | CR¹⁰ | N | N |

-continued

| | X | Q² | Q³ | Q¹ |
|---|---|---|---|---|
| XII-29 | CHR¹⁰ | N | N | N |
| XII-30 | S | N | N | N |
| XII-31 | O | N | N | N |
| XII-32 | NR⁹ | N | N | N |

In some embodiments, a compound of Formula XII exists as a single tautomer or as a mixture of tautomers. One of skill in the art will recognize structures possessing tautomeric forms, and will understand that the illustration of a single tautomer implies the structure of all possible tautomeric forms. In some embodiments, $R^{10}$ is OH, and the compound of Formula XII exists in one, two, or three tautomeric forms of Formula XII, as illustrated in Equation II.

Equation II

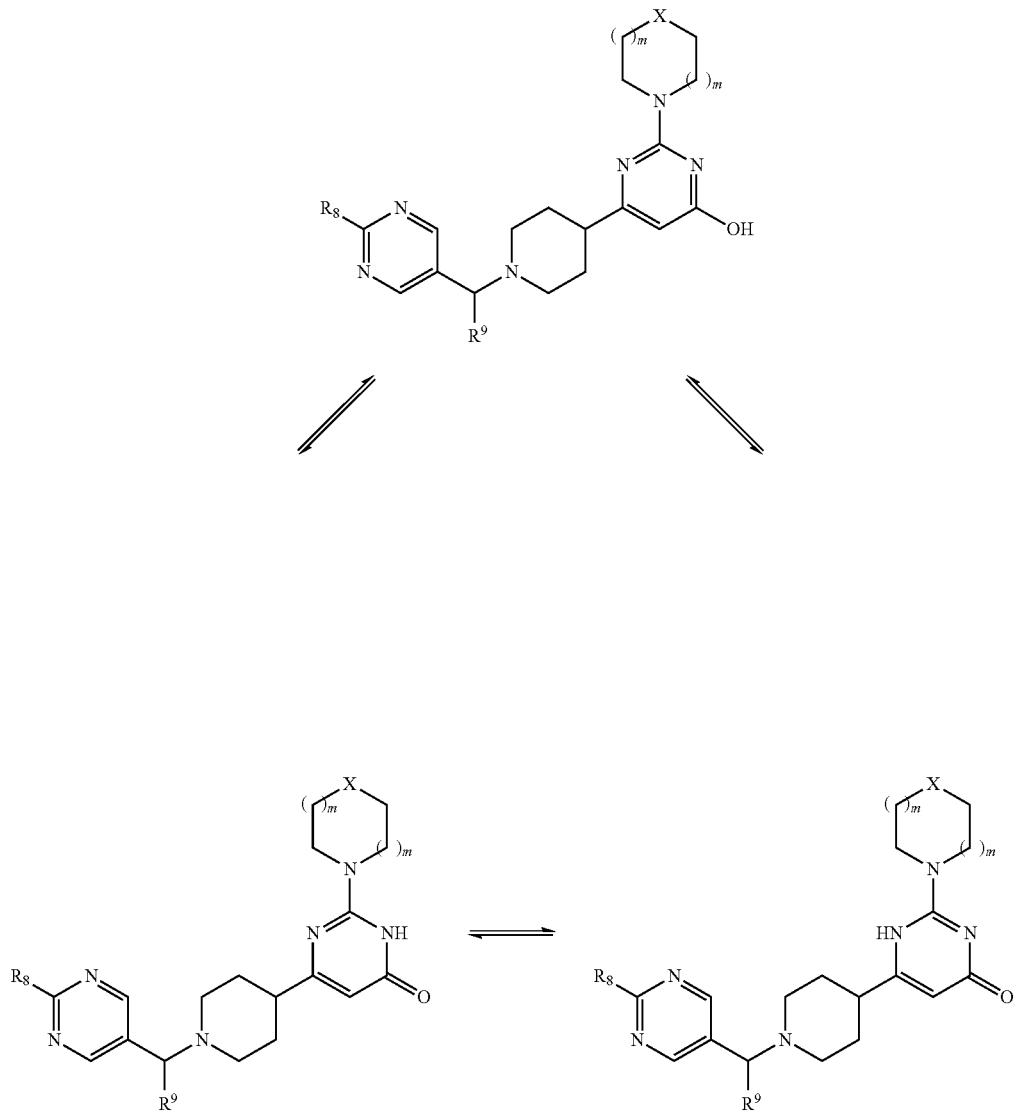

In certain embodiments, a compound of Formula XII has the structure of formula II, and illustrative compounds of Formula XII include compounds IIa-IIjj, or pharmaceutically acceptable salts thereof.
In some embodiments, a compound of Formula XII has the structure:
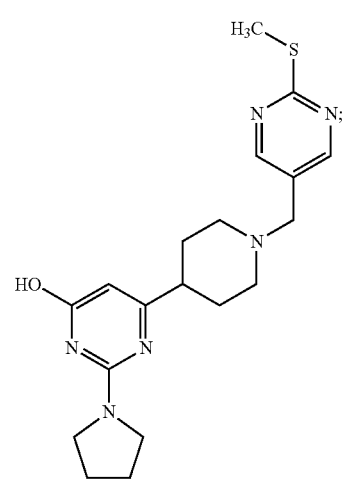
XIIa
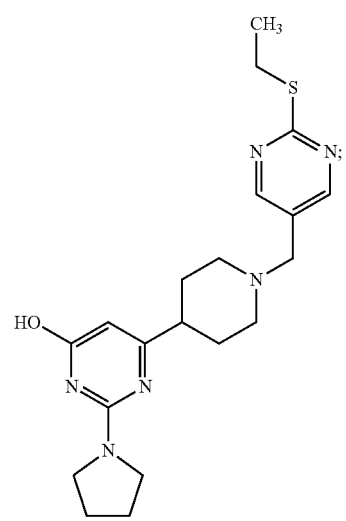
XIIb
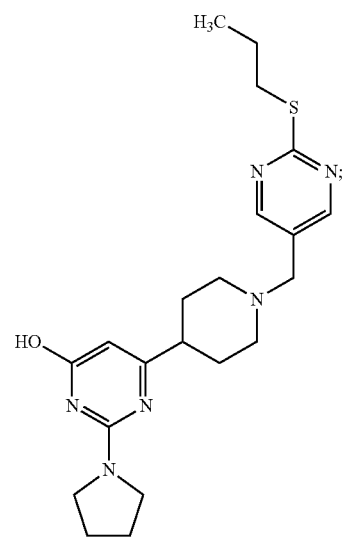
XIIc
-continued
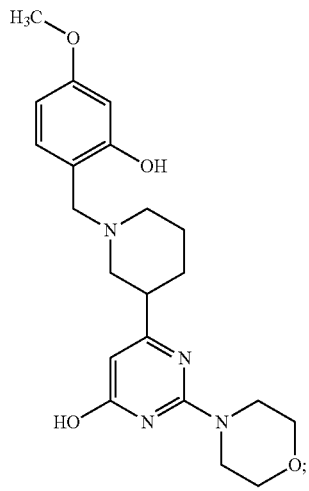
XIId
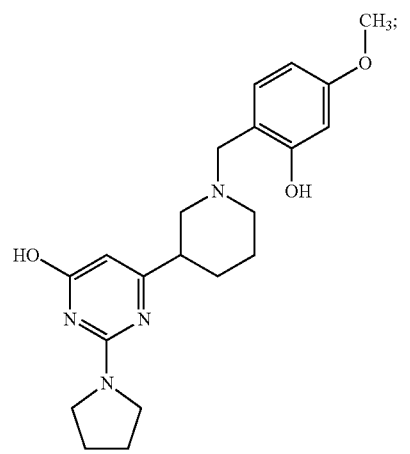
XIIe
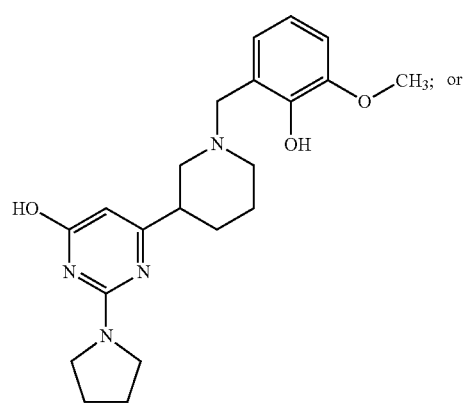
XIIf -continued

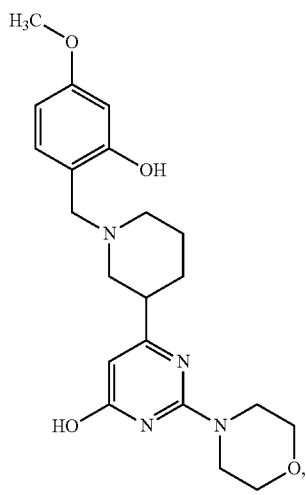

XIIg or a pharmaceutically acceptable salt thereof.

In another embodiment, the invention provides compounds of the following Formula XIII:

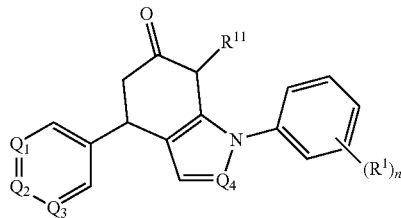

Formula XIII and pharmaceutically acceptable salts thereof, wherein $R^1$ is independently —H, —OH, —NH$_2$, —NH(alkyl), —N(alkyl)(alkyl), hydrocarbyl, —O-hydrocarbyl, aryl, —O-aryl, aralkyl, —O-aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$;

$R^{11}$ is H, hydrocarbyl, aryl, aralkyl, heteroaryl, heterocyclyl, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), or —SO$_2$NH$_2$;

each of $Q^1$, $Q^2$, $Q^3$, and $Q^4$ is independently $CR^{10}$ or N;

n is an integer from 1-4, and each $R^{10}$ is independently —H, —OH, —NH$_2$, —NH(alkyl), —N(alkyl)(alkyl), hydrocarbyl, —O-hydrocarbyl, aryl, —O-aryl, aralykl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$.

In some embodiments, $R^1$ is alkyl. In other embodiments, $R^1$ is 2-alkyl.

In other embodiments, $Q^1$ is H, $Q^2$ is $CR^{10}$ and $R^{10}$ is —OH and $Q^3$ is $CR^{10}$ and $R^{10}$ is O-alkyl. In other embodiments, $Q^1$ is $CR^{10}$ and $R^{10}$ is —O-alkyl, $Q^2$ is $CR^{10}$ and $R^{10}$ is —OH and $Q^3$ is H.

In other embodiments, $Q^4$ is N. In other embodiments, $Q^4$ is $CR^{10}$. In other embodiments, $Q^4$ is C(H).

In some embodiments, $R^{10}$ is H, —OH, or hydrocarbyl. In other embodiments, $R^{10}$ is H. In other embodiments, $R^{10}$ is —OH. In other embodiments, $R^{10}$ is —OMe. In other embodiments, $R^{10}$ is —OEt. In other embodiments, $R^{10}$ is —NH$_2$. In other embodiments, $R^{10}$ is —NHMe. In other embodiments, $R^{10}$ is —NMe$_2$. In other embodiments, $R^{10}$ is hydrocarbyl. In other embodiments, $R^{10}$ is alkyl. In other embodiments, $R^{10}$ is methyl. In other embodiments, $R^{10}$ is ethyl. In other embodiments, $R^{10}$ is phenyl.

In some embodiments, $R^{11}$ is H. In other embodiments, $R^{11}$ is methyl. In other embodiments, $R^{11}$ is ethyl. In other embodiments, $R^{11}$ is benzyl.

In some embodiments, the compounds of Formula XIII are those wherein n is independently an integer from 1-4. In other embodiments, n is 1. In other embodiments, n is 2. In other embodiments, n is 3. In other embodiments, n is 4.

In some embodiments $Q^1$, $Q^2$, $Q^3$, and $Q^4$ of the compounds of Formula XIII are defined as follows:

|  | Q1 | Q2 | Q3 | Q4 |
|---|---|---|---|---|
| XIII-1 | $CR^{10}$ | $CR^{10}$ | $CR^{10}$ | $CR^{10}$ |
| XIII-2 | $CR^{10}$ | N | $CR^{10}$ | $CR^{10}$ |
| XIII-3 | $CR^{10}$ | $CR^{10}$ | N | $CR^{10}$ |
| XIII-4 | $CR^{10}$ | $CR^{10}$ | $CR^{10}$ | N |
| XIII-5 | $CR^{10}$ | N | N | CR10 |
| XIII-6 | $CR^{10}$ | N | $CR^{10}$ | N |
| XIII-7 | $CR^{10}$ | $CR^{10}$ | N | N |
| XIII-8 | $CR^{10}$ | N | N | N |
| XIII-9 | N | $CR^{10}$ | $CR^{10}$ | $CR^{10}$ |
| XIII-10 | N | N | $CR^{10}$ | $CR^{10}$ |
| XIII-11 | N | $CR^{10}$ | N | $CR^{10}$ |
| XIII-12 | N | $CR^{10}$ | $CR^{10}$ | N |
| XIII-13 | N | N | N | $CR^{10}$ |
| XIII-14 | N | N | $CR^{10}$ | N |
| XIII-15 | N | $CR^{10}$ | N | N |
| XIII-16 | N | N | N | N |

In certain embodiments, a compound of Formula XIII has the structure of formula VIII, and illustrative compounds of Formula XIII include compounds VIIIa VIIIc, or pharmaceutically acceptable salts thereof.

In some embodiments, a compound of Formula XIII has the structure:

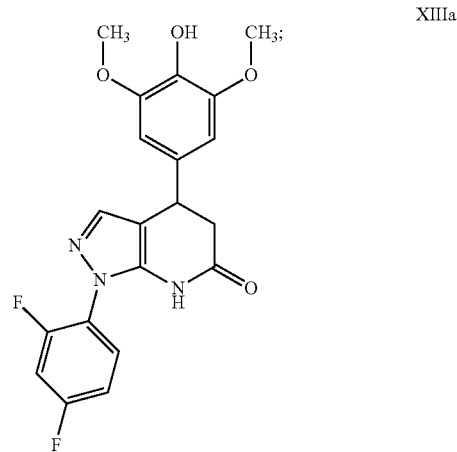

XIIIa

XIIIb
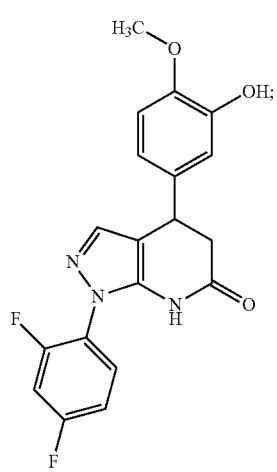
XIIIc
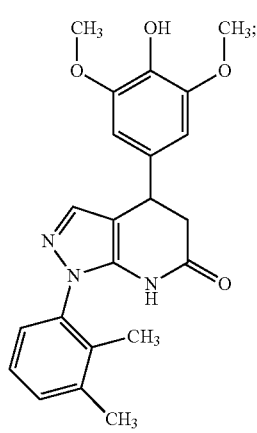
XIIId
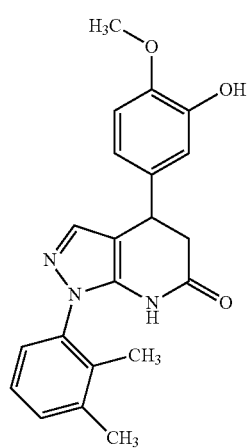
XIIIe
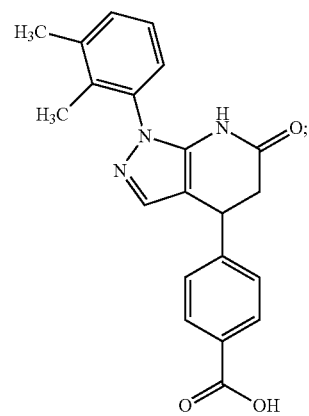
XIIIf
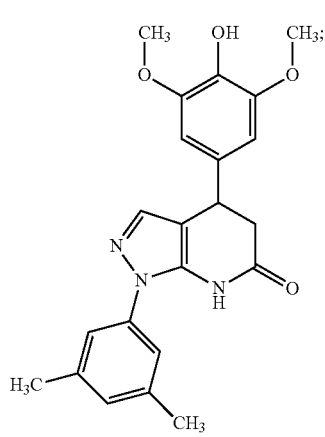
XIIIg
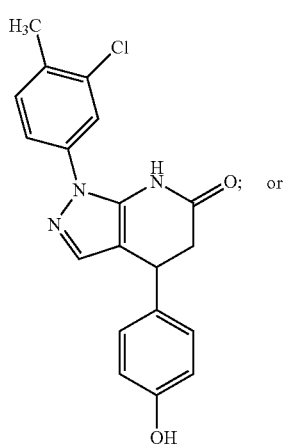

-continued

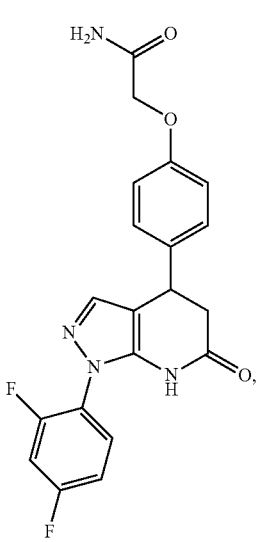

XIIIh or pharmaceutically acceptable salts thereof.

III. Treatment or Prevention of a Condition with the Compounds of the Invention In accordance with the invention, the compounds of the invention are useful for treating or preventing one or more Conditions.

In one embodiment, the invention provides methods for the treatment or prevention of one or more Conditions comprising administering to a subject in need thereof an effective amount of a compound of the invention.

In another embodiment, the invention provides use of one or more compounds of the invention in the manufacture of a medicament useful for the treatment or prevention of one or more Conditions.

In another embodiment, the invention provides one or more compounds of the invention for the treatment or prevention of one or more Conditions.

Non-limiting examples of Conditions that are treatable or preventable by administering one or more compounds of the invention include: (i) a disorder of lipoprotein metabolism including, dyslipidemia, dyslipoproteinemia, lipoprotein overproduction or deficiency, elevation of total cholesterol, elevation of low density lipoprotein concentration, elevation of triglyceride concentration, lipid elimination in bile, metabolic disorder, phospholipid elimination in bile, oxysterol elimination in bile, and peroxisome proliferator activated receptor-associated disorders; (ii) a disorder of glucose metabolism including insulin resistance, impaired glucose tolerance, impaired fasting glucose levels in blood, diabetes mellitus, lipodystrophy, central obesity, peripheral lipoatrophy, diabetic nephropathy, diabetic retinopathy, renal disease, and septicemia; (iii) a cardiovascular disorder or a related vascular disorder including hypertension, coronary artery disease, myocardial infarcation, arrhythmia, atrial fibrillation, heart valve disease, heart failure, cardiomyopathy, pericarditis and impotence; and (iv) a disorder involving abnormal modulation of C-reactive protein or a related disorder including inflammation, ischemic necrosis, colon cancer and a thrombotic disorder; and (v) aging, Alzheimer's Disease, Parkinson's Disease, pancreatitis, pancreatitius, and abnormal bile production.

The invention further provides methods for identifying a biomarker for one or more Conditions, comprising administering an effective amount of a compound of the invention to a subject in need thereof and measuring the level of unesterified cholesterol in the subject's blood. In one embodiment the Condition is a cardiovascular-related disorder. In another embodiment the biomarker is the presence of reverse cholesterol transport from the arterial vessels to the liver or cholesterol elimination in the bile acids, or both.

The invention further provides the use of free cholesterol as a biomarker of the P2Y13 activation having as consequence the functionalisation of the HDL, i.e., its increased potency of a reverse cholesterol transport agent. Accordingly, the invention further provides methods for determining the extent of P2Y13 activation, comprising administering an effective amount of a compound of the invention to a subject in need thereof and measuring the amount of free cholesterol in the subject's blood.

The compounds of the invention and compositions thereof can be administered orally. The compounds of the invention and compositions thereof can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer a compound of the invention. In certain embodiments, more than one compound of the invention is administered to a subject. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration can be left to the discretion of the practitioner, and depends in-part upon the site of the medical condition. In most instances, administration results in the release of the compounds of the invention into the bloodstream.

In specific embodiments, it may be desirable to administer one or more compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, the implant being of a porous, non-porous, or gelatinous material, including membranes, such as sialastic membranes, or fibers. In one embodiment, administration can be by direct injection at the site (or former site) of an atherosclerotic plaque tissue.

In certain embodiments, a compound of the invention can be introduced into the central nervous system by any suitable route, including intraventricular, intrathecal and epidural injection. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds and compositions of the compounds of the invention can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compounds and compositions of the compounds of the invention can be delivered in a controlled release system. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bio-availability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In another embodiment, a controlled-release system can be placed in proximity of the target area to be treated, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, Science 249:1527-1533) may be used.

The present compositions comprise a therapeutically effective amount of a compound of the invention, optionally more than one compound of the invention, together with a suitable amount of a pharmaceutically acceptable vehicle so as to provide a form for administration to the subject.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by E. W. Martin, incorporated by reference in its entirety for teachings of pharmaceutical compositions and methods of administering the same.

In some embodiments, the compounds and compositions of the compounds of the invention are formulated in accordance with routine procedures as a pharmaceutical composition adapted for intravenous administration to humans. Compounds and compositions of the compounds of the invention for intravenous administration can be solutions in sterile isotonic aqueous buffer. The compositions can also include a solubilizing agent. Compositions for intravenous administration optionally include a local anesthetic such as lignocaine. The ingredients can be supplied either separately or mixed together in unit dosage form, for example, as a dry lyophilized powder or water free concentrate in a hermetically sealed container such as an ampoule or sachette. Where the compound of the invention is to be administered by intravenous infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

Compounds and compositions of the compounds of the invention for oral delivery can be in the form of tablets, lozenges, aqueous or oily suspensions, granules, powders, emulsions, capsules, syrups, or elixirs. Compounds and compositions of the compounds of the invention for oral delivery can also be formulated in foods and food mixes. Orally administered compositions can comprise one or more optional agents, for example, sweetening agents such as fructose, aspartame or saccharin; flavoring agents such as peppermint, oil of wintergreen, or cherry; coloring agents; and preserving agents, to provide a pharmaceutically-palatable preparation. The compositions can be coated to delay disintegration and absorption in the gastrointestinal tract thereby providing a sustained action over an extended period of time. Selectively permeable membranes surrounding an osmotically active driving compound are also suitable for orally administered compounds and compositions of the compounds of the invention. A time delay material such as glycerol monostearate or glycerol stearate can also be used. Oral compositions can include standard vehicles such as mannitol, lactose, starch, magnesium stearate, sodium saccharine, cellulose, and magnesium carbonate.

The amount of a compound of the invention that is effective in the treatment of a particular Condition disclosed herein can depend on the nature of the Condition, and can be determined by standard clinical techniques. In vitro or in vivo assays can be employed to help identify optimal dosage ranges. The precise dose to be employed in the compositions can also depend on the route of administration or the severity of the Condition, and can be decided according to the judgment of the practitioner and each subject's circumstances. However, suitable dosage ranges for oral administration are generally about 0.001 mg to 2000 mg of a compound of the invention per kg body mass. In some embodiments, the oral dose is 0.01 mg to 100 mg per kg body mass, 0.1 mg to 50 mg per kg body mass, 0.5 mg to 20 mg per kg body mass, or 1 mg to 10 mg per kg body mass. In some embodiments, the oral dose is 5 mg of a compound of the invention per kg body mass. The dosage amounts described herein refer to total amounts administered; that is, if more than one compound of the invention is administered, the dosages can correspond to the total amount of the compounds of the invention administered. Oral compositions can comprise 10% to 95% active ingredient by mass.

In certain embodiments, the compounds or compositions of the compounds of the invention are administered to a subject, such as a human, as a prophylactic or preventative measure against a Condition as described herein. Compositions of the present invention can be administered as a preventative measure to a subject having a genetic predisposition to a Condition, such as cardiovascular disease, a dyslipidemia, a dyslipoproteinemia, a disorder of glucose metabolism, Alzheimer's disease, Syndrome X, a P2Y13-associated disorder, septicemia, a thrombotic disorder, obesity, pancreatitis, hypertension, a renal disease, cancer, inflammation, or impotence. Examples of such genetic predispositions include but are not limited to the ϵ4 allele of apolipoprotein E, which increases the likelihood of Alzheimer's Disease; a loss of function or null mutation in the lipoprotein lipase gene coding region or promoter (e.g., mutations in the coding regions resulting in the substitutions D9N and N291S; for a review of genetic mutations in the lipoprotein lipase gene that increase the risk of cardiovascular diseases, dyslipidemias and dyslipoproteinemias, see Hayden and Ma, 1992, *Mol. Cell Biochem.* 113:171-176); and familial combined hyperlipidemia and familial hypercholesterolemia.

Compounds or compositions of the compounds of the invention can be administered as a preventative measure to a subject having a non-genetic predisposition to a Condition, such as cardiovascular disease, a dyslipidemia, a dyslipoproteinemia, a disorder of glucose metabolism, Alzheimer's Disease, Syndrome X, a P2Y13-associated disorder, septicemia, a thrombotic disorder, obesity, pancreatitis, hypertension, a renal disease, cancer, inflammation, or impotence. Examples of such non-genetic predispositions include but are not limited to cardiac bypass surgery and percutaneous transluminal coronary angioplasty, which can lead to restenosis, an accelerated form of atherosclerosis; diabetes in women, which can lead to polycystic ovarian disease; and cardiovascular disease, which can lead to impotence. Accordingly, the compositions of the compounds of the invention may be used for the prevention of one disease or disorder and concurrently treating another (e.g., prevention of polycystic ovarian disease while treating diabetes; prevention of impotence while treating a cardiovascular disease).

The present invention provides methods for the treatment or prevention of a cardiovascular disease or a symptom thereof, the methods comprising administering to a subject in need thereof an effective amount of a compound of the invention. In one embodiment, the compound of the invention is present in a composition that further comprises a pharmaceutically acceptable vehicle. As used herein, the term "cardiovascular disease" refers to a disease of the heart or circulatory system. Cardiovascular disease can be associated with dyslipoproteinemia or dyslipidemia, or both. Cardiovascular diseases include but are not limited to arteriosclerosis; atherosclerosis; stroke; ischemia; perivascular disease (PVD); transient ischemic attack (TIA), fulgurant atherosclerosis; organ graft atherosclerosis; endothelium dysfunctions, in particular those dysfunctions affecting blood vessel elasticity; peripheral vascular disease; coronary heart disease; myocardial infarction; cerebral infarction and restenosis. Non-limiting examples of symptoms of cardiovascular disease include angina, shortness of breath, dizziness, nausea, fatigue, irregular heartbeat, and impotence. In some embodiments, treatment of a cardiovascular disease treats one or more symptoms of cardiovascular disease. In some embodiments, treatment of cardiovascular disease treats impotence.

The present invention provides methods for the treatment or prevention of a dyslipidemia, the method comprising administering to a subject in need thereof an effective amount of a compound of the invention. In one embodiment, the compound of the invention is present in a composition that further comprises a pharmaceutically acceptable vehicle.

Dyslipidemias include but are not limited to: hyperlipidemia and low blood levels of high density lipoprotein (HDL) cholesterol. In certain embodiments, the hyperlipidemia is familial hypercholesterolemia; familial combined hyperlipidemia; reduced or deficient lipoprotein lipase levels or activity, including reductions or deficiencies resulting from lipoprotein lipase mutations; hypertriglyceridemia; hypercholesterolemia; high blood levels of ketone bodies (e.g. β-OH butyric acid); high blood levels of Lp(a) cholesterol; high blood levels of low density lipoprotein (LDL) cholesterol; high blood levels of very low density lipoprotein (VLDL) cholesterol and high blood levels of non-esterified fatty acids.

The present invention further provides methods for altering lipid metabolism in a subject, e.g., reducing LDL in the blood of a subject, reducing free triglycerides in the blood of a subject, increasing the ratio of HDL to LDL in the blood of a subject, and inhibiting saponified or non-saponified fatty acid synthesis, the methods comprising administering to a subject in need thereof an effective amount of a compound of the invention. In one embodiment, the compound of the invention is present in a composition that further comprises a pharmaceutically acceptable vehicle.

The present invention provides methods for the treatment or prevention of a dyslipoproteinemia, comprising administering to a subject in need thereof an effective amount of a compound of the invention. In one embodiment, the compound of the invention is present in a composition that further comprises a pharmaceutically acceptable vehicle.

Dyslipoproteinemia are disorders that lead to or are manifested by aberrant levels of circulating lipoproteins. To the extent that levels of lipoproteins in the blood are abnormally high, a compound of the invention is administered to a subject to restore normal levels. Conversely, to the extent that levels of lipoproteins in the blood are abnormally low, a compound of the invention is administered to a subject to restore normal levels. Normal levels of lipoproteins are well known to those of skill in the art.

Dyslipoproteinemias include but are not limited to: high blood levels of LDL; high blood levels of apolipoprotein B (apo B); high blood levels of Lp(a); high blood levels of apo(a); high blood levels of VLDL; low blood levels of HDL; reduced or deficient lipoprotein lipase levels or activity, including reductions or deficiencies resulting from lipoprotein lipase mutations; hypoalphalipoproteinemia; lipoprotein abnormalities associated with diabetes; lipoprotein abnormalities associated with obesity; lipoprotein abnormalities associated with Alzheimer's Disease; and familial combined hyperlipidemia.

The present invention further provides methods for reducing apo C-II levels in the blood of a subject; reducing apo C-III levels in the blood of a subject; elevating the levels of HDL associated proteins, including but not limited to apo A-I, apo A-II, apo A-IV and apo E in the blood of a subject; elevating the levels of apo E in the blood of a subject, or promoting clearance of triglycerides from the blood of a subject, the methods comprising administering to a subject in need thereof an effective amount of a compound of the invention. In one embodiment, the compound of the invention is present in a composition that further comprises a pharmaceutically acceptable vehicle.

The present invention provides methods for the treatment or prevention of a glucose metabolism disorder, the method comprising administering to a subject in need thereof an effective amount of a compound of the invention. In one embodiment, the compound of the invention is present in a composition that further comprises a pharmaceutically acceptable vehicle.

Glucose metabolism disorders can involve aberrant glucose storage and/or utilization. To the extent that one or more indicia of glucose metabolism (i.e., blood insulin, blood glucose) are abnormally high, the compound of the invention is administered to a subject to restore normal levels. Conversely, to the extent that one or more indicia of glucose metabolism are abnormally low, the compound of the invention is administered to a subject to restore normal levels. Normal indicia of glucose metabolism are well known to those of skill in the art.

Glucose metabolism disorders include but are not limited to: impaired glucose tolerance; diabetic retinopathy, diabetic nephropathy, insulin resistance; insulin resistance related cancer, such as breast, colon or prostate cancer; diabetes, including but not limited to non-insulin dependent diabetes mellitus (NIDDM), insulin dependent diabetes mellitus (IDDM), gestational diabetes mellitus (GDM), and maturity onset diabetes of the young (MODY); pancreatitis; hypertension; polycystic ovarian disease; and high levels of blood insulin or glucose, or both.

The present invention further provides methods for altering glucose metabolism in a subject, for example to increase insulin sensitivity or oxygen consumption of a subject, the methods comprising administering to a subject in need thereof an effective amount of a compound of the invention.

In one embodiment, the compound of the invention is present in a composition that further comprises a pharmaceutically acceptable vehicle.

The present invention provides methods for the treatment or prevention of a P2Y13-associated disorder, the method comprising administering to a subject in need thereof an effective amount of a compound of the invention. In one embodiment, the compound of the invention is present in a composition that further comprises a pharmaceutically acceptable vehicle.

Examples of P2Y13-associated disorders include, but are not limited to, rheumatoid arthritis; multiple sclerosis; psoriasis; inflammatory bowel diseases; breast; colon or prostate cancer; low levels of blood HDL; low levels of blood, lymph and/or cerebrospinal fluid apo E; low blood, lymph or cerebrospinal fluid levels of apo A-I; high levels of blood VLDL; high levels of blood LDL; high levels of blood triglyceride; high levels of blood apo B; high levels of blood apo C-III and reduced ratio of post-heparin hepatic lipase to lipoprotein lipase activity. HDL may be elevated in lymph or cerebral fluid, or both.

The present invention provides methods for the treatment or prevention of a hepatic steatosis, including alcoholic and non-alcoholic hepatic steatosis, the method comprising administering to a subject in need thereof an effective amount of a compound of the invention. In one embodiment, the compound of the invention is present in a composition that further comprises a pharmaceutically acceptable vehicle.

The present invention provides methods for the treatment or prevention of a renal disease, the method comprising administering to a subject in need thereof an effective amount of a compound of the invention. In one embodiment, the compound of the invention is present in a composition that further comprises a pharmaceutically acceptable vehicle.

Renal diseases include: a glomerular disease (including but not limited to acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, neoplasia, sickle cell disease, and chronic inflammatory diseases), a tubular disease (including but not limited to acute tubular necrosis and acute renal failure, polycystic renal diseasemedullary sponge kidney, medullary cystic disease, nephrogenic diabetes, and renal tubular acidosis), a tubulointerstitial disease (including but not limited to pyelonephritis, drug and toxin induced tubulointerstitial nephritis, hypercalcemic nephropathy, and hypokalemic nephropathy) acute and rapidly progressive renal failure, chronic renal failure, nephrolithiasis, or tumors (including but not limited to renal cell carcinoma and nephroblastoma). In another embodiment, the renal disease is a vascular disease, including but not limited to hypertension, nephrosclerosis, microangiopathic hemolytic anemia, atheroembolic renal disease, diffuse cortical necrosis, and a renal infarct.

The present invention provides methods for the treatment or prevention of a neurodegenerative disease or disorder, Parkinson's Disease, Alzheimer's Disease, Syndrome X, septicemia, thrombotic disorders, obesity, pancreatitis, hypertension, inflammation, or impotence, comprising administering to a subject in need thereof an effective amount of a compound of the invention. In one embodiment, the compound of the invention is present in a composition that further comprises a pharmaceutically acceptable vehicle.

Treatment or prevention of Alzheimer's Disease can also include treatment or prevention of one or more lipoprotein abnormalities associated with Alzheimer's Disease.

Treatment or prevention of Syndrome X or Metabolic Syndrome can also include treatment or prevention of a symptom thereof, including but not limited to: impaired glucose tolerance, hypertension and dyslipidemia or dyslipoproteinemia.

Treatment or prevention of septicemia can also include treatment or prevention of septic shock.

Treatment or prevention of a thrombotic disorder can also include treatment or prevention of high blood levels of fibrinogen or promotion of fibrinolysis.

The compounds of the invention are also useful to promote weight reduction of the subject.

The compounds of the invention are useful in medical applications for treating or preventing a variety of diseases and disorders such as, but not limited to, cardiovascular disease, stroke, and peripheral vascular disease; dyslipidemia; hypercholesterolemia, atherosclerosis, perivascular disease (PVD), stroke, TIA, fulgurant atherosclerosis Organ Graft atherosclerosis; dyslipoproteinemia; a disorder of glucose metabolism; diabetic nephropathy, diabetic retinopathy, insulin resistance, metabolic syndrome disorders (e.g., Syndrome X); a peroxisome proliferator activated receptor-associated disorder; septicemia; a thrombotic disorder; obesity; pancreatitis; hypertension; renal disease; inflammation; inflammatory muscle diseases, such as polymylagia rheumatica, polymyositis, myopathy, and fibrositis; inflammatory disorders, such as asthma, vasculitis, ulcerative colitis, Crohn's disease, Kawasaki disease, Wegener's granulomatosis, (RA), systemic lupus erythematosus (SLE), multiple sclerosis (MS), and autoimmune chronic hepatitis; arthritis, such as rheumatoid arthritis, juvenile rheumatoid arthritis, and osteoarthritis; osteoporosis, soft tissue rheumatism, such as tendonitis; bursitis; autoimmune disease, such as systemic lupus and erythematosus; scleroderma; ankylosing spondylitis; gout; pseudogout; non-insulin dependent diabetes mellitus; polycystic ovarian disease; hyperlipidemias, such as familial hypercholesterolemia (FH), familial combined hyperlipidemia (FCH); lipoprotein lipase deficiencies, such as hypertriglyceridemia, hypoalphalipoproteinemia, and hypercholesterolemia; lipoprotein abnormalities associated with diabetes; lipoprotein abnormalities associated with obesity. The compounds and compositions of the invention are useful for treatment or prevention of high levels of blood triglycerides, high levels of low density lipoprotein cholesterol, high levels of apolipoprotein B, high levels of lipoprotein Lp(a) cholesterol, high levels of very low density lipoprotein cholesterol, high levels of fibrinogen, high levels of insulin, high levels of glucose, and low levels of high density lipoprotein cholesterol. The compounds and compositions of the invention also have utility for treatment of non-insulin-dependent diabetes mellitus (NIDDM) without increasing weight gain. The compounds of the invention may also be used to reduce the fat content of meat in livestock and reduce the cholesterol content of eggs.

The invention provides novel compounds particularly useful for treating or preventing a variety of diseases and conditions, which include, but are not limited to aging, Alzheimer's Disease, and lipoprotein abnormalities associated with Alzheimer's Disease Parkinson's Disease, cancer, cardiovascular disease, diabetic nephropathy, diabetic retinopathy, a disorder of glucose metabolism, dyslipidemia, dyslipoproteinemia, enhancing bile production, hypertension, impotence, inflammation, insulin resistance, lipid elimination in bile, modulating C reactive protein, obesity, oxysterol elimination in bile, pancreatitis, pancreatitius, impotence; gastrointestinal disease; irritable bowel syndrome; inflammatory bowel disease; a peroxisome proliferator activated receptor-associated disorder, phospholipid elimination in bile, renal disease, septicemia, metabolic syndrome disorders (e.g., Syndrome X), and a thrombotic disorder.

Cardiovascular diseases such as atherosclerosis can require surgical procedures such as angioplasty. Angioplasty can be accompanied by the placement of a reinforcing a metallic tube-shaped structure known as a "stent" into a damaged coronary artery. For more serious conditions, open heart surgery such as coronary bypass surgery can be required. These surgical procedures can entail using invasive surgical devices or implants, and are associated with a high risk of restenosis and thrombosis. Accordingly, the compounds of the invention are useful as coatings on surgical devices (e.g., catheters) or implants (e.g., stents) to reduce the risk of restenosis and thrombosis associated with invasive procedures used in the treatment of cardiovascular diseases. Accordingly, the present invention further provides surgical devices or implants that have a coating that comprises an effective amount of a compound of the invention.

A compound of the invention can be administered to a non-human animal for a veterinary use for treating or preventing a disease or disorder disclosed herein.

In a specific embodiment, the non-human animal is a household pet. In another specific embodiment, the non-human animal is a livestock animal. In another embodiment, the non-human animal is a mammal, for example, a cow, horse, sheep, pig, cat, dog, mouse, rat, rabbit, or guinea pig. In another embodiment, the non-human animal is a fowl species, such as a chicken, turkey, duck, goose, or quail.

In addition to veterinary uses, the compounds and compositions of the invention are useful to reduce the fat content of livestock to produce leaner meats. Alternatively, the compounds and compositions of the invention are useful to reduce the cholesterol content of eggs by administering the compounds to a chicken, quail, or duck hen. For non-human animal uses, the compounds and compositions of the invention can be administered via the animals' feed or orally as a drench composition. Accordingly, the present invention further provides methods for reducing the fat content of livestock or the cholesterol content of eggs, comprising administering an effective amount of a compound of the invention to a subject in need thereof.

A. Treatment or Prevention of Cancer

The compounds of the invention are useful for treating or preventing cancer. Accordingly, the invention provides methods for treating or preventing cancer, comprising administering an effective amount of a compound of the invention to a subject in need thereof. In one embodiment, the methods further comprise administering an effective amount of another anticancer agent. Examples of cancers that the compounds of the invention disclosed herein are useful for treating or preventing include, but are not limited to, the cancers disclosed below in Table 1 and metastases thereof

TABLE 1

| Solid tumors, including but not limited to: | |
| --- | --- |
| fibrosarcoma | basal cell carcinoma |
| myxosarcoma | adenocarcinoma |
| liposarcoma | sweat gland carcinoma |
| chondrosarcoma | sebaceous gland carcinoma |
| osteogenic sarcoma | papillary carcinoma |
| chordoma | papillary adenocarcinomas |
| angiosarcoma | cystadenocarcinoma |
| endotheliosarcoma | medullary carcinoma |
| lymphangiosarcoma | bronchogenic carcinoma |
| lymphangioendotheliosarcoma | renal cell carcinoma |
| synovioma | hepatoma |
| mesothelioma | bile duct carcinoma |

TABLE 1-continued

| Ewing's tumor | choriocarcinoma |
| --- | --- |
| leiomyosarcoma | seminoma |
| rhabdomyosarcoma | embryonal carcinoma |
| colon cancer | Wilms' tumor |
| colorectal cancer | cervical cancer |
| kidney cancer | uterine cancer |
| pancreatic cancer | testicular cancer |
| bone cancer | small cell lung carcinoma |
| breast cancer | bladder carcinoma |
| ovarian cancer | lung cancer |
| prostate cancer | epithelial carcinoma |
| esophageal cancer | skin cancer |
| stomach cancer | melanoma |
| oral cancer | metastatic melanoma |
| nasal cancer | neuroblastoma |
| throat cancer | retinoblastoma |
| squamous cell carcinoma | |
| Blood-borne cancers, including but not limited to: | |
| acute lymphoblastic leukemia ("ALL") | acute myelomonocytic leukemia |
| acute lymphoblastic B-cell leukemia | acute nonlymphocytic leukemia |
| acute lymphoblastic T-cell leukemia | acute undifferentiated leukemia |
| acute myeloblasts leukemia ("AML") | chronic myelocytic leukemia ("CML") |
| acute promyelocyte leukemia ("APL") | chronic lymphocytic leukemia ("CLL") |
| acute monoblastic leukemia | hairy cell leukemia |
| acute erythroleukemic leukemia | multiple myeloma |
| acute megakaryoblastic leukemia | |
| Acute and chronic leukemias, including but not limited to: | |
| lymphoblastic | lymphocytic |
| myelogenous | myelocytic leukemias |
| CNS and brain cancers, including but not limited to: | |
| glioma | acoustic neuroma |
| pilocytic astrocytoma | oligodendroglioma |
| astrocytoma | meningioma |
| anaplastic astrocytoma | vestibular schwannoma |
| glioblastoma multiforme | adenoma |
| medulloblastoma | metastatic brain tumor |
| craniopharyngioma | meningioma |
| ependymoma | spinal tumor |
| pinealoma | medulloblastoma |
| hemangioblastoma | |

In one embodiment, the cancer is lung cancer, breast cancer, colorectal cancer, prostate cancer, a leukemia, a lymphoma, non-Hodgkin's lymphoma, skin cancer, a brain cancer, a cancer of the central nervous system, ovarian cancer, uterine cancer, stomach cancer, pancreatic cancer, esophageal cancer, kidney cancer, liver cancer, or a head and neck cancer. In another embodiment, the cancer is metastatic cancer.

In another embodiment, the cancer is brain cancer or melanoma. In one embodiment, the brain cancer is metastatic brain cancer or a glioma. In one embodiment, the glioma is pilocytic astrocytoma, astrocytoma, anaplastic astrocytoma or glioblastoma multiforme. In one embodiment, the cancer is homologous-recombination deficient, such as BRCA-I or BRCA-2 deficient, or is deficient in one or more proteins of the Fanconi family. In one embodiment, the deficiency is caused by a genetic mutation. In another embodiment, the phenotype resulting from the deficiency is caused by abnormally low expression of BRCA-I or BRCA-2 protein. In another embodiment, the phenotype resulting from the deficiency is caused by abnormally low expression of one or more proteins of the Fanconi family.

In another embodiment, the cancer is leukemia, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemia, such as but not limited to, chronic myelocytic (granulocytic) leukemia, chronic lymphocytic leukemia, hairy cell leukemia; polycythemia Vera; lymphoma such as but not limited to Hodgkin's disease, non-Hodgkin's disease; multiple myeloma such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; dendritic cell cancer, including plasmacytoid dendritic cell cancer, NK blastic lymphoma (also known as cutaneous NK/T-cell lymphoma and agranular (CD4+/CD56+) dermatologic neoplasms); basophilic leukemia; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; a brain tumor such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancer such as but not limited to Cushing's disease, prolactin-secreting tumor, acromegaly, and diabetes insipius; eye cancer such as but not limited to ocular melanoma such as iris melanoma, choroidal melanoma, and cilliary body melanoma, and retinoblastoma; vaginal cancer such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancer such as but not limited to, squamous cell carcinoma, and adenocarcinoma; uterine cancer such as but not limited to endometrial carcinoma and uterine sarcoma; ovarian cancer such as but not limited to, ovarian epithelial carcinoma, borderline tumor, germ cell tumor, and stromal tumor; esophageal cancer such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancer such as but not limited to, adenocarcinoma, fungating (polypoid), ulcerating, superficial spreading, diffusely spreading, malignant lymphoma, liposarcoma, fibrosarcoma, and carcinosarcoma; colon cancer; rectal cancer; liver cancer such as but not limited to hepatocellular carcinoma and hepatoblastoma; gallbladder cancer such as adenocarcinoma; cholangiocarcinomas such as but not limited to papillary, nodular, and diffuse; lung cancer such as non-small cell lung cancer, squamous cell carcinoma (epidermoid carcinoma), adenocarcinoma, large-cell carcinoma and small-cell lung cancer; testicular cancer such as but not limited to germinal tumor, seminoma, anaplastic, classic (typical), spermatocytic, nonseminoma, embryonal carcinoma, teratoma carcinoma, choriocarcinoma (yolk-sac tumor), prostate cancer such as but not limited to, prostatic intraepithelial neoplasia, adenocarcinoma, leiomyosarcoma, and rhabdomyosarcoma; penile cancer; oral cancer such as but not limited to squamous cell carcinoma; basal cancer; salivary gland cancer such as but not limited to adenocarcinoma, mucoepidermoid carcinoma, and adenoidcystic carcinoma; pharynx cancer such as but not limited to squamous cell cancer, and verrucous; skin cancer such as but not limited to, basal cell carcinoma, squamous cell carcinoma and melanoma, superficial spreading melanoma, nodular melanoma, lentigo malignant melanoma, acral lentiginous melanoma; kidney cancer such as but not limited to renal cell carcinoma, adenocarcinoma, hypernephroma, fibrosarcoma, transitional cell cancer (renal pelvis or uterer); Wilms' tumor; bladder cancer such as but not limited to transitional cell carcinoma, squamous cell cancer, adenocarcinoma, carcinosarcoma. In addition, cancer include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In a specific of this embodiment, the cancer is one that is associated with cleavage of notch by γ-secretase including, but not limited to, leukemia, non small cell lung cancer, ovarian cancer, breast cancer, or brain cancer.

In some embodiments, the cancer is colon cancer. In some embodiments, the cancer is colon, breast, lung cancer or melanoma.

In another embodiment, the subject in need of treatment has previously undergone or is presently undergoing treatment for cancer. The treatment includes, but is not limited to, chemotherapy, radiation therapy, surgery or immunotherapy, such as administration of a cancer vaccine. In some embodiments, the compounds of the inventions are used for the prevention of metastasis and invasion from a previous cancer.

The compounds of the invention are also useful for treating or preventing a cancer caused by a virus. Such viruses include human papilloma virus, which can lead to cervical cancer (see, e.g., Hernandez-Avila et al., *Archives of Medical Research* (1997) 28:265-271); Epstein-Barr virus (EBV), which can lead to lymphoma (see, e.g., Herrmann et al., *J. Pathol.* (2003) 199(2):140-5); hepatitis B or C virus, which can lead to liver carcinoma (see, e.g., El-Serag, *J. Clin. Gastroenterol.* (2002) 35(5 Suppl. 2):S72-8); human T cell leukemia virus (HTLV)-I, which can lead to T-cell leukemia (see, e.g., Mortreux et al., *Leukemia* (2003) 17(1):26-38); human herpesvirus-8 infection, which can lead to Kaposi's sarcoma (see, e.g., Kadow et al., *Curr. Opin. Investig. Drugs* (2002) 3(11): 1574-9); and Human Immune deficiency Virus (HIV) infection, which can lead to cancer as a consequence of immunodeficiency (see, e.g., Dal Maso et al., Lancet Oncol (2003) 4(2): 110-9). Each of these references is incorporated herein by reference.

The compounds of the invention are also useful for preventing cancer, or preventing progression of a cancer, including but not limited to the cancers listed in Table 1. Such prophylactic use includes that in which non-neoplastic cell growth such as hyperplasia, metaplasia, or most specifically, dysplasia has occurred. Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a subject, can indicate the desirability of prophylactic or therapeutic administration of a compound of the invention. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. In a specific embodiment, leukoplakia, a benign-appearing hyperplastic or dysplastic lesion of the epithelium, or Bowen's disease, a carcinoma in situ, is treatable or preventable according to the present methods.

In another embodiment, fibrocystic disease (cystic hyperplasia, mammary dysplasia, specifically adenosis (benign epithelial hyperplasia)) is treatable or preventable according to the present methods.

In other embodiments, a subject that has one or more of the following predisposing factors for malignancy can be treated by administration of an effective amount of a compound of the invention: a chromosomal translocation associated with a malignancy (e.g., the Philadelphia chromosome for chronic myelogenous leukemia; t(14;1 8) for follicular lymphoma); familial polyposis or Gardner's syndrome; benign monoclonal gammopathy; a first degree kinship with persons having a cancer or precancerous disease showing a Mendelian (genetic) inheritance pattern (e.g., familial polyposis of the colon, Gardner's syndrome, hereditary exostosis, polyendocrine, adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome); and exposure to carcinogens (e.g., smoking, second-hand smoke exposure, and inhalation of or contacting with certain chemicals).

In one aspect, the present methods for treating or preventing cancer can further comprise the administration of another anticancer agent.

In one embodiment, the present invention provides methods for treating or preventing cancer, comprising the administration of an effective amount of a compound of the invention and another anticancer agent to a subject in need thereof. The compound of the invention and another anticancer agent can be administered concurrently. In this embodiment, the compound of the invention and another anticancer agent can be administered within the same composition, or can be administered from different compositions, via the same or different routes of administration. In another embodiment, the compound of the invention is administered during a time when the other anticancer agent exerts its prophylactic or therapeutic effect, or vice versa.

In another embodiment, the compound of the invention or other anticancer agent is administered in doses commonly employed when such agents are used as monotherapy for the treatment of cancer.

In one embodiment, the compound of the invention or other anticancer agent is administered in doses that are lower than the doses commonly employed when such agents are used as monotherapy for the treatment of cancer.

In another embodiment, the compound of the invention and other anticancer agent act synergistically and are administered in doses that are lower than the doses commonly employed when such agents are used as monotherapy for the treatment of cancer. The dosage of the compound of the invention or other anticancer agent administered as well as the dosing schedule can depend on various parameters, including, but not limited to, the cancer being treated, the subject's general health, and the administering physician's discretion. A compound of the invention can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the other anticancer agent, to a subject in need thereof. In various embodiments a compound of the invention and the other anticancer agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, a compound of the invention and the other anticancer agent are administered within 3 hours. In another embodiment, a compound of the invention and the other anticancer agent are administered at 1 minute to 24 hours apart.

In one embodiment, an effective amount of a compound of the invention and an effective amount of other anticancer agent are present in the same composition. In one embodiment, this composition is useful for oral administration, in another embodiment, this composition is useful for intravenous administration.

In one embodiment, the compositions comprise an amount of a compound of the invention and the other anticancer agent which together are effective to treat or prevent cancer.

In another embodiment, the compositions comprise an effective amount of temozolomide, procarbazine, dacarbazine, interleukin-2, irinotecan, or doxorubicin, a physiologically acceptable carrier, diluent, excipient, or vehicle, and an effective amount of a compound of the invention.

In one embodiment, the amount of a compound of the invention and the other anticancer agent is at least about 0.01% of the combined combination chemotherapy agents by weight of the composition. When intended for oral administration, this amount can be varied from about 0.1% to about 80% by weight of the composition. Some oral compositions can comprise from about 4% to about 50% of combined amount of a compound of the invention and the other anticancer agent by weight of the composition. Other compositions of the present invention are prepared so that a parenteral dosage unit comprises from about 0.01% to about 2% by weight of the composition.

Cancers that can be treated or prevented by administering a compound of the invention and the other anticancer agent include, but are not limited to, the list of cancers set forth above in Table 1.

In one embodiment, the cancer is brain cancer. In specific embodiments, the brain cancer is pilocytic astrocytoma, astrocytoma, anaplastic astrocytoma, glioblastoma multiforme or a metastatic brain tumor.

In one embodiment, the cancer is melanoma. In a specific embodiment, the melanoma is metastatic melanoma.

The compound of the invention and other anticancer agent can act additively or synergistically. A synergistic combination of a compound of the invention and the other anticancer agent, might allow the use of lower dosages of one or both of these agents or less frequent administration of the agents to a subject with cancer. The ability to utilize lower dosages of one or both of the compounds of the invention and other anticancer agent or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

In one embodiment, the administration of an effective amount of a compound of the invention and an effective amount of another anticancer agent inhibits the resistance of a cancer to the other anticancer agent. In one embodiment, the cancer is a tumor.

Suitable other anticancer agents useful in the methods and compositions of the present invention include, but are not limited to temozolomide, a topoisomerase I inhibitor, procarbazine, dacarbazine, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epirubicin, 5-fluorouracil, taxanes such as docetaxel and paclitaxel, leucovorin, levamisole, irinotecan, estramustine, etoposide, nitrogen mustards, BCNU, nitrosoureas such as carmustine and lomustine, vinca alkaloids such as vinblastine, vincristine and vinorelbine, platinum complexes such as cisplatin, carboplatin and oxaliplatin, imatinib mesylate, hexamethylmelamine, topotecan, tyrosine kinase inhibitors, tyrphostins herbimycin A, genistein, erbstatin, and lavendustin A.

In one embodiment, the other anticancer agent is, but is not limited to, a drug listed in Table 2.

TABLE 2

| Alkylating agents, including but not limited to: | | |
|---|---|---|
| Nitrogen mustards: | Cyclophosphamide | Trofosfamide |
| | Ifosfamide | Chlorambucil |
| Nitrosoureas: | Carmustine (BCNU) | Lomustine (CCNU) |
| Alkylsulfonates: | Busulfan | Treosulfan |
| Triazenes: | Dacarbazine | Temozolomide |
| | Procarbazine | |
| Platinum containing complexes: | Cisplatin | Aroplatin |
| | Carboplatin | Oxaliplatin |
| Plant alkaloids, including but not limited to: | | |
| Vinca alkaloids: | Vincristine | Vindesine |
| | Vinblastine | Vinorelbine |
| Taxoids: | Paclitaxel | Docetaxel |
| DNA topoisomerase inhibitors, including but not limited to: | | |
| Epipodophyllins: | Etoposide | 9-aminocamptothecin |
| | Teniposide | Camptothecin |
| | Topotecan | Crisnatol |
| Mitomycins: | Mitomycin C | Anti-metabolites |
| Anti-folates, including but not limited to: | | |
| DHFR inhibitors: | Methotrexate | Trimetrexate |
| IMP dehydrogenase inhibitors: | Mycophenolic acid | EICAR |
| | Tiazofurin | Ribavirin |
| Ribomiclotide reductase inhibitors: | Deferoxamine | hydroxyurea |
| Pyrimidine analogs, including but not limited to: | | |
| Uracil analogs: | 5-Fluorouracil | Doxifluridine |
| | Fluoxuridine | Ralitrexed |
| Cytosine analogs: | Cytarabine (ara C) | Gemcitabine |
| | Cytosine arabinoside | Capecitabine |
| | Fludarabine | |
| Purine analogs: | Mercaptopurine | Thioguanine |
| DNA anti-metabolites: | 3-HP | beta-TGDR |
| | 2'-deoxy-5-fluorouridine | cyclocytidine |
| | 5-HP | guanazole |

TABLE 2-continued

|  |  |  |
|---|---|---|
|  | alpha-TGDR | inosine glycodialdehyde |
|  | aphidicolin glycinate | macebecin II |
|  | ara-C | Pyrazoloimidazole |
|  | 5-aza-2'-deoxycytidine |  |

Hormonal therapies, including but not limited to:

Receptor antagonists:

|  |  |  |
|---|---|---|
| Anti-estrogen: | Tamoxifen | Megestrol |
|  | Raloxifene |  |
| LHRH agonists: | Goserelin | Leuprolide acetate |
| Anti-androgens: | Flutamide | Bicalutamide |

Retinoids/deltoids, including but not limited to:

|  |  |  |
|---|---|---|
|  | Cis-retinoic acid |  |
| Vitamin A derivative: | All-trans retinoic acid (ATRA-IV) |  |
| Vitamin D3 analogs: | EB 1089 | KH 1060 |
|  | CB 1093 |  |

Photodynamic therapies, including but not limited to:

|  |  |  |
|---|---|---|
|  | Vertoporfin (BPD-MA) | Demethoxy-hypocrellin A |
|  | Plithalocyanine | (2BA-2-DMHA) |
|  | Photosensitizer Pc4 |  |

Cytokines, including but not limited to:

|  |  |  |
|---|---|---|
|  | Interferon-α | Tumor necrosis factor |
|  | Interferon-β | Interleukin-2 |
|  | Interferon-γ |  |

Angiogenesis inhibitors, including but not limited to:

|  |  |  |
|---|---|---|
|  | Angiostatin (plasminogen fragment) | MoAb IMC-IC1 1 |
|  | antiangiogenic antithrombin III | Neovastat |
|  | Angiozyme | NM-3 |
|  | ABT-627 | Panzem |
|  | Bay 12-9566 | PI-88 |
|  | Benefin | Placental ribonuclease inhibitor |
|  | Bevacizumab | Plasminogen activator inhibitor |
|  | BMS-275291 | Platelet factor-4 (PF4) |
|  | cartilage-derived inhibitor (CDI) | Prinomastat |
|  | CAI | Prolactin 16kD fragment |
|  | CD59 complement fragment | Proliferin-related protein (PRP) |
|  | CEP-7055 | PTK 787/ZK 222594 |
|  | Col 3 | Retinoids |
|  | Combretastatin A-4 | Solimastat |
|  | Endostatin (collagen XVIII fragment) | Squalamine |
|  | Fibronectin fragment | SS 3304 |
|  | Gro-beta | SU 5416 |
|  | Halofuginone | SU 6668 |
|  | Heparinases | SU1 1248 |
|  | Heparin hexasaccharide fragment | Tetrahydrocortisol-S |
|  | HMV833 | Tetrathiomolybdate |
|  | Human chorionic gonadotropin (hCG) | Thalidomide |
|  | IM-862 | Thrombospondin-1 (TSP-I) |
|  | Interferon α/β/γ | TNP-470 |
|  | Interferon inducible protein (IP-10) | Transforming growth factor-beta (TGF-β) |
|  | Interleukin-12 | Vasculostatin |
|  | Kringle 5 (plasminogen fragment) | Vasostatin (calreticulin fragment) |

TABLE 2-continued

| Antimitotic agents, including but not limited to: | | |
|---|---|---|
| | Marimastat | ZD6126 |
| | Metalloproteinase inhibitors (TIMPs) | ZD 6474 |
| | 2-Methoxyestradiol | farnesyl transferase inhibitors (FTI) |
| | MMI 270 (CGS 27023A) | Bisphosphonates |

| | | |
|---|---|---|
| | Allocolchicine | Maytansine |
| | Halichondrin B | Rhizoxin |
| | Colchicine | Thiocolchicine |
| | colchicine derivative | trityl cysteine |
| | dolstatin 10 | |
| | Others: | |

| | | |
|---|---|---|
| Isoprenylation inhibitors: | | |
| Dopaminergic neurotoxins: | l-methyl-4-phenylpyridinium ion | |
| Cell cycle inhibitors: | Staurosporine | |
| Actinomycins: | Actinomycin D | Dactinomycin |
| Bleomycins: | Bleomycin A2 | Peplomycin |
| | Bleomycin B2 | |
| Anthracyclines: | Daunorubicin | Pirarabicin |
| | Doxorubicin (adriamycin) | Zorabicin |
| | Idarubicin | Mitoxantrone |
| | Epirubicin | |
| MDR inhibitors: | Verapamil | |
| $Ca^{2+}$ATPase inhibitors: | Thapsigargin | |

Other additional anticancer agents that are useful in the compositions and methods of the present invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefmgol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine hydrochloride; hydroxyurea; idarubicin hydrochloride; ifosfamide; ilmofosine; interleukin-2 (including recombinant interleukin-2, or rIL2), interferon alfa-2α; interferon alfa-2β; interferon alfa-n1; interferon alfa-n3; interferon beta-Iα; interferon γ-Iβ; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamyciii; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Further anticancer drugs that are useful in the methods and compositions of the invention include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta Lactam Derivatives; beta-alethine; betaclamycin B; betulinic acid; bFGF inhibitor; bicalutamide; bisantrene; bisaziridinylspermme; bisnafide; bistratene A; bizelesin; breflate; bropirimine; budotitane; buthionine sulfoximine; calcipotriol; calphostin C; camptothecin derivatives; canarypox IL-2; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin Analogue; conagenin; crambescidin 816; crisnatol; cryptopliycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemniii B; didox; diethylnorspermine; dihydro-5-acytidine; dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine Analogue; lipophilic disaccharide peptide; lipophilic platinum complexes; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin Analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drag resistance gene inhibitor; multiple tumor suppressor 1-based therapy; mustard anticancer agents; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel Analogues; paclitaxel derivatives; palauamiiie; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum complexes; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; raboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurirt; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; ver amine; verdins; verteporfin; vinorelbine; vinxaltine; vitaxin; vorozole; zanoterone; zeniplatin; zilascorb; and zinostatin stimalamer.

In another embodiment, the other anticancer agent is interferon-α. In another embodiment, the other anticancer agent is interleukin-2. In one embodiment, the other anticancer agent is an alkylating agent, such as a nitrogen mustard, a nitrosourea, an alkylsulfonate, a triazene, or a platinum-containing agent. In one embodiment, the other anticancer agent is a triazene alkylating agent. In one embodiment, the other anticancer agent is O-6-benzylguanine. In another embodiment, the other anticancer agent is O-6-benzylguanine and temozolomide. In another embodiment, the other anticancer agent is O-6-benzylguanine and procarbazine. In still another embodiment, the other anticancer agent is O-6-benzylguanine and dacarbazine.

The compounds of the invention can be administered to a subject that has undergone or is currently undergoing one or more additional anticancer therapies including, but not limited to, surgery, radiation therapy, or immunotherapy, such as cancer vaccines.

In one embodiment, the invention provides methods for treating or preventing cancer comprising administering to a subject in need thereof an effective amount of (1) a compound of the invention and (2) another anticancer therapy including, but not limited to, surgery, radiation therapy, or immunotherapy, such as a cancer vaccine.

In one embodiment, the other anticancer therapy is radiation therapy. In another embodiment, the other anticancer therapy is surgery. In still another embodiment, the other anticancer therapy is immunotherapy.

In a specific embodiment, the present methods for treating or preventing cancer comprise administering an effective amount of a compound of the invention and radiation therapy. The radiation therapy can be administered concurrently with, prior to, or subsequent to the compound of the invention, in one embodiment at least an hour, five hours, 12 hours, a day, a week, a month, in another embodiment several months (e.g., up to three months), prior or subsequent to administration of the compound of the invention. Where the other anticancer therapy is radiation therapy, any radiation therapy protocol can be administered depending upon the type of cancer to be treated. For example, but not by way of limitation, X-ray radiation can be administered; specifically, high-energy megavoltage (radiation of greater that 1 MeV energy) can be administered for deep tumors, and electron beam and orthovoltage X-ray radiation can be administered for skin cancers. Gamma-ray emitting radioisotopes, such as radioactive isotopes of radium, cobalt and other elements, can also be administered.

Additionally, the invention provides methods of treatment of cancer comprising administering a compound of the invention as an alternative to chemotherapy or radiation therapy where the chemotherapy or the radiation therapy results in a negative side effect in the subject being treated. The subject being treated can, optionally, be treated with another anticancer therapy such as surgery, radiation therapy, or immunotherapy.

The compounds of the invention can also be administered in vitro or ex vivo, such as for the treatment of certain cancers, including, but not limited to leukemias and lymphomas, such treatment involving autologous stem cell transplants. This can involve a process in which the subject's autologous hematopoietic stem cells are harvested and purged of all cancer cells, the subject's remaining bone-marrow cell population is then eradicated via the administration of a compound of the invention or radiation, or both, and the resultant stem cells are infused back into the subject. Supportive care can be subsequently provided while bone marrow function is restored and the subject recovers.

B. Treatment or Prevention of a Neurodegenerative Disease

The invention provides methods for treating or preventing a neurodegenerative disease, comprising administering an effective amount of a compound of the invention to a subject in need thereof. In one embodiment, the compound is present in a composition that further comprises a pharmaceutically acceptable vehicle.

Examples of neurodegenerative diseases include, but are not limited to, Alexander's disease, Alper's disease, Alzheimer's disease, Amyotrophic lateral sclerosis ("ALS"), Ataxia telangiectasia. Batten disease (also known as Spielmeyer-Vogt-Sjogren-Batten disease), Bovine spongiform encephalopathy, Canavan disease, Cockayne syndrome, Corticobasal degeneration, Creutzfeldt-Jakob disease, Huntington's disease, HIV-associated dementia, Kennedy's disease, Krabbe's disease, Lewy body dementia, Machado-Joseph disease (Spinocerebellar ataxia type 3), Multiple sclerosis ("MS"), Multiple System Atrophy, Narcolepsy, Neuroborreliosis, Parkinson's disease, Pelizaeus-Merzbacher Disease, Pick's disease, Primary lateral sclerosis, Prion diseases, Progressive Supranuclear Palsy, Refsum's disease, Sandhoffs disease, Schilder's disease, Subacute combined degeneration of spinal cord secondary to Pernicious Anemia, Spinocerebellar ataxia, Spinal muscular atrophy, Steele-Richardson-Olszewski disease, and Tabes dorsalis. In one embodiment, the neurodegenerative disease is Alzheimer's disease. Other examples of neurdegenerative diseases include, but are not limited to, diffuse Lewy body disease, multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohifart-Kugelberg-Welander disease, spastic paraparesis, progressive multifocal leukoencephalopathy, prion diseases (including Creutzfeldt-Jakob, Gerstmann-Straussler-Scheinker disease, Kuru and fatal familial insomnia), age-related dementia and other conditions with memory loss, such as vascular dementia, diffuse white matter disease (Binswanger's disease), dementia of endocrine or metabolic origin, dementia of head trauma and diffuse brain damage, dementia pugilistica and frontal lobe dementia, cerebral ischemia or infaction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

In one aspect, the present methods for treating or preventing a neurodegenerative disease can further comprise the administration of another anti-neurodegenerative disease agent.

In one embodiment, the present invention provides methods for treating or preventing a neurodegenerative disease, comprising the administration of an effective amount of a compound of the invention and another anti-neurodegenerative disease agent to a subject in need of treatment or prevention of the neurodegenerative disease. The compound of the invention and another anti-neurodegenerative disease agent can be administered separately. The compound of the invention and another anti-neurodegenerative disease agent can also be administered concurrently. In this embodiment, the compound of the invention and another anti-neurodegenerative disease agent can be administered within the same composition, or can be administered from different compositions, via the same or different routes of administration. In another embodiment, the compound of the invention is administered during a time when the other anti-neurodegenerative disease agent exerts its prophylactic or therapeutic effect, or vice versa.

In another embodiment, the compound of the invention or other anti-neurodegenerative disease agent is administered in doses commonly employed when such agents are used as monotherapy for the treatment of a neurodegenerative disease.

In one embodiment, the compound of the invention or other anti-neurodegenerative disease agent is administered in doses that are lower than the doses commonly employed when such agents are used as monotherapy for the treatment of a neurodegenerative disease.

In another embodiment, the compound of the invention and other anti-neurodegenerative disease agent act synergistically and are administered in doses that are lower than the doses commonly employed when such agents are used as monotherapy for the treatment of a neurodegenerative disease. The dosage of the compound of the invention or other anti-neurodegenerative disease agent administered as well as the dosing schedule can depend on various parameters, including, but not limited to, the neurodegenerative disease being treated, the subject's general health, and the administering physician's discretion. A compound of the invention can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the other anti-neurodegenerative disease agent, to a subject in need of treatment or prevention of the neurodegenerative disease. In various embodiments a compound of the invention and the other anti-neurodegenerative disease agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, a compound of the invention and the other anti-neurodegenerative disease agent are administered within 3 hours. In another embodiment, a compound of the invention and the other anti-neurodegenerative disease agent are administered at 1 minute to 24 hours apart.

In one embodiment, an effective amount of a compound of the invention and an effective amount of other anti-neurodegenerative disease agent are present in the same composition. In one embodiment, this composition is useful for oral administration. In another embodiment, this composition is useful for intravenous administration.

In one embodiment, the compositions comprise an amount of a compound of the invention and the other anti-neurodegenerative disease agent which together are effective to treat or prevent a neurodegenerative disease.

The compounds of the invention and other anti-neurodegenerative disease agent can act additively or synergistically. A synergistic combination of a compound of the invention and the other anti-neurodegenerative disease agent, might allow the use of lower dosages of one or both of these agents and/or less frequent administration of the agents to a subject with a neurodegenerative disease. The ability to utilize lower dosages of one or both of the compound of the invention and other anti-neurodegenerative disease agent and/or to administer the agents less frequently can reduce any toxicity associated with the administration of the agents to a subject without reducing the efficacy of the agents in the treatment of a neurodegenerative disease. In addition, a synergistic effect might result in the improved efficacy of these agents in the treatment of a neurodegenerative disease and/or the reduction of any adverse or unwanted side effects associated with the use of either agent alone.

In one embodiment, the administration of an effective amount of a compound of the invention and an effective amount of another anti-neurodegenerative disease agent inhibits the resistance of a neurodegenerative disease to the other anti-neurodegenerative disease agent.

Suitable other anti-neurodegenerative disease agents useful in the methods and compositions of the present invention include, but are not limited to: anti-Alzheimer's agents, such as cholinesterase inhibitors (e.g., tacrine, donepezil hydrochloride, rivastigmine, or galantamine) or partial glutamate antagonists (e.g., memantine); anti-Parkinson's agents, such as levodopa, carbidopa, tolcapone, bromocriptine, pergolide, pramipexole, ropinirole, selegiline, or amantadine; anti-ALS agents, such as riluzole; and anti-MS agents, such as interferon beta-1a, interferon beta-1b, glatiramer acetate, mitoxantrone, or natalizumab.

C. Combination Therapy

Additional agents that can be used in combination with compounds of the invention for the treatment or prevention of a Condition, for example, a disease associated with γ-secretase activity or prevention of diseases associated with γ-secretase activity, include, but are not limited to, a small molecule, a synthetic drug, a peptide (including a cyclic peptide), a polypeptide, a protein, a nucleic acid (e.g., a DNA and RNA nucleotide including, but not limited to, an antisense nucleotide sequence, a triple helix, RNAi, and a nucleotide sequence encoding a biologically active protein, polypeptide or peptide), an antibody, a synthetic or natural inorganic molecule, a mimetic agent, and a synthetic or natural organic molecule. Specific examples of such agents include, but are not limited to, an immunomodulatory agent (e.g., interferon), anti-inflammatory agent (e.g., an adrenocorticoid, a corticosteroid (e.g., beclomethasone, budesonide, flunisolide, fluticasone, triamcinolone, methylprednisolone, prednisolone, prednisone, hydrocortisone), a glucocorticoid, a steroid, and a non-steriodal anti-inflammatory drug (e.g., aspirin, ibuprofen, diclofenac, and a COX-2 inhibitor), a pain reliever, a leukotreine antagonist (e.g., montelukast, a methyl xanthine, zafirlukast, and zileuton), a beta2-agonist (e.g., albuterol, biterol, fenoterol, isoetharie, metaproterenol, pirbuterol, salbutamol, terbutalin formoterol, salmeterol, and salbutamol terbutaline), an anticholinergic agent (e.g., ipratropium bromide and oxitropium bromide), sulphasalazine, penicillamine, dapsone, an antihistamine, an anti-malarial agent (e.g., hydroxychloroquine), an anti-viral agent (e.g., a nucleoside analog (e.g., zidovudine, acyclovir, gangcyclovir, vidarabine, idoxuridine, trifluridine, and ribavirin), foscarnet, amantadine, rimantadine, saquinavir, indinavir, ritonavir, and AZT) and an antibiotic (e.g., dactinomycin (formerly actinomycin), bleomycin, erythomycin, penicillin, mithramycin, and anthramycin (AMC)).

V. Therapeutic or Prophylactic Administration and Compositions of the Invention

Due to their activity, compounds of the invention are advantageously useful in veterinary and human medicine.

When administered to a subject, the compounds of the invention can be administered as a component of a composition that comprises a pharmaceutically acceptable carrier, diluent, excipient, or vehicle. The present compositions, which comprise a compound of the invention, can be administered orally. The compounds of the invention can also be administered by any other convenient route, for example, by infusion or bolus injection, by absorption through epithelial or mucocutaneous linings (e.g., oral, rectal, or intestinal mucosa) and can be administered together with another biologically active agent. Administration can be systemic or local. Various delivery systems are known, e.g., encapsulation in liposomes, microparticles, microcapsules and capsules.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, specifically to the ears, nose, eyes, or skin. In some instances, administration will result in the release of a compound of the invention into the bloodstream.

In one embodiment, the compounds of the invention are administered orally. In other embodiments, it can be desirable to administer the compounds of the invention locally. This can be achieved, for example, and not by way of limitation, by local infusion during surgery, topical application, e.g., in conjunction with a wound dressing after surgery, by injection, by means of a catheter, by means of a suppository or enema, or by means of an implant, the implant being of a porous, non-porous, or gelatinous material, including membranes, such as sialastic membranes, or fibers.

In certain embodiments, it can be desirable to introduce the compounds of the invention into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler of nebulizer, and formulation with an aerosolizing agent, or via perfusion in a fluorocarbon oar, synthetic pulmonary surfactant. In certain embodiments, the compounds of the invention can be formulated as a suppository, with traditional binders and excipients such as triglycerides.

In another embodiment compounds of the invention can be delivered in a vesicle, specifically a liposome (see Langer, Science 249:1527-1533 (1990) and Liposomes in Therapy of Infectious Disease and Cancer 317-327 and 353-365 (1989)).

In yet another embodiment, the compounds of the invention can be delivered in a controlled-release system or sustained-release system (see, e.g., Goodson, in Medical Applications of Controlled Release, supra, vol. 2, pp. 115-138 (1984)). Other controlled or sustained-release systems discussed in the review by Langer, Science 249: 1527-1533 (1990) can be used. In one embodiment a pump can be used (Langer, Science 249: 1527-1533 (1990); Sefton, *CRC Crit. Ref. Biomed. Eng.* 14:201 (1987); Buchwald et al, *Surgery* 88:507 (1980); and Saudek et al., *N. Engl. J. Med.* 321:574 (1989)). In another embodiment polymeric materials can be used (see Medical Applications of Controlled Release (Langer and Wise eds., 1974); Controlled Drug Bioavailability, Drug Product Design and Performance (Smolen and Ball eds., 1984); Ranger and Peppas, *J. Macromol. Sd. Rev. Macromol. Chem.* 2:61 (1983); Levy et al, *Science* 228:190 (1935); During et al, *Ann. Neural.* 25:351 (1989); and Howard et al, *J. Neurosurg.* 71:105 (1989)).

In yet another embodiment a controlled- or sustained-release system can be placed in proximity of a target of the compounds of the invention, e.g., the spinal column, brain, skin, lung, or gastrointestinal tract, thus requiring only a fraction of the systemic dose.

The present compositions can optionally comprise a suitable amount of a pharmaceutically acceptable excipient so as to provide the form for proper administration to the subject.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when the compound of the invention is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also comprise minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see e.g. U.S. Pat. No. 5,698,155). Other examples of suitable pharmaceutical excipients are described in Remington's Pharmaceutical Sciences 1447-1676 (Alfonso R. Gennaro eds., 19th ed. 1995), incorporated herein by reference.

In one embodiment, the compounds of the invention are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving a compound of the invention are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the compounds of the invention can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection.

Generally, the ingredients are supplied either separately or mixed together in unit dosage form, for example, as a dry lyophilized-powder or water-free concentrate in a hermetically sealed container such as an ampule or sachette indicating the quantity of active agent. Where the compounds of the invention are to be administered by infusion, they can be dispensed, for example, with an infusion bottle containing sterile pharmaceutical grade water or saline. Where the compounds of the invention are administered by injection, an ampule of sterile water for injection or saline can be provided so that the ingredients can be mixed prior to administration.

Compounds of the invention can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of Formula I to XI. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, concentration or availability of enzymes, concentration or availability of water, or other physiological conditions or compounds. The amount of the compounds of the invention that is effective in the treatment or prevention of a neurodegenerative disease can be determined by standard clinical techniques. In addition, in vitro or in vivo assays can optionally be employed to help identify optimal dosage ranges. The precise dose to be employed can also depend on the route of administration, and the seriousness of the Condition being treated and can be decided according to the judgment of the practitioner and each subject's circumstances in view of, e.g., published clinical studies. Suitable effective dosage amounts, however, range from about 10 micrograms to about 5 grams about every 4 hours, although they are typically about 500 mg or less per every 4 hours. In one embodiment, the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, and about 5.0 g, every 4 hours. Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered; that is, if more than one compound of the invention is administered, the effective dosage amounts correspond to the total amount administered.

Compositions can be prepared according to conventional mixing, granulating or coating methods, respectively, and the present compositions can comprise, in one embodiment, from about 0.1% to about 99%; and in another embodiment from about 1% to about 70% of the compound of the invention by weight or volume.

The dosage regimen utilizing the compound of the invention can be selected in accordance with a variety of factors including type, species, age, weight, sex and medical condition of the subject; the severity of the Condition to be treated; the route of administration; the renal or hepatic function of the subject; and the specific compound of the invention employed. A compound of the invention can be administered in a single daily dose, or the total daily dosage can be administered in divided doses of two, three or four times daily. Furthermore, a compound of the invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of compound of the invention ranges from about 0.1% to about 15%, w/w or w/v. The compounds of the invention can be assayed in vitro or in vivo for the desired therapeutic or prophylactic activity prior to use in humans. Animal model systems can be used to demonstrate safety and efficacy.

In certain embodiments, a compound of the invention or pharmaceutical composition thereof is administered to a human that has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In some embodiments, a compound of the invention or pharmaceutical composition thereof is administered to a human infant. In other embodiments, a compound of the invention or pharmaceutical composition thereof is administered to a human toddler. In other embodiments, a compound of the invention or pharmaceutical composition thereof is administered to a human child. In other embodiments, a compound of the invention or pharmaceutical composition thereof is administered to a human adult. In yet other embodiments, a compound of the invention or pharmaceutical composition thereof is administered to an elderly human.

In certain embodiments, a compound of the invention or pharmaceutical composition thereof is administered a subject in an immunocompromised state or immunosuppressed state or at risk for becoming immunocompromised or immunosuppressed. In certain embodiments, a compound of the invention or pharmaceutical composition thereof is administered to a subject receiving or recovering from immunosuppressive therapy.

In some embodiments, a compound of the invention or pharmaceutical composition thereof is administered to a patient who is susceptible to adverse reactions to conventional anti-γ-secretase therapies. In some embodiments, a γ-secretase inhibitor or pharmaceutical composition thereof is administered to a patient who has proven refractory to anti-γ-secretase therapies other than γ-secretase inhibitors, but are no longer on these therapies. Among these patients are refractory patients, and patients who are too young for conventional therapies.

In some embodiments, the subject being administered a compound of the invention or pharmaceutical composition thereof has not received therapy prior to the administration of the compound of the invention or pharmaceutical composition thereof.

IV. Kits Comprising a Compound of the Invention

The invention provides kits that can simplify the administration of a compound of the invention to a subject.

A typical kit of the invention comprises a compound of the invention, for example, in unit dosage form. In one embodiment, the unit dosage form is a container, which can be sterile, containing an effective amount of a compound of the invention and a pharmaceutically acceptable carrier, diluent, excipient, or vehicle. The kit can further comprise a label or printed instructions instructing the use of the compound of the invention to treat or prevent a Condition. The kit can also further comprise another prophylactic or therapeutic agent, for example, in unit dosage form, such as a container containing an effective amount of the other prophylactic or therapeutic agent. In one embodiment, the kit comprises a container containing an effective amount of a compound of the invention and an effective amount of another prophylactic or therapeutic agent. Examples of other prophylactic or therapeutic agents include, but are not limited to, those listed above.

Each reference cited herein is hereby incorporated by reference in its entirety.

Syntheses of the Compounds of the Invention
Compounds of Formula I

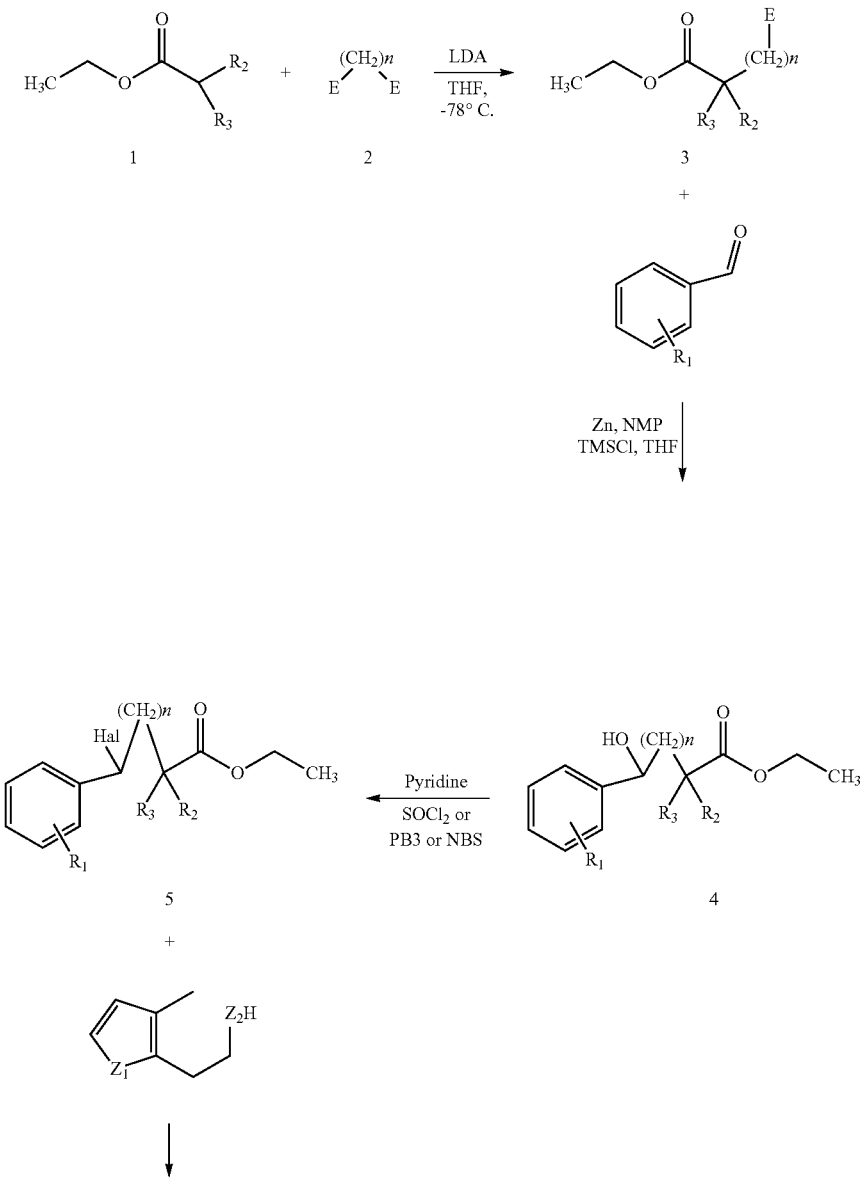

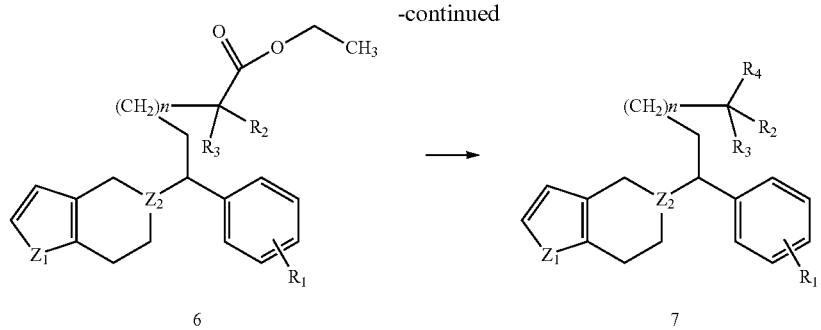

Halo-esters of type 3 can be prepared by reacting compounds 2, wherein E is a suitable leaving group, with compounds 1, wherein $R^2$ and $R^3$ are as defined in Formula I. Suitable leaving groups are well known in the art, but not limited to halides, such as chloride, bromide, and iodide; aryl- or alkylsulfonyloxy, substituted arylsulfonyloxy (e.g., tosyloxy or mesyloxy); substituted alkylsulfonyloxy (e.g., haloalkylsulfonyloxy); ($C_6$)aryloxy or substituted ($C_6$)aryloxy; and acyloxy groups. Compounds 2 are available commercially (e.g., Aldrich Chemical Co., Milwaukee, Wis.) or can be prepared by well-known methods such as halogenation or sulfonation of butanediol. Compounds 1 are also available commercially (e.g., Aldrich Chemical Co., Milwaukee, Wis.) or may be prepared by well-known methods, such as those listed in Larock Comprehensive Organic Transformations; Wiley-VCH: New York, 1999, pp. 1754-1755 and 1765. A review on alkylation of esters of type 1 is given by J. Mulzer in Comprehensive Organic Functional Transformations, Pergamon, Oxford 1995, pp. 148-151 and exemplary synthetic procedures for reacting compounds 1 with compounds 2 are described in U.S. Pat. No. 5,648,387, column 6 and Ackerly, et al., J. Med. Chem. 1995, pp. 1608. The reaction can proceed in the presence of a suitable base. In certain embodiments, a suitable base will have a $pK_a$ of greater than about 25, in yet another embodiment a suitable base will have a $pK_a$ of greater than about 30. Suitable bases include, but are not limited to, alkylmetal bases such as lithium diisopropylamide, methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diethylamide, lithium dicyclohexylamide, sodium hexamethyldisilazide, and lithium hexamethyldisilazide; hydride bases such as sodium hydride and potassium hydride. Metal amide bases, such as lithium diisopropylamide are particularly useful. In certain embodiments of the invention, to react compounds 1 with compounds 2, a solution of about 1 to about 2 equivalents of a suitable base can be added to a stirred solution comprising esters 1 and a suitable organic solvent, under an inert atmosphere, the solution maintained at a constant temperature within the range of about −95° C. to about room temperature, in certain embodiments at about −78° C. to about −20° C. In some embodiments, the base can be diluted in a suitable organic solvent before addition. In some embodiments, the base can be added at a rate of about 1.5 moles per hour. Organic solvents suitable for the reaction of compounds 1 with the compounds 2 include, but are not limited to, dichloromethane, diethyl ether, tetrahydrofuran, dimethylformamide, dimethyl sulfoxide, benzene, toluene, xylene, hydrocarbon solvents (e.g., pentane, hexane, and heptane), and mixtures thereof. After addition of the base, the reaction mixture can be allowed to stir for about 1 to about 2 hours, and a compound 2, which can be dissolved in a suitable organic solvent, is added, in certain embodiments at a rate such that the reaction-mixture temperature remains within about one to two degrees of the initial reaction-mixture temperature. After addition of compounds 2, the reaction-mixture temperature can be adjusted to within a temperature range of about −20° C. to about room temperature, including to about room temperature, and the reaction mixture can be allowed to stir until the reaction is substantially complete as determined by using an appropriated analytical method, such as thin-layer chromatography (TLC) or high-performance liquid chromatography (HPLC). Then the reaction mixture is quenched and compounds 3 can be isolated by workup.

Further, compounds 3 can be reacted with substituted aldehydes by a Grignard reaction to afford alcohols 4. For exemplary procedures for Grignard reactions see March, J. Advanced Organic Chemistry; Reactions Mechanisms, and Structure, 4th ed., 1992, pp. 920-929. In certain embodiments, compounds 3 are treated with Zn or Mg in diethyl ether or tetrahydrofuran, as described in Drake, N. L.; Cooke, G. B. Org. Synth. Coll. Vol. II, 1943, 406. Halides 5 can be synthesized by a variety of methods starting from alcohols 4. One method involves conversion of the alcohol to a leaving group such as a sulfonic ester, such as but not limited to, for example, tosylate, brosylate, mesylate, or nosylate. This intermediate can then be treated with a source of $X^-$, wherein $X^-$ is $I^-$, $Br^-$, or $Cl^-$ in a solvent such as THF or ether. A general method for converting vinyl and phenyl alcohols to thiols involves initially converting the alcohol to a leaving group (e.g., a tosylate) then treating with a halide nucleophile. Exemplary procedures are described in Forrest, O. A.; Gregory, C. F. J. Am. Chem. Soc, 2005, 127, 10482-10483 (NBS/THF), and Possel, O.; van Leusen, A. M. Tetrahedron. Lett, 1977, 48, 4229-4232 (HCl/MeOH).

Halides 5 can be coupled with various heterocycles to produce esters 6. Specifically, 4,5,6,7-tetrahydrothieno[3,2-c]pyridine with $Z^1$=S in the presence of potassium carbonate, as described in Aubert, D.; Touch, P. D.; Ferrand, C.; Ramonville, S.; Maffrand, J. U.S. Pat. No. 4,529,596. 1985. To produce compounds of the invention with $Z^1$=$C_2$ halides 5 are coupled with 6,7-dihydro-5H-[1]pyrindine-3-carboxylic acid as described in Godar E. M., Mariella R. P., J. Org. Chem., 1960, 25, 557-559. To produce esters 6 with $Z^1$=O, halides 5 can be reacted with 4,5,6,7-tetrahydrofuro[3,2-c]pyridine as described in Koike, H.; Asai, F.; Sugidachi, Kimure, T.; Inoue, T.; Nishino, S.; Tsuzaki, Y. U.S. Pat. No. 5,288,726, 1994. Similarly, halides 5 can be reacted with pyrrolo[3,2-c]pyridine-1-carboxylic acid tert-butyl ester, as described in Krichevskii, E. S.; Alekseeva, L. M.;; Granik, V.

G. *Chem. Heterocycl. Compd.* 1990, 1235-1238, to produce compounds of the invention with $Z^1$=N. Esters 6 could undergo subsequent functionalizations as described for instance in Carey, F.; Giuliano, R. *Organic Chemistry*, McGraw-Hill Science/Engineering/Math; 8 edition (2010), Chapter 20. As a specific example, acids of type 7 are obtained by subsequent hydrolysis of the ester groups in the presence of potassium hydroxide (for a general method see *Vogel's Practical Organic Chemistry,* 4th Edition, Longman Inc.: New York 1978, pp 491).

Scheme 2:

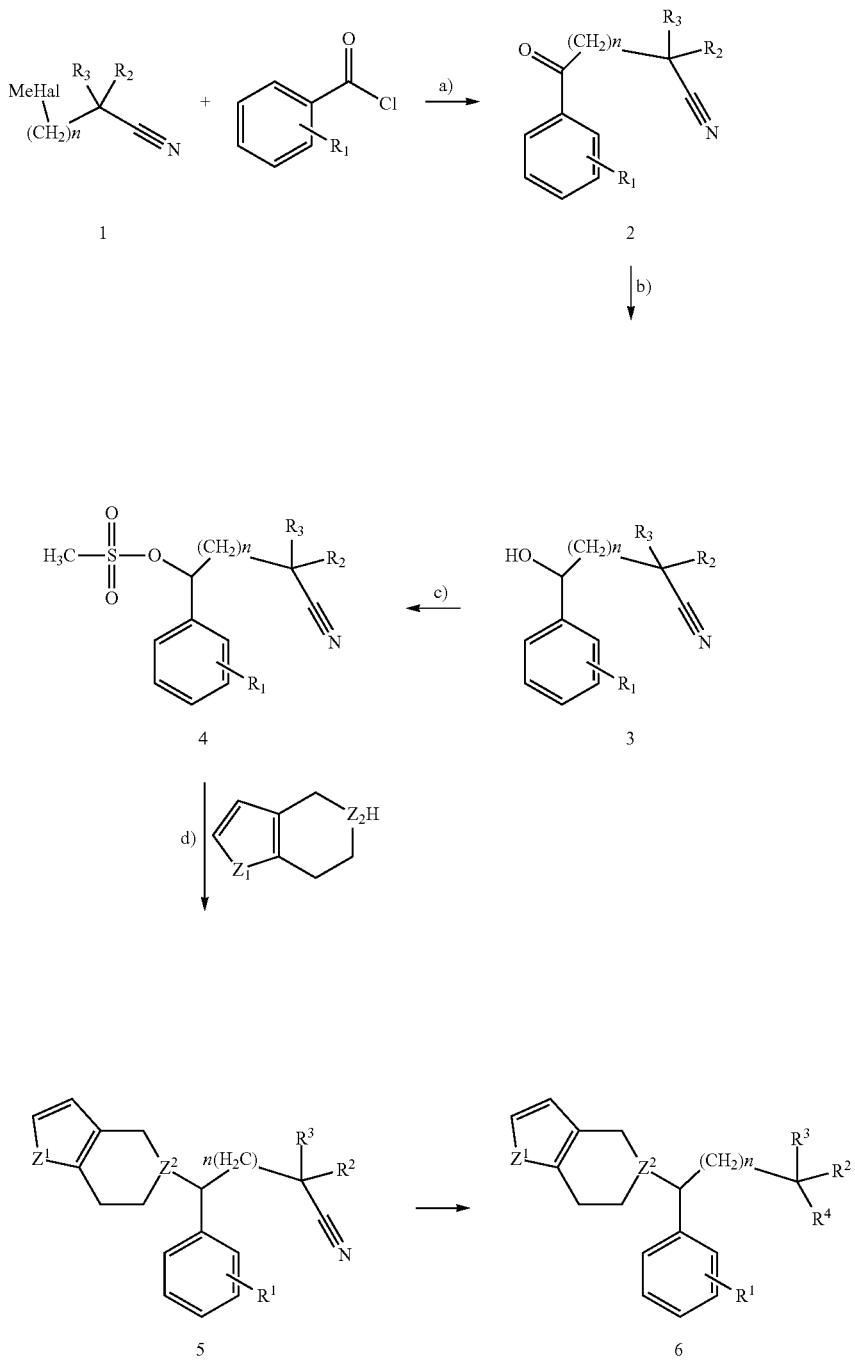

a) CuCN, LiBr, THF, -78 to -10° C.; b) NaBH4, MeOH; c) methanesulfonyl chloride, CH2Cl2; d) Et3N, THF, DMAP Scheme 2 outlines a general method of synthesis for the compounds of the invention. Rieke metals 1 are commercially available, or can be prepared and subjected to the reaction with substituted benzaldehydes as described in Zhu L., Wehmeyer R. M., Rieke R. D., *J. Org. Chem.*, 1991, 56, 1445-1453. The ketone intermediate 2 can be reduced with sodium borohydride to form alcohols 3. The alcohol can be treated with a suitable leaving group in preparation to the subsequent coupling, as described above for the synthesis of derivative 6 in Scheme 1. Suitable leaving groups are well known in the art, for example, but not limited to halides, such as chloride, bromide, and iodide; aryl- or alkylsulfonyloxy, substituted arylsulfonyloxy (e.g., tosyloxy or mesyloxy); substituted alkylsulfonyloxy (e.g., haloalkylsulfonyloxy); ($C_6$)aryloxy or substituted ($C_6$)aryloxy; and acyloxy groups. In certain embodiments of the invention, a compound of type 4 is treated with methanesulfonyl chloride at low temperatures, such as 0-5° C. in the presence of excess triethylamine to form a mesylate. The mesylate 4 is further coupled with the appropriate heterocycle by heating in THF with an excess of triethylamine to form derivative 5. Nitrile derivatives 5 are subjected to transformations to various other functionalities by well-known compendial reactions or via interconversions of carboxylic acid derivatives.

Compounds of Formula II

Scheme 1:

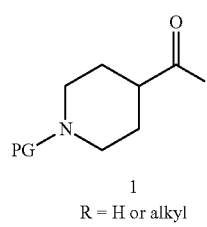

1
R = H or alkyl condensation

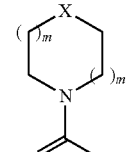

2
$R_1$ = alkyl

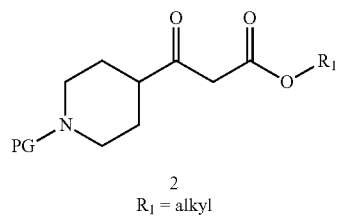

2
$R_1$ = alkyl

+

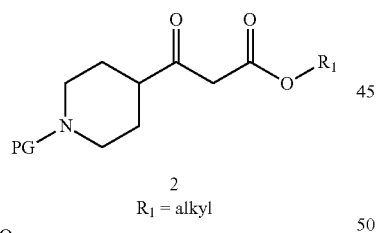

condensation

Scheme 2:

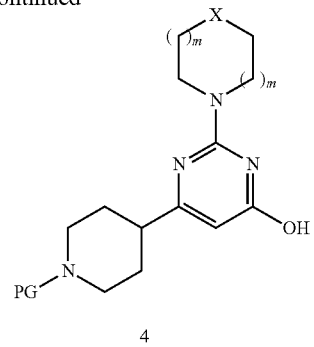

4 halogenation

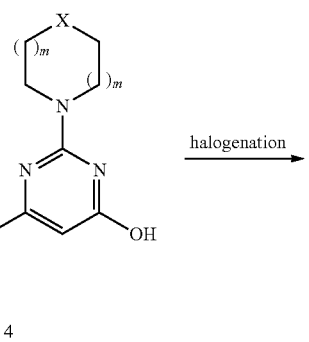

4

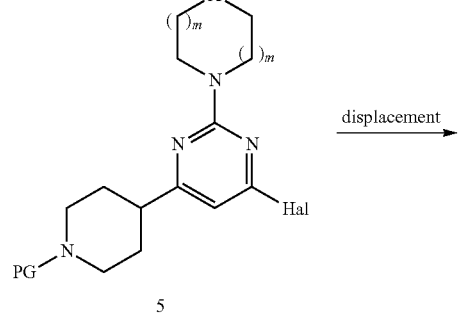

5 displacement

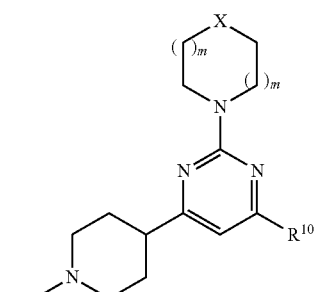

6

Scheme 3:

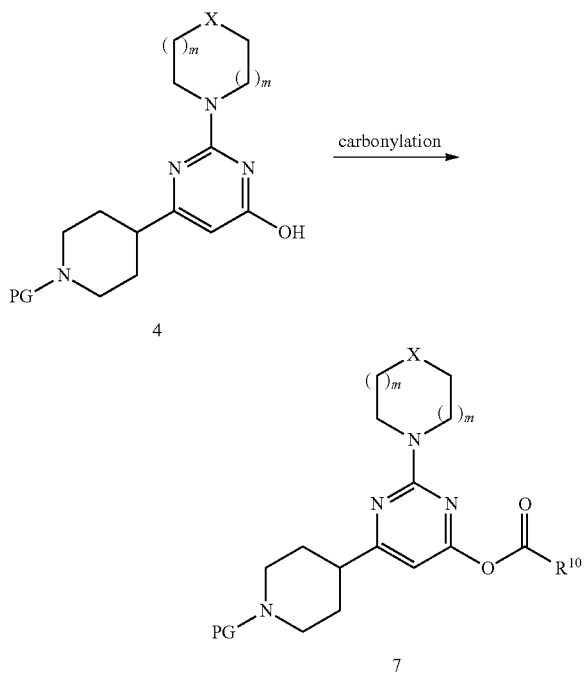

Scheme 4

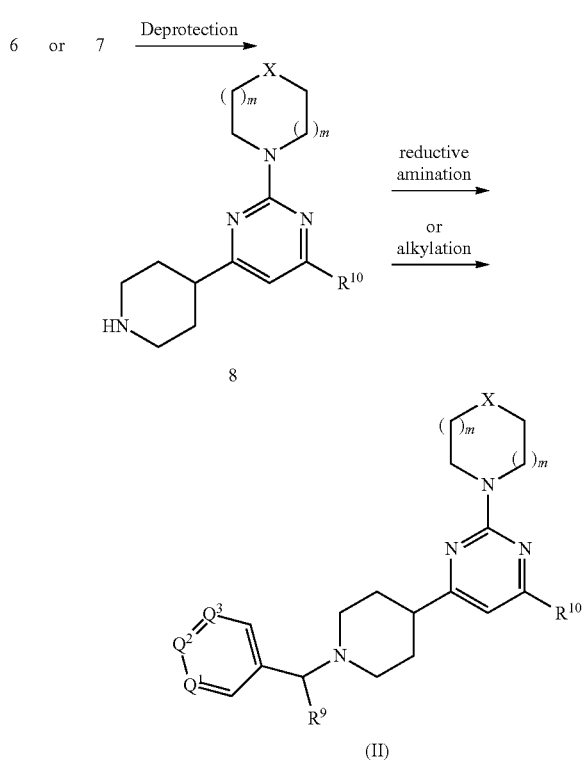

Scheme 1 illustrates a synthesis of pyrimidines of formula 4. The synthesis can be accomplished by condensation of ketoesters of formula 2 and amidines of formula 3. The condensation reaction can be conducted as described in Hull R. et al., 1946, Journal of the Chemical Society pp. 357-362. The ketoesters of formula 2 can be prepared from the commercially available esters of formula 1 (e.g. Matrix Scientific, Columbia, S.C.) by the methods described in Raimundo, Brian C., et al., 2004, Journal of Medicinal Chemistry 47(12), pp. 3111-3131, or the corresponding acid (e.g. Sigma-Aldrich Corp., St. Louis, Mo.) by the method found in Bashford K. E. et al., 2003, Tetrahedron Letters 44, pp. 1627-1629 and Oikawa Y. et al., 1978, Journal of Organic Chemistry 43(10), pp. 2087-2088. The amine present can be commonly protected with but not limited to a t-Boc, CBZ, or benzyl protective group. The amidines of formula 3 (with m being an integer from 0 to 3) are generally commercially available (e.g. Sigma-Aldrich Corp., St. Louis, Mo.) but also can be prepared from the corresponding amine by reaction with 2-methyl-2-thiopseudourea sulfate, which is also commercially available (e.g. Sigma-Aldrich Corp., St. Louis, Mo.). One such nonlimiting procedure is described in Bonafoux D. et al., 2009, Bioorganic & Medicinal Chemistry Letters 19(3), pp. 912-916.

Scheme 2 describes the transformation of pyrimidines of formula 4 to the corresponding halogenated compounds of formula 5 by the use of a halogenating agents including but not limited to $PCl_5$, $PBr_5$, phosphorus oxychloride, and phosphorus oxybromide. An example of this transformation is described by Altenbach R. J., et al., 2008, Journal of Medicinal Chemistry 51(20), pp. 6571-6580. The halogenated compounds of formula 5 can be reacted with a series of carbon, nitrogen, oxygen or sulfur neucleophiles to displace the halogen and generate more the complex pyrimidine analogs of formula 6. The agents used for displacement are commercially available (e.g. Sigma-Aldrich Corp., St. Louis, Mo.) and generally require the presence of additional base including but not limited to triethylamine, diisopropylethylamine, potassium or sodium tert-butoxide, potassium or sodium carbonate, and sodium hydride. Examples of these type of displacement reactions with nitrogen neucleophiles (as in Ghoneim K. M. et al., 1986, Journal of the Indian Chemical Society, 63(10, pp. 914-917), oxygen neuclophiles (as in Dubey P. K. et al., 2006, Indian Journal of Heterocyclic Chemistry 15(4), pp. 405-406), carbon neuclophiles (as in Gillespie R. J. et al, 2009, Bioorganic & Medicinal Chemistry 17(18), pp. 6590-6605), and sulfur neucleophiles (as in Backer H. J. et al, 1942, Recueil des Travaux Chimiques des Pays-Bas et de la Belgique 61, pp. 291-298) are well known in the literature.

Scheme 3 describes the transformation of pyrimidines of formula 4 to the corresponding O-carbonyl pyrimidines of formula 7. The O-carbonyl pyrimidines of formula 7 can be prepared from pyrimidines of formula 4 by addition of the corresponding acid chloride in the presence of base including but not limited to triethylamine, diisopropylethylamine, potassium or sodium tert-butoxide, potassium or sodium carbonate, and sodium hydride. The acid chlorides are commercially available (e.g. Sigma-Aldrich Corp., St. Louis, Mo.) or can be prepared by heating a commercially available acid with chlorinating agents which include but are not limited to thionyl chloride or oxalyl chloride. One example of the carbonylation of pyrimidines is described in Shabbir S. et al., 2010, Tetrahedron 66(35), pp. 7204-7212.

Scheme 4 illustrates the transformation of pyrimidines of formula 6 and formula 7 to the final structures of formula (II). The protective group can be first removed to generate pyrimidines of formula 8 using standard methodologies for the protective group that was used (see Greene T. W. and Wuts P. G., 1999, Protective Groups in Organic Synthesis 3$^{rd}$ edition, Wiley-Interscience, New York for removal of common protective groups). The pyrimidines can then be alkylated with commercially available agents (e.g. Sigma-Aldrich Corp., St. Louis, Mo.) in the presence of a base including but not limited to triethylamine, diisopropylethylamine, potassium or sodium tert-butoxide, potassium or sodium carbonate, and sodium hydride. Procedures described in Levy D. E. et al., 2008, Bioorganic & Medicinal Chemistry Letters, 18(7), pp. 2395-2398 can be used in these types of alkylations. The second commonly methodology that can be used in the transformation of pyrimidines of formula 8 the final structures of formula (II) is reductive amination. Pyrimidines of formula 8 can be treated with a commercially available aldehydes or ketones (e.g. Sigma-Aldrich Corp., St. Louis, Mo.) in the presence of a weak acid (including but not limited to acetic acid, trifluoro acetic acid, or hydrochloric acid) and a reducing reagent (including but not limited to sodium borohydride, sodium cyanoborohydride, and sodium triacetoxyborohydride) to produce the desired final structures of formula (II). The procedures provided in Taibakhsh M. et al, 2011, Synthesis, pp. 490-496 and Abdel-Magid A. F. et al., 1996, Journal Organic Chemistry, 61, pp. 3849-3862 outline methodologies which can be in the reductive amination reactions.

Additionally the compounds of Formula II can be synthesized by methods disclosed in: Abdel-Magid A. F. et al., 1996, "Reductive Amination of Aldehydes and Ketones with Sodium Triacetoxyborohydride. Studies on Direct and Indirect Reductive Amination Procedures(1)", Journal Organic Chemistry, 61, pp. 3849-3862; Altenbach R. J., et al., 2008, "Structure-Activity Studies on a Series of a 2-Aminopyrimidine-Containing Histamine H4 Receptor Ligands", Journal of Medicinal Chemistry 51(20), pp. 6571-6580; Backer H. J. et al, 1942, "Several Sulfanilamido-4-methylpyrimidines", Recueil des Travaux Chimiques des Pays-Bas et de la Belgique 61, pp. 291-298; Bashford K. E. et al., 2003, "The Bohlmann-Ratz Route to Functionalised Pyridine Scaffolds and Their Use in Library Synthesis', Tetrahedron Letter, 44, pp. 1627-1629; Bonafoux D. et al., 2009, "2-Aminoimidazoles Inhibitors of TGF-Beta Receptor 1", Bioorganic & Medicinal Chemistry Letters 19(3), pp. 912-916; Dubey P. K. et al., 2006, "Synthesis of Threobromine Incorporated Pyrimidine", Indian Journal of Heterocyclic Chemistry 15(4), pp. 405-406; Ghoneim K. M. et al., 1986, "Synthesis and Evaluation of some 2-, 4- and 2,4-di-substituted-6-Methylpyrimidine Derivatives for Antimicrobial Activity", Journal of the Indian Chemical Society, 63(10, pp. 914-917; Gillespie R. J. et al, 2009, "Preparation of Pyrimidine Carboxamides as Purine Receptor, Particularly Adenosine Receptor Antagonists", Bioorganic & Medicinal Chemistry 17(18), pp. 6590-6605; Greene T. W. and Wuts P. G., 1999, Protective Groups in Organic Synthesis, 3$^{rd}$ edition, Wiley-Interscience, New York; Hull R. et al., 1946, "Synthetic Antimalarials. III. Some Derivatives of Mono- and Dialkylpyrimidines", Journal of the Chemical Society pp. 357-362; Levy D. E. et al., 2008, "Aryl-indolyl Maleimides as Inhibitors of CaMKII-Delta. Part 2: SAR of the Amine Tether", Bioorganic & Medicinal Chemistry Letters, 18(7), pp. 2395-2398; Oikawa Y. et al., 1978, "Meldrum's Acid in Organic Synthesis. 2. Q General and Versatile Synthesis of Beta-Keto Esters", Journal of Organic Chemistry 43(10), pp. 2087-2088; Raimundo, Brian C. et al, 2004, "Integrating Fragment Assembly and Biophysical Methods in the Chemical Advancement of Small-Molecule Antagonists of IL-2: An Approach for Inhibiting Protein-Protein Interactions", Journal of Medicinal Chemistry, 47(12), pp. 3111-3130; Shabbir S. et al., 2010, "Pyrimidine Based Carboxylic Acid Terminated Aromatic and Semi-aromatic Hyperbranched Polyamide-esters: Synthesis and Characterization", Tetrahedron 66(35), pp. 7204-7212; Taibakhsh M. et al, 2011, "Catalyst-Free One-Pot Reductive Alkylation of Primary and Secondary Amines and N,N-Dimethylation of Amino Acids Using Sodium Borohydride in 2,2,2-Trifluoroethanol", Synthesis, pp. 490-496.

Compounds of Formula III

Scheme 1:

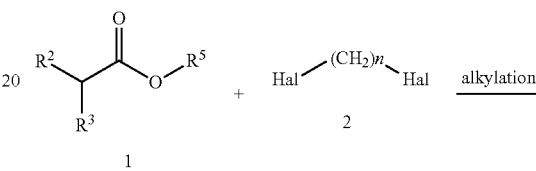

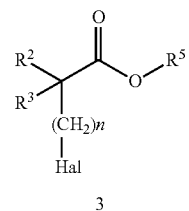

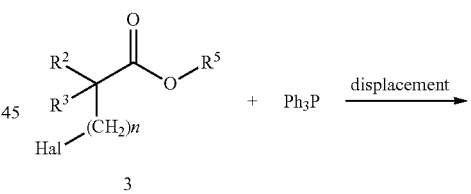

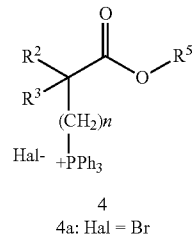

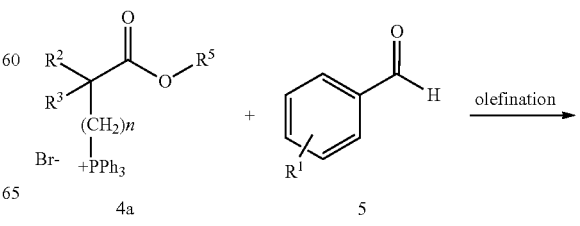

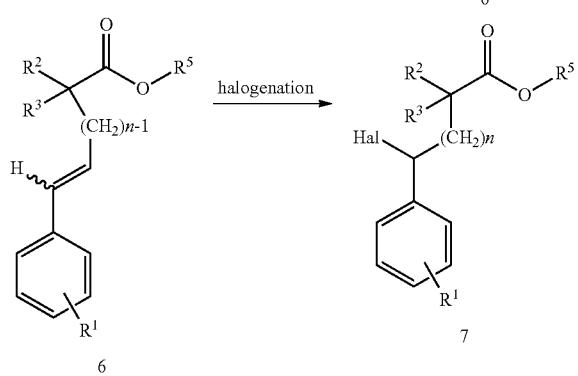

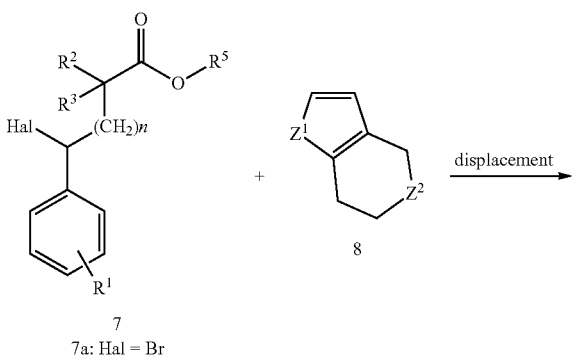

7a: Hal = Br

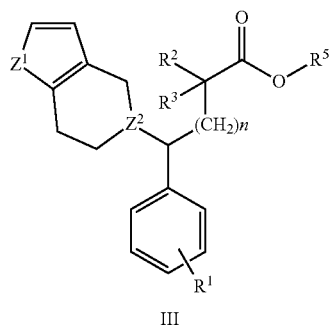

III

Scheme 1 outlines a general synthetic sequence for the preparation of compounds of the Formula III. Commercially available (e.g. Sigma-Aldrich Corp., St. Louis, Mo.) esters, amides, or acids of formula 1 can be treated with base (including but not limited to lithium diisopropylamide, sodium hexamethyldisilylamide, sodium or potassium tert-butoxide) and alkylated with commercially available (e.g. Sigma-Aldrich Corp., St. Louis, Mo.) dihalogenated alkanes of formula 2. The procedures described in Mueller R. et al, 2004, Journal of Medicinal Chemistry, 47(24), pp. 6082-6099 outline a alkylation reaction. The alkylated products of formula 3 can be heated in the presence of triphenylphosphine to prepare the phosphonium salts of formula 4 in the manner described in Parikka K. et al., 2009, Beilstein Journal of Organic Chemistry, 5(22), pp. 1-5. The phosphonium salts of formula 4 can be treated with base (including but not limited to sodium or potassium hydroxide, potassium or sodium tert-butoxide, potassium or sodium carbonate, and sodium hydride) in the presence of commercially available aldehydes (e.g. Sigma-Aldrich Corp., St. Louis, Mo.) of formula 5 to generate olefins of formula 6 in the manner described in Le Bigot Y. et al., 1988, Tetrahedron 44(4), pp. 1057-1072, as a mixture of cis and trans isomers. The mixture of cis and trans isomers of formula 6 can be halogenated by condensation with anhydrous hydrogen halide gas (e.g. hydrogen bromide gas) in acetic acid at low temperature to prepare the halogenated compound of formula 7, in the manner described in Crispi G. et al, 1982, Synthesis 9, pp. 787-788. The final products of formula III can be prepared by heating the halides of formula 7 (e.g. the bromide of 7a) in the presence of base (including but not limited to sodium or potassium hydroxide, potassium or sodium tert-butoxide, potassium or sodium carbonate, and sodium hydride) with commercially available (e.g. Acc Corporation, San Diego Calif. and Ryan Scientific, Mt. Pleasant S.C.) cyclic compounds of formula 8. The displacement products can be prepared as described for similar compounds in the literature (e.g. Cheng D. et al., 2008, Chinese Chemical Letters 19(6), pp. 689-692).

Additionally the compounds of Formula III can be synthesized by methods described in: Cheng D. et al., 2008, "Synthesis and Activity Evaluation of Some Novel Derivatives of 4,5,6,7-Tetrahydrothiono[3,2-c]-pyridine", Chinese Chemical Letters 19(6), pp. 689-692; Crispi G. et al, 1982, "Enamine; 42. A simple Synthesis of 3,4-Diaminobiphenyls", Synthesis (9), pp. 787-788; Le Bigot Y. et al., 1988, "Reactions in a Slightly Hydrated Solid-Liquid Heterogenous Medium: the Wittig Reaction in Alkaline Hydroxide-Aprotic Organic Solvent System", Tetrahedron 44(4), pp. 1057-1072; Mueller R. et al, 2004, "Long Hydrocarbon Chain Keto Diols and Diacids that Favorably Alter Lipid Disorders in Vivo", Journal of Medicinal Chemistry, 47(24), pp. 6082-6099; Parikka K. et al., 2009, "An Expedient Synthesis of 5-n-Alkylresorcinols and Novel 5-n-Alkylresorcinols Hapatens", Beilstein Journal of Organic Chemistry, 5(22) pp. 1-5; Cheng D. et al., 2008, "Synthesis and Activity Evaluation of Some Novel Derivatives of 4,5,6,7-Tetrahydrothiono[3,2-c]pyridine", Chinese Chemical Letters 19(6), pp. 689-692; Crispi G. et al, 1982, "Enamine; 42. A simple Synthesis of 3,4-Diaminobiphenyls", Synthesis (9), pp. 787-788; Le Bigot Y. et al., 1988, "Reactions in a Slightly Hydrated Solid-Liquid Heterogenous Medium: the Wittig Reaction in Alkaline Hydroxide-Aprotic Organic Solvent System", Tetrahedron 44(4), pp. 1057-1072; Mueller R. et al, 2004, "Long Hydrocarbon Chain Keto Diols and Diacids that Favorably Alter Lipid Disorders in Vivo", Journal of Medicinal Chemistry, 47(24), pp. 6082-6099; Parikka K. et al., 2009, "An Expedient Synthesis of 5-n-Alkylresorcinols and Novel 5-n-Alkylresorcinols Hapatens", Beilstein Journal of Organic Chemistry, 5(22) pp. 1-5.

Compounds of Formula IV

Scheme 1:

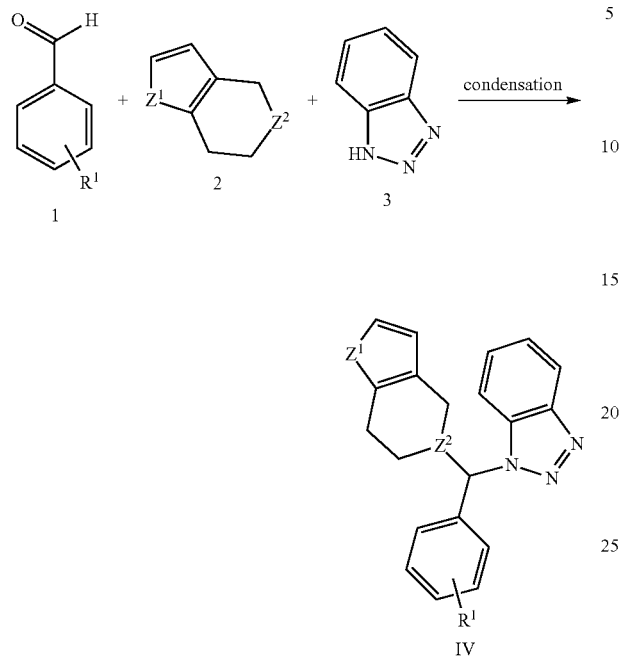

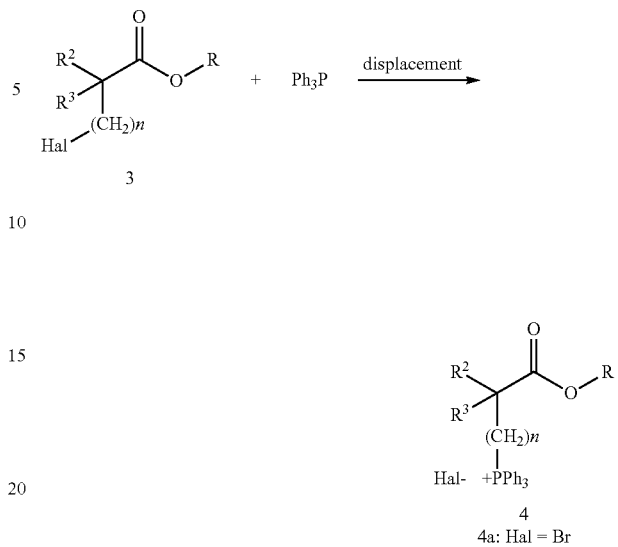

Scheme 1 describes a synthetic route for the preparation of compounds of Formula IV. In certain embodiments, the preparation involves stirring commercially available (e.g. Sigma-Aldrich Corp., St. Louis, Mo.) aldehydes of formula 1, commercially available (e.g. Acc Corporation, San Diego Calif. and Ryan Scientific, Mt. Pleasant S.C.) cyclic compounds of formula 2, and anhydrous benzotriazole 3 in the appropriate solvent, including but not limited to diethyl ether, tetrahydrofuran, dioxane, and toluene. The reactions can be conducted with and without heating the experiments and dry molecular sieves could be used to remove the water in the reaction. The products of formula 4 can then be purified by trituration, crystallization, or column chromatography with the appropriate support (e.g. silica gel or alumina). Examples of the procedure are described in Katritzky A. et al., 1989, "A General Method for the Preparation of Beta-Amino Esters", Synthesis (10), pp. 747-751.

Compounds of Formula V

Scheme 1:

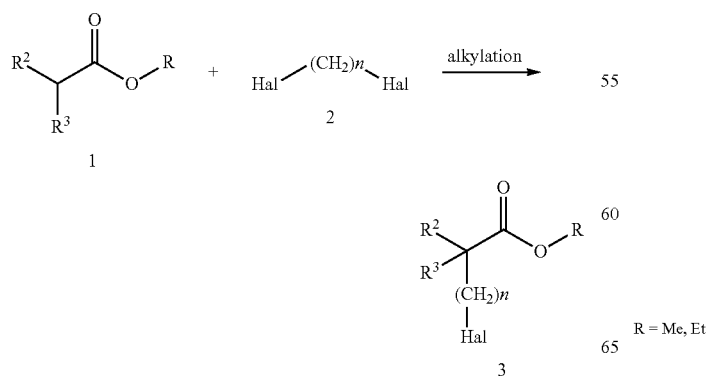

R = Me, Et

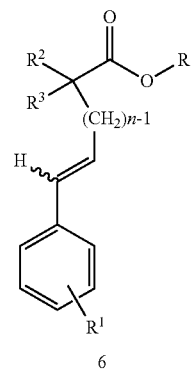

Scheme 2:
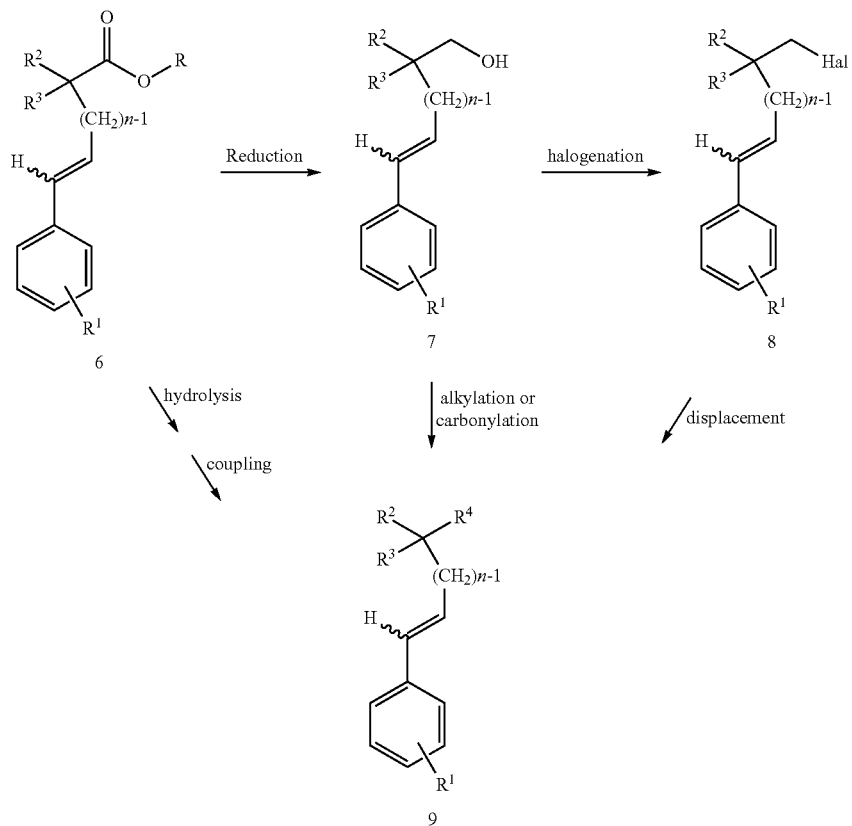
Scheme 3:
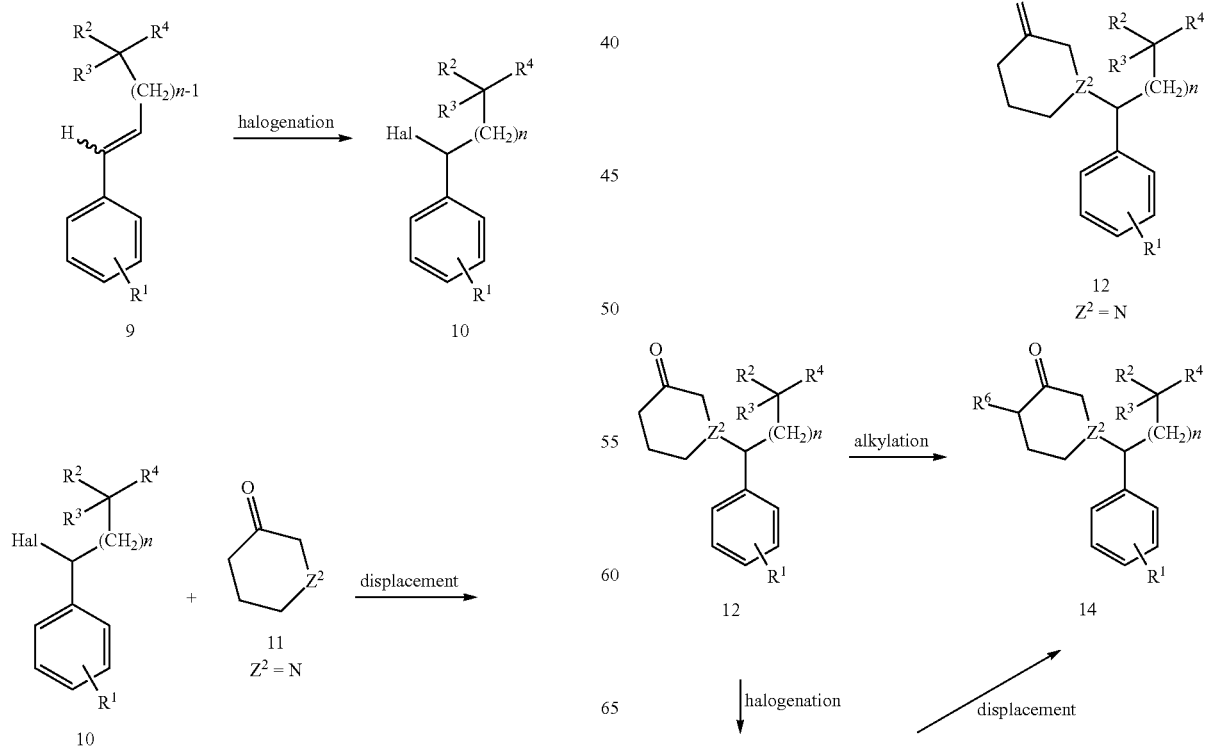

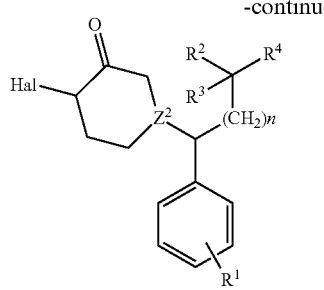

13

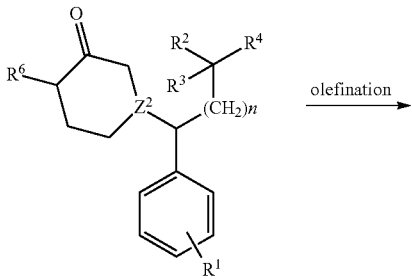

14

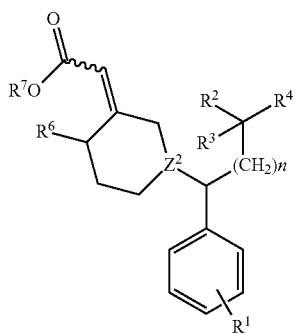

V

Scheme 1 outlines a general synthetic sequence for the preparation of compounds of the formula V. Commercially available (e.g. Sigma-Aldrich Corp., St. Louis, Mo.) esters, amides, or acids of formula 1 can be treated with base (including but not limited to lithium diisopropylamide, sodium hexamethyldisilylamide, sodium or potassium tert-butoxide) and alkylated with commercially available (e.g. Sigma-Aldrich Corp., St. Louis, Mo.) dihalogenated alkanes of formula 2. The procedures described in Mueller R. et al, 2004, Journal of Medicinal Chemistry, 47(24), pp. 6082-6099 outline the alkylation reaction. The alkylated products of formula 3 can be heated in the presence of triphenylphosphine to prepare the phosphonium salts of formula 4 in the manner described in Parikka K. et al., 2009, Beilstein Journal of Organic Chemistry, 5(22), pp. 1-5. The phosphonium salts of formula 4 can be treated with base (including but not limited to sodium or potassium hydroxide, potassium or sodium tert-butoxide, potassium or sodium carbonate, and sodium hydride) in the presence of commercially available aldehydes (e.g. Sigma-Aldrich Corp., St. Louis, Mo.) of formula 5 to generate olefins of formula 6 in the manner described in Le Bigot Y. et al., 1988, Tetrahedron 44(4), pp. 1057-1072, as a mixture of cis and trans isomers.

Scheme 2 illustrates a conversion of esters of formula 6 to halogenated compounds of formula 9. The alcohols of formula 7 can be prepared by reduction of the ester group in compounds of formula 6. A wide variety of reagents are available for reduction of such esters to alcohols, e.g., see M. Hudlicky, Reductions in Organic Chemistry, 2nd ed., 1996 pp. 212-217, hereby expressly incorporated herein by reference. In certain embodiments, the reduction can be performed with a hydride type reducing agent, for example, lithium aluminum hydride, lithium borohydride, lithium triethyl borohydride, diisobutylaluminum hydride, lithium trimethoxyaluminum hydride, or sodium bis(2-methoxy)aluminum hydride. For exemplary, but non-limiting, procedures for reducing esters to alcohols, see Nystrom et al., 1947, J. Am. Chem. Soc. 69:1197; and Moffet et al., 1963, Org. Synth., Collect. 834(4), lithium aluminum hydride; Brown et al., 1965, J. Am. Chem. Soc. 87:5614, lithium trimethoxyaluminum hydride; Cerny et al., 1969, Collect. Czech. Chem. Commun. 34:1025, sodium bis(2-methoxy)aluminum hydride; Nystrom et al., 1949, J. Am. Chem. 71:245, lithium borohydride; and Brown et al., 1980, J. Org. Chem. 45:1, lithium triethyl borohydride. The alcohol present in compounds of formula 7 can be converted to the halide to prepare compounds of formula 8 (for an illustrative discussion of various methods for conversion of alcohols to halides see March, J. Advanced Organic Chemistry; Reactions Mechanisms, and Structure, 4th ed., 1992, pp. 431-433). Compounds of formula 9 can be directly prepared from the ester 6 by hydrolysis of the ester with base followed by standard coupling techniques (using DCC(N,N'-Dicyclohexylcarbodiimide), EDC (1-Ethyl-3-(3-dimethylaminopropyl)carbodiimide), HBTU (O-(Benzotriazol-1-yl)-N,N,N',N'-tetramethyluronium hexafluorophosphate) (for example) with commercially available alcohols, amines, and thiols. Compounds of formula 9 could also be prepared form compounds of formula 7 by alkylation or carbonylation with commercially available alkylating and acylating reagents. Compounds of formula 9 can also be prepared by displacement of the halide present in compounds of formula 8 with commercially available alcohols, amines, and thiols.

In scheme 3, the mixture of cis and trans isomers of formula 9 can be halogenated by condensation with anhydrous hydrogen halide gas (e.g. hydrogen bromide gas) in acetic acid at low temperature to prepare the halogenated compound of formula 10, in the manner described in Crispi G. et al, 1982, Synthesis 9, pp. 787-788. Compounds of the formula 11 ($Z^2$=N) can be prepared as described in Taillier C. et al., 2007, Tetrahedron 63(21), pp. 3589-3592 can coupled with the halides of FIG. 10 in the presence of base (including but not limited to sodium or potassium hydroxide, potassium or sodium tert-butoxide, potassium or sodium carbonate, and sodium hydride) to form compounds of formula 12. The displacement products can be prepared as described for similar compounds in the literature (e.g. Cheng D. et al., 2008, Chinese Chemical Letters 19(6), pp. 689-692). The ketones of formula 12 could be treated with base and alkylated with a series of commercially available alkylating (or acylating) reagents to form compounds of formula 14. The ketones of formula 12 could also be halogenated to form formula 13 compounds by the methods described in Newman M. S. et al., 1945, Organic Synthesis 25 and Mellegaard-Waetzig S. R. et al., 2006, Tetrahedron, pp. 7191-7198. The halogenated compounds of formula 13 could then be displaced with commercially available compounds containing nitrogen, oxygen, or sulfur neuclophiles to prepare the ketones of formula 14. The target compounds of formula V can be prepared by olefination of the ketones of formula 14 with commercially available phosphonates or phosphonium salts in the presence of base.

Additionally the compounds of Formula V can be synthesized by methods disclosed in: Cheng D. et al., 2008, "Synthesis and Activity Evaluation of Some Novel Derivatives of 4,5,6,7-Tetrahydrothiono[3,2-c]-pyridine", Chinese Chemical Letters 19(6), pp. 689-692; Crispi G. et al, 1982, "Enamine; 42. A simple Synthesis of 3,4-Diaminobiphenyls", Synthesis (9), pp. 787-788; M. Hudlicky, Reductions in Organic Chemistry, 2nd ed., 1996 pp. 212-217; Le Bigot Y. et al., 1988, "Reactions in a Slightly Hydrated Solid-Liquid Heterogenous Medium: the Wittig Reaction in Alkaline Hydroxide-Aprotic Organic Solvent System", Tetrahedron 44(4), pp. 1057-1072; March, J. Advanced Organic Chemistry; Reactions Mechanisms, and Structure, 4th ed., 1992, pp. 431-433; Mellegaard-Waetzig S. R. et al., 2006, "Selenium-Catalyzed Oxidative halogenations", Tetrahedron, pp. 7191-7198; Mueller R. et al, 2004, "Long Hydrocarbon Chain Keto Diols and Diacids that Favorably Alter Lipid Disorders in Vivo", Journal of Medicinal Chemistry, 47(24), pp. 6082-6099; Newman M. S. et al., 1945, "2-chlorocyclohexanone", Organic Synthesis 25; Parikka K. et al., 2009, "An Expedient Synthesis of 5-n-Alkylresorcinols and Novel 5-n-Alkylresorcinols Hapatens", Beilstein Journal of Organic Chemistry, 5(22) pp. 1-5; Taillier C. et al., 2007, "Synthesis of 3-Oxooxa and 2-Oxoazacycloak-4-enes by Ring-Closing Metathesis. Application to the Synthesis of an Inhibitor of Cathepsin K", Tetrahedron 63(21), pp. 3589-3592.

Compounds of Formula VI

Scheme 1:

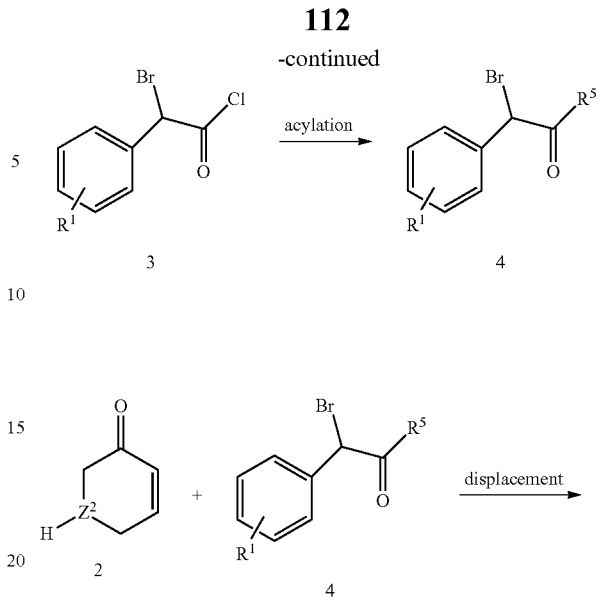

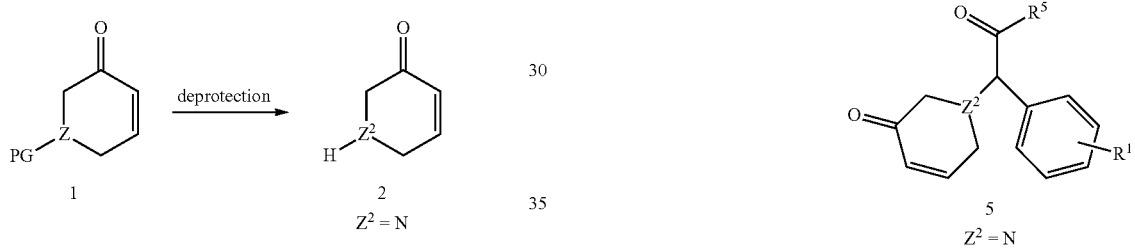

Scheme 2:

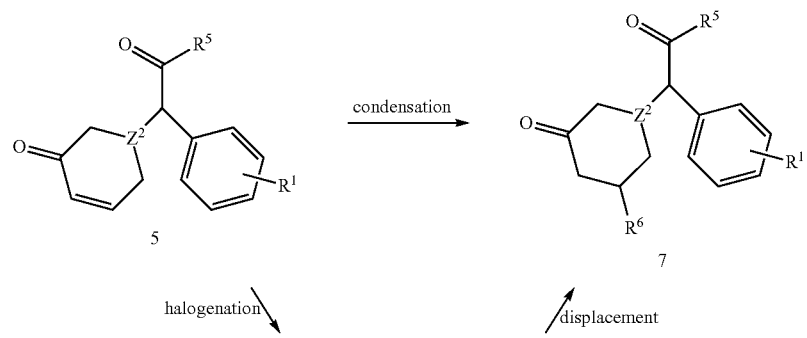

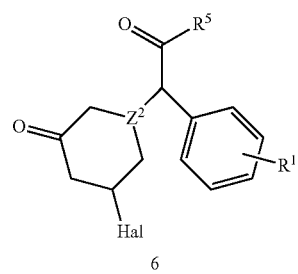

Scheme 3:

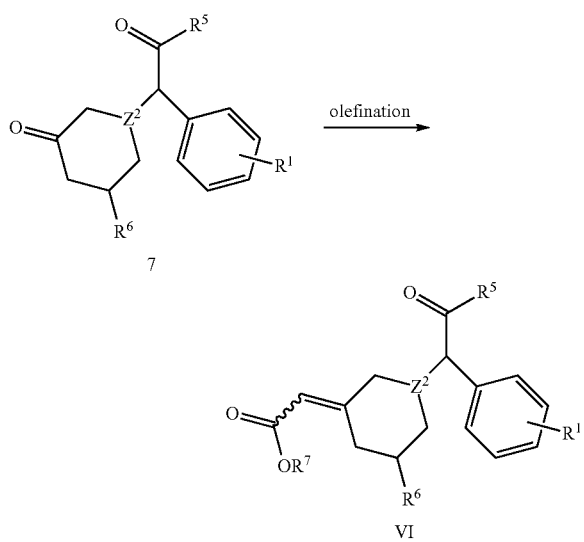

Scheme 1 describes a synthetic route for the preparation of compounds of formula VI. The preparation can involve condensation of compounds with formula 2 and formula 4. Compounds of the formula 1 ($Z^2$=N) can be prepared as described in Taillier C. et al., 2007, Tetrahedron 63(21), pp. 3589-3592 with a boc protective group. The protective group can be removed by stirring in trifluoroacetic acid to prepare the compound of formula 2. The compounds of formula 4 are either commercially available (e.g. Sigma-Aldrich Corp., St. Louis, Mo.) or can be prepared from commercially available compounds of formula 3 by acylation in the presence of a hindered base (e.g. diisopropylethylamine). Equimolar amounts of the compounds of the formula 2 and formula 4 can be heated in polar aprotic solvents (e.g. DMF or acetonitrile) to form the displacement products of formula 5. Similar, but not limiting, displacement reactions are described in the literature (e.g. Cheng D. et al., 2008, Chinese Chemical Letters 19(6), pp. 689-692).

Scheme 2 describes a preparation of analogs of formula 7 from the compounds of formula 5. Analogs of formula 7 can be prepared by direct condensation of commercially available compounds (e.g. Sigma-Aldrich Corp., St. Louis, Mo.) containing sulfur and nitrogen neucleophiles, as described in Kall A. et al., 2010, Synthetic Communications 40(12), pp. 1730-1735 with the compounds of formula 5. Additionally, the compounds of formula 5 could be halogenated by the method described in Marx J. et al., 1983, Tetrahedron 39(9), pp. 1529-1531 to form compound of formula 6. The compounds of formula 6 can be heated with commercially available compounds (e.g. Sigma-Aldrich Corp., St. Louis, Mo.) containing sulfur, nitrogen, or oxygen neucleophiles to form compounds of formula 7 by displacement.

Scheme 3 describes a transformation of the compounds of formula 7 to the target compounds of formula VI by olefination. Commercially available acyl-phosphonium salts or acyl-phosphonates (e.g. Sigma-Aldrich Corp., St. Louis, Mo.) can be treated with base (including but not limited to sodium or potassium hydroxide, potassium or sodium tert-butoxide, potassium or sodium carbonate, lithium diisopropylamide, and sodium hydride) in the presence of compounds of formula 7 to form the final compounds of formula VI. A non-limiting example of a similar procedure is described in Lombardo L. et al., 1987, Synthetic Communications 8(7), pp. 463-468.

Additionally the compounds of Formula VI can be synthesized by methods disclosed in: Cheng D. et al., 2008, "Synthesis and Activity Evaluation of Some Novel Derivatives of 4,5,6,7-Tetrahydrothiono[3,2-c]-pyridine", Chinese Chemical Letters 19(6), pp. 689-692; Kall A. et al., 2010, "Microwave-Induced Aza-Michael reaction in Water. A Remarkably Simple Procedure", Synthetic Communications 40(12), pp. 1730-1735; Lombardo L. et al., 1987, "An Improved Procedure for the Conversion of Carbonyl Compounds to Alpha, Beta-Unsaturated Carboxylic Acids", Synthetic Communications 8(7), pp. 463-468; Marx J. et al., 1983, "A Simple and Convenient Synthesis of Beta-Halo Ketones", Tetrahedron 39(9), pp. 1529-1531; Taillier C. et al., 2007, "Synthesis of 3-Oxooxa and 2-Oxoazacycloak-4-enes by Ring-Closing Metathesis. Application to the Synthesis of an Inhibitor of Cathepsin K", Tetrahedron 63(21), pp. 3589-3592

Compounds of Formula VII

Scheme 1:

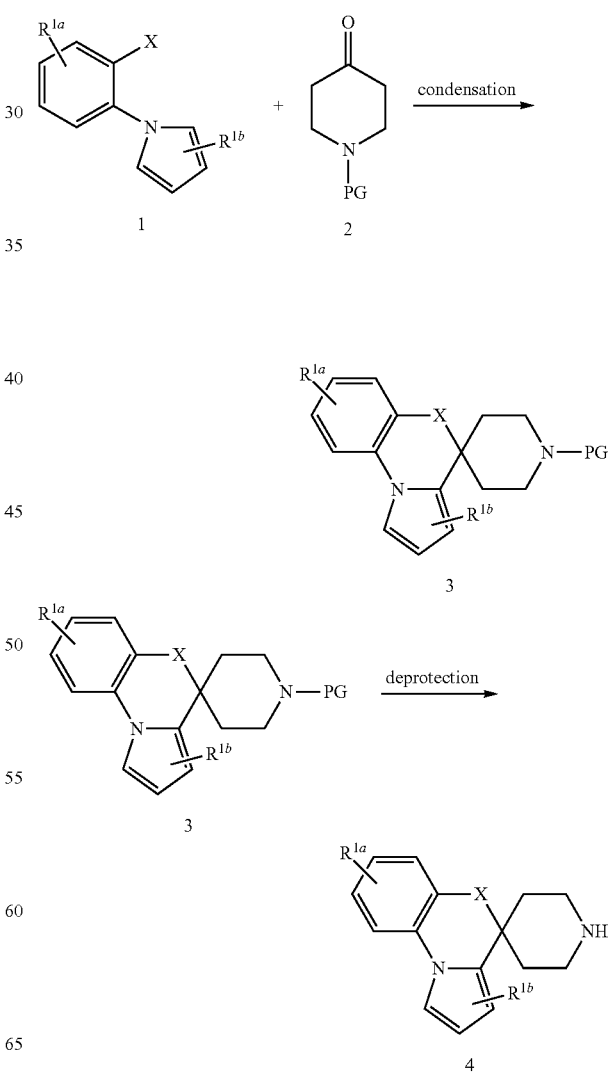

115

-continued

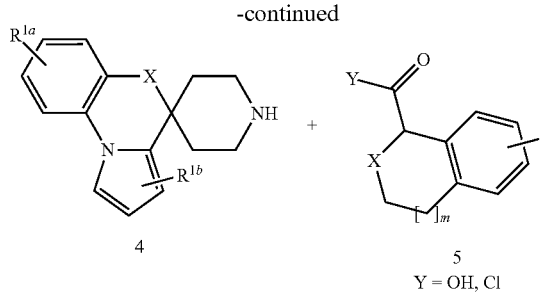

Y = OH, Cl

| acylation

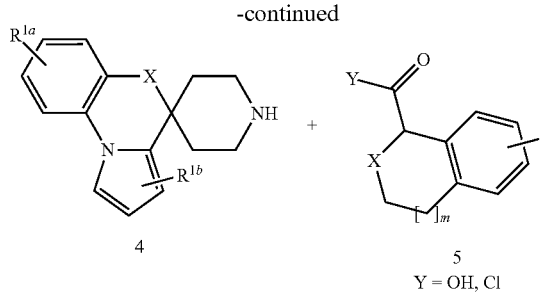

VII

Scheme 1 illustrates a synthesis of compounds of the formula VII. Commercially available (e.g. Sigma-Aldrich Corp., St. Louis, Mo.) analogs of the formula 1 can be condensed with an appropriately protected, commercially available 4-piperidone (e.g. Sigma-Aldrich Corp., St. Louis, Mo.) in the presence of a catalytic amount of acid (e.g. p-toluenesulfonic acid) while heating, as in the procedure described in Raines S. et al., 1976, Journal of Heterocyclic Chemistry 13(4), pp. 711-716. The protective groups can be removed accordingly (see Greene T. W. and Wuts P. G., 1999, Protective Groups in Organic Synthesis $3^{rd}$ edition, Wiley-Interscience, New York for removal of common protective groups) to form amines of formula 4. The amines of formula 4 can be coupled with commercially available (e.g. Sigma-Aldrich Corp., St. Louis, Mo.) acid chlorides in the presence of additional base (including but not limited to triethylamine, diisopropylethylamine, potassium or sodium tert-butoxide, potassium or sodium carbonate, and sodium hydride) of formula 5 to form the target amides of formula VII. Additionally, the target amides of formula VII can be prepared by using standard amide couplings (using but not limited to DCC(N,N'-Dicyclohexylcarbodiimide), EDC (1-Ethyl-3-(3-dimethylaminopropyl)carbodiimide), and HBTU (O-(Benzotriazol-1-yl)-N,N,N',N'-tetramethyluronium hexafluorophosphate)) with the amines of formula 4 and commercial carboxylic acids (e.g. Sigma-Aldrich Corp., St. Louis, Mo.) of formula 5.

Additionally the compounds of Formula VII can be synthesized by methods disclosed in: Greene T. W. and Wuts P. G., 1999, Protective Groups in Organic Synthesis, $3^{rd}$ edition, Wiley-Interscience, New York; Raines S. et al., 1976, "Mannich Reactions. Synthesis of 4,5-Dihydropyrrolo[1,2-a]quinoxalines, 2,3,4,5-Tetrahydro-1H-pyrrolo[1,2-a][1,4]diazapines and 5,6-Dihydropyrrolo[1,2-a][1,4]benzodiazapines", Journal of Heterocyclic Chemistry 13(4), pp. 711-716.

116

Compounds of Formula VIII

Scheme 1:

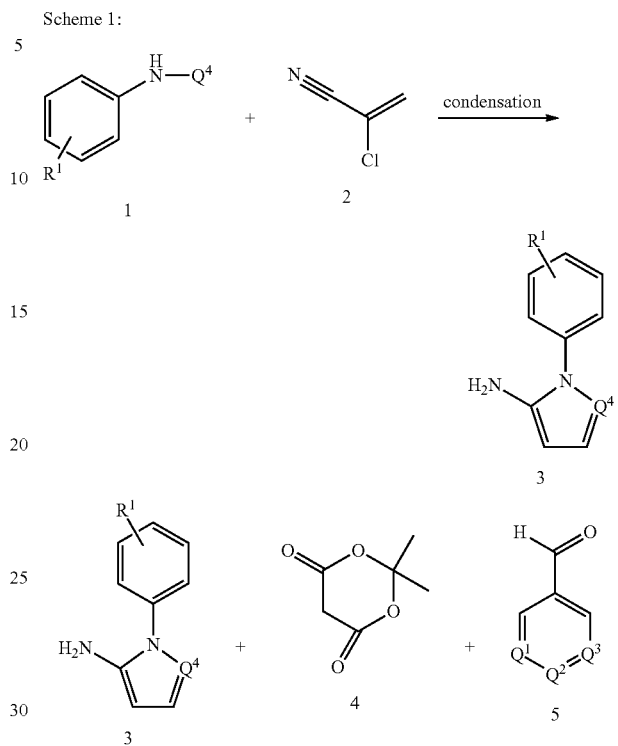

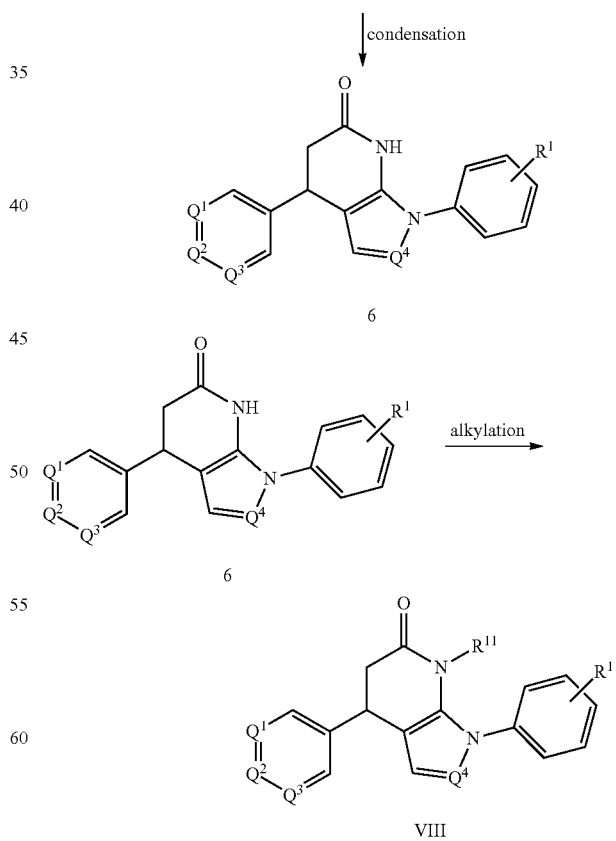

VIII

Scheme 1 illustrates a synthesis of amides of Formula VIII. In order to prepare the intermediates of formula 3, commercially available (e.g. Sigma-Aldrich Corp., St. Louis, Mo.) amines and phenyl hydrazines of formula 1 can be condensed with 2-chloroacrylonitrile 2 by heating in the presence of an excess of acid (e.g. sulfuric acid). There are a few non-limiting examples of this type of condensation in the current literature including the procedure described in Ege G. et al., 1982, Journal of Heterocyclic Chemistry 19(6), pp. 1265-1266. Intermediates of formula 3 can be condensed with commercially available (e.g. Sigma-Aldrich Corp., St. Louis, Mo.) Meldrum's acid 4 and commercially available (e.g. Sigma-Aldrich Corp., St. Louis, Mo.) aldehydes of formula 5 to prepare amides of formula 6 in the manner described in Quiroga J. et al., 1998, Journal of Heterocyclic Chemistry 35(2), pp. 409-412. The amides of formula 6 can be alkylated with a series of commercially available (e.g. Sigma-Aldrich Corp., St. Louis, Mo.) alkylating agents (e.g. alkyl halides, acyl chlorides, chlorosulfonates) in the presence of base (including but not limited to sodium or potassium hydroxide, potassium or sodium tert-butoxide, potassium or sodium carbonate, lithium diisopropylamide, and sodium hydride) to prepare the target compounds of formula VIII.

Additionally the compounds of Formula VIII can be synthesized by methods disclosed in: Ege G. et al., 1982, "Aminopyrazoles. III. Novel One-Flask Preparations of 1=Phenylpyrazol-3-amine", Journal of Heterocyclic Chemistry 19(6), pp. 1265-1266. Quiroga J. et al., 1998, "Reactions of 5-Amino-1-aryl-3-methylpyrazoles with Benzylidene Derivatives of Meldrum's Acid: Synthesis and Characterization of Pyrazolo[3,4-b]pyridinones", Journal of Heterocyclic Chemistry 35(2), pp. 409-412.

Compounds of Formula IX

Scheme 1:

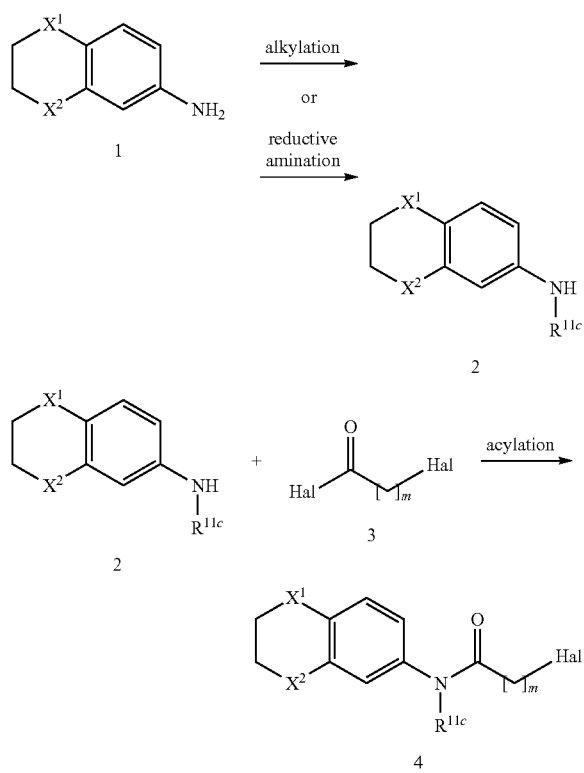

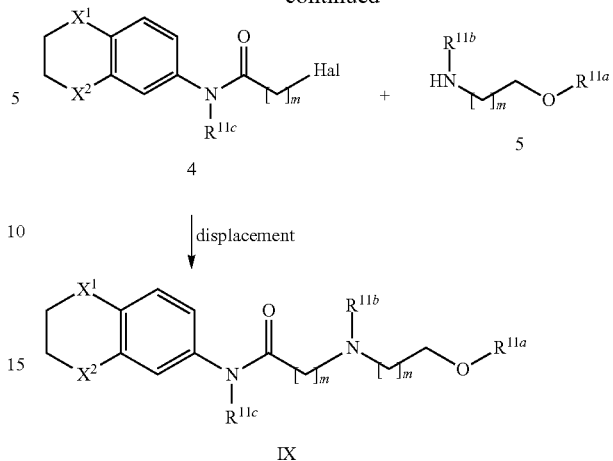

Scheme 2:

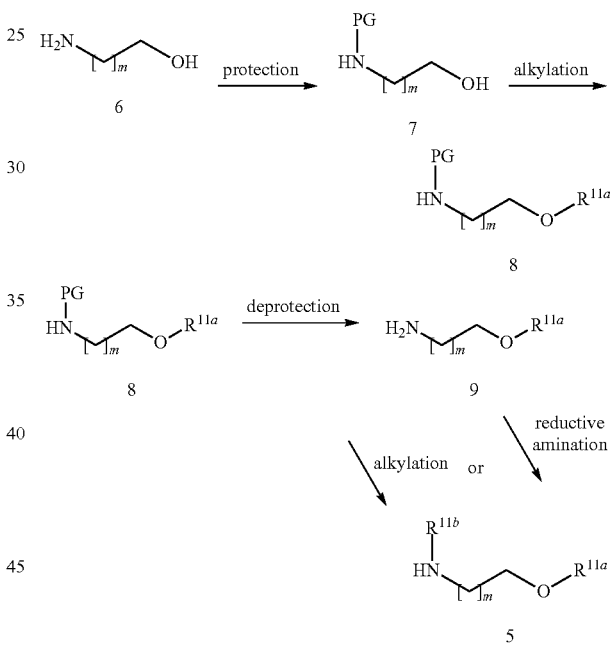

Scheme 1 illustrates a synthesis of amides of formula IX. Commercially available (e.g. Sigma-Aldrich Corp., St. Louis, Mo.) amines of FIG. 1 can be reacted with either alkylating agents (e.g. alkyl halides, acyl chlorides, chlorocarbamates, or chlorosulfonates) to prepare amines of FIG. 2. The amines of FIG. 2 can also be prepared by stirring the amines of FIG. 1 with commercially available aldehydes (e.g. alkyl halides, acyl chlorides, chlorosulfonates) in the presence of a reducing reagent (including but not limited to sodium borohydride, sodium cyanoborohydride, and sodium triacetoxyborohydride). The reductive amination procedure described in Levy D. E. et al., 2008, Bioorganic & Medicinal Chemistry Letters, 18(7), pp. 2395-2398 is commonly used. Amides of formula 4 can be prepared by acylating structures of formula 1 or formula 2 with commercially available halides (e.g. Sigma-Aldrich Corp., St. Louis, Mo.) of formula 3 in the presence of a hindered base (e.g. triethylamine, diisopropylethylamine, diphenylethylamine) as described in Renzi L. et al., 1956, Gazzetta Chimica Italiana 86, pp. 1362-1366. The target compounds of formula IX can be prepared by displacement with amines of formula 5 with the compounds of formula 4 in the presence of base including but not limited to triethylamine, diisopropylethylamine, potassium or sodium tert-butoxide, DMAP, potassium or sodium carbonate, or sodium hydride in the manner described in Demchenko A. M. et al., 2003, Russian Journal of Organic Chemistry 39(7), pp. 1025-1028. Amines of FIG. 5 can be purchased from commercial sources (e.g. Sigma-Aldrich Corp., St. Louis, Mo.) or prepared as illustrated in scheme 2.

Scheme 2 illustrates a general method for the synthesis of amines of formula 5. Commercially available (e.g. Sigma-Aldrich Corp., St. Louis, Mo.) amino-alcohols of formula 6 can be selectively protected on nitrogen with a suitable protective group (boc, benzyl, or CBZ) using common literature procedures. The oxygen present in the formula 7 intermediates can be alkylated with a suitable (e.g. alkyl halides, acyl chlorides, chlorocarbamates, or chlorosulfonates) and commercially available (e.g. Sigma-Aldrich Corp., St. Louis, Mo.) alkylating agents to form intermediates of formula 8. The protective groups can then be removed using standard methodology (see Greene T. W. and Wuts P. G., 1999, Protective Groups in Organic Synthesis, 3rd edition, Wiley-Interscience, New York) to prepare intermediates of formula 9. The amines of formula 5 can be prepared form the amines of formula 9 by either alkylation or reductive amination from commercial available reagents as previously described.

Additionally the compounds of Formula IX can be synthesized by methods disclosed in: Demchenko A. M. et al., 2003, "Synthesis of N5-(Arylcarbonyl)methyl Derivatives of Spinaceamine and 2-Azaspinacaceamine", Russian Journal of Organic Chemistry 39(7), pp. 1025-1028; Greene T. W. and Wuts P. G., 1999, Protective Groups in Organic Synthesis, 3$^{rd}$ edition, Wiley-Interscience, New York; Levy D. E. et al., 2008, "Aryl-indolyl Maleimides as Inhibitors of CaMKII-Delta. Part 2: SAR of the Amine Tether", Bioorganic & Medicinal Chemistry Letters, 18(7), pp. 2395-2398; and Renzi L. et al., 1956, "The 1,4-Benzodioxan Series V. Some Derivatives of 7-Aminobenzodioxan", Gazzetta Chimica Italiana 86, pp. 1362-1366.

The invention is further defined by reference to the following examples.

EXAMPLES

Example 1

5-(2-Chlorophenyl)-5-(6,7-dihydro-4H-thieno[3,2-c]pyridin-5-yl)-2,2-dimethylpentanoic acid, hydrochloride. (Compound Ia Hydrochloride)

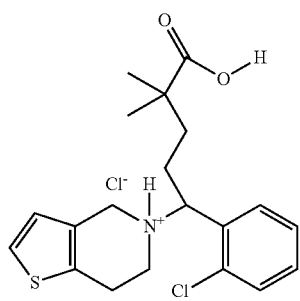 [SMILES: CC(C)(CCC(c1ccccc1Cl)[NH+]1CCc2sccc2C1)C(=O)O ; [Cl-]]

Step 1: Synthesis of 5-(2-chlorophenyl)-2,2-dimethyl-pent-4-enoic acid ethyl ester

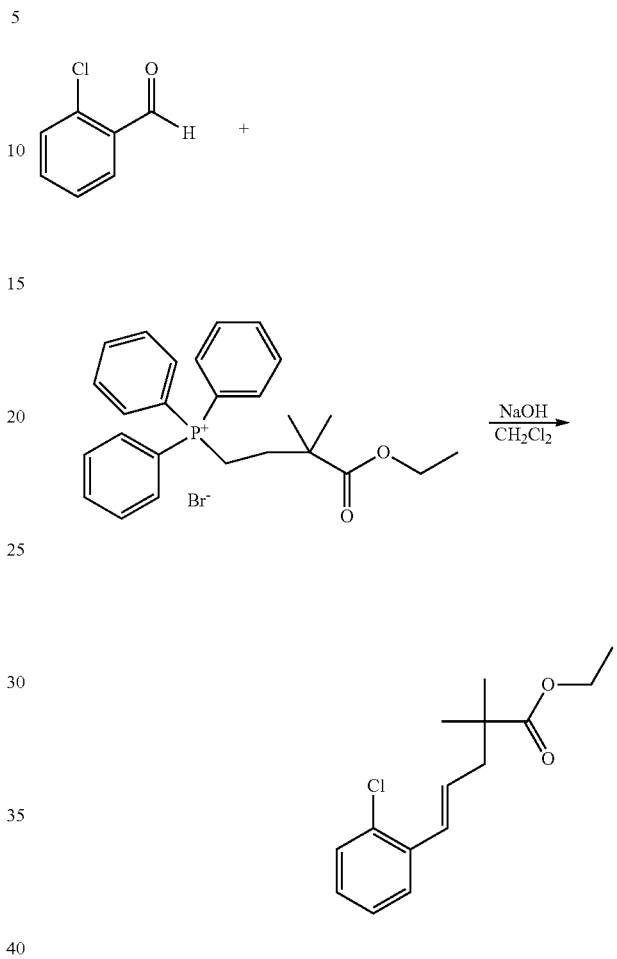

The phosphonium salt (15.0 g, 30.9 mmol) and 2-chlorobenzaldehyde (4.3 g, 30.6 mmol) were dissolved in dichloromethane (100 mL) and mixed vigorously. Sodium hydroxide solution (24 g, 50%) was added drop-wise over 5 minutes. The mixture was allowed to stir for 2 hours at room temperature. Water (100 mL) was added and the layers were separated. The dichloromethane fraction was dried over sodium sulfate, filtered, and concentrated. The remaining orange oil (8.3 g) was purified by column chromatography on silica gel (150 g), eluting with 5% ethyl acetate in heptane, to provide 5-(2-chlorophenyl)-2,2-dimethyl-pent-4-enoic acid ethyl ester (4.02 g, 55% yield) as a colorless oil that was a mixture of trans/cis isomers. $^1$H NMR (300 MHz, CDCl$_3$/TMS): δ=(major fraction; 60:40 mixture trans/cis isomer) 7.46 (dd, 0.6H, J=7.5, 1.5 Hz), 7.35 (dd, 0.4H, J=7.2, 1.5 Hz), 7.32-7.08 (m, 4H), 6.77 (d, 0.6H, j=15.5 Hz), 6.57 (d, 0.4H, j=11.7 Hz), 6.13 (dt, 0.6H, J=15.5, 7.5 Hz), 5.74 (dt, 0.4H, J=11.7, 7.5 Hz), 4.11 (m, 2H), 2.45 (m, 2H), 1.26-1.15 (m, 9H). $^{13}$C NMR (75 MHz, CDCl$_3$/TMS): δ=(major fraction; 60:40 mixture trans/cis isomer) 177.16, 177.12, 135.55, 133.82, 133.62, 132.60, 130.55, 129.53, 129.38, 129.31, 129.26, 129.15, 128.59, 128.15, 126.82, 126.75, 126.22, 60.52, 44.12, 42.79, 42.40, 38.66, 25.19, 25.08, 14.46, 14.34. MS (GC-EI): Calculated for C$_{15}$H$_{19}$O$_2$Cl (MH)$^+$: 267.1146. found 267.1143.

Step 2: Synthesis of 5-bromo-5-(2-chlorophenyl)-2,2-dimethylpentanoic acid ethyl ester

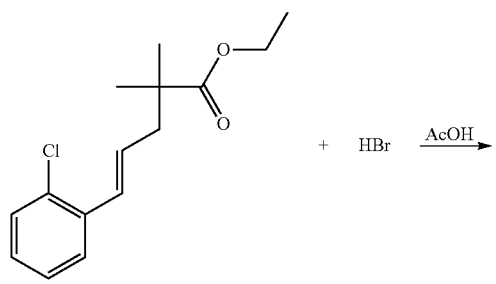

Step 3: Synthesis of 5-(2-chlorophenyl)-5-(6,7-dihydro-4H-thieno[3,2-c]pyridin-5-yl)-2,2-dimethylpentanoic acid ethyl ester. (Compound Ib)

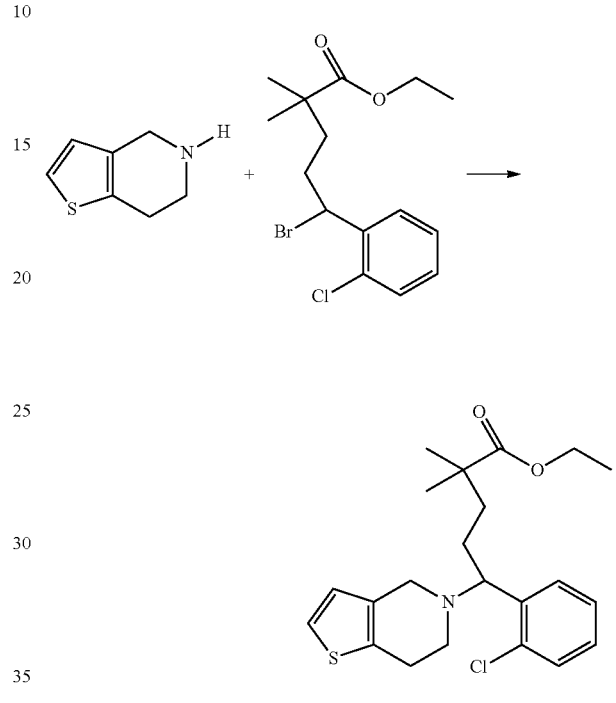

5-(2-Chlorophenyl)-2,2-dimethyl-pent-4-enoic acid ethyl ester (4.0 g, 15.0 mmol) was dissolved in acetic acid (40 mL). The flask was cooled in an ice-water bath and hydrogen bromide gas was bubbled through the solution for five hours as the flask warmed to room temperature. After five hours, the hydrogen bromide gas was stopped and the flask was stored in a freezer overnight (0° C.). After 20 hours at 0° C., the solution was poured in to a mixture of ice and water (200 g). The product was extracted with dichloromethane (2×75 mL). The dichloromethane fractions were combined and washed with saturated sodium bicarbonate solution (200 mL) and water (100 mL). The dichloromethane was dried over sodium sulfate, filtered, and concentrated. The remaining oil (5.13 g) was purified by flash column chromatography on silica gel (200 g), eluting with 5% ethyl acetate in heptane, to provide 5-bromo-5-(2-chlorophenyl)-2,2-dimethylpentanoic acid ethyl ester (3.31 g, 63.5% yield) as a colorless oil. $^1$H NMR (300 MHz, CDCl$_3$/TMS): δ=7.57 (dd, 1H, J=7.5, 1.5 Hz), 7.34-7.16 (m, 3H), 5.39 (t, 1H, J=7.5 Hz), 4.11 (q, 2H, J=7.2 Hz), 2.29-2.04 (m, 2H), 1.77 (dt, 1H, J=12.0, 4.5 Hz), 1.52 (dt, 1H, J=12.0, 4.2 Hz), 1.23 (t, 314, J=7.2 Hz), 1.18 (s, 3H), 1.17 (s, 3H). $^{13}$C NMR (75 MHz, CDCl$_3$/TMS): δ=177.05, 139.06, 132.67, 129.65, 129.31, 128.70, 127.43, 60.49, 50.25, 41.87, 38.78, 34.85, 25.64, 25.08, 14.42. HRMS (CI-TOF): Calculated for C$_{15}$H$_{20}$O$_2$BrCl (MH$^+$): 347. found 267.1146. (eliminates in MS).

4,5,6,7-Tetrahydrothieno[3,2-c]pyridine (0.65 g, 4.61 mmol) and 5-bromo-5-(2-chlorophenyl)-2,2-dimethylpentanoic acid ethyl ester (1.42 g, 4.08 mmol) were dissolved in THF (5 mL) and triethylamine (3 mL) with a few crystals of DMAP. The solution was heated overnight to 85° C. using an oil bath. After 20 hours, the solution was cooled to room temperature and sodium bicarbonate solution (20 mL) was added. After mixing, the product was extracted with dichloromethane (2×25 mL). The combined dichloromethane fractions were dried over sodium sulfate, filtered, and concentrated. The remaining yellow oil was purified by MPLC on a Companion Chromatography station using silica gel (40 g), eluting with a gradient of 100% heptane to 10% ethyl acetate over 20 minutes followed by a second gradient to 100% ethyl acetate at 40 minutes. The second broad fraction was collected and concentrated to produce 5-(2-chlorophenyl)-5-(6,7-dihydro-4H-thieno[3,2-c]pyridin-5-yl)-2,2-dimethylpentanoic acid ethyl ester (Compound Ib, 1.11 g, 67.2% yield) as a light, yellow oil. $^1$H NMR (300 MHz, CDCl$_3$/TMS): δ=7.46 (dd, 1H, J=7.80, 1.5 Hz), 7.38 (dd, 1H, J=7.80, 1.5 Hz), 7.30-7.15 (m, 2H), 7.04 (d, 1H, J=5.1 Hz), 6.70 (d, 1H, J=5.1 Hz), 4.18 (dd, 1H, J=8.7, 4.5 Hz), 4.08 (q, 2H, J=7.2 Hz), 3.79 (d, 1H, J=14.4 Hz), 3.45 (d, 1H, J=14.4 Hz), 2.90-2.62 (m, 4H), 2.0-1.85 (m, 1H), 1.82-1.68 (m, 1H), 1.49 (dt, 1H, J=13.5, 4.2 Hz), 1.30 (dt, 1H, J=13.5, 4.5 Hz), 1.20 (t, 3H, J=7.2 Hz), 1.10 (s, 6H). $^{13}$C NMR (75 MHz, CDCl$_3$/TMS): δ=177.59, 138.99, 134.95, 134.25, 133.59, 129.64, 129.11, 128.07, 126.73, 125.43, 122.61, 63.81, 60.38, 50.63, 47.95, 42.22, 36.43, 28.22, 26.17, 25.52, 25.38, 14.47. MS (MMI-TOF): Calculated for $C_{22}H_{28}NO_2ClS$ (MH$^+$): 406.1602. found 406.1576.

Step 4: 5-(2-Chlorophenyl)-5-(6,7-dihydro-4H-thieno[3,2-c]pyridin-5-yl)-2,2-dimethylpentanoic acid, hydrochloride

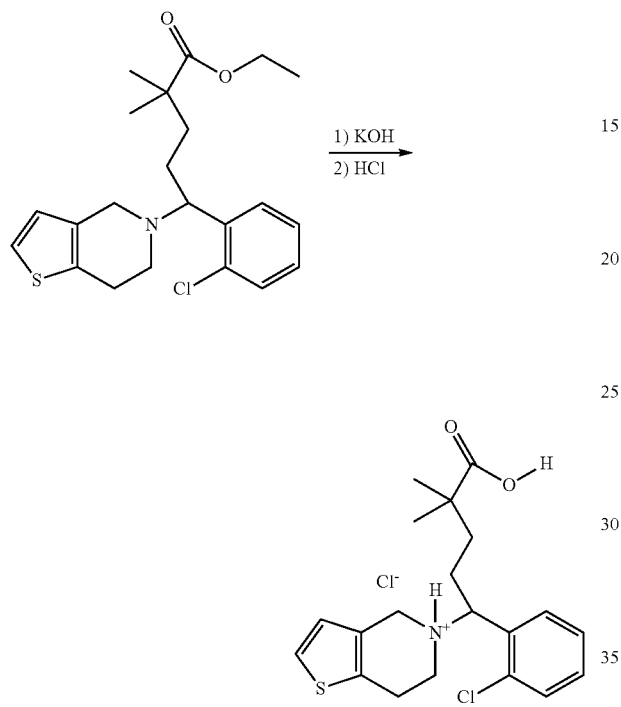

5-(2-Chlorophenyl)-5-(6,7-dihydro-4H-thieno[3,2-c]pyridin-5-yl)-2,2-dimethylpentanoic acid ethyl ester (1.0 g, 2.46 mmol) was dissolved in water (5 mL) and ethanol (5 mL) that contained potassium hydroxide (1 g). The mixture was heated to reflux for 6 hours. After cooling to room temperature, the ethanol was removed under reduced pressure. Water (25 mL) was added and the solution was acidified to pH=5 to 6 with concentrated hydrochloric acid. The product was extracted with dichloromethane (2×25 mL). The combined dichloromethane extracts were dried over sodium sulfate, filtered, and concentrated. The crude product (1.06 g) was purified by column chromatography on silica gel (20 g), eluting with heptane/ethyl acetate (1:1). The product containing fractions were combined, concentrated, and dissolved in dichloromethane (25 mL). The dichloromethane solution was acidified with hydrochloric acid (2N) in diethyl ether (6 mL). The solvents were removed under reduced pressure. The remaining solid was dried to a constant weight at room temperature under high vacuum to provide 5-(2-chlorophenyl)-5-(6,7-dihydro-4H-thieno[3,2-c]pyridin-5-yl)-2,2-dimethylpentanoic acid, hydrochloride salt (Compound Ia hydrochloride, 0.71 g, 69.6% yield) as a off-white solid. $^1$H NMR (300 MHz, DMS-d$_6$/TMS): δ=12.20 (br s, 1H), 11.83 (br s, 0.5H), 11.61 (br s, 0.5H), 8.10 (m, 1H), 7.77-7.41 (m, 4H), 6.97 (d, 1H, J=4.5 Hz), 6.81 (d, 1H, J=4.5 Hz), 4.90-4.70 (m, 1.5H), 4.42-4.37 (m, 0.5H), 4.11-4.01 (m, 1H), 3.90-3.80 (m, 0.5H), 3.51 (m, 0.5H), 3.20-2.84 (m, 2H), 2.37 (m, 1H), 2.14 (m, 1H), 1.28 (m, 1H), 1.04 (s, 3H), 1.02 (s, 3H), 0.90 (m, 1H). (mixture of rotational isomers). $^{13}$C NMR (75 MHz, DMS-d$_6$/TMS): δ=177.64, 134.50, 131.23, 130.89, 129.72, 129.38, 128.02, 127.33, 125.06, 124.68, 64.62, 63.52, 54.63, 49.73, 48.54, 47.93, 47.20, 40.72, 35.21, 25.90 (d), 24.78, 24.37, 21.79, 21.31 (d), 14.99. MS (MMI-TOF): Calculated for $C_{20}H_{25}NO_2Cl_2S$ (MH$^+$): 378.1289. found 378.1271. CHN analysis: Calculated; 57.97; C, 6.08; H, 3.38; N, 17.11; Cl. Found; 56.07; C, 6.25; H, 3.12; N, 18.55; Cl, Best Fit for CHN Data: $C_{20}H_{25}Cl_2NO_2S+0.65H_2O+0.05$ HCl Example 2

6-(2-Chlorophenyl)-6-(6,7-dihydro-4H-thieno[3,2-c]pyridin-5-yl)-2,2-dimethylhexanoic acid, hydrochloride. (Compound Ic Hydrochloride)

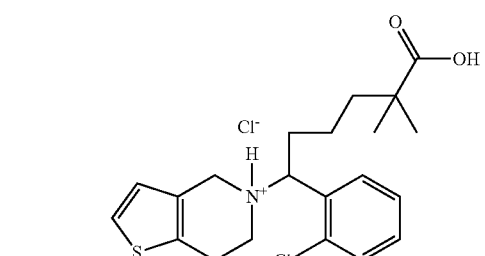

Step 1: Synthesis of (4-Ethoxycarbonyl-4-methyl)triphenylphosphonium bromide

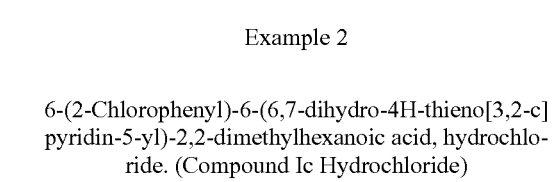

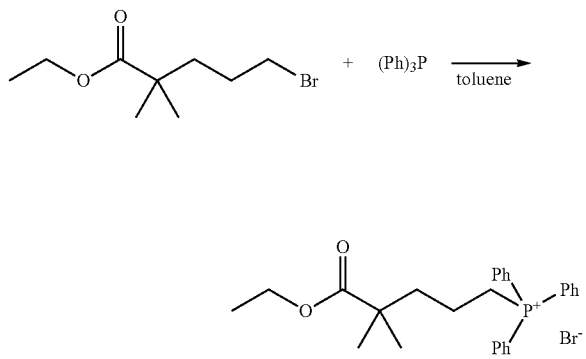 [SMILES: CCOC(=O)C(C)(C)CCCBr ; "(Ph)3P" ; CCOC(=O)C(C)(C)CCC[P+](c1ccccc1)(c1ccccc1)c1ccccc1 ; [Br-]]

Triphenylphosphine (6.6 g, 25.3 mmoL) was added to a solution of 5-bromo-2,2-dimethylpentanoic acid ethyl ester (6 g, 25.3 mmoL) in toluene (55 mL). The solution was heated to reflux (oil bath 122° C.) for 24 h. The toluene was evaporated and the residue was washed with heptane (20 mL) and diethyl ether (20 mL). The remaining solid was dried under high vacuum to provide (4-ethoxycarbonyl-4-methyl)triphenylphosphonium bromide (11 g, 87.3%) as a off-white powder (mp. 245-250° C.). $^1$H NMR (Field: 300 MHz, Solvent: CDCl$_3$/TMS) δ (ppm): 7.94-7.63 (m, 15H), 3.99 (q, 2H, J=6.9 Hz), 3.75 (m, 2H), 1.91 (m, 2H), 1.61 (m, 2H), 1.10 (m, 9H). $^{13}$C NMR (Field: 75 MHz, Solvent: CDCl$_3$/TMS) δ (ppm): 176.79, 134.81, 133.29 (d, J=10 Hz), 130.22 (d, J=12 Hz), 117.79 (d, J=85 Hz), 60.14, 41.94, 40.60 (d, J=16 Hz), 24.95, 22.98 (d, J=50 Hz), 18.37, 14.09. MS (FIA-ESI-TOFM): Calculated for C$_{27}$H$_{32}$BrOP (MH)$^+$: 419.2134. found 419.2138.

Step 2: Synthesis of 6-(2-chlorophenyl)-2,2-dimethylhex-5-enoic acid ethyl ester

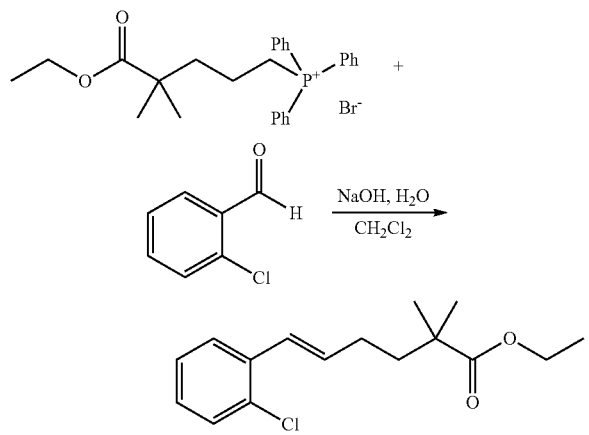

(4-Ethoxycarbonyl-4-methyl)triphenylphosphonium bromide (7 g, 14 mmol) and 2-chlorobenzaldehyde (1.96 g, 14 mmol) in CH$_2$Cl$_2$ (21 mL) were stirred as vigorously as possible and 50% NaOH solution (8 mL) was added drop-wise. After the process, continue stirred for 1.5 h. The mixture was transferred to a separator and dichloromethane (70 mL) and water (70 mL) were added. After mixing the aqueous layer was removed and was extracted with dichloromethane (3×70 mL). The combined organic extracts were washed with brine (50 mL), dried over Na$_2$SO$_4$, concentrated, and purified by column chromatography (silica gel, ethyl acetate/heptane=1/10 to 1/6) to provide 6-(2-chlorophenyl)-2,2-dimethylhex-5-enoic acid ethyl ester (2.81 g, 72.2%) as a yellow oil. $^1$H NMR (Field: 300 MHz, Solvent: CDCl$_3$/TMS) δ (ppm): 7.35-7.08 (m, 4H), 6.46 (d, 1H, J=11.7 Hz), 5.76-5.68 (m, 1H), 4.04 (q, 2H, J=7.2 Hz), 2.23-2.08 (m, 2H), 1.74-1.61 (m, 2H), 1.20 (t, 3H, J=7.2 Hz), 1.13 (s, 6H). (mixture of cis and trans isomers, the major/cis isomer is listed). $^{13}$C NMR (Field: 75 MHz, Solvent: CDCl$_3$/TMS) δ (ppm): 177.34, 135.54, 133.49, 130.34, 129.30, 128.03, 126.40, 126.14, 60.32, 42.13, 40.53, 29.06, 25.33, 14.30. (mixture of cis and trans isomers, the major/cis isomer is listed). MS (GC-CI): Calculated for C$_{16}$H$_{21}$ClO$_2$ (MH)$^+$: 281.1303. found 282.1324

Step 3: Synthesis of 6-bromo-6-(2-chlorophenyl)-2,2-dimethylhexanoic acid ethyl ester

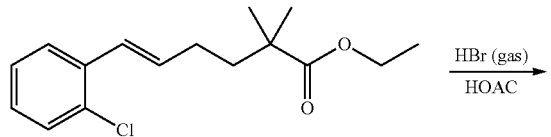

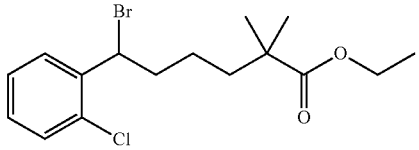

6-(2-Chlorophenyl)-2,2-dimethylhex-5-enoic acid ethyl ester (15 g, 53.6 mmol) was dissolved in glacial acetic acid (150 mL). The solution was cooled in an ice-bath (ca. 15° C.) while dry hydrogen bromide was passed into the solution for 8 h. The reaction mixture was poured into ice-water (250 mL) and extracted with ethyl acetate (3×100 mL). The combined organic extracts were washed with saturated NaHCO$_3$ solution (100 mL), dried over Na$_2$SO$_4$, and concentrated under reduced pressure. The crude product (18 g) was purified by column chromatography (silica gel, ethyl acetate/heptane=1/20 to 1/10) to provide 6-bromo-6-(2-chlorophenyl)-2,2-dimethylhexanoic acid ethyl ester (15.5 g, 80.14%) as a yellow oil. $^1$H NMR (Field: 300 MHz, Solvent: CDCl$_3$/TMS) δ (ppm): 7.58 (d, 1H, J=7.8 Hz), 7.34 (t, 1H, J=7.8 Hz), 7.27 (d, 1H, J=7.2 Hz), 7.21 (t, 1H, J=7.2 Hz), 5.45 (t, 1H, J=8.1 Hz), 4.09 (q, 2H, J=6.9 Hz), 2.19 (m, 2H), 1.55 (m, 2H), 1.24 (t, 3H, J=6.9 Hz), 1.14 (s, 6H). $^{13}$C NMR (Field: 75 MHz, Solvent: CDCl$_3$/TMS) δ (ppm): 177.45, 139.25, 132.64, 129.64, 129.27, 128.75, 127.43, 60.36, 49.97, 42.17, 39.84, 39.51, 25.41, 25.20, 23.67, 14.43. MS (GC-CI): Calculated for C$_{16}$H$_{22}$BrClO$_2$ (MH)$^+$: 361.0564. found 361.0547.

Step 4: Synthesis of 6-(2-chlorophenyl)-6-(6,7-dihydro-4H-thieno[3,2-c]pyridin-5-yl)-2,2-dimethylhexanoic acid ethyl ester. (Compound Ie)

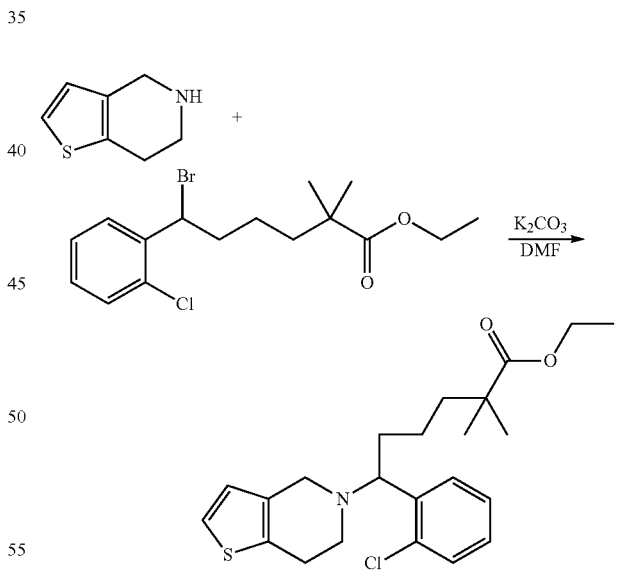

4,5,6,7-tetrahydro-thieno[3,2-c]pyridine hydrochloride (2.5 g, 8.8 mmol) was mixed with sodium hydroxide (2.7 g) in water (80 mL). The corresponding free amine was extracted with dichloromethane (3×20 mL), which was dried over Na$_2$SO$_4$, filtered, and concentrated to provide 4,5,6,7-tetrahydro-thieno[3,2-c]pyridine (1.22 g). 4,5,6,7-Tetrahydro-thieno[3,2-c]pyridine (1.22 g, 8.8 mmol) and 6-bromo-6-(2-chlorophenyl)-2,2-dimethylhexanoic acid ethyl ester (2.5 g, 8.8 mmol) were combined in DMF (90 mL) and potassium carbonate (1.82 g, 13.2 mmol) was added. The mixture was heated to 70° C. for 1 h and then 60° C. overnight. The mixture was cooled to room temperature and water (100 mL) was added. The product was extracted with diethyl ether (3×150 mL). The combined ether extracts were washed with water (3×80 mL), dried over $Na_2SO_4$, filtered, and concentrated under reduced pressure. The crude product was purified by column chromatography (silica gel, ethyl acetate/heptane=1/10) to provide 6-(2-chlorophenyl)-6-(6,7-dihydro-4H-thieno[3,2-c]pyridin-5-yl)-2,2-dimethylhexanoic acid ethyl ester (Compound Ie, 1.26 g, 42.04%) as a yellow oil. $^1$H NMR (Field: 300 MHz, Solvent: $CDCl_3$/TMS) δ (ppm): 7.49 (d, 1H, J=7.8 Hz), 7.37 (d, 1H, J=8.1 Hz), 7.26-7.14 (m, 2H), 7.05 (d, 1H, J=5.4 Hz), 6.70 (d, 1H, J=5.4 Hz), 4.19 (dd, 1H, J=8.7, 4.5 Hz), 4.02 (q, 2H, J=7.2 Hz), 3.81 (d, 1H, J=14.4 Hz), 3.47 (d, 1H, J=14.4 Hz), 2.88-2.66 (m, 4H), 1.95-1.74 (m, 2H), 1.52-1.46 (m, 2H), 1.13 (t, 3H, J=7.2 Hz), 1.15-1.08 (m, 2H), 1.07 (s, 6H). $^{13}$C NMR (Field: 75 MHz, Solvent: $CDCl_3$/TMS) δ (ppm): 177.63, 139.16, 134.91, 134.21, 133.55, 129.53, 129.03, 128.03, 126.81, 124.46, 122.65, 63.47, 60.33, 50.73, 48.04, 42.31, 41.04, 33.48, 26.14, 25.58, 25.12, 21.07, 14.44. MS (GC-CI): Calculated for $C_{23}H_{30}ClNO2S$ $(MH)^+$: 420.1758. found 420.1725.

Step 5: Synthesis of 6-(2-chlorophenyl)-6-(6,7-dihydro-4H-thieno[3,2-c]pyridin-5-yl)-2,2-dimethylhexanoic acid, hydrochloride 6-(2-Chlorophenyl)-6-(6,7-dihydro-4H-thieno[3,2-c]pyridin-5-yl)-2,2-dimethylhexanoic acid ethyl ester (2.5 g, 7.33 mmol) was added to a solution of ethanol (100 mL) and sodium hydroxide (1.8 g, 43.8 mmol) in water (32 mL). The mixture was heated to reflux for 6.5 hours. The solution was evaporated under reduced pressure and water (100 mL) was added to the residue. The water solution was extracted with ethyl acetate/heptane=1/10 (100 mL). The organic layers were discarded and the aqueous solution was adjusted with 10 N hydrochloric acid solution to pH=6. The product was extracted with dichloromethane (3×100 mL), which was dried over $Na_2SO_4$, filtered, and concentrated under reduced pressure to provide 6-(2-chlorophenyl)-6-(6,7-dihydro-4H-thieno[3,2-c]pyridin-5-yl)-2,2-dimethylhexanoic acid (1.6 g, 68.7%) as a yellow oil. 6-(2-Chlorophenyl)-6-(6,7-dihydro-4H-thieno[3,2-c]pyridin-5-yl)-2,2-dimethylhexanoic acid (3.97 g, 10.2 mmol) was dissolved in 36% HCl (0.95 mL) and water (59 mL). After stirring for 10 minutes, the aqueous solution was extracted with ethyl acetate/heptane (20/80, 110 mL). The organic extract was discarded and the aqueous fraction was freeze-dried to provide 6-(2-chlorophenyl)-6-(6,7-dihydro-4H-thieno[3,2-c]pyridin-5-yl)-2,2-dimethylhexanoic acid, hydrochloride salt (Compound Ic hydrochloride, 3.48 g, 79.8% yield, 99.7% purity by HPLC) as a white solid melting at 136-138° C. $^1$H NMR (Field: 300 MHz, Solvent: $CDCl_3$/TMS) δ (ppm): 7.69 (s, 1H), 7.47-7.38 (m, 3H), 7.21 (d, 1H, J=3.9 Hz), 6.71 (d, 1H, J=3.9 Hz), 4.92 (m, 1H), 4.31-4.15 (m, 2H), 3.15-3.05 (m, 4H), 2.24-2.14 (m, 2H), 1.47-1.36 (m, 2H), 1.08-1.06 (m, 2H), 0.99 (s, 6H). (mixture of rotation isomers in NMR). $^{13}$C NMR (Field: 75 MHz, Solvent: $CDCl_3$/TMS) δ (ppm): 181.10, 137.13, 132.80, 132.77, 132.04, 131.79, 130.48, 129.73, 128.73, 126.62, 126.14, 66.14, 51.52, 42.87, 40.92, 32.04, 25.88, 25.47, 23.45, 22.50. MS (FIA-ESI-TOF): Calculated for $C_{21}H_{26}ClNO2S$ $(MH)^+$: 392.1446. found 392.1453. CHN analysis: Calculated; 58.87; C, 6.35; H, 3.27; N, 16.55; Cl, 7.48; S. found; 57.80; C, 6.44; H, 3.15; N, 16.14; Cl, 7.15; S, Best fit for CHN Data: $C_{21}H_{27}Cl_2NO_2S+0.55H_2O$ Example 3

1 2-(2-Chlorophenyl)-2-(6,7-dihydro-4H-thieno[3,2-c]pyridine-5-yl)ethanol. (Compound Is)

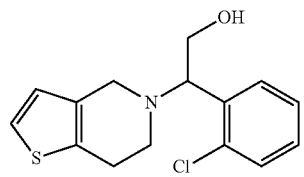 [SMILES: OCC(c1ccccc1Cl)N1CCc2sccc2C1]

To a solution of clopidogrel hydrosulfate (10 g, 23.8 mmol) in deionized water (300 mL) was added sodium bicarbonate (4 g, 47.6 mmol) in small portions. After mixing, t-butyl methyl ether (200 mL) was added and the solution was stirred for one hour. The layers were separated and the aqueous layer was extracted again with t-butyl methyl ether (2×100 mL). The combined organic extracts were washed with brine (100 mL), dried over sodium sulfate, filtered, and concentrated under reduced pressure. The remaining brown oil was dried under high vacuum to a constant weight to afford clopidogrel free base (8.24 g, 106% yield which includes a trace of MTBE). While under a nitrogen atmosphere, a solution of lithium aluminum hydride (0.46 g, 12 mmol) in anhydrous diethyl ether (8 mL) was added drop wise to a solution of clopidogrel free base (3.22 g, 10 mmol) in anhydrous diethyl ether (4 mL). The lithium aluminum hydride was added at a rate to keep the ether refluxing gently. The addition was completed and the mixture was stirred at reflux temperature for an additional 30 minutes. After 30 minutes, the solution was cooled to 0° C. in an ice/water bath. The excess $LiAlH_4$ was decomposed with ethyl acetate (2 mL, added slowly), followed by 6N HCl solution (20 mL added slowly with vigorous stirring). The mixture was transferred to a separatory funnel. The aqueous fraction was separated and extracted with ether (30 mL, which was discarded). The aqueous fraction was adjusted to pH=7 with 6 N NaOH solution (20 mL) and extracted with ether (4×15 mL). The combined ether extracts were washed with brine (20 mL), dried over $MgSO_4$, and concentrated under vacuum to yield 2-(2-chlorophenyl)-2-(6,7-dihydro-4H-thieno[3,2-c]pyridine-5-yl)ethanol (Compound Is, 2.12 g, 75.4% yield) as a white solid. $^1$H NMR (Field: 300 MHz, Solvent: $CDCl_3$/TMS) δ (ppm): 7.45-7.40 (m, 2H), 7.23 (m, 2H), 7.04 (d, 1H, J=5.1 Hz), 6.70 (d, 1H, J=5.1 Hz), 4.47 (dd, 1H, J=6.9, 5.8 Hz), 3.97-3.91 (m, 1H), 3.81-3.74 (m, 2H), 3.62 (d, 1H, J=14.4 Hz), 3.01-2.95 (m, 1H), 2.84 (m, 2H) 2.76-2.68 (m, 1H). $^{13}$C NMR (Field: 75 MHz, Solvent: $CDCl_3$/TMS) δ (ppm): 135.31, 134.92, 133.81, 133.26, 130.03, 129.35, 128.85, 126.72, 125.34, 122.82, 64.53, 61.55, 50.20, 47.67, 26.15. MS (FIR, DIP-CI): Calculated for $C_{15}H_{17}ClNOS$ $(MH)^+$: 294.0714. found 294.0715

Example 4

4-(2-Chlorophenyl)-4-(6,7-dihydro-4H-thieno[3,2-c]pyridine-5-yl)butan-1-ol. (Compound Id)

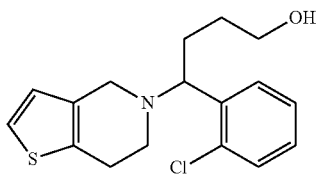 [SMILES: OCCCC(c1ccccc1Cl)N1CCc2sccc2C1]

Step 1. Synthesis of 5-[2-chloro-1-(2-chlorophenyl)ethyl]-4,5,6,7-tetrahydrothieno[3,2-c]pyridine

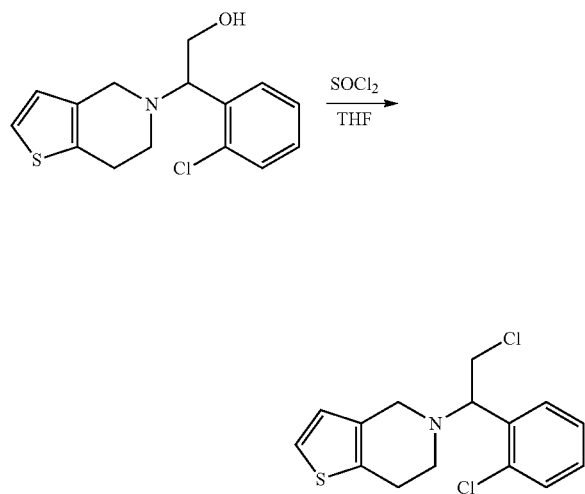

To a solution of 2-(2-chlorophenyl)-2-(6,7-dihydro-4H-thieno[3,2-c]pyridine-5-yl)ethanol (9.7 g, 33.1 mmol) in THF (280 mL) was added thionyl chloride (7.9 g, 66.2 mmol) drop-wise. The solution was stirred at room temperature for 1.5 h (monitored by TLC). The excess thionyl chloride was evaporated under reduced pressure. The residue was dissolved in $CH_2Cl_2$(200 mL), washed with saturated $NaHCO_3$ solution (to pH=7), dried over $Na_2SO_4$, and concentrated under vacuum to provide 5-[2-chloro-1-(2-chlorophenyl)ethyl]-4,5,6,7-tetrahydrothieno[3,2-c]pyridine (10.1 g, 98.1%) as a light yellow oil. $^1$H NMR (Field: 300 MHz, Solvent: $CDCl_3$/TMS) δ (ppm): 7.63 (d, J=6.3 Hz, 1H), 7.36-7.22 (m, 3H), 7.05 (d, J=5.1 Hz, 1H), 6.70 (d, J=5.1 Hz, 1H), 5.62 (t, J=6.3, 1H), 3.71 (s, 2H), 3.10-3.07 (m, 2H), 2.95-2.91 (m, 2H), 2.86-2.84 (m, 2H). $^{13}$C NMR (Field: 75 MHz, Solvent: $CDCl_3$/TMS) δ (ppm): 137.72, 133.43, 132.79, 129.56, 129.47, 129.00, 127.43, 125.31, 122.70, 64.37, 56.60, 53.24, 50.98, 25.24. MS (HR, GC-CI): Calculated for $C_{15}H_{15}Cl_2NS$ $(MH)^+$: 312.0375. found 312.0349.

Step 2. Synthesis of 2-[2-chlorophenyl)-2-(6,7-dihydro-4H-thieno[3,2-c]pyridin-5-yl)ethyl]malonic acid diethyl ester

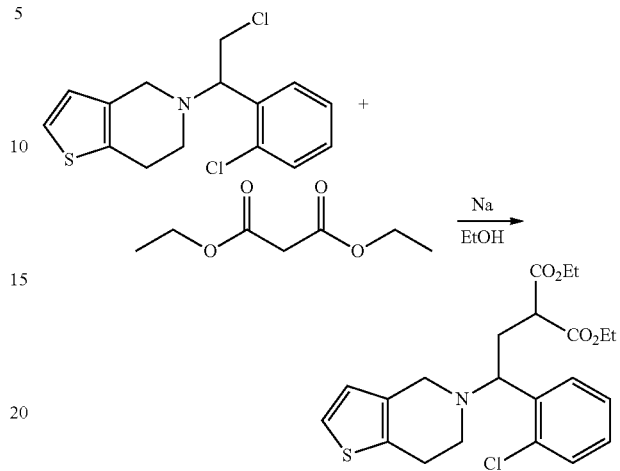

To ethanol (38 mL) under a nitrogen atmosphere was added sodium (1.03 g, 44.9 mmol) in small pieces. The resultant sodium ethoxide solution was cooled and diethyl malonate (7.4 g, 46.2 mmol) was added drop wise. The reaction mixture stirred for 5 minutes at room temperature and then 5-[2-chloro-1-(2-chlorophenyl)ethyl]-4,5,6,7-tetrahydrothieno[3,2-c]pyridine (14 g, 44.9 mmol) in ethanol (30 mL) was added drop wise. The mixture was heated to reflux for 2 hours. After two hours, the solvent was removed under reduced pressure and water (100 mL) was added. The product was extracted with $CH_2Cl_2$ (3×200 mL) and the combined extracts were dried over $Na_2SO_4$, filtered, and concentrated under reduced pressure to provide crude 2-[2-chlorophenyl)-2-(6,7-dihydro-4H-thieno[3,2-c]pyridin-5-yl)ethyl]malonic acid diethyl ester (17 g, 86.7%) as a brown oil. $^1$H NMR (Field: 300 MHz, Solvent: $CDCl_3$/TMS) δ (ppm): 7.36 (d, J=7.8 Hz, 1H), 7.15 (m, 3H), 7.02 (d, J=5.1 Hz, 1H), 6.69 (d, J=5.1 Hz, 1H), 4.45-4.37 (m, 1H), 3.96-3.74 (m, 5H), 3.6 (d, J=14.4 Hz, 1H), 3.48 (d, J=14.4 Hz, 1H), 3.00-2.95 (m, 1H), 2.81-2.60 (m, 4H), 1.05 (t, J=7.2 Hz, 3H), 0.94 (t, J=7.2 Hz, 3H). $^{13}$C NMR (Field: 75 MHz, Solvent: $CDCl_3$/TMS) δ (ppm): 168.01, 167.77, 138.09, 134.28, 133.92, 133.34, 129.81, 127.98, 127.76, 126.88, 125.05, 122.38, 61.57, 61.50, 61.23, 56.56, 53.25, 50.72, 40.02, 25.21, 13.88, 13.81. MS (HR, GC-CI): Calculated for $C_{22}H_{27}ClNO_4S$ $(MH)^+$: 436.1344. found 436.1318

Step 3. Synthesis of 4-(2-chlorophenyl)-4-(6,7-dihydro-4H-thieno[3,2-c]pyridine-5-tl)butyric acid ethyl ester. (Compound If)

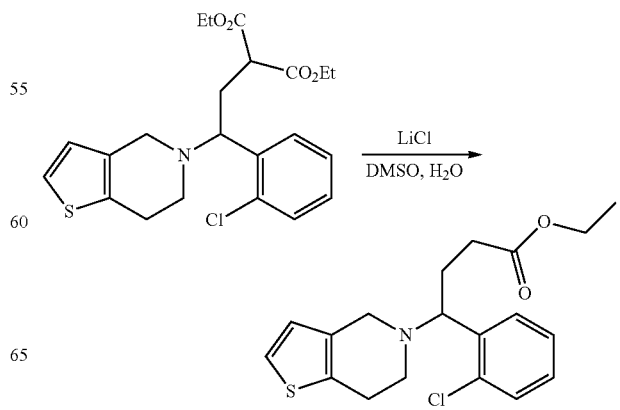

A mixture of 2-[2-chlorophenyl)-2-(6,7-dihydro-4H-thieno[3,2-c]pyridin-5-yl)ethyl]malonic acid diethyl ester (17.5 g, 40.2 mmol) and lithium chloride (6.8 g, 161.9 mmol) in DMSO (230 mL) and water (3.9 mL) was heated to reflux (oil bath, ca. 190° C.) with stirring for 4 hours. The reaction mixture was cooled to room temperature, diluted with water (150 mL) and extracted with ethyl acetate (3×150 mL). The combined organic extracts were washed with water (3×80 mL), brine (80 mL), and dried over MgSO$_4$. The product was filtered, concentrated under reduced pressure, and dried under high vacuum. The procedure generated a crude product (15.4 g). The crude product was purified by column chromatography (silica gel, ethyl acetate/heptane 1:3) to provide 4-(2-chlorophenyl)-4-(6,7-dihydro-4H-thieno[3,2-c]pyridine-5-tl)butyric acid ethyl ester (Compound If, 11.1 g, 76.1% yield) as a light yellow oil. $^1$H NMR (Field: 300 MHz, Solvent: CDCl$_3$/TMS) δ (ppm): 7.34 (d, J=7.8 Hz, 1H), 7.24-7.10 (m, 3H), 7.03 (d, J=5.1 Hz, 1H), 6.71 (d, J=5.1 Hz, 1H), 4.15-4.02 (m, 1H), 3.92 (q, J=7.2 Hz, 2H), 3.67 (d, J=14.4 Hz, 1H), 3.51 (d, J=14.4 Hz, 1H), 2.97-2.80 (m, 4H), 2.75-2.53 (m, 4H), 1.06 (t, J=7.2 Hz, 3H). $^{13}$C NMR (Field: 75 MHz, Solvent: CDCl$_3$/TMS) δ (ppm): 172.25, 139.97, 134.09, 133.99, 133.46, 129.77, 127.76, 127.60, 127.01, 125.22, 122.46, 62.68, 60.32, 53.43, 51.14, 38.41, 36.49, 25.59, 14.20. MS (HR, GC-CI): Calcd. C$_{19}$H$_{23}$ClNO$_2$S (MH)$^+$ 364.1133. found 364.1152.

Step 4. Synthesis of 4-(2-chlorophenyl)-4-(6,7-dihydro-4H-thieno[3,2-c]pyridine-5-yl)butan-1-ol

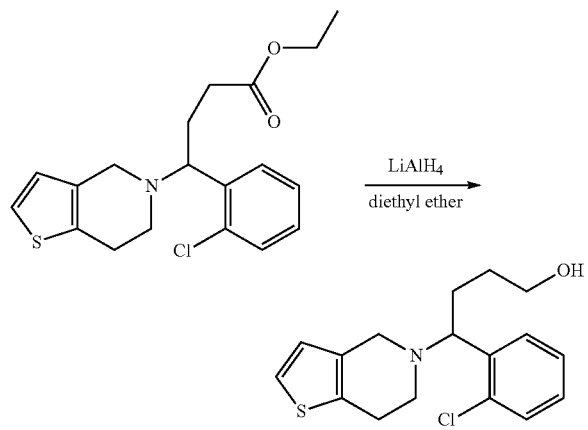

4-(2-Chlorophenyl)-4-(6,7-dihydro-4H-thieno[3,2-c]pyridine-5-tl)butyric acid ethyl ester (1.0 g, 2.75 mmol) in anhydrous diethyl ether (3 mL) was added drop wise, under a nitrogen atmosphere, to a solution of lithium aluminum hydride (0.13 g, 3.31 mmol) in anhydrous diethyl ether (7 mL). The lithium aluminum hydride was added at a rate that kept the ether at a gentle reflux. When the addition was completed, the mixture was stirred at reflux for an additional 30 minutes. The reaction was cooled to 0° C. with ice-water bath. The excess LiAlH$_4$ was decomposed with ethyl acetate (1 mL, added slowly). This was followed by 6 N HCl solution (10 mL) added slowly with vigorous stirring. The water was separated and extracted with ether (30 mL, later discarded). The aqueous portion was neutralized with 6 N NaOH solution (15 mL, to pH=7) and extracted with ether (3×20 mL). The combined organic layers were washed with brine (15 mL), dried over MgSO$_4$, and concentrated under reduced pressure to provide 4-(2-chlorophenyl)-4-(6,7-dihydro-4H-thieno[3,2-c]pyridine-5-yl)butan-1-ol (Compound Id, 0.77 g, 87.2% yield) as a yellow, viscous oil. $^1$H NMR (Field: 300 MHz, Solvent: CDCl$_3$/TMS) δ (ppm): 7.36 (d, 1H, J=7.5 Hz), 7.25-7.12 (m, 3H), 7.07 (d, 1H, J=5.1 Hz), 6.72 (d, 1H, J=5.1 Hz), 6.55 (br s, 1H), 3.82-3.54 (m, 5H), 3.2-3.13 (m, 1H), 2.95 (br t, 2H, J=4.8 Hz), 2.82-2.75 (m, 1H), 2.70-2.60 (m, 2H), 2.06-1.90 (m, 2H). $^{13}$C NMR (Field: 75 MHz, Solvent: CDCl$_3$/TMS) δ (ppm): 142.33, 133.14, 133.06, 132.63, 129.70, 127.75, 127.68, 127.28, 125.16, 123.11, 63.80, 62.19, 53.41, 51.01, 39.78, 39.43, 24.88. MS (HR, DIP-CI): Calculated for C$_{17}$H$_{21}$ClNOS (MH)$^+$: 322.1027. found 322.1006.

Example 5

1-[(2-Chlorophenyl)-(6,7-dihydro-4H-thieno[3,2-c]pyridin-5-yl)-methyl]-1H-benzotriazole. (Compound IVa)

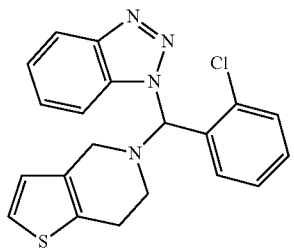 [SMILES: Clc1ccccc1C(N1CCc2sccc2C1)n1nnc2ccccc21]

4,5,6,7-Tetrahydro-thieno[3,2-c]pyridine (0.5 g, 3.59 mmol), benzotriazole (428 mg, 3.59 mmol), and 2-chlorobenzaldehyde (504 mg, 3.59 mmol) were dissolved in diethyl ether and stirred for 3 days in the presence of molecular sieves (4 Å) under an argon atmosphere at room temperature. After 3 days, the ether was filtered and washed with saturated sodium bicarbonate solution (20 mL). The ether was dried over sodium sulfate, filtered and concentrated. The remaining colorless foam was dissolved in heptane/diethyl ether (5 mL/1 mL) and stored in a freezer (−10° C.) overnight. After 20 hours at −10° C., the heptane was decanted and the remaining oil was dried under high vacuum at room temperature until a constant weight was achieved to provide 1-[(2-Chlorophenyl)-(6,7-dihydro-4H-thieno[3,2-c]pyridin-5-yl)-methyl]-1H-benzotriazole (Compound IVa, 0.84 g, 61.7% yield) as a colorless foam that appeared to be an 80:20 mixture of isomers by NMR. $^1$H NMR (300 MHz, CDCl$_3$/TMS): δ=8.08 (d, 1H, J=8.1 Hz), 7.91-7.79 (m, 2H), 7.55 (d, 1H, J=8.4 Hz), 7.53-7.24 (m, 4H), 7.11 (s, 1H), 7.04 (d, 1H, J=5.1 Hz), 6.61 (d, 1H, J=5.1 Hz), 3.90 (d, 1H, J=14.4 Hz), 3.69 (d, 14.4 Hz), 3.21-2.95 (m, 2H), 2.88 (m, 2H). (major isomer). $^{13}$C NMR (75 MHz, CDCl$_3$/TMS): δ=145.48, 133.78, 133.45, 132.94, 132.65, 130.10, 129.40, 127.50, 126.98, 126.56, 124.97, 124.00, 122.79, 119.80, 110.39, 84.85, 49.59, 47.28, 25.50. (major isomer). MS (HR, DIP-CI): Calculated for (MH$^+$): 379.0779. found 379.0752.

Example 6

7-(2-Chlorophenyl)-7-(6,7-dihydro-4H-thieno[3,2-c]pyridin-5-yl)-2,2-dimethylheptanoic acid, hydrochloride. (Compound Ig Hydrochloride)

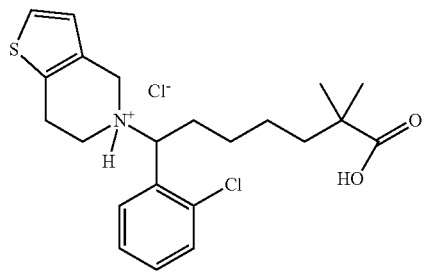 [SMILES: CC(C)(CCCCC(c1ccccc1Cl)[NH+]1CCc2sccc2C1)C(=O)O ; [Cl-]]

Step 1. Synthesis of (5-Ethoxycarbonyl-5-methyl-hexyl)-triphenylphosphonium bromide

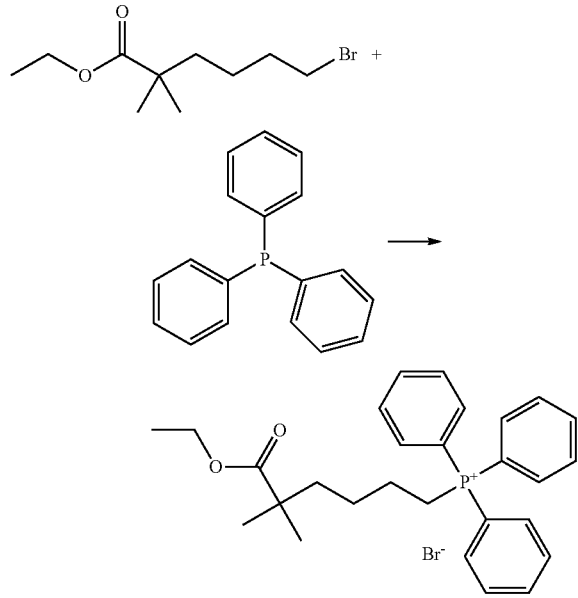

6-Bromo-2,2-dimethylhexanoic acid ethyl ester (38.0 g, 0.15 mol) and triphenylphosphine (40.0 g, 0.15 mol) were dissolved in toluene (100 mL) and heated to reflux for 24 hours under an argon atmosphere. After 24 hours of heating, the flask was allowed to cool to room temperature and stirred for an additional 24 hours at room temperature. After 48 hours, the toluene was removed under reduced pressure. The remaining material was dissolved in dichloromethane (100 mL) and added drop-wise to t-butyl methyl ether (600 mL). The ether was decanted away from the precipitate, which was dried to a constant weight under high vacuum to provide (5-ethoxycarbonyl-5-methylhexyl)-triphenylphosphonium bromide (71.5 g, 93.1% yield) as a light yellow foam. $^1$H NMR (300 MHz, CDCl$_3$/TMS): S=7.87-7.57 (m, 15H), 4.05 (l, 2H, J=7.2 Hz), 3.67 (m, 2H), 1.78-1.45 (m, 6H), 1.20 (t, 3H, J=7.2 Hz), 1.12 (s, 6H). $^{13}$C NMR (75 MHz, CDCl$_3$/TMS): δ=177.02, 134.56 (d, 3C, J=2.4 Hz), 132.94 (d, 6C, J=10.1 Hz), 129.99 (d, 6C, J=12.6 Hz), 117.44 (d, 3C, J=85.4 Hz), 59.78, 41.47, 39.12, 25.44 (d, 1H, J=15.5 Hz), 24.62, 22.59 (d, 1H, J=4.1 Hz), 21.96, 13.83. HRMS (ESI-TOF): Calculated for (M$^+$): 433.2291. Found: 433.2330.

Step 2. Synthesis of 7-(2-Chlorophenyl)-2,2-dimethyl-hept-6-enoic acid ethyl ester

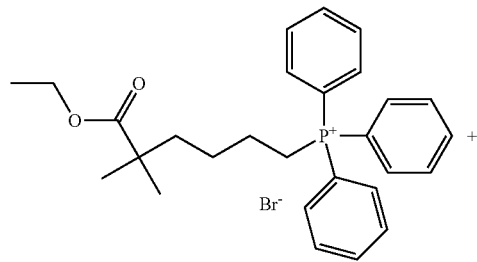

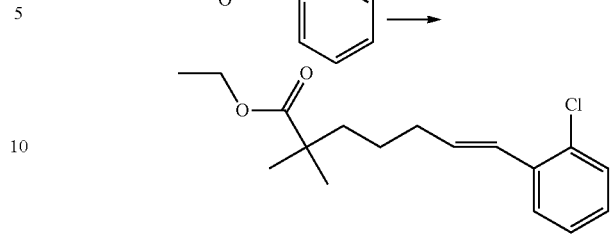

(5-Ethoxycarbonyl-5-methylhexyl)-triphenylphosphonium bromide (35.0 g, 0.0619 mol) was dissolved in dichloromethane (100 mL) containing 2-chlorobenzaldehyde (8.70 g, 0.0619 mol). A solution of sodium hydroxide (10 g, 0.25 mol) in water (10 mL) was added in portions over ten minutes. The mixture stirred for 2 hours at room temperature. After two hours, the layers were separated and the dichloromethane fraction was washed with water (2×150 mL), dried over sodium sulfate, filtered, and concentrated under reduced pressure. The remaining brown oil (18.99 g) was filtered through silica gel (200 g), eluting with ethyl acetate/heptane (1:9). The product containing fractions were combined and concentrated under reduced pressure. The remaining yellow oil (10.5 g) was contaminated with 2-chlorobenzaldehyde (30-40%). The material was reprocessed by dissolving in fresh dichloromethane (100 mL) with additional phosphonium salt (25 g, 0.048 mol). Sodium hydroxide (10 g, 0.25 mol) in water (10 mL) was added in portions and the mixture was allowed to stir for 4 hours at room temperature. The layers were separated and the dichloromethane fraction was washed with water (2×100 mL), dried over sodium sulfate, filtered, and concentrated under reduced pressure. The remaining brown oil was purified by column chromatography on silica gel (200 g), eluting with ethyl acetate/heptane (1:9). The product-containing fractions were combined and concentrated under reduced pressure to provide 7-(2-chlorophenyl)-2,2-dimethylhept-6-enoic acid ethyl ester (12.0 g, 60% yield) as a light, yellow liquid. $^1$H NMR (300 MHz, CDCl$_3$/TMS): δ=7.47 (d, 0.4H, J=7.5 Hz), 7.36-7.07 (m, 3.6H), 6.74 (d, 0.4H, J=15.6 Hz), 6.50 (d, 0.6H, J=11.4 Hz), 6.16 (dt, 0.4H, J=15.6, 7.2 Hz), 5.75 (dt, 0.6H, d=11.4, 7.2 Hz), 4.10 (m, 2H), 2.26-2.12 (m, 2H), 1.61-1.34 (m, 4H), 1.29-1.17 (m, 3H), 1.14 (s, 6H). (mixture of cis/trans isomers). $^{13}$C NMR (75 MHz, CDCl$_3$/TMS): δ=177.59, 135.63 (2 peaks), 133.67, 133.45, 133.31, 132.38, 130.31, 129.41, 129.19, 127.84, 127.73, 126.57, 126.47, 126.24, 126.00, 60.16, 42.12, 42.07, 40.22, 33.56, 28.83, 25.21, 25.16, 24.69, 14.30. (mixture of cis/trans isomers). HRMS (MMI-TOF): Calculated for C$_{22}$H$_{29}$Cl$_2$NO$_2$S (MH$^+$): 406.1202. Found 406.1594.

Step 3. Synthesis of 7-Bromo-7-(2-chlorophenyl)-2,2-dimethylheptanoic acid ethyl ester

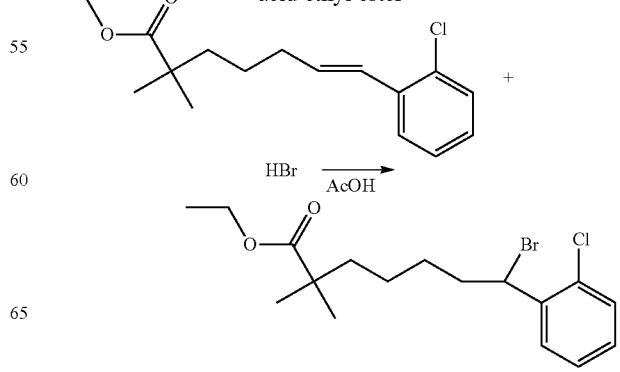

7-(2-Chlorophenyl)-2,2-dimethylhept-6-enoic acid ethyl ester (11.75 g, 0.040 mole) was dissolved in acetic acid (80 mL) under an argon atmosphere. The flask was cooled in an ice-water bath. Hydrogen bromide gas was passed slowly through the solution for 3 hours while the solution slowly warmed to room temperature. Ice (250 g) was added and after mixing, the product was extracted with ethyl acetate (2×100 mL). The ethyl acetate extracts were combined and washed with saturated sodium bicarbonate solution (3×75 mL) and water (100 mL). The solution was dried over sodium sulfate, filtered, and concentrated under reduced pressure. The remaining oil (14.06 g) was purified by column chromatography on silica gel (250 g), eluting with 3:1 (followed by 2:1) heptane/ethyl acetate. The product-containing fractions were combined and concentrated under reduced pressure to provide 7-bromo-7-(2-chlorophenyl)-2,2-dimethylheptanoic acid ethyl ester (12.9 g, 86% yield) as a clear oil. $^1$H NMR (300 MHz, CDCl$_3$/TMS): δ=7.57 (d, 1H, J=7.50 Hz), 7.33-7.15 (m, 3H), 5.43 (t, 1H, J=6.9 Hz), 4.08 (q, 2H, J=7.2 Hz), 2.30-2.21 (m, 2H), 1.55-1.42 (m, 3H), 1.34-1.19 (m, 5H), 1.13 (s, 6H). $^{13}$C NMR (75 MHz, CDCl$_3$/TMS): δ=177.72, 139.41, 132.69, 129.67, 129.28, 128.92, 127.48, 60.36, 50.17, 42.26, 40.57, 39.19, 28.59, 25.38, 25.34, 24.45, 14.50. MS (HR, DIP-CI): Calculated for (MH$^+$): 375.0726. found 375.0726.

Step 4. Synthesis of 7-(2-Chlorophenyl)-7-(6,7-dihydro-4H-thieno[3,2-c]pyridin-5-yl)-2,2-dimethylheptanoic acid ethyl ester. (Compound Ih)

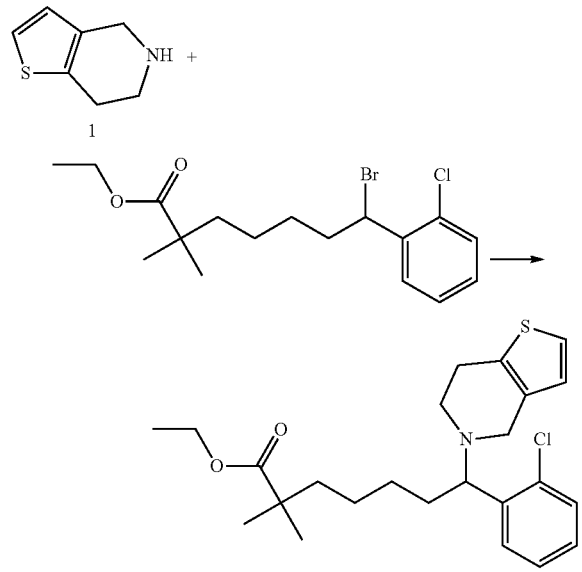

The hydrochloride salt of 4,5,6,7-tetrahydro-thieno[3,2-c]pyridine (3.2 g, 18.9 mmol) was dissolved in water (120 mL) and 50% sodium hydroxide solution (10 mL) was added. The corresponding free base was extracted with dichloromethane (2×25 mL), which was dried over sodium sulfate, filtered, and concentrated. The remaining oil (2.58 g, 18.9 mmol) was dissolved in DMF (10 mL) under an argon atmosphere. Potassium carbonate (5 g) and 7-bromo-7-(2-chlorophenyl)-2,2-dimethylheptanoic acid ethyl ester (7.0 g, 18.63 mmol) were added and the mixture stirred for 44 hours at 75° C. The flask was cooled to room temperature and water (50 mL) was added. The product was extracted with dichloromethane (2×75 mL), which was dried over sodium sulfate, filtered, and concentrated. The remaining brown oil (8.94 g) was purified by column chromatography on silica gel (140 g), eluting with heptane-ethyl acetate (4:1 to 2:1). The product containing fractions were combined, concentrated, and dried to a constant weight under high vacuum at room temperature to provide 7-(2-chlorophenyl)-7-(6,7-dihydro-4H-thieno[3,2-c]pyridin-5-yl)-2,2-dimethylheptanoic acid ethyl ester (Compound Ih, 3.85 g, 49% yield) as a clear oil. $^1$H NMR (300 MHz, CDCl$_3$/TMS): δ=7.53 (dd, 1H, J=7.5, 1.2 Hz), 7.40 (dd, 1H, J=7.8, 1.2 Hz), 7.31-7.18 (m, 2H), 7.08 (d, 1H, 15.1 Hz), 6.74 (d, 1H, J=5.1 Hz), 4.22 (dd, 1H, J=8.7, 4.5 Hz), 4.12 (q, 2H, J=7.2 Hz), 3.83 (d, 1H, J=14.1 Hz), 3.49 (d, 1H, J=14.1 Hz), 2.92-2.68 (m, 4H), 2.08-1.73 (m, 2H), 1.46 (m, 2H), 1.30-1.19 (m, 7H), 1.15 (s, 6H). $^{13}$C NMR (75 MHz, CDCl$_3$/TMS): S=178.00, 139.41, 134.99, 134.26, 133.62, 129.53, 128.13, 128.03, 126.87, 125.51, 122.67, 63.69, 60.37, 50.79, 48.15, 42.33, 40.84, 33.11, 26.19, 25.40, 14.55. HRMS (DIP-CI): Calculated for (M+H$^+$): 434.1921. found 434.1871.

Step 5. Synthesis of 7-(2-chlorophenyl)-7-(6,7-dihydro-4H-thieno[3,2-c]pyridin-5-yl)-2,2-dimethylheptanoic acid, hydrochloride

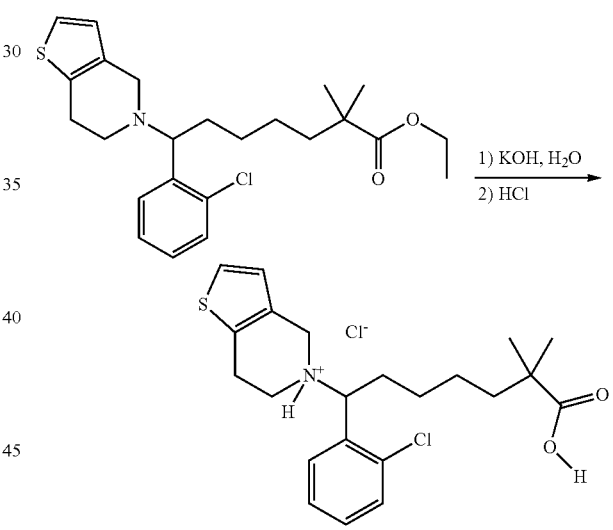

7-(2-Chlorophenyl)-7-(6,7-dihydro-4H-thieno[3,2-c]pyridin-5-yl)-2,2-dimethylheptanoic acid ethyl ester (2.80 g, 7.23 mmol) was dissolved in ethanol (40 mL) and water (25 mL) containing potassium hydroxide (10 g, 250 mmol). The mixture was heated to reflux for 24 hours. After 24 hours, the flask was cooled to room temperature and concentrated. Water (50 mL) was added and extracted with 10% ethyl acetate in heptane. The aqueous fraction was acidified (to pH=6) with concentrated hydrochloric acid and the product was extracted with dichloromethane (2×100 mL). The dichloromethane extracts were combined, dried over sodium sulfate, filtered and concentrated. The remaining tan oil (3.0 g) was purified by flash column chromatography on silica gel (100 g), eluting with heptane-ethyl acetate (2:1) to provide 7-(2-chlorophenyl)-7-(6,7-dihydro-4H-thieno[3,2-c]pyridin-5-yl)-2,2-dimethylheptanoic acid as a white solid (2.1 g, 71.6% yield). The product was dissolved in water (ASTM 1, 200 mL) containing hydrochloric acid (1%) and acetone (25 mL). Most of the acetone and excess hydrochloric acid was removed under reduced pressure. The remaining water (200 mL) was freeze-dried to provide 7-(2-chlorophenyl)-7-(6,7-dihydro-4H-thieno[3,2-c]pyridin-5-yl)-2,2-dimethylheptanoic acid, hydrochloride salt (Compound Ig hydrochloride, 2.2 g, mp 97-100° C., 99.47% purity by HPLC) as a white solid. $^1$H NMR (300 MHz, DMSO-$d_6$): δ=12.25 (br s, 0.5H), 12.12 (br s, 0.5H), 8.24 (br s, 1H), 7.60-7.38 (m, 4H), 6.94 (d, 1H, J=4.5 Hz), 6.77 (d, 1H, J=4.5 Hz), 4.90-4.68 (m, 1.5H), 4.38 (dd, 0.5H, J=14.4, 5.4 Hz), 4.01 (m, 1H), 3.80 (dd, 0.5H, J=14.4, 5.1 Hz), 3.60-3.30 (m, 1.5H), 3.20-2.85 (m, 2H), 2.42 (m, 1H), 2.23 (m, 1H), 1.40-1.0 (m, 5H), 1.01 (s, 6H), 0.79 (m, 1H). (mixture of rotational isomers). $^{13}$C NMR (75 MHz, DMSO-$d_6$): δ=178.41, 134.70, 134.60, 131.83, 131.49, 131.23, 131.05, 129.93, 129.75, 128.38, 128.35, 128.10, 125.43, 125.26, 124.87, 124.86, 64.35, 63.17, 49.87, 48.70, 48.00, 47.13, 41.16, 30.78, 30.30, 30.12, 25.77, 25.02, 24.14, 21.78, 21.37. (mixture of rotational isomers). HRMS (MMI-TOF): Calculated for $C_{22}H_{29}Cl_2NO_2S$ (MH$^+$): 406.1202. found 406.1594.

Example 7

8-(2-chlorophenyl)-8-(6,7-dihydro-4H-furo[3,2-c]pyridin-5-yl)-2,2-dimethyloctanoic acid, hydrochloride. (Compound Io Hydrochloride)

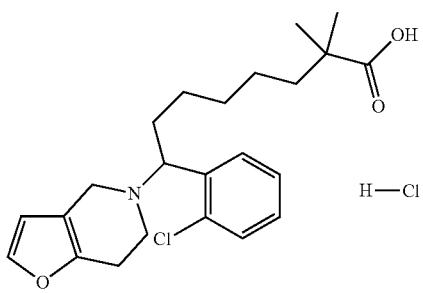 [SMILES: CC(C)(CCCCCC(c1ccccc1Cl)N1CCc2occc2C1)C(=O)O ; Cl]

Step 1. Synthesis of 2-(2-nitrovinyl)-furan

2-Furaldehyde (18.2 g, 190 mmol) and ammonium acetate (13 g, 169 mmol) were added to nitromethane (169 mL) and the mixture was heated to reflux for 45 min. The solution was concentrated and dichloromethane (250 mL) was added. The dichloromethane solution was washed with water (2×250 mL), dried over sodium sulfate, and filtered to obtain the crude product. Purification by column chromatography (silica gel, ethyl acetate/heptane=1/10 to 2/3) afforded pure 2-(2-nitrovinyl)-furan (14 g, 53.0%) as a yellow powder (M.P. 71-74° C.). $^1$H NMR (Field: 300 MHz, Solvent: CDCl$_3$/TMS) δ (ppm): 7.78 (d, 1H, J=13.2 Hz), 7.59 (m, 1H), 7.52 (d, 1H, J=13.5 Hz), 6.90 (d, 1H, J=3.6 Hz), 6.58 (m, 1H). $^{13}$C NMR (Field: 75 MHz, Solvent: CDCl$_3$/TMS) δ (ppm): 146.90, 146.67, 134.93, 125.51, 120.12, 113.46.

Step 2: Synthesis of 2-furan-2-yl-ethylamine

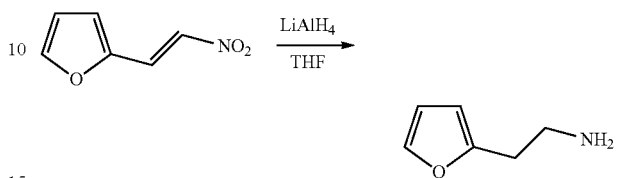

To a mixture of lithium aluminum hydride (13.4 g, 353 mmol) in dry THF (400 ml) was added drop-wise over 30 minutes 2-(2-nitrovinyl)-furan (14 g, 101 mmol) in THF (100 ml) at 0° C., under argon atmosphere. The cooling was stopped and the flask was heated reflux for addition 3.5 hours. The reaction mixture was cooled to room temperature, water (13 mL) was slowly added with vigorous stirring. After the water was added, 15% sodium hydroxide solution (13 mL) was added, followed again by water (36 mL). After stirring vigorously for 10 min, the solids were filtered and washed with diethyl ether (3×150 mL). The combined filtrates were dried over Na$_2$SO$_4$, filtered, and concentrated under reduced pressure to yield 2-furan-2-yl-ethylamine (11 g, 85.6% yield) as a brown oil. $^1$H NMR (Field: 300 MHz, Solvent: CDCl$_3$/TMS) δ (ppm): 7.31 (m, 1H), 6.29 (d, 1H, J=2.1 Hz), 6.05 (d, 1H, J=2.1 Hz), 2.96 (t, 2H, J=6.6 Hz), 2.76 (t, 2H, J=6.6 Hz), 1.84 (br, 2H). $^{13}$C NMR (Field: 75 MHz, Solvent: CDCl$_3$/TMS) δ (ppm): 153.82, 141.21, 110.15, 106.00, 40.79, 32.35.

Step 3: Synthesis of 6,7-dihydro-4H-furo[3,2-c]pyridine-5-carboxylic acid tert-butyl ester

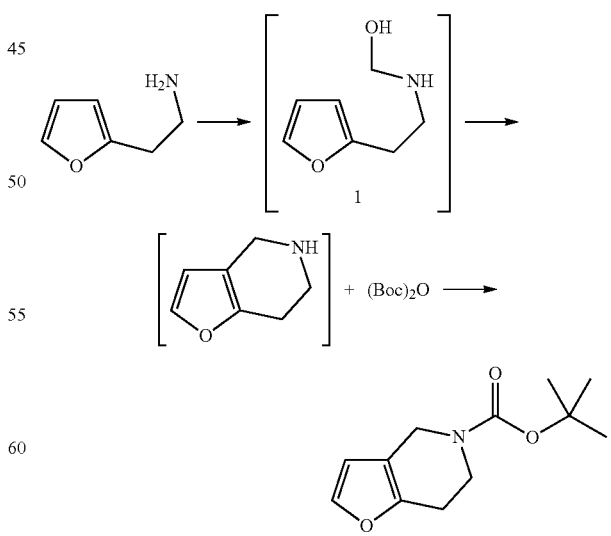

Formalin (37% aqueous formaldehyde, 4 g, 49.2 mmol) was added drop-wise to 2-furan-2-yl-ethylamine (5.5 g, 43.3 mmol, neat) and the mixture was allowed to stir for 30 minutes at room temperature. The crude intermediate 1 was extracted with diethyl ether (3×80 mL). The diethyl ether extracts were combined, dried over sodium sulfate, filtered, and concentrated. DMF (35 mL) was saturated with hydrogen chloride gas by passing hydrogen chloride through the solution for one hour. The remaining oil was dissolved in DMF (10 mL) and added to the DMF/HCl solution. After mixing at room temperature for 3 hours, the DMF was removed under high vacuum. Methyl t-butyl ether was added and the traces of DMF were removed by extraction with water (100 mL) that had been adjusted to pH=11 with saturated sodium bicarbonate solution. The ether solution was dried over sodium sulfate, filtered, and concentrated. The remaining crude intermediate 4,5,6,7-tetrahydrofuro[3,2-c]pyridine (0.87 g, 7.1 mmol) in dichloromethane (50 mL) was added drop-wise to di-tert-butyldicarbonate (1.6 g, 7.4 mmol) in CH$_2$Cl$_2$ (50 mL) at room temperature. The reaction mixture was stirred at same temperature for 1.5 hours, monitored by TLC. The solvent was evaporated by reduced pressure and the crude product was purified by column chromatography (silica gel, ethyl acetate/heptane=1/9) to afford pure 6,7-dihydro-4H-furo[3,2-c]pyridine-5-carboxylic acid tert-butyl ester (0.56 g, 35.4%) as a yellow oil. $^1$H NMR (Field: 300 MHz, Solvent: CDCl$_3$/TMS) δ (ppm): 7.19 (s, 1H), 6.13 (d, 1H, J=1.5 Hz), 4.25 (s, 2H), 3.63 (m, 2H), 2.59 (d, m), 1.44 (s, 9H). $^{13}$C NMR (Field: 75 MHz, Solvent: CDCl$_3$/TMS) δ (ppm): 154.78, 146.85, 141.23, 108.19, 85.03, 79.82, 41.58, 40.05, 28.52, 23.90.

Step 4: Synthesis of 4,5,6,7-Tetrahydrofuro[3,2-c]pyridine hydrochloride

To 6,7-dihydro-4H-furo[3,2-c]pyridine-5-carboxylic acid tert-butyl ester (0.56 g, 2.51 mmol) in methanol (50 mL) was added concentrated hydrochloric acid solution (37%, 1.4 mL). The mixture stirred at room temperature for 5.5 hours, monitored by TLC. The methanol was evaporated under reduced pressure to yield 4,5,6,7-tetrahydrofuro[3,2-c]pyridine hydrochloride (0.5 g, 100% yield) as a yellow powder. $^1$H NMR (Field: 300 MHz, Solvent: CD$_3$OD/TMS) δ (ppm): 7.47 (s, 1H), 6.42 (s, 1H), 4.20 (s, 2H), 3.57 (m, 2H), 3.03 (m, 2H). $^{13}$C NMR (Field: 75 MHz, Solvent: CDCl$_3$/TMS) δ (ppm): 147.23, 143.89, 112.23, 109.50, 43.10, 42.37, 21.70.

Step 5: 8-(2-chlorophenyl)-8-(6,7-dihydro-4H-furo [3,2-c]pyridin-5-yl)-2,2-dimethyloctanoic acid ethyl ester. (Compound Ip)

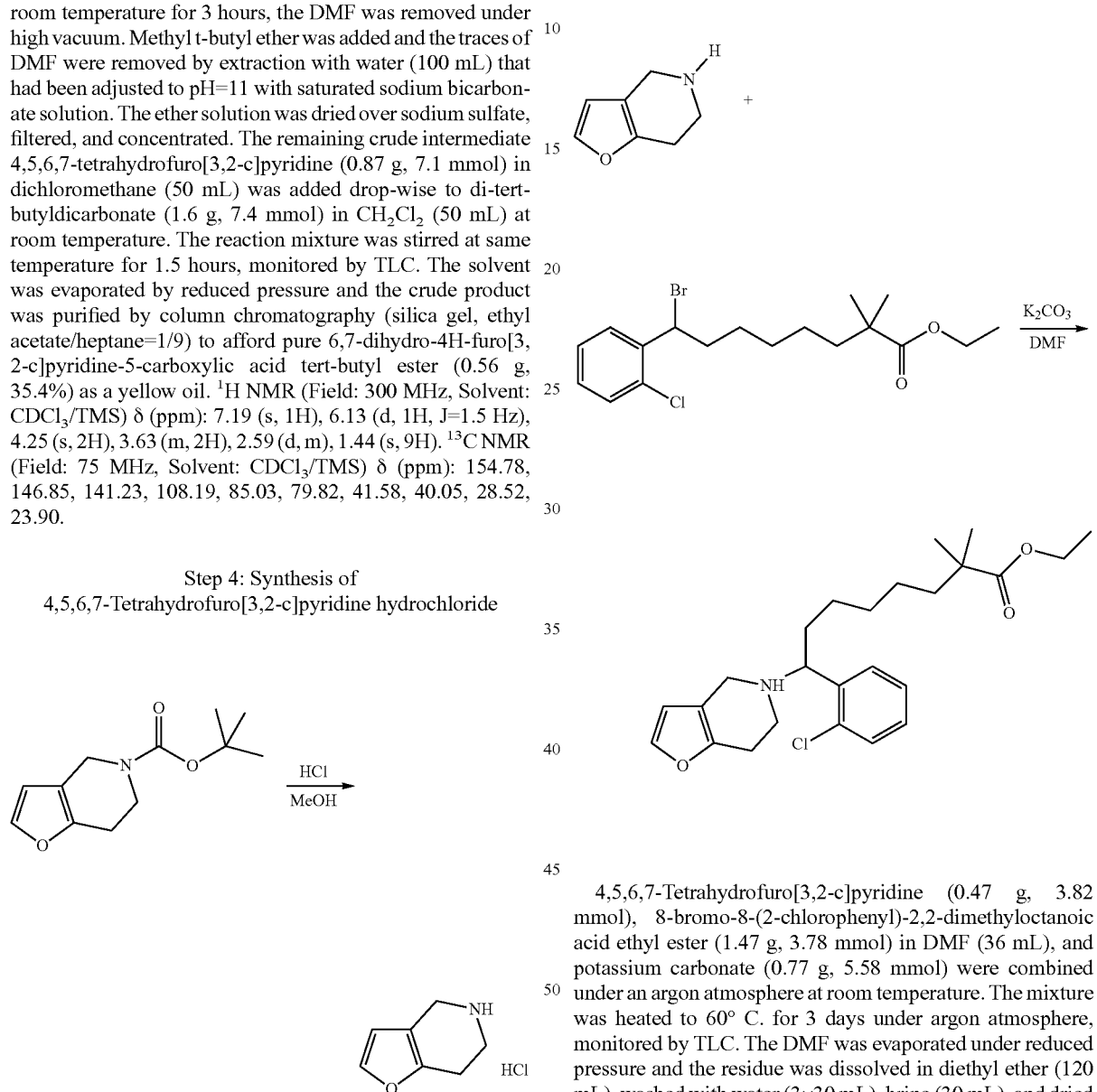

4,5,6,7-Tetrahydrofuro[3,2-c]pyridine (0.47 g, 3.82 mmol), 8-bromo-8-(2-chlorophenyl)-2,2-dimethyloctanoic acid ethyl ester (1.47 g, 3.78 mmol) in DMF (36 mL), and potassium carbonate (0.77 g, 5.58 mmol) were combined under an argon atmosphere at room temperature. The mixture was heated to 60° C. for 3 days under argon atmosphere, monitored by TLC. The DMF was evaporated under reduced pressure and the residue was dissolved in diethyl ether (120 mL), washed with water (3×30 mL), brine (30 mL), and dried over Na$_2$SO$_4$. The crude oil was purified by column chromatography (silica gel, ethyl acetate/heptane 1/9) to afford pure 8-(2-chlorophenyl)-8-(6,7-dihydro-4H-furo[3,2-c]pyridin-5-yl)-2,2-dimethyloctanoic acid ethyl ester (Compound Ip, 0.50 g, 30.3% yield) as a yellow oil. $^1$H NMR (Field: 300 MHz, Solvent: CD$_3$OD/TMS) δ (ppm): 7.48 (d, 1H, J=7.5 Hz), 7.36 (d, 1H, J=7.8 Hz), 7.32-7.15 (m, 3H), 6.17 (s, 1H), 4.20 (dd, 1H, J=9.0, 4.8 Hz), 4.08 (q, 2H, J=7.2 Hz), 3.62 (d, 1H, J=13.5 Hz), 3.11 (d, 1H, J=13.5 Hz), 2.88-2.58 (m, 4H), 1.95-1.70 (m, 2H), 1.45-1.40 (m, 2H), 1.30-1.0 (m, 15H). $^{13}$C NMR (Field: 75 MHz, Solvent: CDCl$_3$/TMS) δ (ppm): 178.01, 149.01, 140.94, 139.50, 135.00, 129.57, 129.04, 128.03, 126.85, 115.92, 108.90, 63.43, 60.36, 47.65, 47.54, 42.36, 40.91, 33.27, 30.57, 25.67, 25.41, 25.06, 24.73, 14.55. HRMS (HR, DART-TOF): Calculated for (M+H)+: 432.2300. found 432.2316.

Step 6: Synthesis of 8-(2-chlorophenyl)-8-(6,7-dihydro-4H-furo[3,2-c]pyridin-5-yl)-2,2-dimethyloctanoic acid, hydrochloride

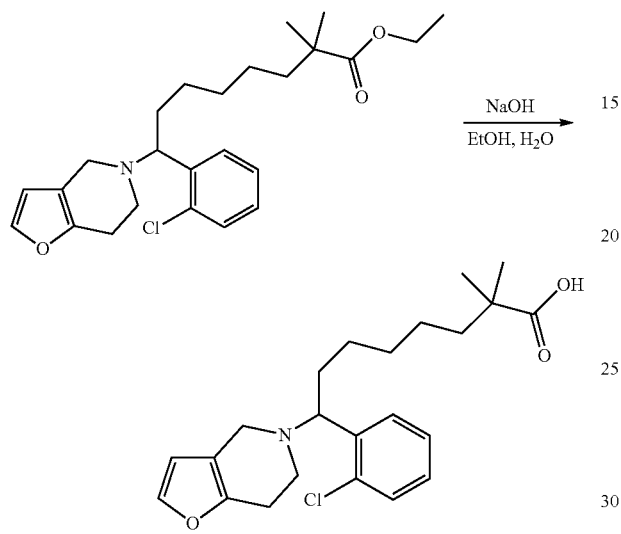

8-(2-Chlorophenyl)-8-(6,7-dihydro-4H-furo[3,2-c]pyridin-5-yl)-2,2-dimethyloctanoic acid ethyl ester (0.5 g, 1.16 mmol) was added to a mixture of ethanol (20 mL) and sodium hydroxide (0.32 g, 8.0 mmol) in water (6.6 mL). The mixture was heated to reflux for 6.5 hours. Evaporated solvent under reduced pressure and water (20 mL) was added to the residue. The aqueous solution was washed with a mixture of ethyl acetate/heptane 1/10 (10 mL), and the extract was discarded. The aqueous fraction was acidified with concentrated hydrochloric acid to pH=6 and the product was extracted with dichloromethane (3×20 mL). The combined dichloromethane extracts were dried over sodium sulfate, filtered, and concentrated under reduced pressure to provide 8-(2-chlorophenyl)-8-(6,7-dihydro-4H-furo[3,2-c]pyridin-5-yl)-2,2-dimethyloctanoic acid (0.25 g, 46.9%) as a yellow oil. The material was dissolved in diethyl ether (5 mL) and added to hydrochloric acid solution (2N HCl in diethyl ether, 0.34 mL). Water (12 mL) was added and after mixing the aqueous portion was separated and freeze dried to provide 8-(2-chlorophenyl)-8-(6,7-dihydro-4H-furo[3,2-c]pyridin-5-yl)-2,2-dimethyloctanoic acid, hydrochloride salt (Compound Io hydrochloride, 0.16 g, light yellow powder, 59.3% yield). $^1$H NMR (Field: 300 MHz, Solvent: CD$_3$OD/TMS) δ (ppm): 7.77 (br s, 1H), 7.63-7.48 (m, 5H), 6.37 (br s, 1H), 5.05 (m, 1H), 4.18 (m, 1H), 3.62 (m, 1H), 3.02 (m, 2H), 2.36-2.24 (m, 2H), 1.42-1.40 (m, 2H), 1.32 (m, 2H), 1.20-1.18 (m, 4H), 1.11 (s, 6H), 1.08-0.92 (m, 1H). $^{13}$C NMR (Field: 75 MHz, Solvent: CD$_3$OD/TMS) δ (ppm): 181.70, 147.11, 144.55, 137.40, 132.15, 131.89, 130.08, 128.21, 129.87, 112.37, 109.71, 66.34, 52.10, 50.05, 43.07, 41.60, 35.10, 31.67, 30.56, 26.64, 25.85, 22.31. HRMS (FIR, DIP-CI): Calculated for C$_{23}$H$_{30}$ClNO$_3$ (M+H)+: 404.1987. Found 404.2009. CHN analysis: Calculated; 62.73; C, 7.09; H, 3.18; N, 16.10; Cl. found; 59.13; C, 7.04; H, 3.03; N, 13.58; Cl.

Example 8

8-(2-Chlorophenyl)-2,2-dimethyl-8-(1,4,6,7-tetrahydropyrrolo[3,2-c]pyridin-5-yl)-octanoic acid, hydrochloride. (Compound Iq Hydrochloride)

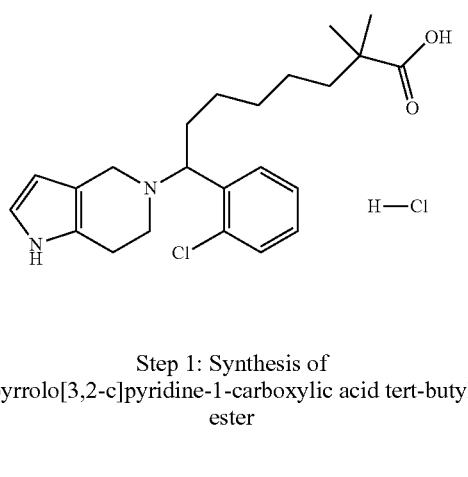

Step 1: Synthesis of pyrrolo[3,2-c]pyridine-1-carboxylic acid tert-butyl ester

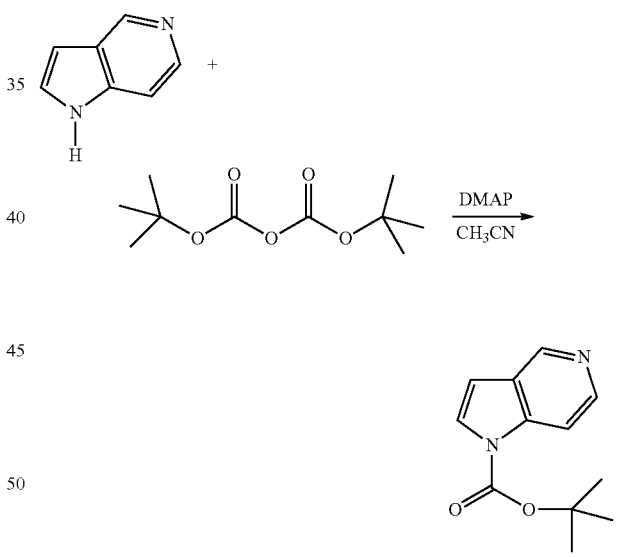

Dimethylaminopyridine (DMAP) (2.08 g, 16.9 mmol) in acetonitrile (20 mL) was added drop wise to 5-azaindole (2.0 g, 16.9 mmol) in acetonitrile (70 mL) at room temperature. After stirring for 2 hours, di-tert-butyldicarbonate (3.68 g, 16.9 mmol) was added in portion at same temperature. After 2.5 hours, the solvent was evaporated under reduced pressure and the residue (5.4 g) was purified by column chromatography (silica gel, ethyl acetate/heptane 1/10 to 1/2) to provide pyrrolo[3,2-c]pyridine-1-carboxylic acid tert-butyl ester (2.72 g, 92.4% yield) as a bright yellow oil. $^1$H NMR (Field: 300 MHz, Solvent: CD$_3$OD/TMS) δ (ppm): 8.87 (s, 1H), 8.48 (d, 1H, J=5.7 Hz), 7.98 (d, 1H, J=5.1 Hz), 7.60 (d, 1H, J=3.3 Hz), 6.63 (d, 1H, J=3.0 Hz), 1.68 (s, 9H). $^{13}$C NMR (Field: 75

MHz, Solvent: CDCl₃/TMS) δ (ppm): 148.82, 143.75, 143.51, 139.50, 126.69, 109.83, 105.46, 84.60, 28.05.

Step 2: Synthesis of 1-tert-butoxycarbonyl-5-[1-(2-chlorophenyl)-7-methyloctyl]-1H-pyrrolo[3,2-c]pyridin-5-ium bromide)

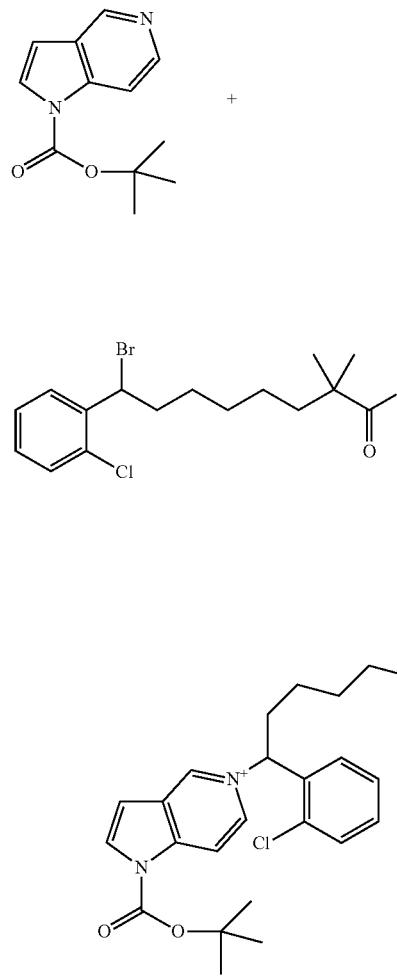

A mixture of pyrrolo[3,2-c]pyridine-1-carboxylic acid tert-butyl ester (0.81 g, 3.73 mmol), 8-bromo-8-(2-chlorophenyl)-2,2-dimethyloctanoic acid ethyl ester (1.44 g, 3.73 mmol), and acetonitrile (25 mL) were stirred at 45° C. for 52 hours. The solvent was evaporated under reduced pressure and residue was washed with diethyl ether (3×20 mL) to afford 1-tert-butoxycarbonyl-5-[1-(2-chlorophenyl)-7-methyloctyl]-1H-pyrrolo[3,2-c]pyridin-5-ium bromide (1.37 g, 60.6% yield) as a yellow oil. ¹H NMR (Field: 300 MHz, Solvent: CD₃OD/TMS) δ (ppm): 10.52 (s, 1H), 8.84 (d, 1H, J=7.2 Hz), 8.23 (d, 1H, J=7.8 Hz), 7.91 (t, 1H, J=3.6 Hz), 7.54-7.31 (m, 4H), 7.39 (s, 1H), 6.95 (s, 1H), 6.42 (t, 1H, J=7.2 Hz), 4.09 (q, 2H, J=7.2 Hz), 2.67 (m, 1H), 1.70 (s, 9H), 1.42-1.19 (m, 8H), 1.21 (t, 3H, J=6.9 Hz), 1.10 (s, 6H). ¹³C NMR (Field: 75 MHz, Solvent: CDCl₃/TMS) δ (ppm): 178.00, 147.44, 140.17, 136.60, 133.19, 131.97, 131.45, 130.42, 130.03, 128.64, 113.10, 108.61, 88.15, 71.55, 60.34, 42.23, 40.54, 34.54, 29.69, 28.13, 26.42, 25.28, 24.92, 14.46.

HRMS (HR, DIP-CI): Calculated for C₃₀H₄₀ClN₂O₂ (M+H)⁺: not found (decomposed on analysis).

Step 3: Synthesis of 5-[1-(2-chlorophenyl)-7-ethoxycarbonyl-7-methyloctyl]-4,5,6,7-tetrahydropyrrolo[3,2-c]pyridine-1-carboxylic acid tert-butyl ester

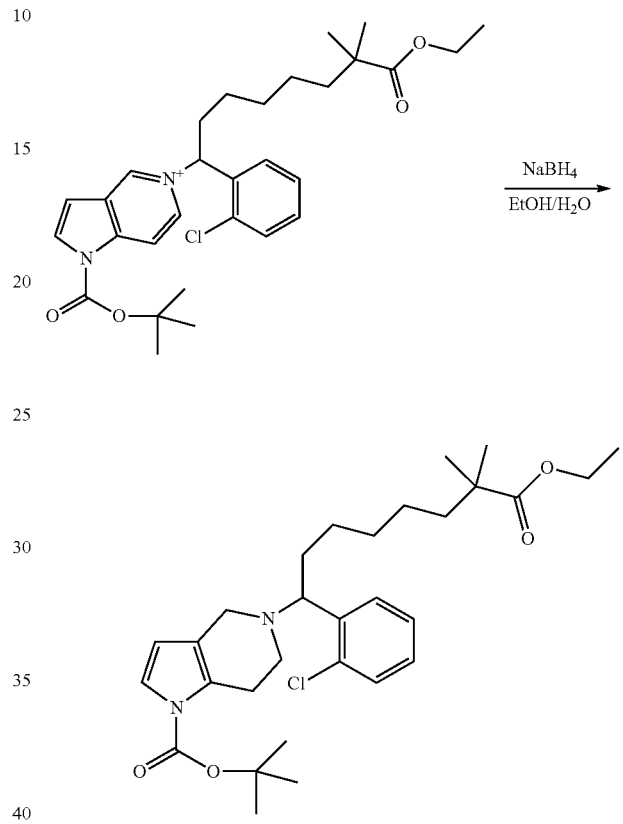

Portions of sodium borohydride (0.16 g, 4.28 mmol) were added to a solution of 1-tert-butoxycarbonyl-5-[1-(2-chlorophenyl)-7-methyloctyl]-1H-pyrrolo[3,2-c]pyridin-5-ium bromide (1.3 g, 2.14 mmol) in 70% EtOH (30 mL) at room temperature over 30 minutes. Once the addition was complete, the mixture was stirred for 0.5 hours. The solvent was evaporated under reduced pressure and water (60 mL) was added. The product was extracted with dichloromethane (3×80 mL). The combined organic extracts were dried over sodium sulfate, filtered, and concentrated. The resultant tertiary amine was purified by column chromatography (silica gel, ethyl acetate/heptane=1/10 to 1/3) to yield 5-[1-(2-chlorophenyl)-7-ethoxycarbonyl-7-methyloctyl]-4,5,6,7-tetrahydropyrrolo[3,2-c]pyridine-1-carboxylic acid tert-butyl ester (0.53 g, 46.9%) as a yellow oil. ¹H NMR (Field: 300 MHz, Solvent: CD₃OD/TMS) δ (ppm): 7.52 (d, 1H, J=7.8 Hz), 7.37 (d, 1H, J=7.8 Hz), 7.27 (t, 1H, J=6.6 Hz), 7.19 (t, 1H, J=7.5 Hz), 7.12 (d, 1H, J=3.3 Hz), 5.95 (d, 1H, J=3.3 Hz), 4.16-4.13 (m, 1H), 4.09 (q, 2H, J=7.2 Hz), 3.31 (d, 1H, J=13.8 Hz), 2.85-2.59 (m, 4H), 1.95-1.76 (m, 2H), 1.55 (s, 9H), 1.45-1.40 (m, 2H), 1.28-1.14 (m, 6H), 1.21 (t, 3H, J=7.2 Hz), 1.11 (s, 6H). ¹³C NMR (Field: 75 MHz, Solvent: CDCl₃/TMS) δ (ppm): 178.00, 149.47, 139.70, 134.90, 129.45, 129.15, 127.89, 127.60, 126.80, 120.94, 119.76, 109.18, 83.24, 63.80, 60.30, 48.78, 42.32, 40.88, 33.20, 30.56, 28.31, 26.45, 25.44, 25.38, 25.03, 14.52. HRMS (HR): Calculated for $C_{30}H_{43}ClN_2O_2$ (M+H)+: 531.2990. found 531.2933.

Step 4: Synthesis of 8-(2-chlorophenyl)-2,2 dimethyl-8-(1,4,6,7-tetrahydro-pyrrolo[3,2-c]pyridine-5-yl)-octanoic acid ethyl ester. (Compound Ir)

25.08, 24.07, 14.56. HRMS (HR, DART-TOF): Calculated for $C_{25}H_{35}ClN_2O_2$ (M+H)+: 431.2460. found 431.2476.

Step 5: Synthesis of 8-(2-chlorophenyl)-2,2 dimethyl-8-(1,4,6,7-tetrahydro-pyrrolo[3,2-c]pyridine-5-yl)-octanoic acid (Compound Iq)

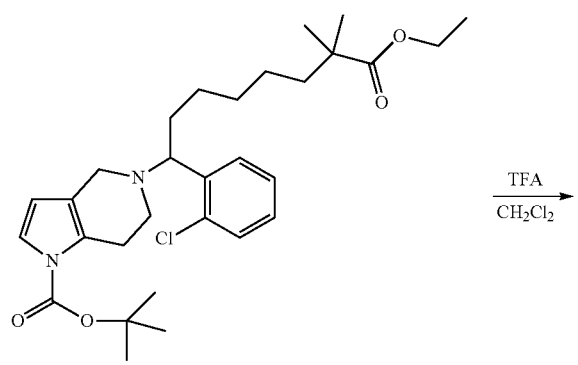

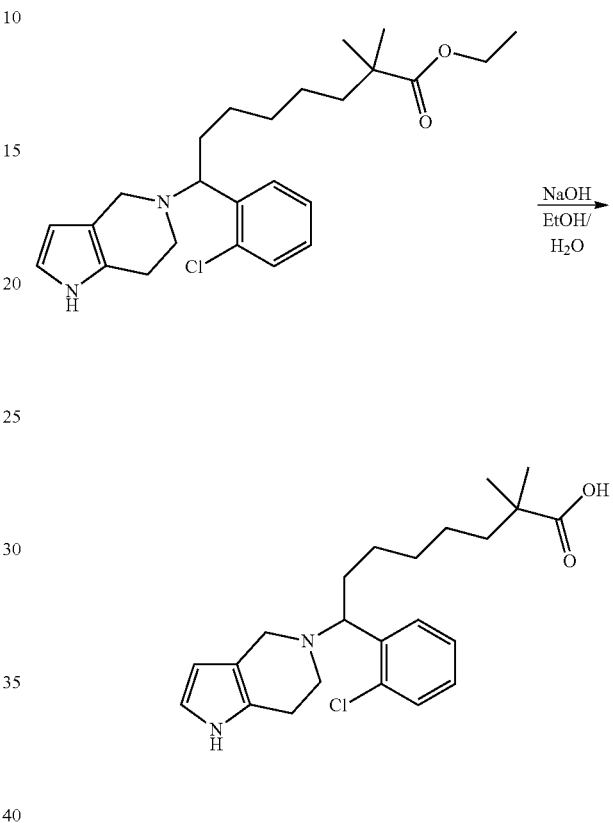

5-[1-(2-Chlorophenyl)-7-ethoxycarbonyl-7-methyloctyl]-4,5,6,7-tetrahydropyrrolo[3,2-c]pyridine-1-carboxylic acid tert-butyl ester (0.12 g, 0.23 mmol) was dissolved in dichloromethane (5 mL) with stirring under an argon atmosphere. TFA (0.48 mL, 4.75 mmol) was added to the solution. After 1 hour, TLC showed the starting material was gone. The mixture was poured into ice cold water (50 mL) and extracted with dichloromethane (3×20 mL). The combined organic layers were dried over sodium sulfate, filtered, and concentrated under reduced pressure. The crude product was purified by column chromatography (silica gel, ethyl acetate/heptane=1/9 to 1/3) to afford 8-(2-chlorophenyl)-2,2 dimethyl-8-(1,4,6,7-tetrahydro-pyrrolo[3,2-c]pyridine-5-yl)-octanoic acid ethyl ester (Compound Ir, 65 mg, 65.9% yield) as a yellow oil. $^1$H NMR (Field: 300 MHz, Solvent: $CD_3OD$/TMS) δ (ppm): 7.80 (s, 1H), 7.54 (d, 1H, J=7.5 Hz), 7.37 (d, 1H, J=7.8 Hz), 7.26-7.16 (m, 2H), 6.60 (s, 1H), 5.94 (s, 1H), 4.17 (m, 1H), 4.08 (q, 2H, J=7.2 Hz), 3.75 (d, 1H, J=13.2 Hz), 3.35 (d, 1H, J=13.2 Hz), 2.83-2.57 (m, 4H), 2.01-1.56 (m, 4H), 1.45-1.40 (m, 2H), 1.21 (t, 3H, J=7.2 Hz), 1.24-1.11 (m, 4H), 1.11 (s, 6H). $^{13}$C NMR (Field: 75 MHz, Solvent: $CDCl_3$/TMS) δ (ppm): 178.14, 140.07, 134.95, 129.43, 129.25, 127.82, 126.79, 125.12, 116.43, 115.93, 105.80, 63.89, 60.37, 48.79, 48.32, 42.37, 40.94, 33.34, 30.64, 25.55, 25.41, 8-(2-Chlorophenyl)-2,2 dimethyl-8-(1,4,6,7-tetrahydropyrrolo[3,2-c]pyridine-5-yl)-octanoic acid ethyl ester (0.11 g, 0.25 mmol) was added to a mixture of ethanol (15 mL), water (1.35 mL), and sodium hydroxide (0.07 g, 1.75 mmol). The mixture was heated to reflux (95-98° C. oil bath) for 11 hours. After cooling to room temperature, the solvent was evaporated under reduced pressure. Water (10 mL) was added to the residue and adjusted to pH=6 with 10 N hydrochloric acid. The product was extracted with dichloromethane (3×10 mL). The combined organic layers were washed with water (10 mL), brine (10 mL), dried over $Na_2SO_4$. After filtration, the dichloromethane solution was concentrated under reduced pressure to obtain crude product. The crude product was purified by column chromatography (silica gel, ethyl acetate/heptane=3/7) to afford 8-(2-chlorophenyl)-2,2 dimethyl-8-(1,4,6,7-tetrahydro-pyrrolo[3,2-c]pyridine-5-yl)-octanoic acid (Compound Iq, 0.06 g, 59.8% yield) as a yellow oil. $^1$H NMR (Field: 300 MHz, Solvent: $CD_3OD$/TMS) δ (ppm): 7.60 (d, 1H, J=7.5 Hz), 7.48 (d, 1H, J=7.8 Hz), 7.41-7.30 (m, 2H), 6.58 (d, 1H, J=2.7 Hz), 5.89 (d, 1H, J=2.7 Hz), 4.56-4.52 (m, 1H), 3.96 (d, 1H, J=13.5 Hz), 3.65 (d, 1H, J=13.5 Hz), 2.97-2.65 (m, 4H), 2.00-1.87 (m, 2H), 1.43-1.39 (m, 2H), 1.28-1.18 (m, 6H), 1.11 (s, 6H). $^{13}$C NMR (Field: 75 MHz, Solvent: $CD_3OD$/TMS) δ (ppm) 183.09, 136.97, 136.77, 131.03, 130.05, 130.31, 128.80, 124.29, 118.35, 113.24, 105.71, 65.49, 50.79, 49.81, 43.48, 42.01, 33.13, 30.39, 26.74, 26.19, 25.98, 23.34.

Step 6: Synthesis of 8-(2-Chlorophenyl)-2,2-dimethyl-8-(1,4,6,7-tetrahydro-pyrrolo[3,2-c]pyridin-5-yl)-octanoic acid, hydrochloride

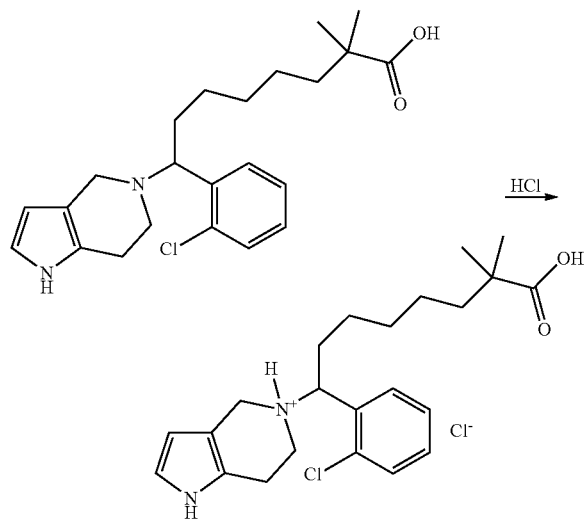

8-(2-Chlorophenyl)-2,2 dimethyl-8-(1,4,6,7-tetrahydro-pyrrolo[3,2-c]pyridine-5-yl)-octanoic acid (0.09 g, 0.22 mmol) was dissolved in diethyl ether (5 mL) and added to HCl solution (2N HCl in diethyl ether). Water (5 mL) was added and after mixing the organic layer was discarded. The aqueous solution was freeze dried to afford 8-(2-chlorophenyl)-2,2 dimethyl-8-(1,4,6,7-tetrahydro-pyrrolo[3,2-c]pyridine-5-yl)-octanoic acid, hydrochloride salt (Compound Iq hydrochloride, 0.09 g, 86.5% yield) as a light yellow powder. $^1$H NMR (Field: 300 MHz, Solvent: $CD_3OD/TMS$) δ (ppm): 10.28 (br, 1H), 7.61 (br s, 1H), 7.48-7.40 (m, 3H), 6.57 (d, 1H, J=10.8 Hz), 5.86-5.70 (2 s, 1H), 4.79-4.52 (m, 3H), 4.19-3.86 (m, 2H), 3.45-2.77 (m, 4H), 2.22-2.06 (m, 2H), 1.26-0.65 (m, 8H), 0.97 (s, 6H). (mixture of conformation isomers in NMR). $^{13}$C NMR (Field: 75 MHz, Solvent: $CDCl_3/TMS$) δ (ppm) 181.66, 137.12, 132.64, 132.39, 129.68, 122.62, 119.72, 109.61, 105.95, 105.76, 66.09, 51.79, 50.73, 43.06, 41.57, 37.95, 31.80, 30.52, 26.59, 25.78, 21.67. HRMS (HR, DIP-CI): Calculated for $C_{23}H_5ClN_2O_2$ (M+H)$^+$: 403.2147. found 403.2158. CHN analysis: Calculated; 62.87; C, 7.34; H, 6.37; N, 16.14 Cl. found; 60.04; C, 7.05; H, 5.92; N, 15.88 Cl.

Example 9

(3-Carboxymethylene-5-mercaptopiperidin-1-yl)-(2-chlorophenyl)-acetic acid methyl ester, hydrochloride. (Compound VIa Hydrochloride)

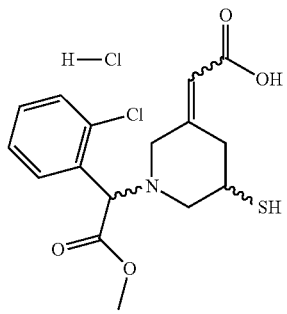

Step 1: Synthesis of Allyl-(1-hydroxyallyl)-carbamic acid tert-butyl ester

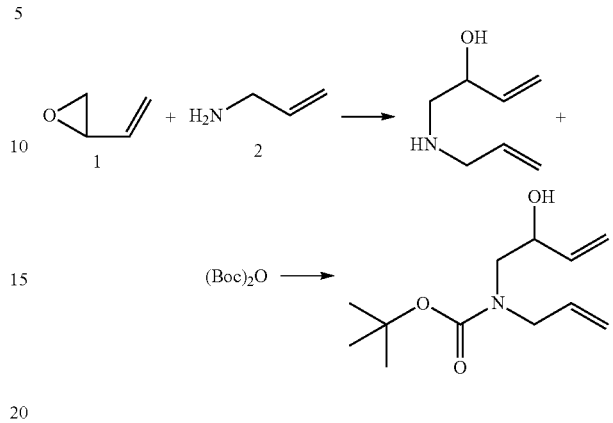

Butadiene monoxide (1, 5.0 g, 71.3 mmol) was added to allylamine (2, 16 mL) and water (1 mL) while cooling at 15° C. The mixture was heated to reflux (100° C.) for 6 hours. After cooling to room temperature, the volatile material was removed under reduced pressure at room temperature. The remaining oil containing the allyl amine was dissolved in dioxane (100 mL) and water (20 mL). The flask was cooled in a water bath and 1M sodium hydroxide solution (80 mL) was added. Di-tert-butyl dicarbonate (17.95 g, 82.2 mmol) was added and the solution was allowed to stir overnight at room temperature. After 18 hours, most of the dioxane was removed under reduced pressure. The remaining water/dioxane solution (40 mL) was extracted with diethyl ether (2×100 mL). The ether was dried over sodium sulfate, filtered, and concentrated under reduced pressure. The remaining oil (19.0 g) was purified by column chromatography on silica gel (250 g), eluting with heptane/ethyl acetate (4:1 to 1:1) to provide allyl-(1-hydroxyallyl)-carbamic acid tert-butyl ester (10.5 g, 65% yield) as a clear oil. $^1$H NMR (300 MHz, $CDCl_3$/TMS): δ=5.82-5.67 (m, 2H), 5.28-5.02 (m, 4H), 4.25 (m, 1H), 3.80-3.65 (m, 2H), 3.22 (m, 1H), 1.39 (s, 9H). $^{13}$C NMR (75 MHz, $CDCl_3$/TMS): δ=138.52, 135.38, 133.88, 117.42, 116.34, 115.58, 80.30, 72.53, 63.42, 61.04, 53.41, 51.77, 28.50.

Step 2: Synthesis of 3-Hydroxy-3,6-dihydro-2H-pyridine-1-carboxylic acid tert-butyl ester

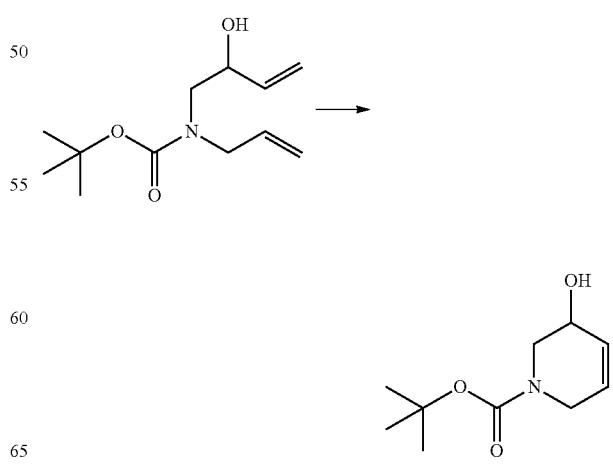

Allyl-(1-hydroxyallyl)-carbamic acid tert-butyl ester (5.0 g, 21.9 mmol) in dichloromethane (350 mL) was sparged with argon gas for 5 minutes. The flask was placed under an argon atmosphere and Grubb catalyst I (0.48 g) was added. The mixture was stirred overnight under argon at room temperature. After 18 hours, the solution was concentrated and the remaining oil purified by column chromatography on silica gel (150 g), eluting with heptane/ethyl acetate (4:1 to 1:1). The product containing fractions were combined, concentrated under reduced pressure, and dried to a constant weight under high vacuum at room temperature to provide 3-hydroxy-3,6-dihydro-2H-pyridine-1-carboxylic acid tert-butyl ester (4.20 g, 96% yield) as a thick, brown oil. $^1$H NMR (300 MHz, CDCl$_3$/TMS): δ=5.85-5.65 (m, 2H), 4.13 (m, 1H), 3.80 (s, 2H), 3.66 (m, 1H), 3.26 (m, 1H), 1.39 (s, 9H). $^{13}$C NMR (75 MHz, CDCl$_3$/TMS): δ=155.06, 128.81, 126.79, 80.11, 67.53, 66.83, 63.60, 47.38, 43.36, 28.56.

Step 3: Synthesis of
3-Oxo-3,6-dihydro-2H-pyridine-1-carboxylic acid
tort-butyl ester

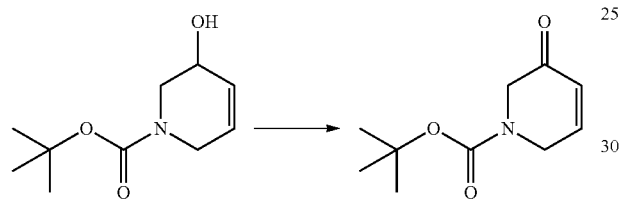

3-Hydroxy-3,6-dihydro-2H-pyridine-1-carboxylic acid tert-butyl ester (3.1 g, 17.3 mmol) was dissolved in dichloromethane (30 mL) under an argon atmosphere. Pyridinium chlorochromate (5 g, 23 mmol) was added in portions over 1 hour. The dichloromethane solution was filtered through silica gel (100 g), eluting with dichloromethane. The crude brown solid (2.84 g) was purified by MPLC (Companion) on a silica cartridge (40 g), eluting with 100% heptane followed by a gradient of ethyl acetate/heptane (0 to 60%). The product containing fractions were combined, concentrated, and dried under high vacuum for 1 hour at room temperature to provide 3-oxo-3,6-dihydro-2H-pyridine-1-carboxylic acid tert-butyl ester (2.1 g, 61% yield) as a clear oil that solidified on standing at low temperature. $^1$H NMR (300 MHz, CDCl$_3$/TMS): δ=6.95 (m, 1H), 6.08 (d, 1H, J=10.5 Hz), 4.15 (m, 2H), 4.02 (br s, 2H), 1.39 (s, 9H). $^{13}$C NMR (75 MHz, CDCl$_3$/TMS): δ=193.11, 154.02, 147.17, 127.40, 80.89, 51.97, 42.69, 28.41.

Step 4: Synthesis of 1,6-Dihydro-2H-pyridin-3-one,
trifluoroacetic acid salt

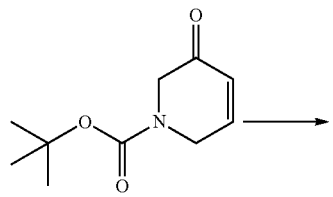

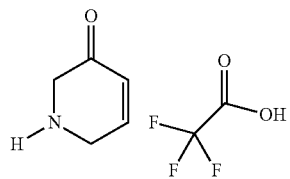

3-Oxo-3,6-dihydro-2H-pyridine-1-carboxylic acid tert-butyl ester (0.42 g, 2.13 mmol) was dissolved in dichloromethane (5 mL) under an argon atmosphere. Trifluoroacetic acid (1.5 mL) was added and the mixture stirred for 4 hours at room temperature. The TFA/dichloromethane solution was concentrated under reduced pressure and dried under high vacuum for 1 hour at room temperature. The remaining brown oil containing 1,6-dihydro-2H-pyridin-3-one, trifluoroacetic acid salt (0.44 g, 97% yield) was used immediately for the next step. $^1$H NMR (300 MHz, CDCl$_3$-CD$_3$OD/TMS): δ=7.12 (d, 1H, J=10.5 Hz), 6.8 (br, 2H), 6.32 (d, 1H, J=10.5 Hz), 4.06 (m, 2H), 3.90 (br s, 2H). $^{13}$C NMR (75 MHz, CDCl$_3$-CD$_3$OD/TMS): δ=187.85, 160.79 (q, J=38 Hz), 132.63, 128.31, 115.71 (q, J=284 Hz), 49.32, 41.11.

Step 5: Synthesis of Bromo-(2-chlorophenyl)-acetic
acid methyl ester

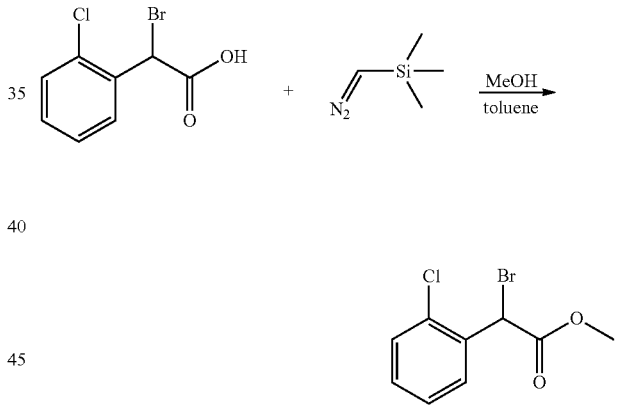

Methanol (1 mL) was added to toluene (10 mL) under an argon atmosphere at room temperature. The flask was cooled in a water bath and 2M (trimethylsilyl)diazomethane (5 mL, 10 mmol) was added, followed by α-bromo-2-chlorophenyl acetic acid (2.2 g, 8.81 mmol) in portions over 5 minutes. After 10 additional minutes, the toluene/methanol was removed under reduced pressure. The crude oil was purified by MPLC (companion) on a silica cartridge (40 g) with a gradient of ethyl acetate in heptane (10% to 50%) over 20 minutes. The product containing fractions were combined, concentrated, and dried under high vacuum for 1 hour at room temperature to provide bromo-(2-chlorophenyl)-acetic acid methyl ester (2.0 g, 86% yield) as a clear liquid that solidified at low temperatures (−10° C.). $^1$H NMR (300 MHz, CDCl$_3$/TMS): δ=7.75 (d, 11-1, J=6.9 Hz), 7.39-7.26 (m, 3H), 5.91 (s, 1H), 3.80 (s, 3H). $^{13}$C NMR (75 MHz, CDCl$_3$/TMS): δ=168.29, 133.82, 133.30, 130.93, 130.47, 129.83, 127.66, 53, 80, 43.08.

Step 6: Synthesis of (2-Chlorophenyl)-(3-oxo-3,6-dihydro-2H-pyridin-1-yl)-acetic acid methyl ester

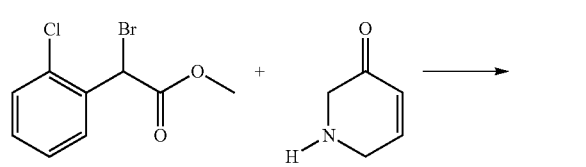

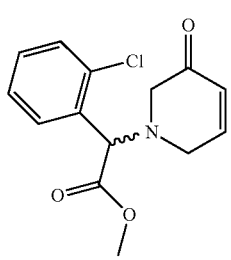

1,6-Dihydro-2H-pyridin-3-one, trifluoroacetic acid salt (1.27 g, 6.0 mmol) and bromo-(2-chlorophenyl)-acetic acid methyl ester (1.50 g, 6.15 mmol) were dissolved in DMF (5 mL) under an argon atmosphere at room temperature. Potassium carbonate (2 g, 14.5 mmol) was added and the mixture stirred for 3 hours at room temperature. Water (25 mL) was added and the product was extracted with dichloromethane (2×25 mL). The dichloromethane extracts were combined, dried over sodium sulfate, filtered, and concentrated. The remaining oil was purified on silica gel (30 g), eluting with heptane-ethyl acetate (3:1). The product containing fractions were combined, concentrated under reduced pressure, and dried under high vacuum for 2 hours at room temperature to provide (2-chlorophenyl)-(3-oxo-3,6-dihydro-2H-pyridin-1-yl)-acetic acid methyl ester (0.50 g, 29.7% yield) as a light yellow oil. $^1$H NMR (300 MHz, CDCl$_3$/TMS): δ=7.50-7.39 (m, 2H), 7.30-7.26 (m, 2H), 7.02-6.97 (m, 1H), 6.09 (d, 1H, J=10.5 Hz), 4.94 (s, 1H), 3.70 (s, 3H), 3.49 (m, 2H), 3.39 (d, 1H, J=15.9 Hz), 3.31 (d, 1H, J=15.9 Hz). $^{13}$C NMR (75 MHz, CDCl$_3$/TMS): δ=194.81, 170.41, 148.28, 134.74, 132.10, 129.95, 129.73, 129.69, 127.44, 126.99, 66.70, 57.89, 52.14, 49.16. HRMS (GC-CI): Calculated for (M+H$^+$): 280.0740. found 280.0727.

Step 7: Synthesis of (2-chlorophenyl)-(3-mercapto-5-oxopiperidin-1-yl)-acetic acid methyl ester

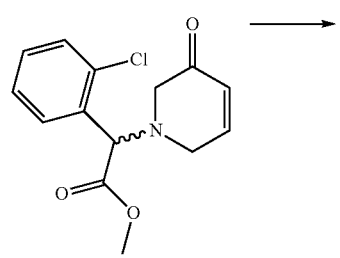

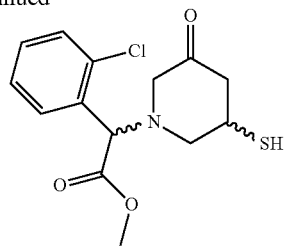

(2-Chlorophenyl)-(3-oxo-3,6-dihydro-2H-pyridin-1-yl)-acetic acid methyl ester (0.45 g, 1.6 mmol) was dissolved in methanol (100 mL) under an argon atmosphere. A few drops of triethylamine were added and argon gas was passed through the solution for 5 minutes. The argon was stopped and hydrogen sulfide was bubbled through the solution for 45 minutes. The hydrogen sulfide was stopped and the solution was placed under an argon atmosphere for 30 additional minutes. The excess hydrogen sulfide was removed by bubbling argon through the solution for 10 minutes. The methanol was removed under reduced pressure and crude (2-chlorophenyl)-(3-mercapto-5-oxopiperidin-1-yl)-acetic acid methyl ester (0.48 g, 96% yield, yellow glass) was used directly for the next step. $^1$H NMR (300 MHz, CDCl$_3$/TMS): δ=7.40-7.20 (m, 4H), 4.88 (3×s, 1H), 3.70 (s, 3H), 3.40-3.00 (m, 4H), 2.90-2.60 (m, 2H), 2.45-2.15 (m, 1H). $^{13}$C NMR (75 MHz, CDCl$_3$/TMS): δ=203.04, 170.75, 135.07, 132.49, 130.30, 129.96, 129.85, 127.04, 67.06, 60.38 (4 peaks), 57.19 (2 peaks), 52.29, 45.88 (3 peaks), 39.06 (4 peaks). HRMS (GC-CI): Calculated for (M+H$^+$): 314.0618. found 314.0588.

Step 8: Synthesis of 3-tert-butoxycarbonylmethyl-ene-5-mercaptopiperidin-1-yl)-(2-chlorophenyl)-acetic acid methyl ester. (Compound VIb)

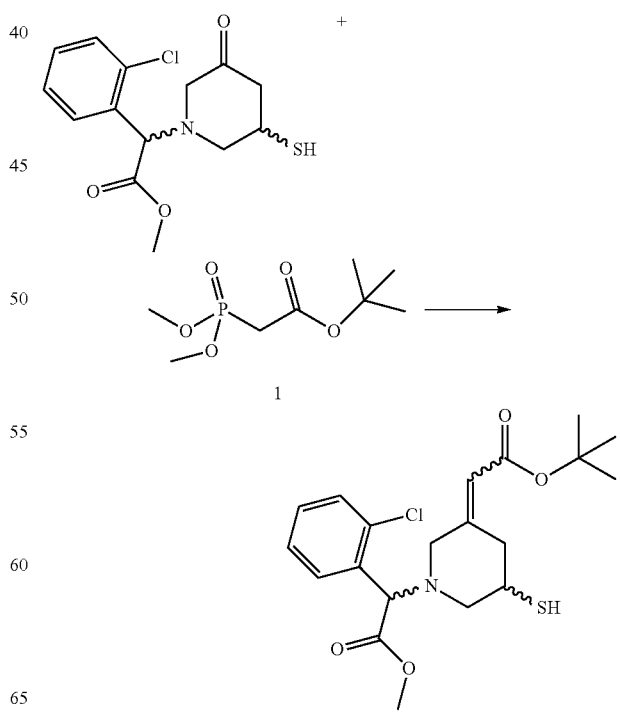

The crude (2-chlorophenyl)-(3-mercapto-5-oxopiperidin-1-yl)-acetic acid methyl ester (0.36 g, 1.14 mmol) was dissolved in THF (5 mL, argon sparged) and added to a mixture of tert-butyl P,P-dimethylphosphonoacetate (0.50 g, 2.23 mmol) and 60% sodium hydride (0.075 g, 1.87 mmol) in THF (4 mL, argon sparged), at room temperature under an argon atmosphere. After 20 minutes, dichloromethane (25 mL, argon sparged) was added and the mixture was washed with water (25 mL, argon sparged). The dichloromethane solution was dried over sodium sulfate, filtered, and concentrated under reduced pressure. The remaining yellow oil was purified by column chromatography on silica gel (15 g), eluting with heptane-ethyl acetate (4:1, argon sparged) to provide 3-tert-butoxycarbonylmethylene-5-mercaptopiperidin-1-yl)-(2-chlorophenyl)-acetic acid methyl ester (0.28 g, 59% yield) as a clear gel that was kept under an argon atmosphere at low temperature to prevent oxidation to the disulfide. $^1$H NMR (300 MHz, CDCl$_3$/TMS): δ=7.60-7.15 (m, 4H), 5.55 (m, 1H), 4.77 (m, 1H), 3.67 (s, 3H), 3.20-2.00 (m, 7H), 1.41 (m, 9H). $^{13}$C NMR (75 MHz, CDCl$_3$/TMS): δ=170.63 (2×), 165.26 (2×), 151.09 (3×), 134.64, 133.11 (4×), 129.83 (5×), 127.21, 118.35 (2×), 80.32 (2×), 67.57 (5×), 57.28 (6×), 52.28, 42.49-40.14 (8×), 34.54, 28.38 (2×). HRMS (DIP-CI): Calculated for (M+H$^+$): 412.1349. found 412.1312.

Step 9: Synthesis of (3-Carboxymethylene-5-mercaptopiperidin-1-yl)-(2-chlorophenyl)-acetic acid methyl ester, hydrochloride

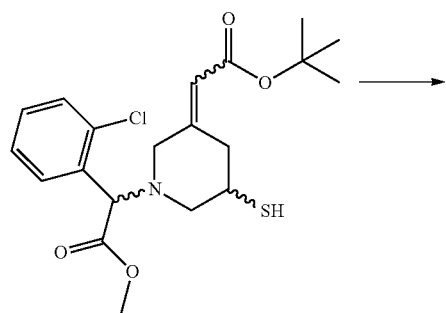

3-tert-Butoxycarbonylmethylene-5-mercaptopiperidin-1-yl)-(2-chlorophenyl)-acetic acid methyl ester (0.18 g, 0.43 mmol) was dissolved in a 1:1 mixture of dichloromethane and trifluoroacetic acid (6 mL, sparged with argon) that had been sparged with argon. The solution stirred for 3 hours under an argon atmosphere at room temperature. Dichloromethane (25 mL) was added and then washed with 5% sodium bicarbonate solution (2×25 mL, sparged with argon). The dichloromethane was dried over sodium sulfate, filtered, and concentrated under reduced pressure. Dichloromethane (5 mL, sparged with argon) was added and the salt was formed by adding 2N hydrochloric acid in diethyl ether (2 mL, sparged with argon). Additional diethyl ether (25 mL, sparged with argon) was added and the solid precipitate was filtered and dried under high vacuum for 3 hours at room temperature to provide (3-carboxymethylene-5-mercaptopiperidin-1-yl)-(2-chlorophenyl)-acetic acid methyl ester, hydrochloride salt (Compound VIa hydrochloride, 0.12 g, 70% yield) a slightly pink solid. $^1$H NMR (300 MHz, DMSO/TMS): δ=7.65-7.25 (m, 4H), 5.71 (m, 1H), 4.91 (m, 1H), 3.66 (s, 3H), 3.40-2.00 (m, 7H). (mixture of 8 isomers). $^{13}$C NMR (75 MHz, DMSO/TMS): δ=169.60-165.99 (6 peaks), 194.52 (4 peaks), 133.46-127.01 (13 peaks), 119.50-117.50 (6 peaks), 66.94-65.45 (7 peaks), 56.74-49.17 (12 peaks), 33.31 (br). HRMS (DIP-CI): Calculated for (M+H): 356.0723. found 356.0712. CHN analysis: Calculated; 48.99; C, 4.88; H, 3.51; N. found; 49.25; C, 5.00; H, 3.57; N.

Example 10

8-(2-Chlorophenyl)-8-(6,7-dihydro-4H-thieno[3,2-c]pyridin-5-yl)-2,2-dimethyloctanoic acid. (Compound Im)

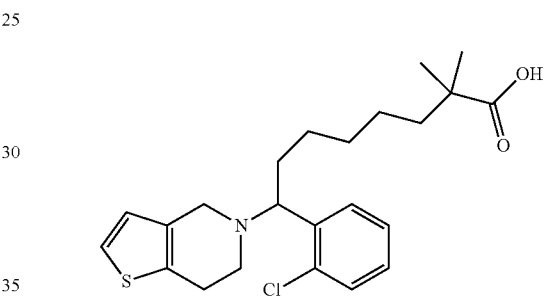

Step 1: Synthesis of 6-Ethoxycarbonyl-6-methylheptyl)triphenylphosphonium bromide

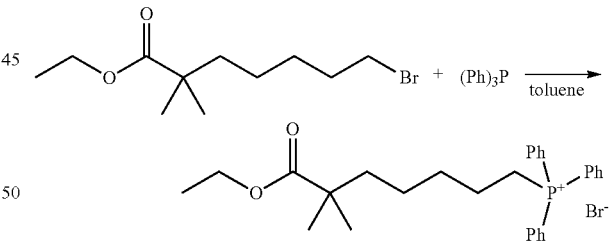

Triphenylphosphine (14.8 g, 56.6 mmoL) was added to a solution of 7-bromo-2,2-dimethylheptanoic acid ethyl ester (15.0 g, 56.6 mmoL) in toluene (110 mL). The solution was heated to reflux (oil bath 122° C.) for 24 h. The toluene was evaporated and the residue was washed with heptane (2×60 mL), diethyl ether (2×60 mL), and dried in high vacuum to a constant weight to provide 6-ethoxycarbonyl-6-methylheptyl)triphenylphosphonium bromide (24.39 g, 81.8% yield) as a off-white powder (m.p. 165-170° C.). $^1$H NMR (Field: 300 MHz, Solvent: CDCl$_3$/TMS) δ (ppm): 7.88-7.82 (m, 9H), 7.75-7.72 (m, 6H), 4.06 (q, 2H, J=6.9 Hz), 3.76 (m, 2H), 1.64 (m, 4H), 1.46-1.41 (m, 2H), 1.20 (t, 51-I, J=6.9 Hz), 1.10 (s, 6H). $^{13}$C NMR (Field: 75 MHz, Solvent: CDCl$_3$/TMS) δ (ppm): 177.82, 134.99, 133.69 (d, J=10 Hz), 130.57 (d, J=12

Hz), 117.69 (d, J=85 Hz), 60.29, 42.12, 40.09, 30.94 (d, J=16 Hz), 25.26 (d, J=41 Hz), 23.18 (d, J=41 Hz), 14.40. HRMS (FIA-ESI-TOFM)): Calculated for $C_{29}H_{36}BrO_2P$ (M+H)$^+$ 447.2447. found 447.2446.

Step 2: Synthesis of 8-(2-chlorophenyl)-2,2-dimethyl-oct-7-enoic acid ethyl ester

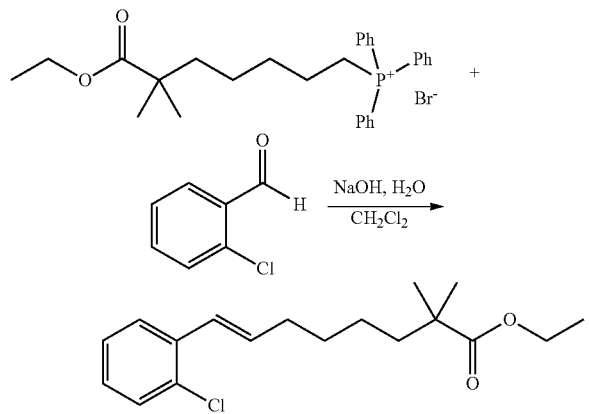

6-Ethoxycarbonyl-6-methylheptyl)triphenylphosphonium bromide (24 g, 45.5 mmol) and 2-chlorobenzaldehyde (6.38 g, 45.5 mmol) in $CH_2Cl_2$ (60 mL) were stirred as vigorously as possible and 50% NaOH solution (24 mL) was added drop-wise. After the addition was complete, the mixture continued to stir for 3 hours. The mixture was transferred to a separator and washed with dichloromethane (200 mL) and water (200 mL). The aqueous portion was extracted with dichloromethane (3×150 mL). The combined dichloromethane extracts were washed with brine (150 mL), dried over $Na_2SO_4$, concentrated, and purified by column chromatography (silica gel, ethyl acetate/heptane=1/10 to 1/6) to provide 8-(2-chlorophenyl)-2,2-dimethyl-oct-7-enoic acid ethyl ester (10 g, 71.6% yield) as a yellow oil. $^1$H NMR (Field: 300 MHz, Solvent: CDCl$_3$/TMS) δ (ppm): 7.46 (dd, 1H, J=7.5, 1.5 Hz), 7.36-7.06 (m, 3H), 6.49 (d, 1H, J=11.4 Hz), 5.74 (m, 1H), 4.09 (m, 2H), 2.20 (m, 2H), 1.58-1.36 (m, 4H), 1.21 (m, 5H), 1.13 (s, 6H). (major isomer). $^{13}$C NMR (Field: 75 MHz, Solvent: CDCl$_3$/TMS) δ (ppm): 177.76, 135.78, 134.00, 133.69, 130.48, 129.52, 127.94, 126.69, 126.27, 60.25, 42.26, 40.68, 33.14, 30.27, 28.46, 25.28, 24.73, 14.32. (major isomer). HRMS (FIA-ESI-TOFM): Calculated for $C_{18}H_{25}ClO_2$ (M+Na): 331.1435. found 331.1446.

Step 3: Synthesis of 8-bromo-8-(2-chlorophenyl)2,2-dimethyloctanoic acid ethyl ester

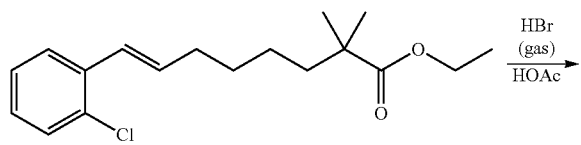

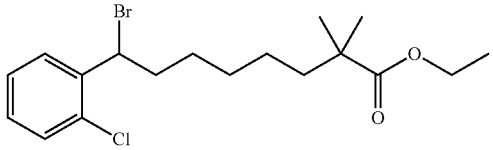

8-(2-Chlorophenyl)-2,2-dimethyl-oct-7-enoic acid ethyl ester (7 g, 22.8 mmol) was dissolved in glacial acetic acid (60 mL). The solution was cooled in an ice-bath (ca. 15° C.), while dry hydrogen bromide was passed into the solution for 8 h. The reaction mixture was poured into ice-water (130 mL) and extracted with ethyl acetate (3×50 mL). The combined organic layers were washed with saturated $NaHCO_3$ solution (100 mL), dried over $Na_2SO_4$, and concentrated under reduced pressure. The crude product (10 g) was purified by column chromatography (200 g silica gel, eluting with ethyl acetate/heptane=1/20 to 1/10) to furnish 8-bromo-8-(2-chlorophenyl)2,2-dimethyloctanoic acid ethyl ester (7.46 g, 81.8% yield) as a yellow oil. $^1$H NMR (Field: 300 MHz, Solvent: CDCl$_3$/TMS) δ (ppm): 7.59 (d, 1H, J=7.8 Hz), 7.34 (t, 1H, J=7.5 Hz), 7.26 (d, 1H, J=6.9 Hz), 7.19 (t, 1H, J=7.2 Hz), 5.45 (t, 1H, J=7.5 Hz), 4.09 (q, 2H, J=7.2 Hz), 2.26-2.09 (m, 4H), 1.52-1.46 (m, 2H), 1.41-1.31 (m, 2H), 1.28-1.18 (m, 2H), 1.20 (t, 3H, J=7.2 Hz), 1.14 (s, 6H). $^{13}$C NMR (Field: 75 MHz, Solvent: CDCl$_3$/TMS) δ (ppm): 177.80, 139.43, 132.65, 129.64, 129.24, 128.88, 127.45, 60.28, 50.30, 42.25, 39.21, 29.48, 27.98, 25.36, 24.88, 14.49. HRMS (GC-Cl): Calculated for $C_{18}H_{26}BrClO_2$ (M+H)$^+$389.0883. found 389.0867.

Step 4: Synthesis of 8-(2-chlorophenyl)-8-(6,7-dihydro-4H-thieno[3,2-c]pyridin-5-yl)-2,2-dimethyloctanoic acid ethyl ester. (Compound In)

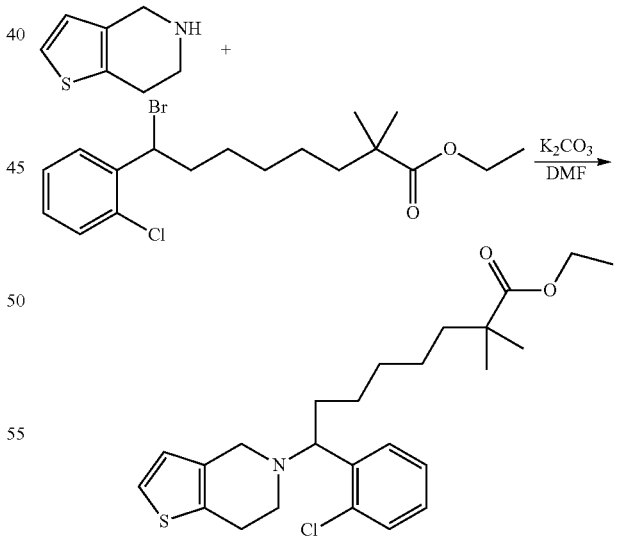

4,5,6,7-tetrahydrothieno[3,2-c]pyridine hydrochloride (1.30 g, 7.19 mmol) was added to sodium hydroxide (1.38 g) in water (86 mL) and extracted with dichloromethane (3×20 mL). The dichloromethane was dried over sodium sulfate, filtered, and concentrated to prepare the free base (1.0 g). 4,5,6,7-Tetrahydrothieno[3,2-c]pyridine free base (1.0 g, 7.19 mmol) and 8-bromo-8-(2-chlorophenyl)2,2-dimethyloctanoic acid ethyl ester (2.8 g, 7.19 mmol) were dissolved in DMF (75 mL) with potassium carbonate (1.49 g, 10.79 mmol). The mixture was heated to 65-70° C. overnight. After 18 hours, the mixture was cooled to room temperature and water (50 mL) was added. The product was extracted with diethyl ether (3×50 mL). The combined organic extracts were washed with water (3×50 mL), dried over sodium sulfate, and concentrated under reduced pressure. The crude product was purified by column chromatography on silica gel, eluting with ethyl acetate/heptane (1/10) to provide 8-(2-chlorophenyl)-8-(6,7-dihydro-4H-thieno[3,2-c]pyridin-5-yl)-2,2-dimethyloctanoic acid ethyl ester (Compound In, 1.4 g, 43.5%) as a yellow oil. $^1$H NMR (Field: 300 MHz, Solvent: CDCl$_3$/TMS) δ (ppm): 7.49 (dd, 1H, J=7.5, 1.5 Hz), 7.35 (dd, 1H, J=8.1, 1.2 Hz), 7.24 (dt, 1H, J=7.5, 1.0 Hz), 7.16 (dt, 1H, J=7.8, 1.5 Hz), 7.02 (d, 1H, J=5.0 Hz), 6.68 (d, 1H, J=5.0 Hz), 4.18 (dd, 1H, J=8.7, 4.2 Hz), 4.08 (q, 2H, J=6.9 Hz), 3.82 (d, 1H, J=14.1 Hz), 3.48 (d, 1H, J=14.1 Hz), 2.88-2.66 (m, 4H), 1.96-1.76 (m, 2H), 1.46-1.41 (m, 2H), 1.26-1.18 (m, 6H), 1.21 (t, 3H, J=6.9 Hz), 1.11 (s, 6H). $^{13}$C NMR (Field: 75 MHz, Solvent: CDCl$_3$/TMS) δ (ppm): 177.92, 134.92, 134.21, 133.53, 129.48, 129.06, 127.94, 126.77, 125.44, 122.60, 63.67, 60.27, 50.73, 48.08, 42.29, 40.85, 33.02, 30.52, 26.13, 25.39, 25.01, 14.51. HRMS (FIA-ESI-TOFM): Calculated for C$_{25}$H$_{34}$ClNO$_2$S (M+H)$^+$: 448.2072. found 448.2067.

Step 5: Synthesis of 8-(2-chlorophenyl)-8-(6,7-dihydro-4H-thieno[3,2-c]pyridin-5-yl)-2,2-dimethyloctanoic acid (Compound Im)

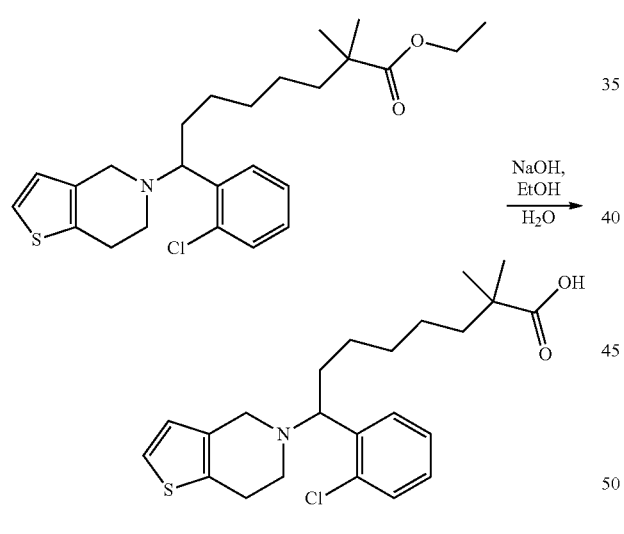

8-(2-Chlorophenyl)-8-(6,7-dihydro-4H-thieno[3,2-c]pyridin-5-yl)-2,2-dimethyloctanoic acid ethyl ester (0.86 g, 1.92 mmol) was added to a solution of ethanol (32 mL) and sodium hydroxide (0.53 g, 13.4 mmol) in water (10.4 mL). The mixture was heated to reflux for 6.5 hours. The solution was concentrated under reduced pressure and water (43 mL) was added to the residue. Any starting material was extracted with ethyl acetate/heptane (1/10, 43 mL). The heptane extract was discarded. The remaining aqueous solution was adjusted with 10 N hydrochloric acid solution to pH=6. The product was extracted with CH$_2$Cl$_2$ (3×40 mL), dried over Na$_2$SO$_4$, concentrated and purified by column chromatography (silica gel, ethyl acetate/heptane=1/10 to 1/3) to provide 8-(2-chlorophenyl)-8-(6,7-dihydro-4H-thieno[3,2-c]pyridin-5-yl)-2,2-dimethyloctanoic acid (Compound Im, 0.35 g, 43.8% yield, 99.6% purity by HPLC) as a yellow oil. $^1$H NMR (Field: 300 MHz, Solvent: CDCl$_3$/TMS) δ (ppm): 10.43 (br, 1H), 7.52 (d, 1H, J=7.50 Hz), 7.39 (d, 1H, J=8.10 Hz), 7.28-7.15 (m, 2H), 7.03 (d, 1H, J=5.0 Hz), 6.69 (d, 1H, J=5.0 Hz), 4.24 dd, 1H, J=9.3, 4.2 Hz), 3.83 (d, 1H, J=14.40 Hz), 3.51 (d, 1H, J=14.40 Hz), 2.92-2.73 (m, 4H), 1.99-1.81 (m, 2H), 1.46-1.41 (m, 2H), 1.28-1.15 (m, 6H), 1.13 (s, 6H). (t, 3H, J=7.2 Hz), 1.15-1.08 (m, 2H), 1.07 (s, 6H). $^{13}$C NMR (Field: 75 MHz, Solvent: CDCl$_3$/TMS) δ (ppm): 184.02, 138.85, 135.16, 133.87, 133.42, 129.60, 129.17, 128.17, 126.92, 125.52, 122.74, 63.53, 50.54, 47.90, 42.29, 40.70, 32.95, 30.52, 25.75, 25.64, 25.26, 24.96. HRMS (FIA-ESI): Calculated for C$_{23}$H$_{30}$ClNO$_2$S (M+H)$^+$: 420.1759. found 420.1779. CHN analysis: Calculated; 65.77; C, 7.20; H, 3.33; N. found; 60.77; C, 6.68; H, 3.11; N. Best fit for CHN: C$_{23}$H$_{30}$ClNO$_2$S+HCl Example 11

7-(2-chlorophenyl)-7-(6,7-dihydro-4H-furo[3,2-c]pyridin-5-yl)-2,2-dimethylheptanoic acid, hydrochloride. (Compound Ii Hydrochloride)

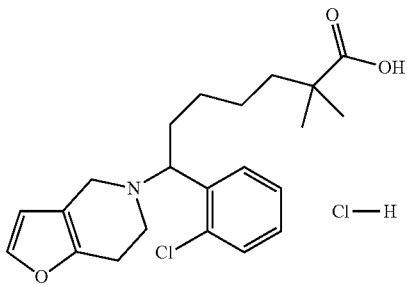 [SMILES: CC(C)(CCCCC(c1ccccc1Cl)N1CCc2occc2C1)C(=O)O ; Cl]

Step 1: Synthesis of 7-(2-chlorophenyl)-7-(6,7-dihydro-4H-furo[3,2-c]pyridin-5-yl)-2,2-dimethylheptanoic acid ethyl ester. (Compound Ij)

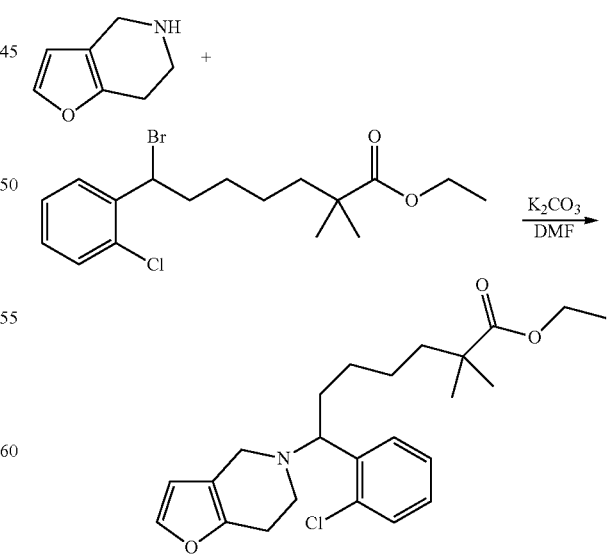

4,5,6,7-Tetrahydrofuro[3,2-c]pyridine (0.16 g, 1.3 mmol), 7-bromo-7-(2-chlorophenyl)-2,2-dimethylheptanoic acid ethyl ester (0.49 g, 1.3 mmol) in DMF (13 mL), and potassium carbonate (0.27 g, 1.95 mmol) were combined under an argon atmosphere at room temperature. The mixture was heated to 65° C. overnight under an argon atmosphere. The reaction continued at 65° C. for 48 hours. After cooling to room temperature and concentration under reduced pressure, the crude product (0.28 g) was purified by column chromatography (silica gel, ethyl acetate/heptane=1/20 to 1/5) to afford 7-(2-chlorophenyl)-7-(6,7-dihydro-4H-furo[3,2-c]pyridin-5-yl)-2,2-dimethylheptanoic acid ethyl ester (Compound Ij, 0.26 g, 48.1% yield) as a yellow oil. $^1$H NMR (Field: 300 MHz, Solvent: CDCl$_3$/TMS) δ (ppm): 7.42 (d, 1H, J=7.5 Hz), 7.29 (d, 1H, J=7.2 Hz), 7.17 (t, 1H, J=8.7 Hz), 7.14 (s, 1H), 7.09 (t, 1H, J=8.1 Hz), 6.08 (s, 1H), 4.12 (t, 1H, J=4.2 Hz), 4.01 (q, 2H, J=7.2 Hz), 3.98 (d, 1H, J=14.4 Hz), 3.26 (d, 1H, J=13.5 Hz), 2.79-2.53 (m, 4H), 1.90-1.73 (m, 2H), 1.35-1.32 (m, 2H), 1.20-1.06 (m, 7H), 1.04 (s, 6H). $^{13}$C NMR (Field: 75 MHz, Solvent: CDCl$_3$/TMS) δ (ppm): 177.91, 148.97, 140.89, 139.39, 134.93, 129.50, 129.00, 128.02, 126.84, 115.82, 108.84, 63.33, 60.54, 47.61, 47.51, 42.28, 40.78, 33.21, 26.23, 25.35, 24.65, 14.50.

Step 2: Synthesis of 7-(2-chlorophenyl)-7-(6,7-dihydro-4H-furo[3,2-c]pyridin-5-yl)-2,2-dimethylheptanoic acid, hydrochloride

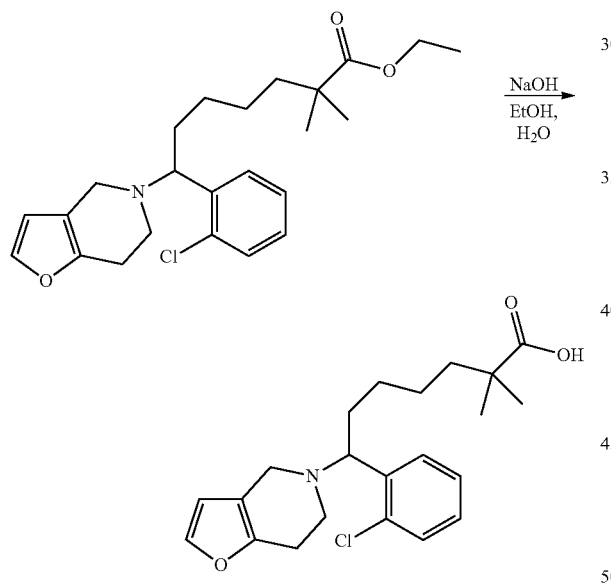

7-(2-Chlorophenyl)-7-(6,7-dihydro-4H-furo[3,2-c]pyridin-5-yl)-2,2-dimethylheptanoic acid ethyl ester (0.26 g, 0.62 mmol) was added to a mixture solution of ethanol (10 mL) and sodium hydroxide (0.17 g, 4.4 mmol) in water (3.3 mL), the mixture was heated to reflux for 6.5 hours, when the TLC showed the starting material was gone. The ethanol was removed under reduced pressure and additional water (15 mL) was added to the residue. The aqueous portion was washed with a mixture of ethyl acetate/heptane 1/10 (10 mL), which was discarded. The aqueous fraction was adjusted with concentrated hydrochloric acid to pH=6. The product was extracted with dichloromethane (3×15 mL). The combined dichloromethane layers were dried over sodium sulfate, filtered, and concentrated under reduced pressure. The product acid was obtained (0.17 g, 70.1% yield, 97.23% purity by HPLC) as a yellow oil. A portion of the material (0.15 g, 0.38 mmol) was dissolved in diethyl ether (5 mL) and added to 2N HCl in ether (0.21 mL). The solid precipitate was extracted with water (10 mL) and freeze dried to provide 7-(2-chlorophenyl)-7-(6,7-dihydro-4H-furo[3,2-c]pyridin-5-yl)-2,2-dimethylheptanoic acid (Compound Ii hydrochloride, 0.11 g, 68.8% yield, 99.08% purity by HPLC) as a light yellow powder. $^1$H NMR (Field: 300 MHz, Solvent: CD$_3$OD/TMS) δ (ppm): 7.80 (br s, 1H), 7.61-7.48 (m, 4H), 6.43 (s, 0.5H), 6.29 (s, 0.5H), 5.07 (m, 1H), 4.68 (d, 0.5H, J=13.8 Hz), 4.30 (d, 0.51-1, J=13.8 Hz), 4.25-3.95 (m, 1H), 3.64-3.40 (m, 1H), 3.09-2.95 (m, 2H), 2.40-2.27 (m, 2H), 1.46-0.87 (m, 6H), 1.11 (s, 6H), 1.09 (br s, 1H). (mixture of rotational isomers). $^{13}$C NMR (Field: 75 MHz, Solvent: CD$_3$OD/TMS) δ (ppm): 181.47, 147.11, 141.52, 137.12, 132.84, 132.09 131.86, 130.50, 129.75, 112.35, 109.69, 66.20 (br), 43.03, 41.40, 33.10, 31.71, 30.18, 27.36, 25.92, 25.70, 25.63, 23.80, 22.26, 14.50. (mixture of rotational isomers). HRMS (DIP-CI): Calculated for C$_{22}$H$_{28}$ClNO$_3$ (M+H)$^+$: 390.1830. found 390.1792. CHN Analysis: Calculated for C$_{22}$H$_{29}$NCl$_2$O$_3$S: 61.97; C, 6.86; H, 3.28; N, 16.61 Cl. found 60.28; C, 6.88; H, 3.13; N, 16.24 Cl.

Example 12

7-(2-Chlorophenyl)-2,2-dimethyl-7-(1,4,6,7-tetrahydropyrrolo[3,2-c]pyridin-5-yl)-heptanoic acid, hydrochloride. (Compound Ik Hydrochloride)

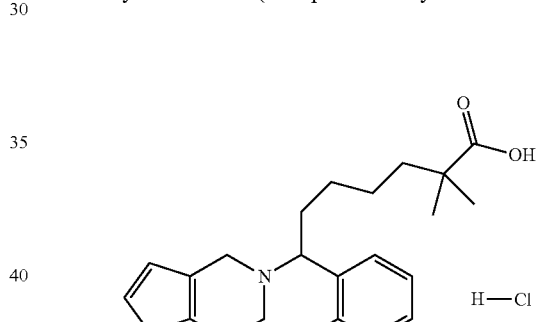

Step 1: Synthesis of 1-tert-butoxycarbonyl-5-[1-(2-chlorophenyl)-6-methylheptyl]-1H-pyrrolo[3,2-c]pyridin-5-ium bromide

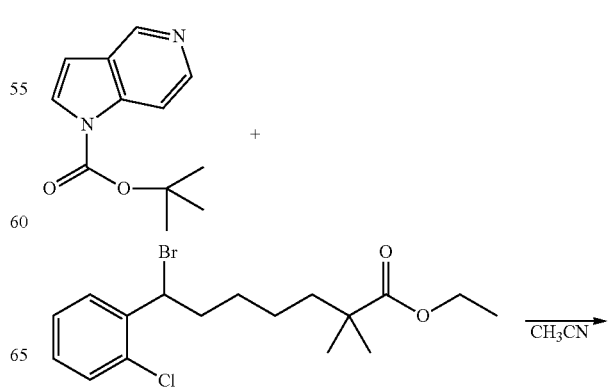

-continued

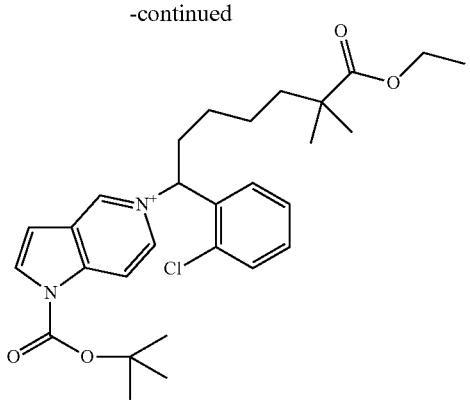

A mixture of tert-butyl 1H-pyrrolo[3,2-c]pyridine-1-carboxylate (0.81 g, 3.73 mmol), 7-bromo-7-(2-chlorophenyl)-2,2-dimethyloctanoic acid ethyl ester (1.40 g, 3.73 mmol) in acetonitrile (25 mL) was stirred and warmed to 45° C. After 52 hours, the reaction was completed. The solvent was evaporated under reduced pressure, the residue was washed with diethyl ether (3×20 mL) to afford 1-tert-butoxycarbonyl-5-[1-(2-chlorophenyl)-6-methylheptyl]-1H-pyrrolo[3,2-c]pyridin-5-ium bromide (1.47 g, 66.5% yield) as a yellow oil. $^1$H NMR (Field: 300 MHz, Solvent: CD$_3$OD/TMS) δ (ppm): 10.54 (s, 1H), 8.84 (d, 1H, J=6.9 Hz), 8.23 (d, 1H, J=7.8 Hz), 7.72 (s, 1H), 7.53 (t, 1H, J=4.2 Hz), 7.45 (t, 1H, J=7.2 Hz), 7.39 (d, 1H, J=3.6 Hz), 7.31 (s, 1H), 6.96 (s, 1H), 6.47 (t, 1H, J=7.2 Hz), 4.10 (q, 2H, J=5.7 Hz), 2.72 (d, 21-1, J=6.6 Hz), 2.40 (m, 1H), 1.69 (s. 9H), 1.50-1.32 (m, 4H), 1.21 (t, 3H, J=3.3 Hz), 1.12 (s, 6H). (crude mixture. HRMS (DIP-CI): failed, decomposed on analysis.

Step 2: Synthesis of 5-[1-(2-chlorophenyl)-6-ethoxycarbonyl-6-methylheptyl]-4,5,6,7-tetrahydro-pyrrolo[3,2-c]pyridine-1-carboxylic acid tert-butyl ester

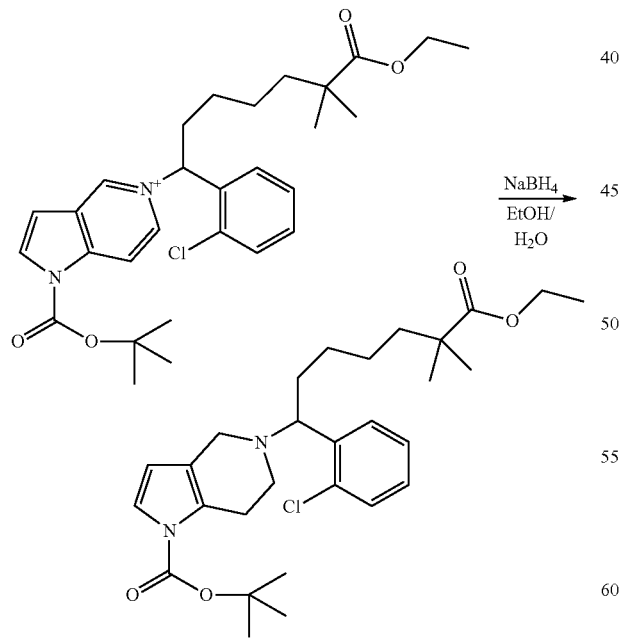

To a solution of 1-tert-butoxycarbonyl-5-[1-(2-chlorophenyl)-6-methylheptyl]-1H-pyrrolo[3,2-c]pyridin-5-ium bromide (2.4 g, 4.0 mmol) in 70% EtOH (60 mL) was added (at room temperature, with vigorous stirring, and in portions) sodium borohydride (0.30 g, 8.0 mmol). When the sodium borohydride was completely added, the stirring was terminated and mixture was stirred for 0.5 hours. The solvent was evaporated under reduced pressure and water (60 mL) was added. The product was extracted with dichloromethane (3×150 mL) and the combined organic extracts were dried over sodium sulfate, filtered, and concentrated under reduced pressure. The crude residue was purified by column chromatography (silica gel, ethyl acetate/heptane=1/10 to 1/3) to yield 5-[1-(2-chlorophenyl)-6-ethoxycarbonyl-6-methylheptyl]-4,5,6,7-tetrahydro-pyrrolo[3,2-c]pyridine-1-carboxylic acid tert-butyl ester (1.45 g, 60.9% yield) as a yellow oil. $^1$H NMR (Field: 300 MHz, Solvent: CD$_3$OD/TMS) δ (ppm): 7.50 (dd, 1H, J=7.5, 1.2 Hz), 7.37 (d, 1H, J=8.1, 1.5 Hz), 7.27-7.10 (m, 3H), 5.94 (d, 1H, J=3.3 Hz), 4.16-4.13 (m, 1H), 4.09 (q, 2H, J=6.9 Hz), 3.62 (d, 1H, J=14.1 Hz), 3.28 (d, 1H, J=13.5 Hz), 2.85-2.60 (m, 4H), 1.98-1.76 (m, 2H), 1.55 (s, 9H), 1.42 (t, 2H, J=6.9 Hz), 1.28-1.16 (m, 4H), 1.21 (t, 3H, J=7.2 Hz), 1.11 (s, 6H). $^{13}$C NMR (Field: 75 MHz, Solvent: CDCl$_3$/TMS) δ (ppm): 177.98, 149.49, 139.66, 134.90, 129.44, 129.15, 127.93, 127.60, 126.84, 120.92, 119.77, 109.20, 83.26, 63.76, 60.33, 48.81, 48.19, 42.30, 40.80, 33.23, 32.13, 28.31, 26.07, 25.35, 22.96, 14.52. HRMS (DART-TOF): Calculated for C$_{20}$H$_{41}$ClN$_2$O$_2$ (M+H)$^+$: 517.2828. found 517.2833.

Step 3: Synthesis of 7-(2-chlorophenyl)-2,2 dimethyl-7-(1,4,6,7-tetrahydro-pyrrolo[3,2-c]pyridine-5-yl)-heptanoic acid ethyl ester. (Compound I1)

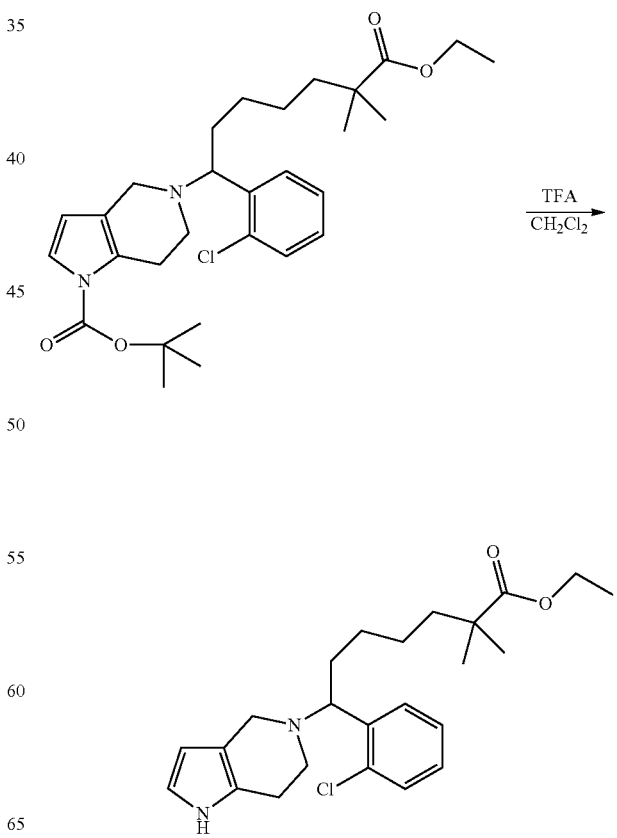

5-[1-(2-Chlorophenyl)-6-ethoxycarbonyl-6-methylheptyl]-4,5,6,7-tetrahydro-pyrrolo[3,2-c]pyridine-1-carboxylic acid tert-butyl ester (1.0 g, 1.94 mmol) was dissolved in dichloromethane (40 mL) under an argon atmosphere. Trifluoroacetic acid (4.0 mL, 40.7 mmol) was added to the solution. After 2 hours, the mixture was poured into ice/water (90 mL) and extracted with dichloromethane (3×20 mL). The combined organic layers were dried over sodium sulfate, filtered, and concentrated under reduced pressure. The crude product was purified by column chromatography (silica gel, ethyl acetate/heptane=1/9 to 1/3) to afford 7-(2-chlorophenyl)-2,2 dimethyl-7-(1,4,6,7-tetrahydro-pyrrolo[3,2-c]pyridine-5-yl)-heptanoic acid ethyl ester (Compound Il, 330 mg, 41.2% yield) as a yellow oil. $^1$H NMR (Field: 300 MHz, Solvent: CDCl$_3$/TMS) δ (ppm): 7.93 (br, 1H), 7.53 (d, 1H, J=7.5 Hz), 7.35 (d, 1H, J=7.8 Hz), 7.26-7.13 (m, 2H), 6.58 (s, 1H), 5.93 (s, 1H), 4.16 (dd, 1H, J=9.3, 3.9 Hz), 4.10 (q, 2H, J=7.2 Hz), 3.75 (d, 1H, J=13.5 Hz), 3.39 (d, 1H, J=13.2 Hz), 2.80-2.56 (m, 4H), 2.04-1.78 (m, 2H), 1.44-1.39 (m, 2H), 1.21 (t, 3H, J=6.9 Hz), 1.26-1.16 (m, 4H), 1.11 (s, 6H). $^{13}$C NMR (Field: 75 MHz, Solvent: CDCl$_3$/TMS) δ (ppm): 178.01, 139.87, 134.94, 129.40, 129.22, 127.86, 126.81, 125.01, 116.45, 115.70, 105.69, 63.80, 60.37, 48.78, 48.29, 42.31, 40.81, 33.29, 26.15, 25.36, 23.95, 14.52. HRMS (DART-TOF): Calculated for $C_{24}H_{33}ClN_2O_2$ (M+H)$^+$: 717.2303, 417.2295 found.

Step 4: Synthesis of 7-(2-chlorophenyl)-2,2 dimethyl-7-(1,4,6,7-tetrahydro-pyrrolo[3,2-c]pyridine-5-yl)-heptanoic acid. (Compound Ik)

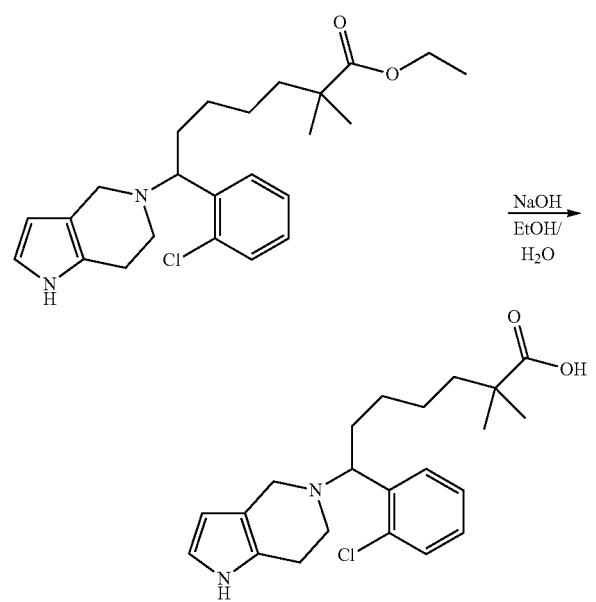

7-(2-Chlorophenyl)-2,2 dimethyl-7-(1,4,6,7-tetrahydro-pyrrolo[3,2-c]pyridine-5-yl)-heptanoic acid ethyl ester (0.21 g, 0.51 mmol) was added to a mixture of ethanol (10 mL), water (2.70 mL), and sodium hydroxide (0.14 g, 3.54 mmol). The mixture was heated to reflux (95-98° C. oil bath) for 16 hours. After 26 hours, the flask was cooled to room temperature and the solvent was evaporated under reduced pressure. Water (15 mL) was added to the residue and the product was extracted with diethyl ether (15 mL). The extract was discarded and the aqueous portion was adjusted pH=6 with 10 N hydrochloric acid. The product was extracted with dichloromethane (3×15 mL) and the combined dichloromethane layers were washed with water (20 mL) and brine (20 mL). The dichloromethane solution was dried over sodium sulfate, filtered, and concentrated in under reduced pressure. The crude product was purified by column chromatography (silica gel, MeOH/CH$_2$Cl$_2$=1/9) to afford 7-(2-chlorophenyl)-2,2 dimethyl-7-(1,4,6,7-tetrahydro-pyrrolo[3,2-c]pyridine-5-yl)-heptanoic acid (Compound Ik, 0.11 g, 57.9% yield) as a yellow oil. $^1$H NMR (Field: 300 MHz, Solvent: DMSO/TMS) δ (ppm): 12.10 (br, 1H), 10.30 (br, 1H), 7.53 (m, 1H), 7.43 (d, 1H, J=7.2 Hz), 7.36-7.25 (m, 2H), 6.50 (s, 1H), 5.71 (s, 1H), 4.10 (m, 1H), 3.39 (m, 5H), 2.75 (m, 1H), 1.14 (m, 2H), 1.34 (m, 2H), 1.23-1.07 (m, 4H), 1.03 (s, 6H). $^{13}$C NMR (Field: 75 MHz, Solvent: DMSO/TMS) δ (ppm) 178.45, 178.97, 133.83, 129.07, 128.23, 126.93, 123.97, 115.83, 113.99, 104.19, 63.11, 48.27, 47.60, 41.19, 40.06, 31.59, 25.84, 25.03, 24.96, 24.55, 23.34.

Step 5: Synthesis of 7-(2-Chlorophenyl)-2,2-dimethyl-7-(1,4,6,7-tetrahydropyrrolo[3,2-c]pyridin-5-yl)-heptanoic acid, hydrochloride

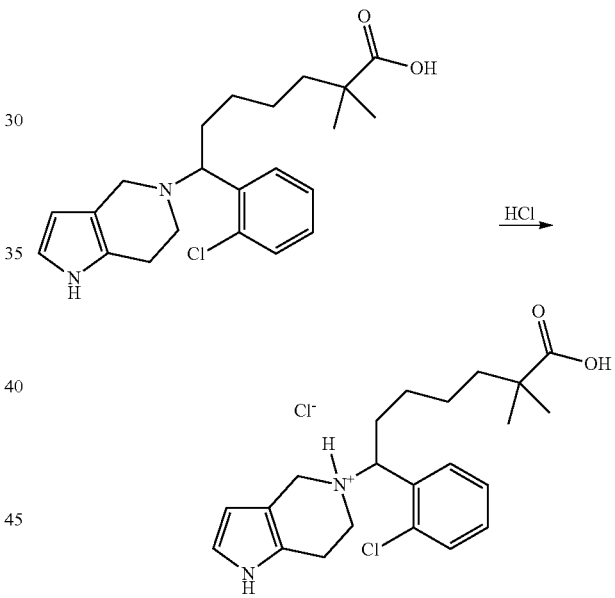

7-(2-Chlorophenyl)-2,2 dimethyl-7-(1,4,6,7-tetrahydropyrrolo[3,2-c]pyridine-5-yl)-heptanoic acid (0.26 g, 0.67 mmol) was dissolved in diethyl ether (15 mL) and hydrogen chloride solution (2N HCl in diethyl ether) was added. The ether solution was extracted with water (15 mL) and the organic layer was discarded. The aqueous solution was freeze dried to afford 7-(2-chlorophenyl)-2,2 dimethyl-7-(1,4,6,7-tetrahydro-pyrrolo[3,2-c]pyridine-5-yl)-heptanoic acid, hydrochloride (Compound Ik hydrochloride, 0.19 g, 61.9% yield) as a light yellow powder (purity 97.33% by HPLC, mp. 168-172° C.). $^1$H NMR (Field: 300 MHz, Solvent: CD$_3$OD/TMS) δ (ppm): 10.26 (br s, 1H), 7.65 (br s, 1H), 7.45-7.38 (m, 4H), 6.54-6.50 (2 s, 1H), 5.84 (s, 0.5H), 5.66 (s, 0.5H), 4.79 (m, 1H), 4.51 (m, 1H), 4.14-3.82 (m, 2H), 3.43-2.76 (m, 4H), 2.43-2.09 (m, 2H), 1.25-1.14 (m, 4H), 1.39-0.65 (m, 2H), 0.96 (s, 6H). (mixture of conformational isomers). $^{13}$C NMR (Field: 75 MHz, Solvent: CDCl$_3$/TMS) δ (ppm) 181.52, 137.17, 132.64, 132.32, 131.75, 130.09, 129.79, 122.85, 119.88, 109.70, 106.00, 65.79, 51.79, 51.10, 42.98, 41.43, 31.84, 27.28, 25.096, 25.76, 21.78. MS (HR, DIP-CI): Calculated for $C_{22}H_{30}Cl_2N_2O_2$ (M+H)$^+$: 389.1994. found 389.1996. CHN analysis: Calculated; 62.12; C, 7.11; H, 6.59; N, 16.67; Cl. Found; 59.23; C, 7.04; H, 6.26; N, 16.93; Cl.

Example 13

6-[1-(2-Dimethylaminopyrimidin-5-ylmethyl)-piperidin-4-yl]-2-morpholin-4-yl-pyrimidin-4-ol, Compound IIa

Step 1: Synthesis of 4-(2-ethoxycarbonylacetyl)-piperidine-1-carboxylic acid tert-butyl ester

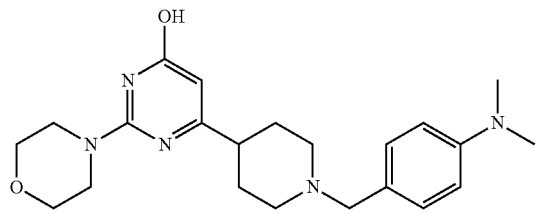 [SMILES: CN(C)c1ccc(CN2CCC(c3cc(O)nc(N4CCOCC4)n3)CC2)cc1]

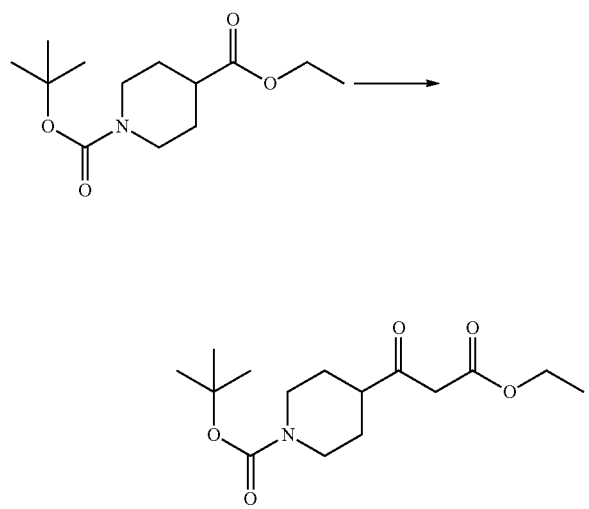 [SMILES: CCOC(=O)C1CCN(C(=O)OC(C)(C)C)CC1 ; CCOC(=O)CC(=O)C1CCN(C(=O)OC(C)(C)C)CC1]

Piperidine-1,4-dicarboxylic acid 1-tert-butyl ester 4-ethyl ester (0.50 g, 1.94 mmol) in DMF (5 mL) was mixed with ethyl acetate (0.38 mL, 3.88 mmol) and potassium tert-butoxide (0.33 g, 2.92 mmol). The mixture was heated to 50° C. for 20 hours. After cooling to room temperature, water was added (50 mL) and the product was extracted with diethyl ether. The ether extract was dried over sodium sulfate, filtered and concentrated. The crude product was purified by column chromatography on silica gel, eluting with heptane-ethyl acetate to provide 4-(2-ethoxycarbonylacetyl)-piperidine-1-carboxylic acid tert-butyl ester (0.27 g, 47% yield). $^1$H NMR (300 MHz, CDCl$_3$/TMS): δ=4.20 (q, 2H, J=7.2 Hz), 4.18-4.05 (m, 2H), 3.50 (s, 2H), 2.86-2.70 (m, 2H), 2.68-2.55 (m, 1H), 1.90-1.78 (m, 2H), 1.60-1.50 (m, 2H), 1.45 (s, 9H), 1.28 (t, 3H, J=7.2 Hz). $^{13}$C NMR (75 MHz, CDCl$_3$/TMS): δ=204.21, 167.20, 154.67, 79.91, 61.70, 48.93, 47.56, 43.41, 28.73, 27.56, 14.46.

Step 2: Synthesis of 4-(6-hydroxy-2-morpholin-4-ylpyrimidin-4-yl)-piperidine-1-carboxylic acid tert-butyl ester

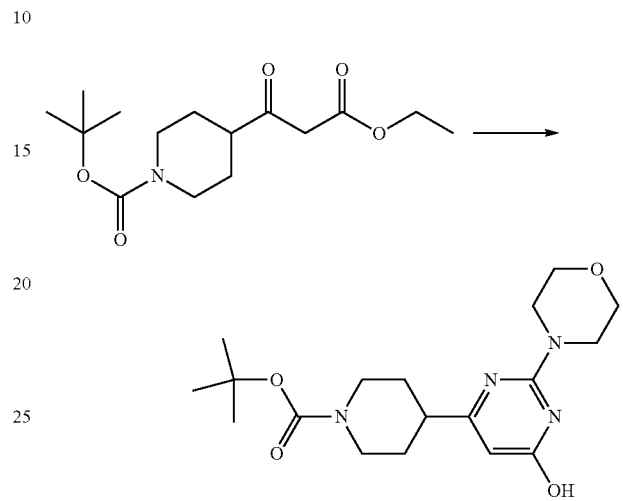

Morpholine-4-carboxamidine hydrobromide (0.267 g) and 4-(2-ethoxycarbonylacetyl)-piperidine-1-carboxylic acid tert-butyl ester (0.38 g, 1.27 mmol) were stirred in ethanol (10 mL) and diazobicycloundecane (285 μl) was added. The reaction stirred for 18 hours at room temperature. The ethanol was removed under reduced pressure and water (25 mL) was added. The solution was acidified (to pH=4) with acetic acid. The product was extracted with dichloromethane (4×30 mL). The dichloromethane was removed and crude product was purified twice on silica gel (Combiflash), eluting with 10% methanol in dichloromethane to provide 4-(6-hydroxy-2-morpholin-4-ylpyrimidin-4-yl)-piperidine-1-carboxylic acid tert-butyl ester (0.15 g, 40.5% yield) as a white solid. $^1$H NMR (300 MHz, CDCl$_3$/TMS): δ=5.63 (s, 1H), 4.25-4.05 (m, 2H), 3.75 (m, 8H), 2.75-2.65 (m, 2H), 2.47-2.35 (m, 1H), 1.00-1.75 (m, 2H), 1.70-1.50 (m, 2H), 1.46 (s, 9H). $^{13}$C NMR (75 MHz, CDCl$_3$/TMS): δ=173.35, 166.87, 154.96, 154.06, 98.88, 79.70, 66.72, 45.13, 44.24, 30.64, 28.82, 27.58.

Step 3: Synthesis of 2-morpholin-4-yl-6-piperidin-4-yl-pyrimidin-4-ol, hydrochloride salt

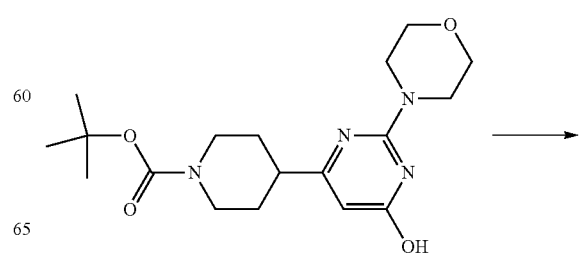

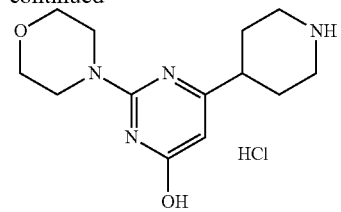

4-(6-Hydroxy-2-morpholin-4-ylpyrimidin-4-yl)-piperidine-1-carboxylic acid tert-butyl ester (0.19 g, 0.52 mmol) was added to 2 N hydrogen chloride in diethyl ether and stirred for 18 hours at room temperature. The resultant product was isolated by filtration and washed with ether to provide 2-morpholin-4-yl-6-piperidin-4-yl-pyrimidin-4-01, hydrochloride salt (0.16 g, 91% yield) as a white solid. $^1$H NMR (300 MHz, CD$_3$OD/TMS): δ=6.17 (s, 1H), 3.90-3.78 (m, 8H), 3.60-3.50 (m, 2H), 3.26-3.1 (m, 3H), 2.32-2.20 (m, 2H), 2.00-1.80 (m, 2H). $^{13}$C NMR (75 MHz, CD$_3$OD/TMS): δ=171.60, 164.86, 155.10, 97.63, 66.93, 45.13, 46.92, 44.81, 38.29, 28.41.

Step 4: Synthesis of 6-[1-(2-Dimethylaminopyrimidin-5-ylmethyl)-piperidin-4-yl]-2-morpholin-4-yl-pyrimidin-4-ol

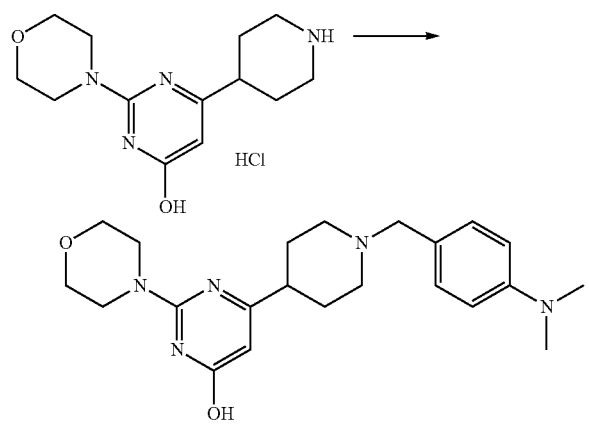

2-Morpholin-4-yl-6-piperidin-4-yl-pyrimidin-4-ol, hydrochloride salt (0.16 g, 0.47 mmol), 2-dimethylamino-pyrimidine-5-carboxaldehyde (86 mg, 0.57 mmol), and one drop of acetic acid were mixed in dry dichloromethane (10 mL) for 3 hours at room temperature. Sodium cyanoborohydride (88 mg, 1.42 mmol) was added and the mixture stirred for 3 days. The mixture was poured into saturated sodium bicarbonate solution and extracted with dichloromethane (3×50 mL). The material was purified on silica gel, eluting with 10% methanol in dichloromethane to provide 6-[1-(2-Dimethylaminopyrimidin-5-ylmethyl)-piperidin-4-yl]-2-morpholin-4-yl-pyrimidin-4-ol (Compound IIa, 0.11 g, 69% yield) as a white solid. CHN Analysis: Calculated for C$_{20}$H$_{29}$N$_7$O$_2$: 60.13; C, 7.32; H, 24.54; N. found 57.31; C, 7.11; H, 23.68; H. Bestfit is C$_{20}$H$_{29}$N$_7$O$_2$+1H$_2$O; 57.54; C, 7.48; H, 23.48; N. $^1$H NMR (300 MHz, CDCl$_3$/CD$_3$OD/TMS): δ=8.26 (s, 2H), 5.65 (s, 1H), 3.85-3.60 (m, 8H), 3.42 (m, 2H), 3.19 (s, 6H), 3.15-2.85 (m, 3H), 2.40-2.00 (m, 2H), 2.18-1.60 (m, 4H). $^{13}$C NMR (75 MHz, CDCl$_3$/CD$_3$OD/TMS): δ=173.66, 161.63, 158.91, 153.90, 116.63, 98.76, 66.56, 57.62, 53.12, 44.94, 43.65, 37.48, 30.26.

Example 14

Preparation of N-(2,3-Dihydrobenzo[1,4]dioxin-6-yl)-2-(2-methoxy-ethylamino)-acetamide, Compound XIa

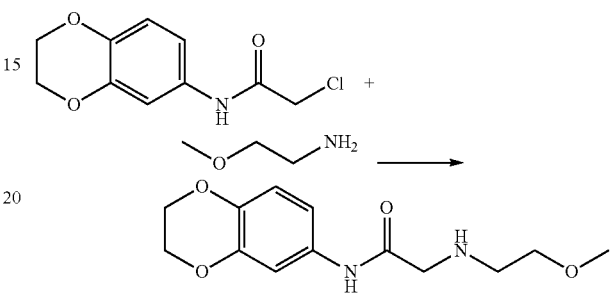

A mixture of 2-chloro-N-(2,3-dihydro-1,4-benzodioxin-6-yl)acetamide (2 mmol), potassium carbonate (10 mmol), 2-methoxyethylamine (2 mmol) and anhydrous DMF (4 mL) was stirred for 2 hours at 100° C. (monitored by TLC). The mixture was cooled to room temperature, treated with cold water (30 mL). The precipitate was collected by filtration, washed with diethyl ether and dried to afford N-(2,3-dihydro-benzo[1,4]dioxin-6-yl)-2-(2-methoxy-ethylamino)-acetamide (Compound XIa, 96 mg, 36%). $^1$H NMR (300 MHz, CDCl$_3$/TMS): δ=9.29 (s, 1H), 7.24 (d, 1H, J=2.4 Hz), 6.97 (dd, 1H, J=8.7, 2.4 Hz), 6.78 (d, 1H, J=8.7 Hz), 4.32-4.15 (m, 4H), 3.46 (t, 2H, J=4.8 Hz), 3.36 (s, 3H), 3.34 (s, 2H), 2.82 (t, 2H, J=4.8 Hz), 2.17 (s, 1H). $^{13}$C NMR (75 MHz, CDCl$_3$/CD$_3$OD/TMS): δ=169.48, 143.16, 139.87, 131.43, 116.84, 112.74, 108.89, 71.41, 64.28, 64.12, 58.68, 52.57, 49.35.

Example 15

Preparation of 6-[1-(3-Hydroxy-4-methoxybenzyl)-piperidin-4'-yl]-2-piperidin-1-yl-pyrimidin-4-ol, Compound IIb

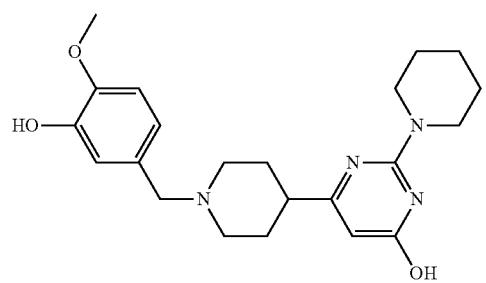 [SMILES: COc1ccc(CN2CCC(c3cc(O)nc(N4CCCCC4)n3)CC2)cc1O]

Step 1: Synthesis of 4-(2-Ethoxycarbonyl-acetyl)-piperidine-1-carboxylic acid tert-butyl ester

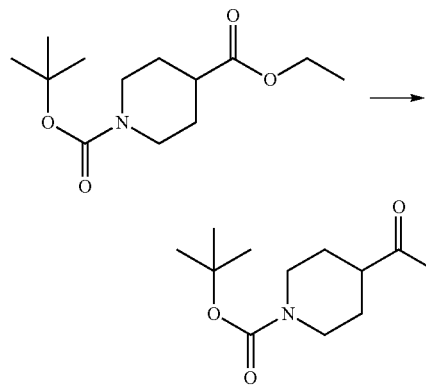

Piperidine-1,4-dicarboxylic acid 1-tert-butyl ester 4-ethyl ester (0.50 g, 1.94 mmol) in DMF (5 mL) was mixed with ethyl acetate (0.38 mL, 3.88 mmol) and potassium tert-butoxide (0.33 g, 2.92 mmol). The mixture was heated to 50° C. for 20 hours. After cooling to room temperature, water was added (50 mL) and the product was extracted with diethyl ether. The ether extract was dried over sodium sulfate, filtered and concentrated. The crude product was purified by column chromatography on silica gel, eluting with heptane-ethyl acetate to provide 4-(2-ethoxycarbonyl-acetyl)-piperidine-1-carboxylic acid tert-butyl ester (0.27 g, 47% yield).

Step 2: Synthesis of 4-(6-Hydroxy-2-piperidin-1-yl-pyrimidin-4-yl)-piperidine-1-carboxylic acid tert-butyl ester

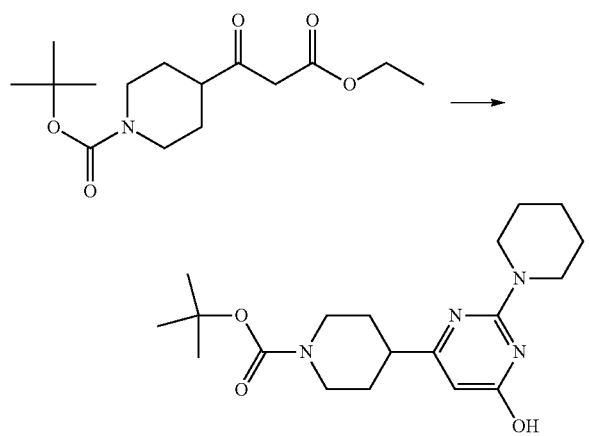

Sodium (1 mol) was dissolved in anhydrous ethanol (400 mL). To the obtained solution, Piperidine-1-carboxamidine (0.5 mol) was carefully added in portions. Then 4-(2-ethoxycarbonyl-acetyl)-piperidine-1-carboxylic acid tert-butyl ester (0.5 mol) was added dropwise, and the mixture was stirred at reflux for 4-6 h (monitored by TLC), cooled to room temperature, concentrated, diluted with water (300 mL) and acidified with acetic acid to pH-4. The formed precipitate was collected by filtration, washed with water and dried to afford 4-(6-hydroxy-2-piperidin-1-yl-pyrimidin-4-yl)-piperidine-1-carboxylic acid tert-butyl ester (89 g, 49%).

Step 3: Synthesis of 6-Piperidin-4-yl-2-piperidin-1-yl-pyrimidin-4-ol, hydrochloride salt

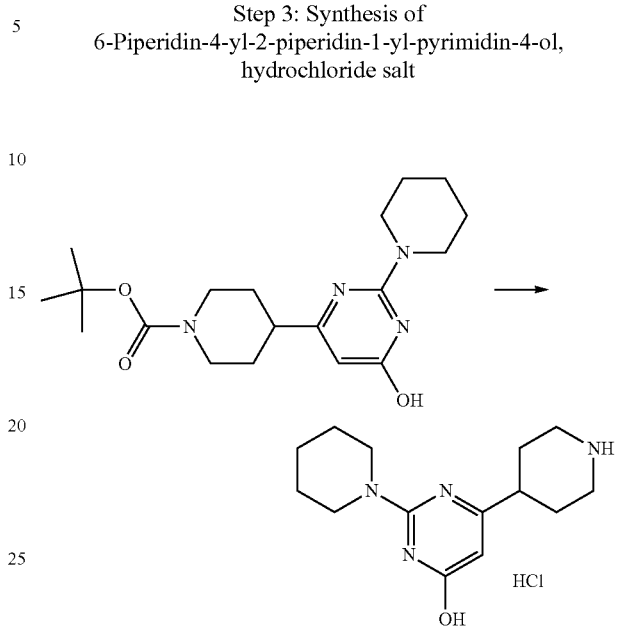

A suspension of 4-(6-hydroxy-2-piperidin-1-yl-pyrimidin-4-yl)-piperidine-1-carboxylic acid tert-butyl ester (0.05 mol) in 15% HCl in dioxane (100 mL) was stirred at reflux for 2 hours. After reaction was completed the mixture was cooled, precipitate was filtered, washed with dry ether and dried to obtain 6-piperidin-4-yl-2-piperidin-1-yl-pyrimidin-4-ol, hydrochloride salt (12 g, 81%).

Step 4: Synthesis of 6-[1-(3-Hydroxy-4-methoxy-benzyl)-piperidin-4-yl]-2-piperidin-1-yl-pyrimidin-4-ol

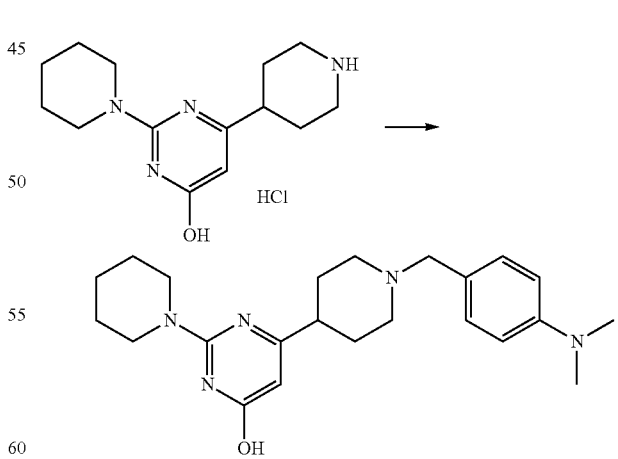

A mixture of 6-Piperidin-4-yl-2-piperidin-1-yl-pyrimidin-4-ol, hydrochloride salt (2.0 mmol), 3-hydroxy-4-methoxy-benzaldehyde (2.6 mmol), triethylamine (4.0 mmol) and 3 drops of acetic acid in dry dichloromethane (20 mL) was stirred at room temperature for 3 hours. Then sodium triacetoxyborohydride (6.0 mmol) was added in portions and stirring was continued for 48 hours (monitored by TLC). The mixture was quenched with saturated aqueous sodium bicarbonate solution (20 mL), and the product was extracted with dichloromethane (2×10 mL). The extracts were washed with brine and dried over sodium sulfate. The solvent was evaporated in vacuo to give a crude product. Purification via column chromatography (silica gel, ethyl acetate/hexane) afforded 6-[1-(3-hydroxy-4-methoxy-benzyl)-piperidin-4-yl]-2-piperidin-1-yl-pyrimidin-4-ol (Compound IIb, 542 mg, 68%).

Example 16

Preparation of 6-(1-(4-(methylamino)benzyl)piperidin-4-yl)-2-(piperidin-1-yl)pyrimidin-4-ol, Compound IIc

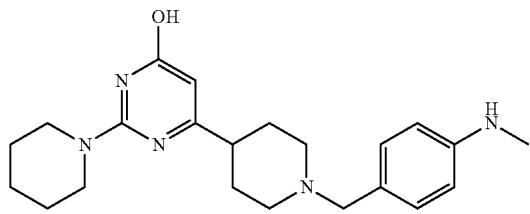 [SMILES: CNc1ccc(CN2CCC(c3cc(O)nc(N4CCCCC4)n3)CC2)cc1]

Step 1: Synthesis of 4-(2-Ethoxycarbonyl-acetyl)-piperidine-1-carboxylic acid tert-butyl ester

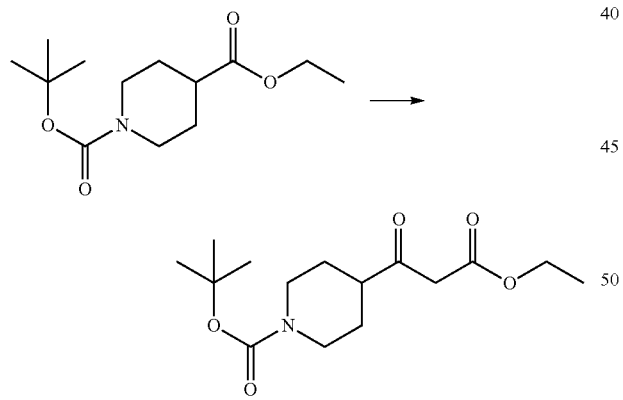

Piperidine-1,4-dicarboxylic acid 1-tert-butyl ester 4-ethyl ester (0.50 g, 1.94 mmol) in DMF (5 mL) was mixed with ethyl acetate (0.38 mL, 3.88 mmol) and potassium tert-butoxide (0.33 g, 2.92 mmol). The mixture was heated to 50° C. for 20 hours. After cooling to room temperature, water was added (50 mL) and the product was extracted with diethyl ether. The ether extract was dried over sodium sulfate, filtered and concentrated. The crude product was purified by column chromatography on silica gel, eluting with heptane-ethyl acetate to provide 4-(2-ethoxycarbonyl-acetyl)-piperidine-1-carboxylic acid tert-butyl ester (0.27 g, 47% yield).

Step 2: Synthesis of tert-butyl 4-(6-hydroxy-2-(piperidin-1-yl)pyrimidin-4-yl)piperidine-1-carboxylate

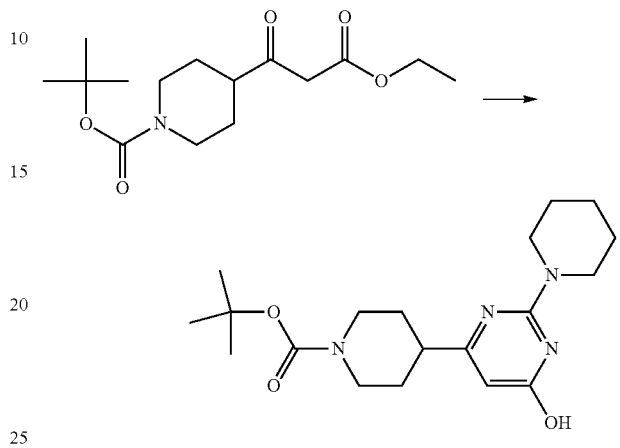

Sodium (1 mol) was dissolved in anhydrous ethanol (400 mL). To the obtained solution, Piperidine-1-carboxamidine (0.5 mol) was carefully added in portions. Then 4-(2-ethoxycarbonyl-acetyl)-piperidine-1-carboxylic acid tert-butyl ester (0.5 mol) was added dropwise, and the mixture was stirred at reflux for 4-6 h (monitored by TLC), cooled to room temperature, concentrated, diluted with water (300 mL) and acidified with acetic acid to pH-4. The formed precipitate was collected by filtration, washed with water and dried to afford 4-(6-hydroxy-2-piperidin-1-yl-pyrimidin-4-yl)-piperidine-1-carboxylic acid tertbutyl ester (80 g, 44%).

Step 3: Synthesis of 2-(piperidin-1-yl)-6-(piperidin-4-yl)pyrimidin-4-ol hydrochloride

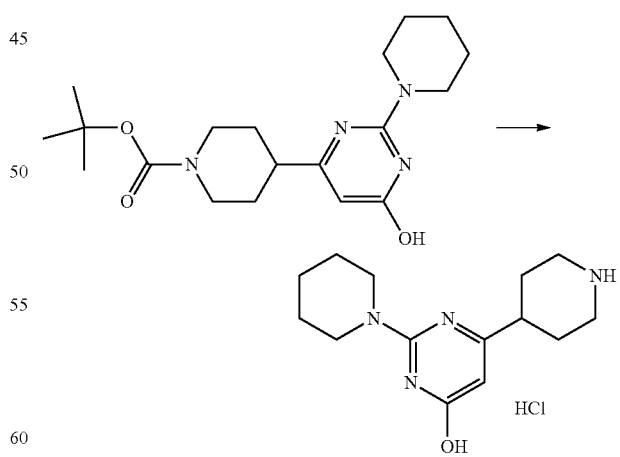

A suspension of 4-(6-hydroxy-2-piperidin-1-yl-pyrimidin-4-yl)-piperidine-1-carboxylic acid tert-butyl ester (0.05 mol) in 15% HCl in dioxane (100 mL) was stirred at reflux for 2 hours. After reaction was completed the mixture was cooled, precipitate was filtered, washed with dry ether and dried to obtain 2-morpholin-4-yl-6-Piperidin-4-yl-2-piperidin-1-yl-pyrimidin-4-ol, hydrochloride salt (12 g, 82%).

Step 4: Synthesis of 6-(1-(4-(methylamino)benzyl)piperidin-4-yl)-2-(piperidin-1-yl)pyrimidin-4-ol

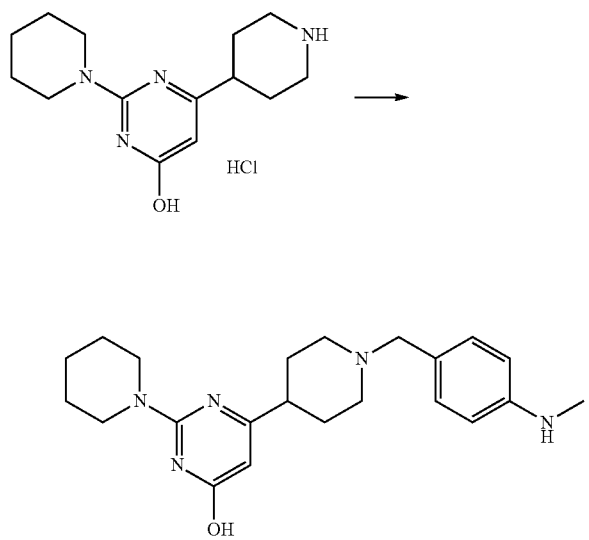

A mixture of 6-piperidin-4-yl-2-piperidin-1-yl-pyrimidin-4-ol, hydrochloride salt (2.0 mmol), 2-methylaminopyrimidine-5-carbaldehyde (2.6 mmol), triethylamine (4.0 mmol) and 3 drops of acetic acid in dry dichloromethane (20 mL) was stirred at room temperature for 3 hours. Then sodium triacetoxyborohydride (6.0 mmol) was added in portions and stirring was continued for 48 hours (monitored by TLC). The mixture was quenched with saturated aqueous sodium bicarbonate solution (20 mL), and the product was extracted with dichloromethane (2×10 mL). The extracts were washed with brine and dried over sodium sulfate. The solvent was evaporated in vacuo to give a crude product. Purification via column chromatography (silica gel, ethyl acetate/hexane) afforded 6-[1-(2-methylaminopyrimidin-5-ylmethyl)-piperidin-4-yl]-2-piperidin-1-yl-pyrimidin-4-ol (Compound IIc, 637 mg, 83%).

Example 17

Preparation of isochroman-1-yl(5'H-spiro[piperidine-4,4'-pyrrolo[1,2-a]quinoxaline]-1-yl)methanone, Compound VIIa

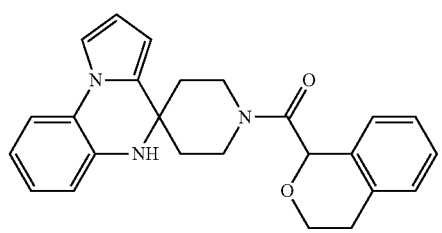 [SMILES: O=C(C1OCCc2ccccc21)N1CCC2(CC1)Nc1ccccc1-n1cccc12]

Step 1: Synthesis of 4,5-Dihydro-pyrrolo[1,2-a]quinoxaline-spiro-4-piperidine-1-carboxylic acid tert-butyl ester

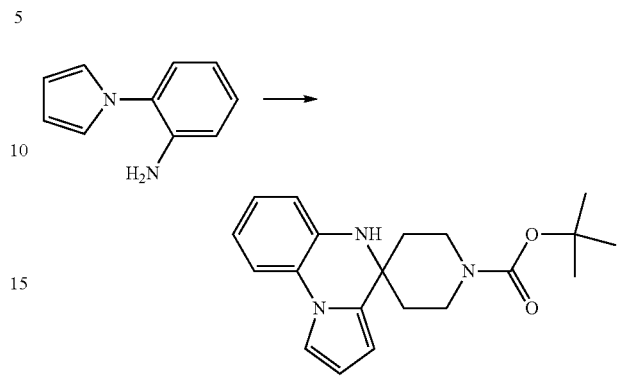

2-Pyrrol-1-yl-phenylamine (0.05 mol) and N-Boc-piperidone (0.05 mol) were dissolved in ethanol (50 mL), p-toluenesulphonic acid monohydrate as catalyst was added, stirred reaction mixture was heated to reflux during 2-3 h under argon. The reaction was monitored by TLC. Formed product was filtered, washed with cold ethanol and dried affording 4,5-dihydro-pyrrolo[1,2-a]quinoxaline-spiro-4-piperidine-1-carboxylic acid tert-butyl ester (7 g, 44%). $^1$H NMR (300 MHz, CDCl$_3$/TMS) δ 7.30 (d, J=7.5 Hz, 1H), 7.18-7.12 (m, 1H), 6.97 (t, J=7.4 Hz, 1H), 6.84 (t, J=7.6 Hz, 1H), 6.78 (d, J=8.1 Hz, 1H), 6.30 (t, J=3.0 Hz, 1H), 6.07-6.02 (m, 1H), 4.21 (s, 1H), 3.95-3.77 (m, 2H), 3.30-3.17 (m, 2H), 2.15-1.90 (m, 2H), 1.90-1.78 (m, 2H), 1.47 (s, 9H). $^{13}$C NMR (75 MHz, CDCl$_3$/TMS) δ 154.55, 133.87, 133.03, 125.53, 124.59, 119.45, 116.06, 114.49, 114.26, 109.83, 102.62, 79.69, 51.10, 39.58, 35.50, 28.38.

Step 2: Synthesis of the free amine

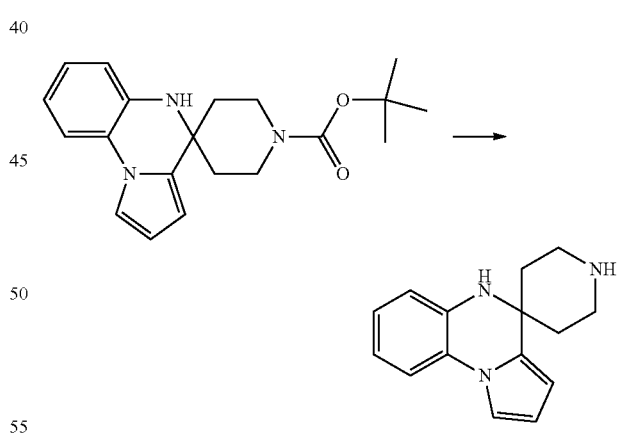

4,5-Dihydro-pyrrolo[1,2-a]quinoxaline-spiro-4-piperidine-1-carboxylic acid tert-butyl ester (0.1 mol) was dissolved in isopropanol (100 mL) and was heated to reflux. To vigorous stirred mixture 30-40 mL HCl (14-16%) in dioxane was added drop-wise. The gas was evolved. Product hydrochloride was formed as white precipitate. The mixture was heated to reflux for 30-40 minutes to complete the reaction. Filtration gave 4,5-dihydropyrrolo[1,2-a]quinoxaline-spiro-4-piperidine, hydrochloride salt. 4,5-Dihydropyrrolo[1,2-a]quinoxaline-spiro-4-piperidine, hydrochloride salt was dissolved in water (50 mL) and quenched with solid potassium carbonate to pH 7-8. The precipitate was collected by filtration affording 4,5-dihydro-pyrrolo[1,2-a]quinoxalinespiro-4-piperidine (22 g 94%) as free base. $^{1}$H NMR (300 MHz, CDCl$_{3}$/TMS) δ 7.28 (d, J=7.8 Hz, 1H), 7.15-7.11 (m, 1H), 6.96 (t, J=7.5 Hz, 1H), 6.86-6.76 (m, 2H), 6.29 (t, J=3.0 Hz, 1H), 6.08-6.04 (m, 1H), 4.39 (s, 1H), 3.69 (s, 1H), 3.07-2.85 (m, 4H), 2.03-1.90 (m, 2H), 1.90-1.79 (m, 2H). $^{13}$C NMR (75 MHz, CDCl$_{3}$/TMS) δ 134.13, 134.01, 125.45, 124.49, 119.11, 115.88, 114.41, 114.02, 109.77, 102.53, 66.96, 51.26, 42.07, 36.54.

Step 3: Synthesis of isochroman-1-yl(5'H-spiro[piperidine-4,4'-pyrrolo[1,2-a]quinoxaline]-1-yl)methanone

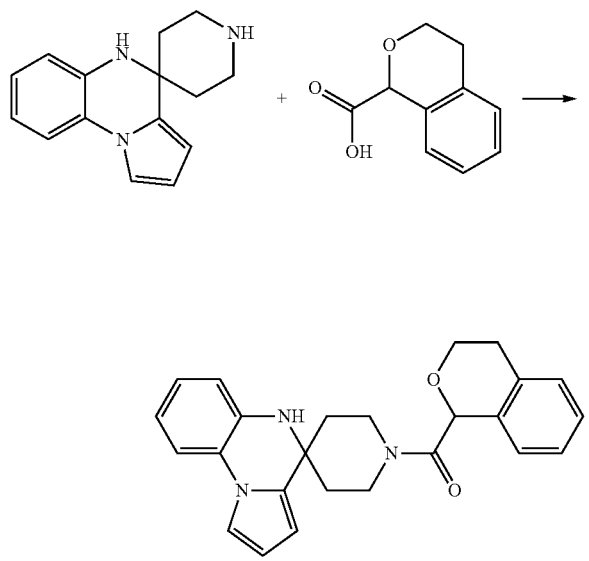

A mixture of 4,5-dihydropyrrolo[1,2-a]quinoxaline-spiro-4-piperidine (2.0 mmol), triethylamine (2 mmol), isochroman-1-carboxylic acid (2 mmol) and Benzotriazole-1-yloxy-tris-(dimethylamino)-phosphonium hexafluorophosphate (2 mmol) in dichloromethane (10 mL) was stirred at room temperature for 16 hours. The mixture was quenched with saturated aqueous sodium bicarbonate solution (10 mL), stirred for 2 hours, and the product was extracted with dichloromethane (2×10 mL). The combined organic layers were dried over sodium sulfate and concentrated at reduced pressure to give a crude product. Purification via column chromatography (silica gel, ethyl acetate/hexane) afforded isochroman-1-yl(5'H-spiro[piperidine-4,4'-pyrrolo[1,2-a]quinoxaline]-1-yl)methanone. $^{1}$H NMR (300 MHz, CDCl$_{3}$/TMS) δ 7.31-7.05 (m, 6H), 6.96 (dd, J=13.6, 6.1 Hz, 1H), 6.87-6.71 (m, 2H), 6.30 (t, J=3.1 Hz, 0.5H), 6.25 (t, J=3.1 Hz, 0.5H), 6.07 (d, J=2.1 Hz, 0.5H), 5.88 (d, J=2.1 Hz, 0.5H), 5.52 (s, 1H), 4.28-4.03 (m, 3H), 3.91-3.68 (m, 2H), 3.48-3.12 (m, 2H), 3.10-2.96 (m, 1H), 2.12-1.78 (m, 2.5H), 1.68-1.54 (m, 2H), 1.44-1.36 (m, 0.5H). $^{13}$C NMR (75 MHz, CDCl$_{3}$/TMS) δ 168.30, 133.82, 132.75, 132.61, 132.31, 132.18, 129.01, 127.24, 126.29, 125.68, 124.63, 119.64, 116.30, 114.50, 114.36, 109.91, 102.92, 102.61, 79.59, 79.39, 64.55, 51.36, 41.63, 41.50, 38.67, 36.30, 35.69, 35.52, 28.00.

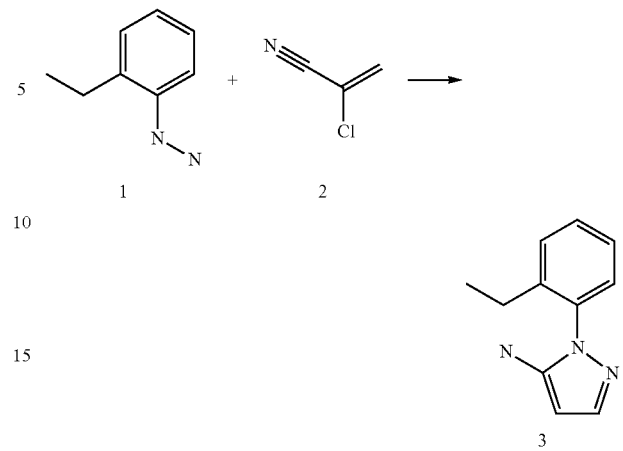

To a solution (2-Ethyl-phenyl)-hydrazine 1 (35 mmol) and disodium ethylenediaminetetraacetate (20 mg) in methanol (60 ml), 2-chloroacrylonitrile 2 (105 mmol) was added dropwise at 60° C., and the mixture was stirred under reflux for 8 hours. Then concentrated sulfuric acid (94 mmol) was added and the mixture was further heated for 6 hours. After cooling to room temperature the mixture was quenched with anhydrous sodium carbonate (105 mmol) and the solvent was removed under reduced pressure. The residue was treated with water (100 mL) and the product extracted with ethyl acetate (3*100 mL). The combined organic extracts were dried over anhydrous magnesium sulfate and the solvent was removed under reduced pressure. The residue was purified by column chromatography to give (28 mmol) of 2-(2-Ethylphenyl)-2H-pyrazol-3-ylamine 3. $^{1}$H NMR (300 MHz, CDCl$_{3}$/TMS) δ 7.44-7.35 (m, 3H), 7.30-7.25 (m, 2H), 5.57 (d, J=2.1 Hz, 1H), 3.57 (br s, 2H), 2.49 (q, J=7.6 Hz, 2H), 1.10 (t, J=7.6 Hz, 3H), $^{13}$C NMR (75 MHz, CDCl$_{3}$/TMS) δ 145.20, 142.60, 139.62, 135.93, 129.47, 129.41, 127.88, 126.55, 88.70, 24.04, 14.34.

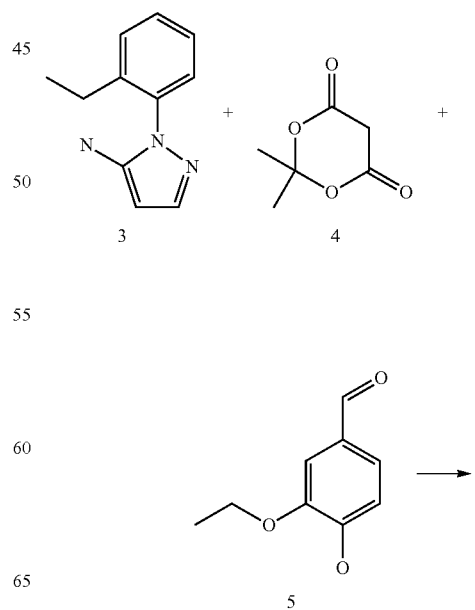

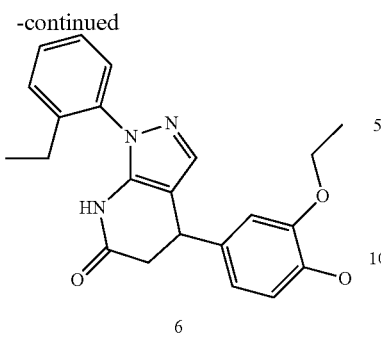

To 2-(2-Ethyl-phenyl)-2H-pyrazol-3-ylamine 3 (25.9 mmol) in EtOH (150 mL) was added 3-Ethoxy-4-hydroxy-benzaldehyde 5 (28.5 mmol), followed by Meldrum's Acid 4 (28.5 mmol). The reaction mixture was heated to 75° C., then after 2 hours, the reaction mixture was cooled to room temperature, and concentrated under reduced pressure. The residue was treated with water (100 mL) and the product was extracted with dichloromethane (200 mL). The organic extract was dried over anhydrous magnesium sulfate and the solvent was removed at reduced pressure. The residue was purified by column chromatography t to provide (11 mmol) of 4-(3-Ethoxy-4-hydroxy-phenyl)-1-(2-ethyl-phenyl)-1,4,5,7-tetrahydro-pyrazolo[3,4-b]pyridin-6-one 6. $^1$H NMR (300 MHz, CDCl$_3$/TMS) δ 7.44-7.35 (m, 3H), 7.30-7.25 (m, 2H), 5.57 (d, J=2.1 Hz, 1H), 3.57 (br s, 2H), 2.49 (q, J=7.6 Hz, 2H), 1.10 (t, J=7.6 Hz, 3H); $^{13}$C NMR (75 MHz, CDCl$_3$/TMS) δ 145.20, 142.60, 139.62, 135.93, 129.47, 129.41, 127.88, 126.55, 88.70, 24.04, 14.34.

Example 17

Preparation of 6-[1-(2-Amino-pyrimidin-5-ylmethyl)-piperidin-4-yl]-2-piperidin-1-yl-pyrimidin-4-ol, Compound IId

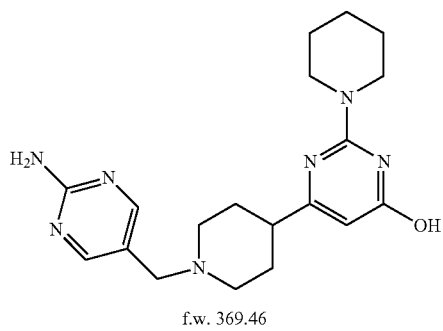 [SMILES: Nc1ncc(CN2CCC(c3cc(O)nc(N4CCCCC4)n3)CC2)cn1]

f.w. 369.46

To a mixture of ethyl N-Boc-piperidine-4-carboxylate (0.5 mol) and ethyl acetate (3 mol) t-BuOK (1.5 mol) was added in some portions at 0 C. The mixture was stirred at room temperature for 3 h (monitored by TLC), concentrated up to a half of volume, diluted with water (200 mL) and extacted with ether. Organic layer was dried over sodium sulfate and evaporated in vacuo. Purification by column chromatography (silica gel, ethyl acetate/hexane) afforded 4-(2-ethoxycarbonyl-acetyl)-piperidine-1-carboxylic acid tert-butyl ester (78 g, 52%)

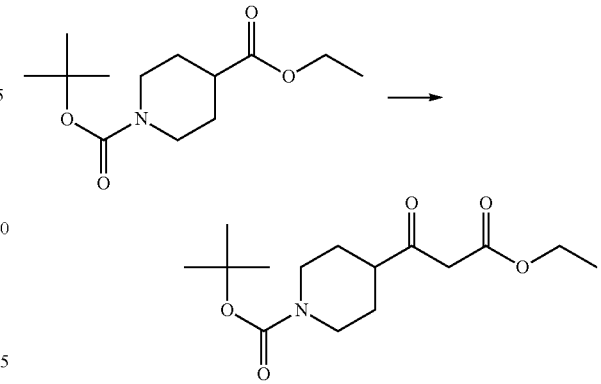

Sodium (1 mol) was dissolved in anhydrous ethanol (400 mL). To the obtained solution, Piperidine-1-carboxamidine (0.5 mol) was carefully added in portions. Then 4-(2-Ethoxy-carbonyl-acetyl)-piperidine-1-carboxylic acid tert-butyl ester (0.5 mol) was added dropwise, and the mixture was stirred at reflux for 4-6 h (monitored by TLC), cooled to room temperature, concentrated, diluted with water (300 mL) and acidified with acetic acid to pH-4. The formed precipitate was collected by filtration, washed with water and dried to afford 4-(6-Hydroxy-2-piperidin-1-yl-pyrimidin-4-yl)-piperidine-1-carboxylic acid tert-butyl ester (82 g, 45%).

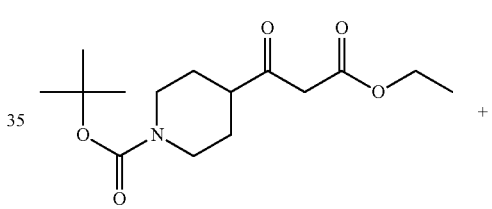

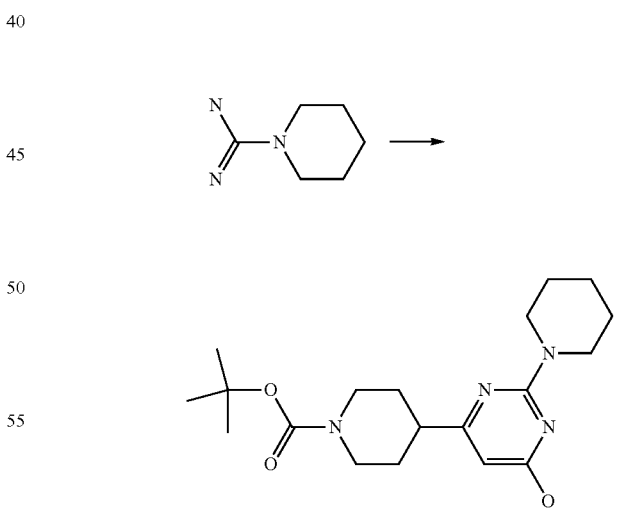

A suspension of 4-(6-hydroxy-2-piperidin-1-yl-pyrimidin-4-yl)-piperidine-1-carboxylic acid tert-butyl ester (0.05 mol) in 15% HCl in dioxane (100 mL) was stirred at reflux for 2 hours. After reaction was completed the mixture was cooled, precipitate was filtered, washed with dry ether and dried to obtain 6-Piperidin-4-yl-2-piperidin-1-yl-pyrimidin-4-ol as hydrochloride (12 g, 82%).

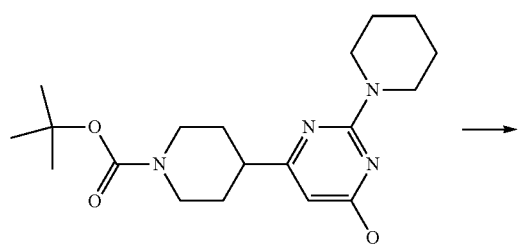
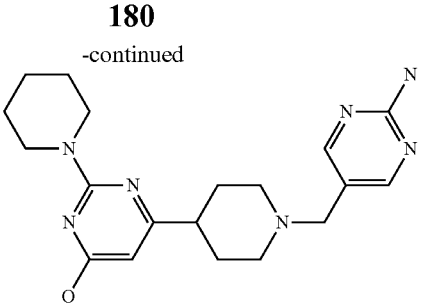

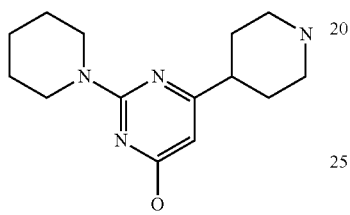

A mixture of 6-piperidin-4-yl-2-piperidin-1-yl-pyrimidin-4-ol (2.0 mmol), 2-amino-pyrimidine-5-carbaldehyde (2.6 mmol), triethylamine (4.0 mmol) and 3 drops of acetic acid in dry dichloromethane (20 mL) was stirred at room temperature for 3 hours. Then sodium triacetoxyborohydride (6.0 mmol) was added in portions and stirring was continued for 48 hours (monitored by TLC). The mixture was quenched with saturated aqueous sodium bicarbonate solution (20 mL), and the product was extracted with dichloromethane (2×10 mL). The extracts were washed with brine and dried over sodium sulfate. The solvent was evaporated in vacuo to give a crude product. Purification via column chromatography (silica gel, ethyl acetate/hexane) afforded 6-[1-(2-Amino-pyrimidin-5-ylmethyl)-piperidin-4-yl]-2-piperidin-1-yl-pyrimidin-4-ol (606 mg, 82%)

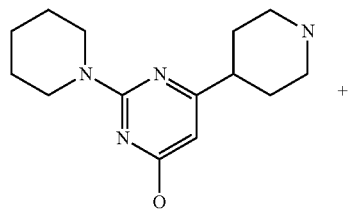

Example 18

Preparation of isochroman-1-yl(5'H-spiro[piperidine-4,4'-pyrrolo[1,2-a]quinoxaline]-1-yl)methanone, Compound VIIa

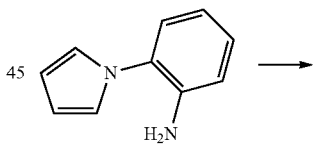

f.w. = 399.50

Step 1: Synthesis of 4,5-Dihydro-pyrrolo[1,2-a]quinoxaline-spiro-4-piperidine-1-carboxylic acid tert-butyl ester

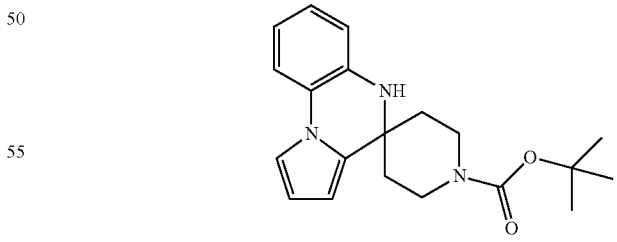

f.w. = 158.20 f.w. = 339.44

2-Pyrrol-1-yl-phenylamine (0.05 mol) and N-Boc-piperidone (0.05 mol) were dissolved in ethanol (50 mL), p-toluenesulphonic acid monohydrate as catalyst was added, stirred reaction mixture was heated to reflux during 2-3 h under argon. The reaction was monitored by TLC. Formed product was filtered, washed with cold ethanol and dried affording 4,5-dihydro-pyrrolo[1,2-a]quinoxaline-spiro-4-piperidine-1-carboxylic acid tert-butyl ester (7 g, 44%).

Step 2: Synthesis of the Free Amine

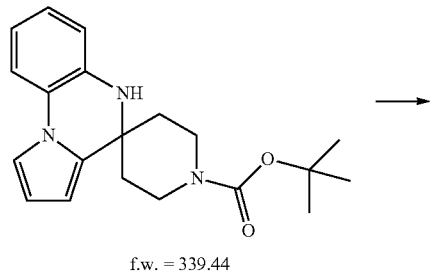

f.w. = 339.44

→ f.w. = 275.78

4,5-Dihydro-pyrrolo[1,2-a]quinoxaline-spiro-4-piperidine-1-carboxylic acid tert-butyl ester (0.1 mol) was dissolved in isopropanol (100 mL) and was heated to reflux. To vigorous stirred mixture 30-40 mL HCl (14-16%) in dioxane was added drop-wise. The gas was evolved. Product hydrochloride was formed as white precipitate. The mixture was heated to reflux for 30-40 minutes to complete the reaction. Filtration gave 4,5-dihydropyrrolo[1,2-a]quinoxaline-spiro-4-piperidine, hydrochloride salt. 4,5-Dihydropyrrolo[1,2-a]quinoxaline-spiro-4-piperidine, hydrochloride salt was dissolved in water (50 mL) and quenched with solid potassium carbonate to pH 7-8. The precipitate was collected by filtration affording 4,5-dihydro-pyrrolo[1,2-a]quinoxalinespiro-4-piperidine (22 g 94%) as free base.

Step 3: Synthesis of isochroman-1-yl(5'H-spiro[piperidine-4,4'-pyrrolo[1,2-a]quinoxaline]-1-yl)methanone

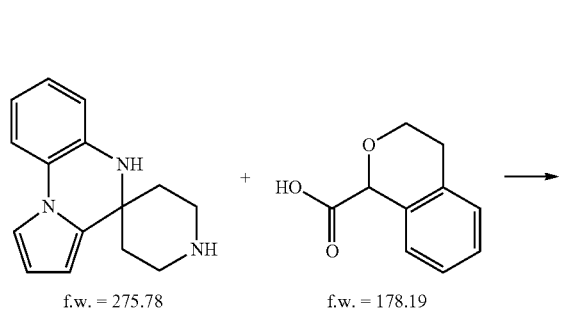

f.w. = 275.78          f.w. = 178.19

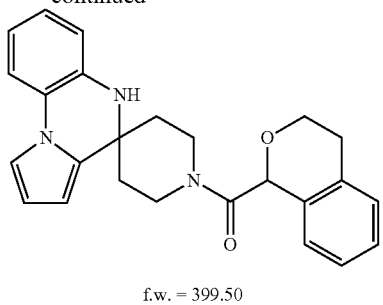

f.w. = 399.50

A mixture of 4,5-dihydropyrrolo[1,2-a]quinoxaline-spiro-4-piperidine (2.0 mmol), triethylamine (2 mmol), isochroman-1-carboxylic acid (2 mmol) and Benzotriazole-1-yl-oxy-tris-(dimethylamino)-phosphonium hexafluorophosphate (2 mmol) in dichloromethane (10 mL) was stirred at room temperature for 16 hours. The mixture was quenched with saturated aqueous sodium bicarbonate solution (10 mL), stirred for 2 hours, and the product was extracted with dichloromethane (2×10 mL). The combined organic layers were dried over sodium sulfate and concentrated at reduced pressure to give a crude product. Purification via column chromatography (silica gel, ethyl acetate/hexane) afforded isochroman-1-yl(5'H-spiro[piperidine-4,4'-pyrrolo[1,2-a]quinoxaline]-1-yl)methanone (Compound VIIa, 527 mg, 66%).

Biological Assays

Example 19

Agonist Activity of Illustrative Compounds of the Invention Using P2Y13 Receptor Transfected Cell Line.v Compounds were assayed for their agonist activity on P2Y13 GPCR transfected cells using a Ca++ flux assay (associated to fluorescent dye detection) with the Reference Compound as positive reference. Two cell lines, 1321N1-P2Y13 stably expressing human P2Y13 receptor, and 1321N1 parental cell line as control, were used in this assay. 1321N1 Parental and 1321N1 P2Y13 were seeded into T25 flasks at 3 million cells per flask, respectively. Cells were incubated at 37 degrees Celsius in 5% $CO_2$ overnight. The day after, cells were transfected with Gqi5 protein using Fugene transfection reagent (Roche's Fugene Reagent).

After 24 hours of transfection, cells were collected from flasks and seeded in 384-well plates at 8000 cells per well. The assays were carried out 48 hours after Gqi5 transfection.

Methods:

The Ca++ flux assay was conducted according to the manufacturer's protocol (Molecular Devices FLIPR Calcium 4 Assay kit (R8142). Briefly, cell culture media were aspirated from the wells and replaced with 25 μL of Hank's buffer or PBS buffer. 25 μL of Ca++ dye was added into each assay well. The plate was incubated for 1 hour at 37° C. in 5% $CO_2$. After the incubation, the plate was transferred to FlexStation III (FlexStation III (Molecular Devices)). The compounds were automatically injected into each well.

Results:

EC$_{50}$ values for illustrative compounds of the invention were obtained. The results are set forth in FIG. 1 and in Table 3. The EC$_{50}$ values were also compared to those the Reference Compound.

Figure 2:
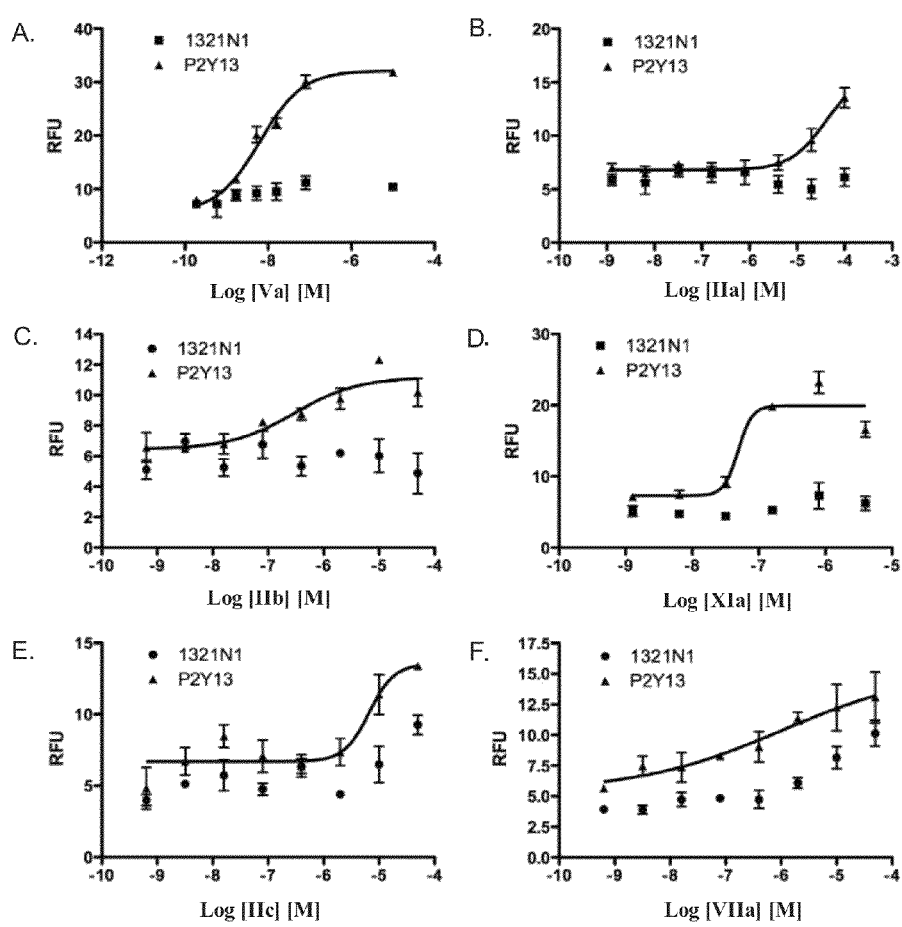
FIG. 2A-F: Activity of illustrative compounds of the invention (dark triangles) on 1321 N1 cells transfected with P2Y13 receptor and compared with a positive Reference Compound: Compound Va (FIG. 2A), Compound IIa (FIG. 2B), Compound IIb (FIG. 2C), Compound XIa (FIG. 2D), Compound IIc (FIG. 2E), Compound VIIa (FIG. 2F). Non transfected 1321 N1 cells were used as negative control (dark circle). Each data point was a mean of triplicate wells.

Additional illustrative compounds of the invention were assayed for their agonist activity on P2Y13 receptor transfected cells and are presented in FIG. 2 and the EC$_{50}$ summarized in Table 4.

TABLE 3

EC$_{50}$ of representative compounds on P2Y13 receptor activity measured from data of FIG. 1.

| Compound of the Invention | EC$_{50}$ (M) |
|---|---|
| Compound Va | 5,516e−005 |// 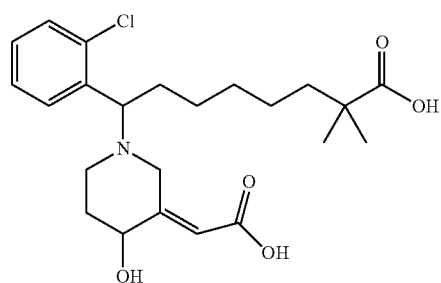 [SMILES: CC(C)(CCCCCC(c1ccccc1Cl)N1CCC(O)/C(=C/C(=O)O)C1)C(=O)O]
| Compound Ih (R- isomer) | 4,237e−005 |// 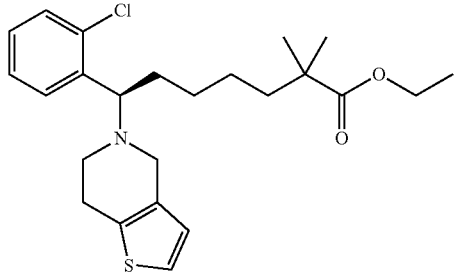 [SMILES: CCOC(=O)C(C)(C)CCCC[C@H](c1ccccc1Cl)N1CCc2sccc2C1]
| Compound Ih (S- isomer) | 3,372e−005 |// 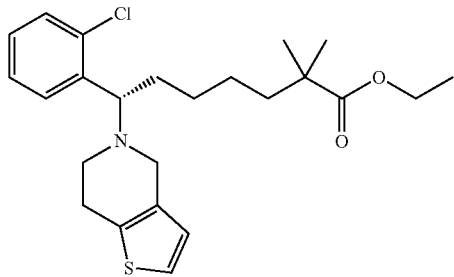 [SMILES: CCOC(=O)C(C)(C)CCCC[C@@H](c1ccccc1Cl)N1CCc2sccc2C1]

TABLE 4

Values of EC$_{50}$ on P2Y13 receptor activity measured from data of Figure 2.

| Compound of the Invention | EC$_{50}$ (M) |
|---|---|
| Compound IIa | 4,032e−005 |
| Compound IIb | 2,987e−007 |
| Compound IIc | 6,629e−006 |
| Compound VIIa | 4,032e−005 |
| Compound XIa | 4,889e−008 |
| Reference Compound | 6,322e−009 |

The chemical name of the Reference Compound is Dichloro-(((((2R,3S,4R,5R)-3,4-dihydroxy-5-(6-(2-(methylthio)ethylamino)-2-(3,3,3-trifluoropropylthio)-9H-purin-9-yl)tetrahydrofuran-2-yl)methoxy)(hydroxy)phosphoryloxy)(hydroxy)phosphoryl)-methylphosphonic acid. The Reference Compound is also known as Cangrelor®. Its chemical structure is depicted below:

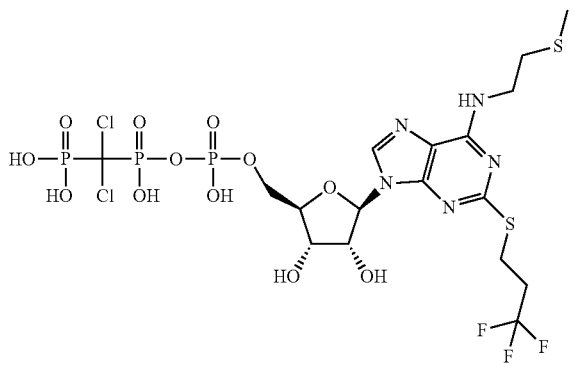 [SMILES: CSCCNc1nc(SCCC(F)(F)F)nc2c1ncn2[C@@H]1O[C@H](COP(=O)(O)OP(=O)(O)C(Cl)(Cl)P(=O)(O)O)[C@@H](O)[C@H]1O]

In Vitro HDL Internalization in Human Hepatocytes (HepG2) Cells.

Figure 3:
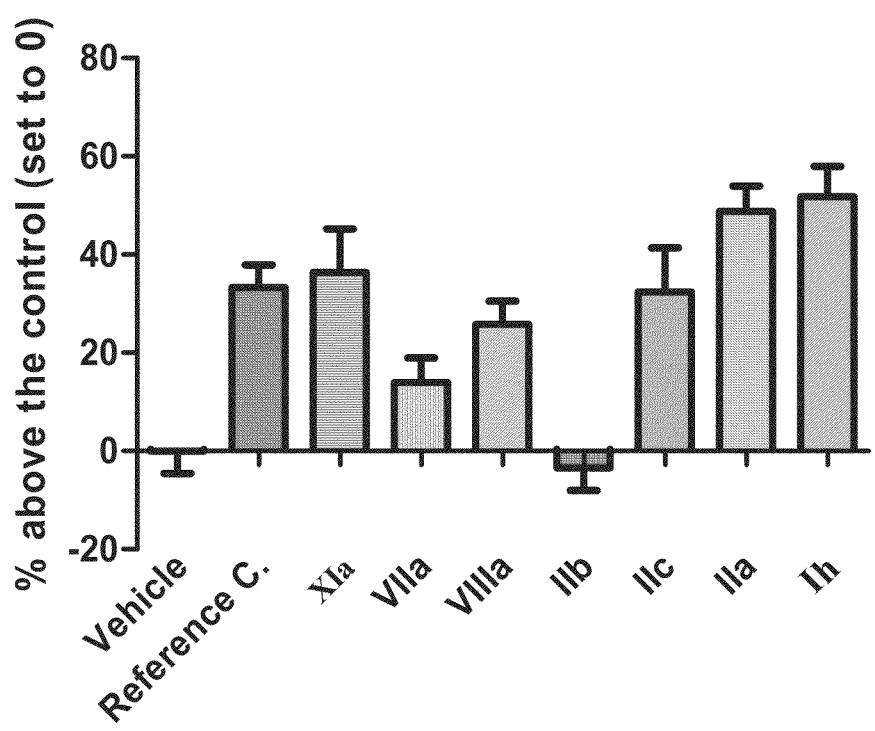
FIG. 3: Single-dose effect of the selected molecules on HDL internalization by HepG2 cells. Cells were incubated for 10 min at 37° C. with 75 μg/ml $^3$H cholesterol Cholesteryl Oleate [Cholesteryl-1,2-$^3$H(N)] HDL, Reference Compound (100 nM) and illustrative compounds of the invention (1 μM). Data are expressed as the percentage of internalized radioactivity with respect to the control value (set as 0). *p<0.005, **p<0.0001.
Figure 14:
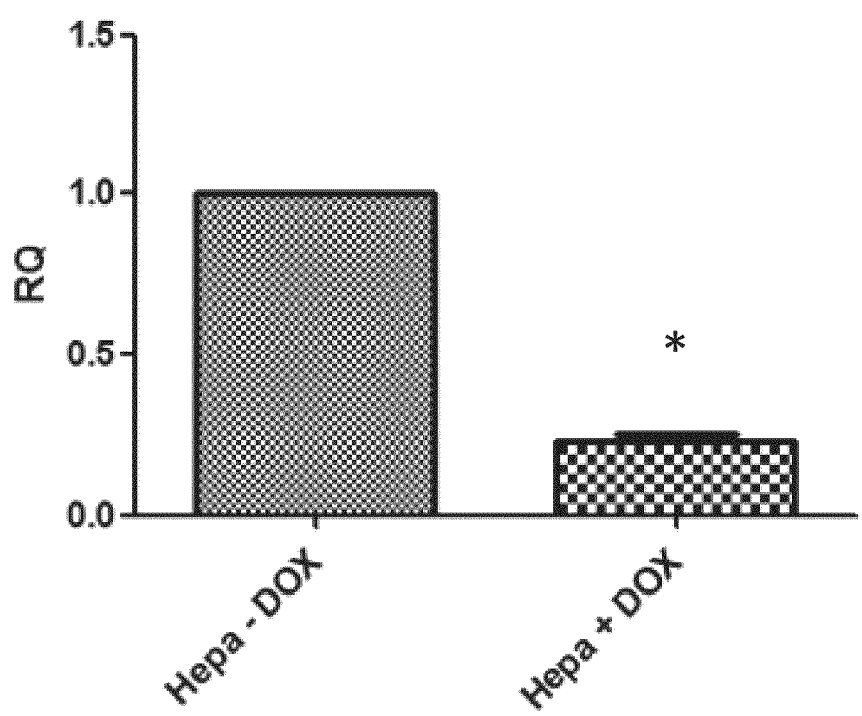
FIG. 14: P2Y13 knock-down in Hepa 1-6 cells. Hepa 1-6 cells were transduced with lentiviral particles coding the P2Y13 shRNA (MOI 40) inducible by the addition of doxycycline. The cell pool was treated or not for 72 hours with doxycycline (10 µM final concentration) and the P2Y13 mRNA expression was measured by QPCR.$*p<0.0001$.
Figure 15:
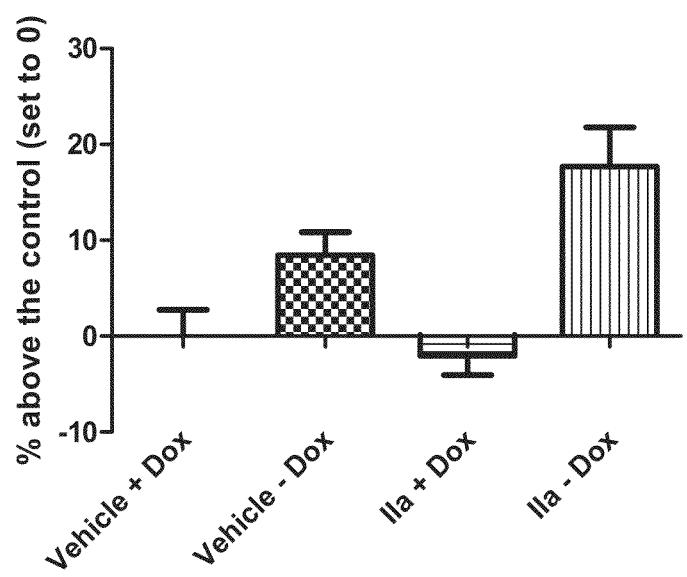
FIG. 15: HDL uptake on P2Y13 knock-down Hepa 1-6 cells. Hepa 1-6 cells transduced with lentiviral particles coding the P2Y13 shRNA were induced by the addition of doxycycline for 72 hours. Cells were incubated for 10 min at 37° C. with 75 µg/ml $^3$H cholesterol ether HDL and Compound IIa (1 µM). Data are expressed as the percentage of internalized radioactivity with respect to the control value (set as 0).$*p<0.05$, $**p<0.005$.

The effect of illustrative compounds of the invention on HDL internalization was measured by an in vitro assay on HepG2 cells (FIG. 3). $^3$H cholesterol Cholesteryl Oleate [Cholesteryl-1,2-$^3$H(N)] labeled HDL] (available from PerkinElmer http://www.perkinelmer.com/Catalog/Product/ID/NET746L001MC) was loaded on HepG2 cells in presence of illustrative compounds of the invention (final concentration 1 µM). The Reference Compound was previously reported to increase the HDL uptake in HepG2 cells in vitro (Jacquet S, Malaval C, Martinez L O, Sak K, Rolland C, Perez C, Nauze M, Champagne E, Tercé F, Gachet C, Perret B, Collet X, Boeynaems J M, Barbaras R. The nucleotide receptor P2Y13 is a key regulator of hepatic high-density lipoprotein (HDL) endocytosis. *Cell Mol Life Sci.* 2005 November; 62(21):2508-15) and was used as a positive control of the HDL uptake by HepG2 cells. It was determined that Compounds XIa, IIc, IIa and Ih (R-isomer) have a strong impact on HDL uptake by HepG2 cells; Compounds IIb, VIIa and VIIIa have a modest impact on HDL uptake by HepG2 cells.

Consequences on Bile Acids Physiology after IV Injection of the Selected Molecules.

Bile acids are derived from cholesterol and their synthesis is the predominant pathway for catabolism of cholesterol. The HDL uptake by the liver is directly connected with the bile acids secretion and the bile cholesterol clearance. To demonstrate the effect of illustrative compounds of the invention on the bile physiology, the compounds were injected into the tail of C57B16 mice and 4 hours later the mice were sacrificed and the bile content was analyzed (FIG. 5). An increase of bile acids concentration as well as of the bile volume was observed. All the compounds responded as well as or even better than the control compound (Reference Compound).

Dose Response of the Selected Molecules on Bile Physiology.

The dose response after oral gavage was determined for illustrative compounds of the invention. The chosen doses were 0.003, 0.03 and 0.3 mg/kg. The selected compounds of the invention were administrated by oral gavage and 6 hours later the mice are sacrificed and the bile content was analyzed (FIGS. 6-11). Dose dependent increases in bile acids, bile cholesterol and bile phospholipids were observed for all concentrations of all the compounds. Compounds IIa, VIIIa, IIIc and XIa showed an effect at 0.003 mg/kg; Compounds IIb and VIIa showed an effect at 0.3 mg/kg.

Consequences on Bile Acids Physiology after One Week Daily Treatment with Compound IIa In the previous experiments, illustrative compounds of the invention were administrated once and the impact on bile physiology was measured after 6 hours. Compound IIa was administrated by oral gavage once daily for a week to allow observation of the consequences on bile physiology of a longer treatment. On the day of sacrifice, the conditions were similar to the dose response experiments. The net impact of Compound IIa on the bile secretion was observed. The volume of the individual bile was also affected with a significant increase compare to vehicle treatment.

P2Y13 Knock-Down in Hepa 1-6 Cells

In order to relate the specific P2Y13 HDL uptake to the illustrative compounds of the invention, a knock-down P2Y13 in a mouse liver cell line (Hepa 1-6) was investigated. Lentiviral particles coding for the mouse P2Y13 shRNA and inducible by the addition of doxycycline onto the cells (pTRIPZ vector from Open Biosystem) were used. In presence of doxycycline, a decrease of the P2Y13 mRNA (FIG. 11) was observed. The uptake of HDL on this cell line was measured in the presence and the absence of Compound IIa and doxycycline (FIG. 12). A significant decrease of HDL uptake (8.5%) was observed when the cells were treated with doxycycline (group vehicle—p<0.05). This decrease was also observed in presence of Compound IIa (17.5%—p<0.005), thus showing that the target of Compound IIa is P2Y13.

Materials and Methods

A bile acids kit was purchased from Diazyme; Phospholipids and total cholesterol kits were purchased from Biolabo; mice C57B16 were purchased from Janvier. Mouse pGIPZ lentiviral P2Y13 shRNAmir (RMM4431-98723221) was purchased from Openbiosystem and subcloned into pTRIZ (doxycycline inducible vector). The 1 mL of lentiviral production was prepared by Vectalys (France) with 1.2$^E$8 transducing units per mL. The mouse P2Y13 primers (Mm 00546978-m1), GAPDH primers (Mm03302249-g1) and ribosomal 18S primers (Mm02601777-g1) for real-time PCR assays were purchased from Applied. HepG2 cells (HB-8065) and Hepa 1-6 (CRL-1830) were obtained from the ATCC.

Lipoprotein Preparation

Lipoproteins were purified from mice plasma by sequential ultracentrifugation on KBr gradient. HDL were obtained at a density d=1.21. The purified HDL were dialysed against PBS and used for the uptake experiments.

HDL Labeling $^3$H cholesterol Cholesteryl Oleate [Cholesteryl-1,2-$^3$H (N)] (Perkin Elmer) solution (250 µL) was dried and resuspended in acetone (250 µL). The solution was mixed with Lipoprotein delipidated serum (20 mL at 40 mg/mL) and DTNB (0.4 µM final concentration). HDL (7 mg) was added and incubated overnight at 4° C. on gentle rotation. The HDL was purified on KBr gradient as previously described.

HepG2 and shP2Y13 Transduced Hepa 1-6 HDL Uptake

Transduced Hepa 1-6 cells were plated at 300,000 cells/well in 6x-well plates. These cells were treated every day with doxycycline (10 µM) for 3 days (for P2Y13 extinction) or not (control for plasmid"leakage") The day of uptake, the cells were washed once with DMEM and incubated for 1 hour in DMEM at 37° C. 75 µg of radio-labeled HDL (6500 dpm/µg of HDL3.) were added to the medium and incubated for 10 minutes at 37° C. The cells were washed once with DMEM (2 mL) and incubated for 1.5 hours in DMEM at 4° C., whereupon dissociation occurred. Then the cells were washed once more with cold DMEM (2 ml) and the incorporated cholesterol ether was retrieved from HepG2 cells by the addition of hexane:isopropanol (3:2) solution (1 mL).

HDL Uptake

Hepatocytes were plated at 300,000 cells/well in 6x-well plates. Two days later, the cells were washed once with DMEM and incubated for 1 hour in DMEM at 37° C. 75 µg of radio-labeled HDL (6500 dpm/µg) were added to the medium and incubated for 10 minutes at 37° C. The cells were washed once with DMEM (2 mL) and incubated for 1.5 hours in DMEM at 4° C., whereupon dissociation occurred. Then the cells were washed once more with cold DMEM (2 mL) and the incorporated cholesterol ether was retrieved from HepG2 cells by the addition of hexane:isopropanol (3:2) solution (1 mL).

Cholesterol Efflux

Cholesterol efflux capacity was quantified as previously described (Wang et al., 2007), in blood samples from rabbit plasma collected before administration of the dose on day 0 and after 4 weeks of administrations of Compound IIa. Briefly, oxidised LDL (25 µg/ml), labelled with [$^3$H]-cholesterol (2 µCi/ml; Perkin-Elmer), were added to J774 macrophages in culture for 24 h in 2.5% serum medium. [$^3$H]-cholesterol release was measured after 6 h incubation of 2.5% (v/v) rabbit plasma or β-lipoprotein free-plasma (PTA kit—Biolabo, France). All assays were performed in triplicate. A rabbit plasma (calibrator) was included on each plate and the values were normalized by dividing plasma samples by this calibrator plasma to determine the normalized cholesterol efflux capacity of the samples.

Animal Protocol

Animal housing and care were in compliance with the recommendations of Directive 86/609/EEC, and protocol approvals were obtained from institutional ethics committees.

ApoE$^{-/-}$ mice "flow cessation model":

Left carotid of apoE$^{-/-}$ mice were ligatured and placed on Western diet. These mice were given Compound IIa once a day at 100 µg/kg (0.5% CMC, 0.2% Tween80) for 2 weeks.

ApoE$^{-/-}$ "high-cholesterol diet model":

Mice were placed for two month on Western diet (0.2% cholesterol, 21% butter milk) then dosed with Compound IIa once a day at 100 µg/kg (0.5% CMC, 0.2% Tween80) for 4 more weeks. The mice were sacrificed and the aortas were collected for biochemical and immunohistological characterizations. One set of aorta (n=10) was detached at the base of the heart and placed in a glass tube with 3 ml of chloroform-methanol 2:1 (v/v), and stigmasterol as the internal standard. Then analyzed as described above. Another set of aortas (n=10) were first extensively washed with PBS, then with 4% paraformaldehyde (5000) and finally with tissue tek OCT (500 µl). Next the aorta was embedded in OCT and frozen at −20° C. Three step frozen sections of 10 µm separated one from the other were processed and stained with Oil red 0 (ORO), Sirius red and hematoxylin/eosin. Macrophages were detected using F4/80 primary rat monoclonal antibody (Abeam) and VCAM was detected using rat anti mouse CD106 (AbDSerotec).

New Zealand Rabbits.

After 2 months of High Cholesterol Diet feeding (0.5% cholesterol) and a wash-out period of 2 weeks, the animals were treated (by oral gavage) once day with Compound IIa at 30, 100 and 300 µg/kg for 4 weeks. Blood samples were collected before the dose administration on day 0 and after 4 weeks of administrations of Compound IIa. After final bleeding, the liver, gallbladder, heart, thoracic and abdominal aorta from heart (left ventricle) to iliac arteries were sampled.

Macrophages and Oil Red O Staining of Mice ApoE$^{-/-}$ Carotids.

The left carotid fixed in formalin was embedded in OCT and frozen at −20° C. Four step frozen sections of 50 µm separated one from the other were processed and stained with Oil red O(ORO). Macrophages were detected using primary rat monoclonal anti CD-68 antibody (Abeam).

Rabbit Aortas Staining.

Rabbit aortas were fixed in neutral formalin buffer and embedded in paraffin. Longitudinal 3 µm sections were stained with Hematoxylin-Eosin-Saffron for histology analysis. The tissue sections were deparaffinized and incubated in protein-free block to inhibit the nonspecific binding of primary monoclonal antibodies used for the immunostaining of rabbit monocytes and macrophages (RAM11 obtained from Dako Corp. 1:100 dilution) and smooth muscle cell-specific actin (HHF35 obtained from Dako Corp. 1:100 dilution). Secondary biotinylated anti-goat antibody was used at 1:300 dilution (Dako).

Hepa 1-6 Transduction

The lentiviral production in HEK 293T and authorization for lentiviral production was obtained by Vectalys. Hepa 1-6 cells were plated at 75,000 cells in a 24-well plate a day before the transduction. 24 hours after transduction, the number of cells was counted. Medium of other wells was removed and replaced with 1 ml of DMEM 10% serum containing 8 µg/ml of polybrene. Cells were transduced by adding 40 transducing units of viral vector (1.2E8TU/ml) per cells. 17 hours after transduction the medium was replaced and the pool of transduced Hepa cells was established.

QPCR

For quantitative PCR experiment the RNA was purified from cultured cells with the RiboPure™ Kit (AM1924 Ambion). The RNA was reverse transcribed to single-stranded cDNA with the High Capacity RNA-to-cDNA kit (4387406 Applied BioSystem). The QPCR was performed using the Taqman technology according to the manufacturer procedure (Applied Biosystems).

Analysis

Bile Acids.

Bile acids were diluted in PBS (1:5000) and the concentration was measured according to the manufacturer protocol with slight modifications. Concentrations of bile acids in the standard curve were varied from 50 to 200 mM and the enzymatic reaction was performed for 20 minutes. 4 µl of 1:5000 bile dilution was used for concentration determination.

Bile Phospholipids.

Bile phospholipids were measured according to the manufacturer protocol. Briefly, the standards were varied from 0 to 20 µg/ml and 4 µl of bile was measured in the assay. The reaction was performed for 5 minutes at 37° C.

Bile Cholesterol.

Bile phospholipids were measured according to the manufacturer protocol. Briefly, the standards were varied from 0 to 60 µg/ml and 4 µl of bile (dilution 1:10) was measured in the assay. The reaction was performed for 5 minutes at 37° C.

Example 20

Effect of Compound IIa on the P2Y13R Pathway

Compound IIa demonstrated a dramatic effect on the inhibition of the atherosclerosis progression in mice through the stimulation of HDL-P2Y13r pathway. The specificity of P2Y13r pathway in vivo using adenovirus carrying P2Y13r-shRNA in infected apoE−/− mice was also shown. Moreover, Compound IIa induced the regression of pre-established atherosclerotic plaques in aortas of the rabbits fed with cholesterol chow. These results demonstrate that P2Y13r plays a strong pivotal role in the HDL metabolism and atherosclerosis, and that P2Y13r is a useful therapeutic target for exploring biology of atherosclerosis.

Heterocyclic compounds that were designed as orally active P2Y13 receptor agonists were used. These compounds were selected based on their specific binding and activity in 1321N1 cells expressing P2Y13 receptors (not shown) (Kim, Y. C. et al. Synthesis of pyridoxal phosphate derivatives with antagonist activity at the P2Y13 receptor. Biochem Pharmacol 70, 266-274 (2005)). The compounds were further tested for their propensity to stimulate the [$^3$H]-cholesterol-labelled-HDL uptake in vitro in mouse hepatocytes (Hepa) and human hepatoma cells (HepG2). Specificity of the uptake was also confirmed using P2Y13 siRNA probe (not shown). It was hypothesized that administration of P2Y13r agonists in animals would increase the reverse cholesterol transport, i.e., the HDL uptake by the liver and subsequently enhancing bile acid and bile cholesterol secretion. First, when C57B1/6J mice were intravenously given Compound IIa (10 nmol/kg), after 4 h of treatment an increase of bile acids (BA) and free cholesterol secretion into bile was observed, the effect being slightly higher than with Cangrelor (The Medicines Company), a known agonist of P2Y13r (FIGS. 16 A and B) (Jacquet, S. et al. The nucleotide receptor P2Y13 is a key regulator of hepatic high-density lipoprotein (HDL) endocytosis. *Cell Mol Life Sci* 62, 2508-2515 (2005)). The stimulation of the bile acid and cholesterol secretion in the bile of animals given P2Y13r agonist by oral gavage at doses as low as 30 µg/kg was confirmed (FIGS. 16 C and D). This increase in bile acid secretion observed with P2Y13r agonists could be a consequence of either a secretion of BA from an intra-hepatic pool to the bile duct (Schwartz, C. C., Halloran, L. G., Vlahcevic, Z. R., Gregory, D. H. & Swell, L. Preferential utilization of free cholesterol from high-density lipoproteins for biliary cholesterol secretion in man. *Science* 200, 62-64 (1978)) or a de novo synthesis of BA by the liver following stimulation of the HDL uptake by the P2Y13r pathway. An increase in liver bile acid content at 30 µg/kg of P2Y13r agonist in agreement with the stimulation of the HDL uptake by the liver which in turn results in an increase in the BA synthesis was clearly shown (FIG. 16 E). It is noteworthy that the plasma cholesterol and HDL were not significantly affected (FIG. 16 F) after 4 h of treatment with the exception of the unesterified cholesterol, which could represent specific HDL cholesterol liver uptake as already described (Schwartz, C. C., Halloran, L. G., Vlahcevic, Z. R., Gregory, D. H. & Swell, L. Preferential utilization of free cholesterol from high-density lipoproteins for biliary cholesterol secretion in man. *Science* 200, 62-64 (1978)). To further delineate the implication of the HDL in the increase of bile secretion after treatment of the mice with Compound IIa, in vivo liver uptake analysis of [3H]-cholesterol labelled mouse HDL (FIG. 16G), [3H]-cholesterol ester labelled mouse HDL (FIG. 16H) and [3H]-cholesterol labelled mouse LDL (FIG. 16I) was performed. The intravenous treatment of the animals with 10 nmole/kg with the P2Y13r agonist showed a specific stimulation of the uptake of the HDL as compared to LDL, which supports the hypothesis of a stimulation of the HDL-mediated reverse cholesterol transport The effect of the stimulation of the P2Y13r pathway by the agonists on the atherosclerotic plaque lesions in apoE−/− mice that are very susceptible to develop atherosclerosis on a short term Western (i.e. high-cholesterol) diet was investigated. To be closer to human pathology, atherosclerotic lesions were developed using the methodology described as "flow cessation model" in apoE−/− mice (Godin, D., Ivan, E., Johnson, C., Magid, R. & Galis, Z. S. Remodeling of carotid artery is associated with increased expression of matrix metalloproteinases in mouse blood flow cessation model. *Circulation* 102, 2861-2866 (2000); Ivan, E. et al. Expansive arterial remodeling is associated with increased neointimal macrophage foam cell content: the murine model of macrophage-rich carotid artery lesions. *Circulation* 105, 2686-2691 (2002); Lessner, S. M., Martinson, D. E. & Galis, Z. S. Compensatory vascular remodeling during atherosclerotic lesion growth depends on matrix metalloproteinase-9 activity. *Arterioscler Thromb Vasc Biol* 24, 2123-2129 (2004)). Briefly, the left carotid artery of the mouse was ligated to cause local inflammation, resulting in well-defined atherosclerotic lesions after 2 weeks of feeding with Western diet. The concomitant dosing with the P2Y13r agonist for 2 weeks along with high-cholesterol diet showed a dose-dependent inhibition of the progression of the atherosclerosis lesions compared to control animals based on the lesion cholesterol content (Riedmüller K, Metz S, Bonaterra G A, Kelber O, Weiser D, Metz J, Kinscherf R. Cholesterol diet and effect of long-term withdrawal on plaque development and composition in the thoracic aorta of New Zealand White rabbits. *Atherosclerosis* 210 407-13 (2010)) (FIG. 17A). The quantification of plaque components by histo-pathological analysis of the treated carotids with hematoxylin-eosin (FIG. 17B, E, H), oil-red O staining (FIG. 17C, F, I) and with CD68 antibody (specific of the macrophages), (FIG. 17D, G, J) further confirmed this observation. The staining clearly showed a decrease in lipid content of the carotids of the treated animals. The P2Y13r agonist inhibition of cholesterol deposit was also observed in the non-inflammatory right carotids of the "flow cessation model" apoE$^{-/-}$ mice (for example, 18.2+/−3.6 and 7.5+/−3.4 nmole/mg of tissue for vehicle and Compound IIa at 100 µg/kg, respectively.

To certify the P2Y13r specificity, prior to carotid ligation and Western diet, the mice were infected with adenovirus carrying either mock or specific shRNA targeted against the P2Y13r where a strong knock-down of P2Y13r was observed (FIG. 18 A). The concomitant dosing with the P2Y13r agonists (at 0.1 mg/kg/day) for 2 weeks along with high-cholesterol diet showed a remarkable decrease in the cholesterol content (60% decrease) of the ligated carotids in mock adenovirus, indicating a significant inhibition of the progression of the atherosclerosis lesions as compare to control animals (FIG. 18 B). This observation was further confirmed by histo-pathological analysis of the treated carotids with hematoxylin-eosin and oil-red O staining (not shown). The effects of P2Y13r agonist on cholesterol content in carotids were abolished in mice treated with shRNA targeted against the P2Y13r, strengthening the specificity of the P2Y13r in this model when P2Y13r expression was knocked-down (FIG. 18 B). This specific role of P2Y13r was also observed on plasma cholesterol content (FIG. 18 C) and more specifically on LDL and VLDL cholesterol (FIGS. 18 E and D, respectively), the main lipoprotein classes in this particular animal model, where a decrease was observed in mock adenovirus P2Y13r agonist-treated mice and abolished in to P2Y13r shRNA agonist-treated mice. These data represent the first evidence that the stimulation of P2Y13r could have a positive influence on the atherosclerosis progression.

The prevention of progression of the plaque in aorta was further evaluated in the cholesterol diet-fed apoE−/− mice (FIG. 19). After 8 weeks of diet followed by 4 weeks treatment at 100 μg/kg/day of Compound IIa, the treated animals had significant decreases in plaque area (FIGS. 4B, 4G and 4J), cholesterol content (FIG. 19A), VCAM1 expression using specific antibody CD106 (FIGS. 4F, 4I and 4L), decreased macrophage content (F4/80 antibody—FIG. 19C) of the aortic wall and the plaque and a decrease of the lipid staining (FIGS. 19D, H and K). The collagen content of the wall was improved (FIG. 19E).

The issue of whether stimulation of the P2Y13r pathway could affect the regression of atherosclerosis pre-induced in the high-cholesterol diet fed rabbits was also addressed. These animals, after 2 months of high-cholesterol diet (0.5% cholesterol in the diet) followed by a 3 weeks wash-out period, developed atherosclerotic lesions in the aorta. In addition, they expressed cholesteryl ester transfer protein (CETP, not expressed in mice) and also presented a lipoprotein pattern similar to the human. Following lesion induction and washout period, these animals were treated with Compound IIa given orally at doses up to 0.3 mg/kg for 4 weeks. There was significant regression of the atherosclerotic plaques in aorta (30% decrease) of the agonist treated animals as measured by the cholesterol content of the entire artery (FIG. 20 A). Again, the immuno-histological analysis of different parts of the aortas (from proximal-to-distal) using hematoxylin-eosin, HHF35 antibody (specific for smooth muscle cells) and RAM11 antibody (specific for macrophages) confirmed the regression of the plaques (not shown). The lipoprotein profiles analyzed by HPLC showed a trend towards an increase of the HDL cholesterol (FIG. 20 D) as well as the rabbit apoA-I, as measured by SELDI-TOF analysis, while the VLDL and LDL decreased slightly (FIGS. 20 B and C, respectively). No change in mRNA expressions (as measured by QPCR) of LDL receptors and SR-BI was observed in the liver of treated rabbits (not shown). These observations indicated that the activation of P2Y13r did not have direct impact on the β-lipoprotein metabolism, also confirmed by the modest modulation of the plasma VLDL, LDL apoB and triglycerides. As observed previously in mice (FIG. 16), the bile acid content in the liver increased in the rabbits treated with P2Y13r agonists (FIG. 20G) strengthening the role of P2Y13r pathway in the observed effects in the rabbits. This relatively modest effect on the plasma HDL levels could be due to a neo-synthesis of new HDL particles, which would compensate the uptake of mature HDL by the liver due to Compound IIa effect. As a confirmation, the observed increase in plasma apoA-I (FIG. 21A) associated with the increase in the apoA-I mRNA expression in the liver (FIG. 21B) is in favour of the generation of new HDL particles in the circulation.

In addition, due to the efficient HDL turnover mediated by P2Y13r and their strong capacity to efflux cholesterol from macrophages, the nascent HDL particles could efficiently promote regression of the atherosclerotic plaques.

To evaluate this hypothesis, the size of HDL particles in the treated animals were analyzed using Lipoprint® technique. The HDL content of the treated animals showed a very consistent pattern with a specific decrease in large HDL and increase of the "intermediate" size HDL particles as compare to control animals (FIGS. 21 C and D). These intermediate HDL particles are considered as more potent particles for the removal of cholesterol from atherosclerotic plaques by promoting efflux of cholesterol from the macrophages presents in the lesion (Khera, A. V. et al. Cholesterol efflux capacity, high-density lipoprotein function, and atherosclerosis. *N Engl J Med* 364, 127-135 (2011); deGoma, E. M., deGoma, R. L. & Rader, D. J. Beyond high-density lipoprotein cholesterol levels evaluating high-density lipoprotein function as influenced by novel therapeutic approaches. *J Am Coll Cardiol* 51, 2199-2211 (2008)). Finally, the measurement of cholesterol efflux in [3H]-cholesterol loaded J774 macrophages using either the plasma (FIG. 21E) or apoB-particles-depleted plasma (FIG. 21F) from the treated animals showed a dose-dependent efflux of cholesterol after treatment with the P2Y13r agonist, indicating that plasma HDL from treated animals are more powerful to efflux cholesterol from macrophages (Khera, A. V. et al. Cholesterol efflux capacity, high-density lipoprotein function, and atherosclerosis. *N Engl J Med* 364, 127-135 (2011)).

In conclusion, it was demonstrated for the first time in vivo that P2Y13 receptors are key partners in the HDL metabolism, i.e., in the reverse cholesterol transport process and in their final major physiological function, i.e., atherosclerosis protection. These data support a mechanism in which the stimulation of the HDL uptake or endocytosis by the liver via P2Y13r pathway promotes cholesterol catabolism by the liver and secretion in the bile. It is likely that the uptake of large HDL particles by the liver also stimulates de novo synthesis of nascent HDL particles and hence improves the efflux capacity of the serum. In another words, it was demonstrated in vivo that positive direct intervention on the functionality of the HDL, instead of acting only on the level of HDL, could have dramatic impact on the atherosclerotic pathology. These data also support that P2Y13r agonists, such as Compound IIa and the other compounds of the invention, are highly useful as pharmacological therapeutics for the treatment of atherosclerotic disease or its complications.

What is claimed is:

1. A compound of Formula (I):

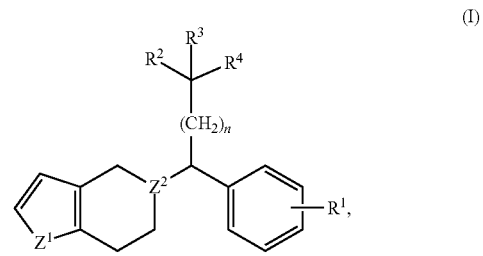

or a pharmaceutically acceptable salt thereof, wherein each of $R^1$, $R^2$, and $R^3$ is independently —H, —OH, —NH$_2$, —NH(alkyl), —N(alkyl)(alkyl), hydrocarbyl, —O-hydrocarbyl, aryl, —O-aryl, aralkyl, —O-aralkyl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), —N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), or —SO$_2$NH$_2$;

$R^4$ is —OH, —COOH, or —C(O)O(alkyl), $Z^1$ is S;

$Z^2$ is N; and n is an integer from 1-6.

2. The compound or pharmaceutically acceptable salt of the compound of claim 1, wherein $R^1$ is 2-halo.

3. The compound or pharmaceutically acceptable salt of claim 2, wherein each of $R^2$ and $R^3$ is independently —H or alkyl.

4. The compound of claim 1, wherein the compound is:
Ia
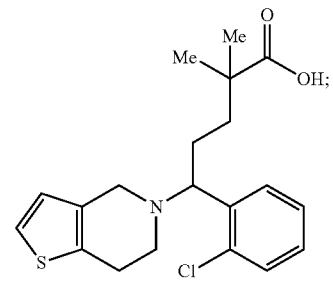
Ib
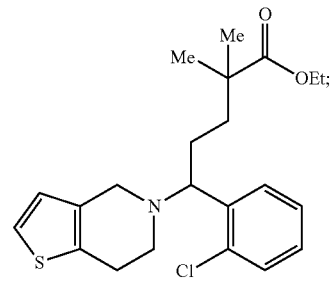
Ic
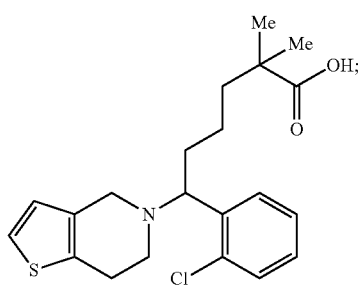
Id
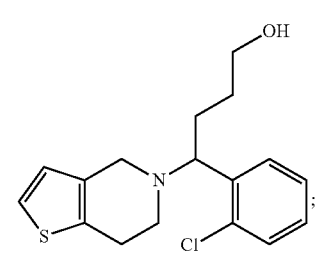
Ie
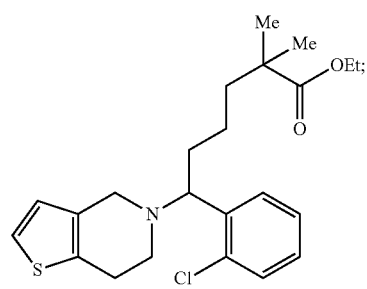
-continued
If
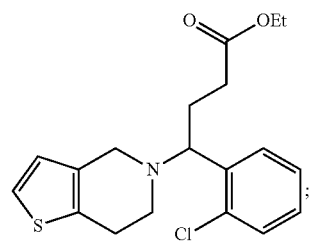
Ig
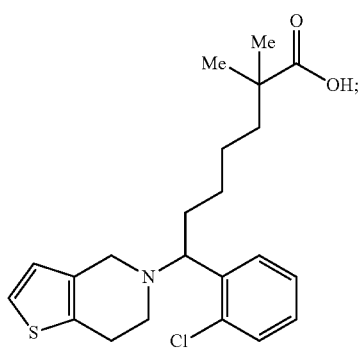
Ih
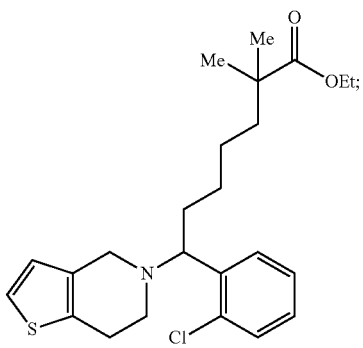
Im
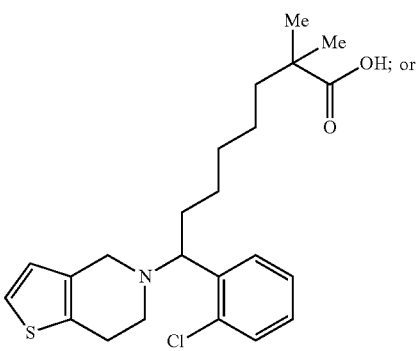

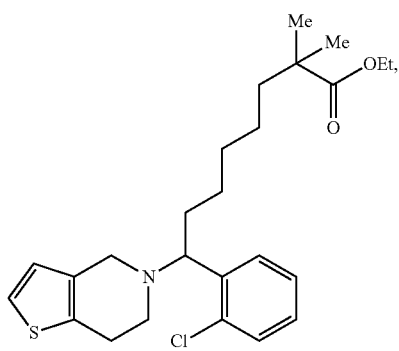

or a pharmaceutically acceptable salt of any of the foregoing.

5. A composition comprising an effective amount of a compound or pharmaceutically acceptable salt of the compound of claim 1 and a pharmaceutically acceptable vehicle or carrier.

6. The composition of claim 5, wherein the composition is formulated for oral administration.

7. The composition of claim 5, wherein the composition is in the form of a tablet or capsule.

8. The composition of claim 5, wherein the compound or salt thereof is present in an amount of about 1 mg to about 1,000 mg.

9. The compound of claim 1, wherein the compound is:

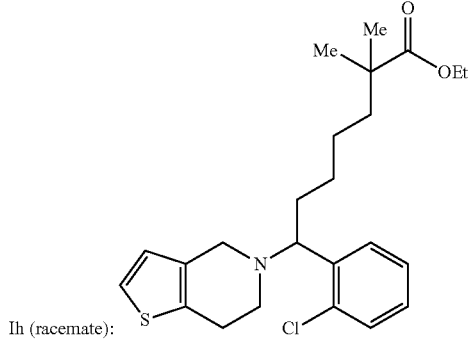 [SMILES: CCOC(=O)C(C)(C)CCCCC(c1ccccc1Cl)N1CCc2sccc2C1]

Ih (racemate):

or a pharmaceutically acceptable salt thereof.

10. The compound of claim 1, wherein the compound is:

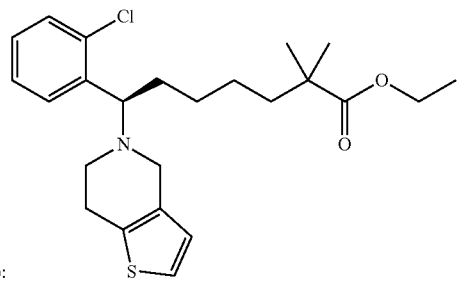

Ih (R-isomer):

or a pharmaceutically acceptable salt thereof.

11. The compound of claim 1, wherein the compound is:

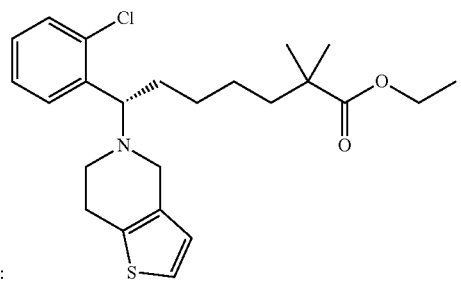

Ih (S-isomer):

or a pharmaceutically acceptable salt thereof.

* * * * *